(12) United States Patent
Cowens et al.

(10) Patent No.: US 8,765,383 B2
(45) Date of Patent: Jul. 1, 2014

(54) METHODS OF PREDICTING CANCER RISK USING GENE EXPRESSION IN PREMALIGNANT TISSUE

(75) Inventors: Wayne Cowens, Tiburon, CA (US); Maureen T. Cronin, Los Altos, CA (US); Carl L. Millward, Burlingame, CA (US); Francois Collin, Berkeley, CA (US); Michael Crager, Redwood City, CA (US)

(73) Assignee: Genomic Health, Inc., Redwood City, CA (US)

( * ) Notice: Subject to any disclaimer, the term of this patent is extended or adjusted under 35 U.S.C. 154(b) by 336 days.

(21) Appl. No.: 12/755,368

(22) Filed: Apr. 6, 2010

(65) Prior Publication Data
US 2010/0291573 A1    Nov. 18, 2010

Related U.S. Application Data

(60) Provisional application No. 61/167,503, filed on Apr. 7, 2009, provisional application No. 61/243,708, filed on Sep. 18, 2009.

(51) Int. Cl.
*C12Q 1/68*    (2006.01)
(52) U.S. Cl.
CPC .................................. *C12Q 1/6886* (2013.01)
USPC ........................................ 435/6.14; 435/6.12
(58) Field of Classification Search
CPC .................................................... C12Q 1/6886
See application file for complete search history.

(56) References Cited

U.S. PATENT DOCUMENTS

| | | |
|---|---|---|
| 2002/0042088 A1 | 4/2002 | Macina et al. |
| 2003/0219760 A1 | 11/2003 | Gordon et al. |
| 2004/0053317 A1 | 3/2004 | Glinskii |
| 2006/0211036 A1 | 9/2006 | Chou et al. |
| 2007/0099209 A1 | 5/2007 | Clarke et al. |
| 2007/0105133 A1 | 5/2007 | Clarke et al. |
| 2008/0131885 A1 | 6/2008 | Pratilas et al. |
| 2009/0298701 A1 | 12/2009 | Baker et al. |
| 2010/0075323 A1* | 3/2010 | Terng et al. ................. 435/6 |

FOREIGN PATENT DOCUMENTS

| | | |
|---|---|---|
| WO | WO2005076005 A2 | 8/2005 |
| WO | WO2007025044 A2 | 3/2007 |
| WO | WO 2007/082099 | 7/2007 |
| WO | WO 2009/045115 | 4/2009 |

OTHER PUBLICATIONS

Strausberg et al, In Microarrays and Cancer Research, Warrington et al (eds.), Eaton Publishing, Westborough, MA, pp. xi-xvi.*
Notterman et al, In Microarrays and Cancer Research, Warrington et al (eds.), Eaton Publishing, Westborough, MA, pp. 81-111 at pp. 61-62.*
International Search Report and Written Opinion of the International Searching Authority issued in International Application No. PCT/US 10/30285, 11 pages (Sep. 9, 2010).
Karamouzis et al., "Differential Expression of Retinoic Acid Receptor Beta (RAR) and the AP-1 Transcription Factor in Normal, Premalignant and Malignant Human Laryngeal Tissues," European Journal of Cancer, 40:761-773 (2004).
Supplementary European Search Report issued in EP App. No. 10762395, 6pages (Jul. 11, 2012).

* cited by examiner

*Primary Examiner* — James Martinell
(74) *Attorney, Agent, or Firm* — Bozicevic, Field & Francis LLP

(57) ABSTRACT

The present disclosure provides methods for assessing a patient's cancer risk and/or recurrence risk, which methods comprise assaying, in a biological sample obtained from the gastrointestinal (GI) tract of the patient, an expression level of a risk gene. The present disclosure also provides methods involving a cancer risk/recurrence risk sequence, i.e. the V600E mutation of the BRAF gene, which is useful for assessing cancer risk and/or recurrence risk in a patient.

18 Claims, 1 Drawing Sheet

Mutant Amplicon (V660E)
TATTTCTTCATGAAGACCTCACAGTAAAAATAGGTGATTTTGGTCTAGCTACAGAGA
AATCTCGATGGAGTGGGTC
ATAAAGAAGTACTTCTGGAGTGTCATTTTTATCCACTAAAACCAGATCGATGTCTCT
TTAGAGCTACCTCACCCAG Wild Type
TATTTCTTCATGAAGACCTCACAGTAAAAATAGGTGATTTTGGTCTAGCTACAGTGA
AATCTCGATGGAGTGGGTC
ATAAAGAAGTACTTCTGGAGTGTCATTTTTATCCACTAAAACCAGATCGATGTCACT
TTAGAGCTACCTCACCCAG

METHODS OF PREDICTING CANCER RISK USING GENE EXPRESSION IN PREMALIGNANT TISSUE

CROSS-REFERENCE TO RELATED APPLICATIONS

This application claims priority benefit of U.S. provisional application Ser. No. 61/167,503, filed Apr. 7, 2009 and U.S. provisional application Ser. No. 61/243,708, filed Sep. 18, 2009, each of which applications is incorporated herein in its entirety.

INTRODUCTION

The gastrointestinal (GI) tract is a series of distinct but connected anatomical areas, including the esophagus, stomach, small bowel, colon and rectum. Cancers of the GI tract are the second most common cause of cancer-related mortality in Europe and the U.S., and a major health issue around the world.

Under current practice, definitive screening of the GI tract for cancer requires endoscopy, biopsy of morphologically abnormal mucosa, and confirmation of the diagnosis by histological analysis of biopsied tissues. Consequently, a large number of endoscopic procedures are performed annually. As an example, approximately 25% of colonoscopies identify premalignant lesions. About 0.25% of colonoscopy patients experience serious complications from the procedure such as perforation of the colon, rectal bleeding, diverticulitis, cardiovascular events, severe abdominal pain, or death.

In cases where premalignant lesions are found, no firm data exist to guide surveillance decisions, such as the timing of a follow-up procedure. Current methods of cancer risk assessment have significant shortcomings, not the least of which is that for many patients, classification of lesions discovered fails to yield a definitive assessment. In many instances, physicians presented with identical endoscopic and histological findings reach different conclusions as to the level of cancer risk present and the appropriate course of surveillance. The uncertainty inherent in clinical classification based on endoscopic and histological findings applies broadly to many premalignant lesions of the gastrointestinal mucosa. Improved methods are needed for assessing the risk of progression to cancer based on evaluation of premalignant lesions and for making informed cancer surveillance and treatment decisions.

SUMMARY

The present disclosure provides methods for assessing a patient's cancer risk and/or recurrence risk, which methods comprise assaying, in a biological sample obtained from the gastrointestinal (GI) tract of the patient, an expression level of a risk gene. The present disclosure also provides methods involving a cancer risk/recurrence risk sequence, i.e. the V600E mutation of the BRAF gene, which is useful for assessing cancer risk and/or recurrence risk in a patient.

The present disclosure provides methods for determining cancer risk for a human patient, the methods comprising measuring a normalized expression level of a risk gene listed in Tables 8a or 8b, or a co-expressed gene thereof listed in Table 9 or Table 10, in a biological sample obtained from the gastrointestinal (GI) tract of the patient, using the normalized expression level to generate a score indicative of the cancer risk for the patient, wherein the normalized expression level of risk genes in Table 8a, and co-expressed genes thereof, are positively correlated with an increased cancer risk, and wherein the normalized expression level of risk genes in Tables 8b, and co-expressed genes thereof, are negatively correlated with an increased cancer risk; and generating a report based on the score. The biological sample can comprise cells from a premalignant lesion. The cancer risk determined can be a synchronous risk, and the score provide information concerning a likelihood that the patient has a co-existant malignant lesion of the GI tract. The cancer risk determined can be a progression risk, and the score provide information concerning a likelihood that the patient will develop a malignant lesion of the GI tract. The risk gene can be a comparable risk gene. The measuring step in such methods can be conducted using polymerase chain reaction (PCR), and can be quantitative PCR. The measuring step in such methods can quantify an mRNA expression level for the risk gene. The measuring step in such methods can quantify a polypeptide expression level for the risk gene.

The present disclosure provides methods for determining cancer risk for a human patient, comprising measuring a normalized expression level of a risk gene listed in Tables 4a-5b, or a co-expressed gene thereof listed in Table 9 or Table 10, in a biological sample obtained from the lower gastrointestinal (GI) tract of the patient; using the normalized expression level to generate a score indicative of the cancer risk for the patient, wherein the normalized expression level of risk genes in Table 4a and 5a, and co-expressed genes thereof, are positively correlated with an increased cancer risk, and wherein the normalized expression level of risk genes in Table 4b and 5b, and co-expressed genes thereof, are negatively correlated with an increased cancer risk; and generating a report based on the score. The biological sample can comprise cells from a premalignant lesion. The cancer risk determined can be a synchronous risk, and the score provide information concerning a likelihood that the patient has a co-existant malignant lesion of the lower GI tract. The cancer risk determined can be a progression risk, and the score provide information concerning a likelihood that the patient will develop a malignant lesion in the lower GI tract. The measuring step in such methods can be conducted using PCR, and can be quantitative PCR. The measuring step in such methods can quantify an mRNA expression level for the risk gene. The measuring step in such methods can quantify a polypeptide expression level for the risk gene. Such methods can further include analyzing a sequence of BRAF from the biological sample to detect a V600E mutation.

The present disclosure provides methods for determining cancer risk for a human patient, comprising measuring a normalized expression level of a cancer risk gene listed in Tables 6a, 6b, 7a, or 7b, or a co-expressed gene thereof listed in Table 9, in a biological sample obtained from the upper gastrointestinal (GI) tract of the patient; using the normalized expression level to generate a score indicative of the cancer risk for the patient, wherein the normalized expression level of cancer risk genes in Tables 6a and 7a, and co-expressed genes thereof, are positively correlated with an increased cancer risk, and wherein the normalized expression level of cancer risk genes in Tables 6b and 7b, and co-expressed genes thereof, are negatively correlated with an increased cancer risk; and generating a report based on the score. The biological sample can comprise cells from a premalignant lesion. The cancer risk determined can be a synchronous risk, and the score provide information concerning a likelihood that the patient has a co-existant malignant lesion of the upper GI tract. The cancer risk determined can be a progression risk, and the score provide information concerning a likelihood that the patient will develop a malignant lesion in the upper GI tract. The measuring step in such methods can be conducted using PCR, and can be quantitative PCR. The measuring step in such methods can quantifies an mRNA expression level for the risk gene. The measuring step in such methods can quantify a polypeptide expression level for the risk gene.

The present disclosure provides methods for determining recurrence risk for a human patient with a gastrointestinal (GI) cancer after surgery, comprising measuring a normalized expression level of a risk gene listed in Tables 4a-7b, or a co-expressed gene thereof listed in Table 9 or Table 10, in a biological sample obtained from the gastrointestinal (GI) tract of the patient; using the normalized expression level to generate a score indicative of the recurrence risk for the patient, wherein the normalized expression level of risk genes in Table 4a and 5a, and co-expressed genes thereof, are positively correlated with an increased recurrence risk, and wherein the normalized expression level of risk genes in Tables 4b and 5b, and co-expressed genes thereof, are negatively correlated with an increased recurrence risk; and generating a report based on the score. The biological sample in such methods can include cells of a malignant tumor obtained from the patient during surgery. The measuring step in such methods can be conducted using PCR, and can be quantitative PCR. The measuring step in such methods can quantifies an mRNA expression level for the risk gene. The measuring step in such methods can quantify a polypeptide expression level for the risk gene.

BRIEF DESCRIPTION OF THE DRAWINGS

FIG. 1 shows the mutant (SEQ ID NO: 1) and wild type (SEQ ID NO:2) amplicons used in qRT-PCR to determine the respective expression levels of the V600E mutant and wild type alleles of BRAF.

DETAILED DESCRIPTION

Definitions

As used herein, the term "gastrointestinal tract" or "GI tract" refers to the esophagus, stomach, colon, ileum, jejunum, rectum, anus, and all connections between these segments. As used herein, the term "upper GI tract" means the mouth, pharynx, esophagus, and stomach. As used herein, the term "lower GI tract" means the small and large intestines, rectum and anus.

As used herein, the term "stomach" includes the fundus, corpus (or body), and the antrum (or pylorus). As used here, the term "esophagus" includes the esophagus and the gastroesophageal junction (GEJ), also known as the cardiac sphincter, lower esophageal sphincter, cardia, and cardias.

As used herein, the term "cancer risk" refers to synchronous risk and/or progression risk.

As used herein, the term "synchronous risk" refers to the likelihood that a patient identified as having a premalignant lesion of the GI tract also has another anatomically distinct lesion, either malignant or pre-malignant. The terms "synchronous" and "metaschronous" may be used herein interchangeably to refer to simultaneous occurrence. For example, a synchronous lesion is one that exists in temporal (but necessarily anatomic) proximity to a known lesion.

As used herein, the term "progression risk" refers to the likelihood that a patient having a premalignant lesion in the gastrointestinal (GI) tract will develop a malignant lesion of the GI tract within a defined time interval.

As used herein, the term "recurrence risk" refers to the likelihood that a patient diagnosed with cancer of the GI tract, after surgery, will have a cancer recurrence at the same anatomical location, or an event at an anatomically distant location of the GI tract, within a defined time interval.

As used herein, the term "risk gene" refers to a gene, the expression level of which is correlated, positively or negatively, with cancer risk and/or recurrence risk. The term "progression risk gene" refers specifically to a gene, the expression level of which is correlated, positively or negatively, with progression risk. The term "synchronous risk gene" refers specifically to a gene, the expression level of which is correlated, positively or negatively, with synchronous risk. The term "recurrence risk gene" refers specifically to a gene, the expression level of which is correlated, positively or negatively, with recurrence risk.

As used herein, a "comparable risk gene" refers to a risk gene for the upper GI tract that is a member of the same gene family as a risk gene for the lower GI tract, or vice versa. The comparable risk gene may be part of a family of genes. For example, the collagens are a superfamily of proteins that play a role in maintaining the integrity of various tissues, and a statistically significant correlation exists between members of this family and increased cancer risk in the upper GI tract (e.g., COL12A1, COL4A1, COL6A3) and the lower GI tract (e.g., COL1A1, COL3A1, COL6A1, COL6A3, COL12A1). Thus, for example, increased expression of COL12A1 in a premalignant lesion obtained from the upper GI tract may be indicative of an increased cancer risk for the entire GI tract. As shown in Tables 4a-7b and 12a-12b, comparable risk genes include collagens, calcium binding (e.g., S100A2, S100A8, and S100A9), cell differentiation (e.g., CD18, CD105, CD248, CD31), heat shock proteins (e.g., HSPA1A, HSPA8), chemokine ligands (e.g., CXCL5, CXCL9, CXCL10, CXCL12), early growth response (e.g., EGR1, EGR3), dual specificity phosphatases (e.g., DUSP2, DUSP4, DUSP6), human leukocyte antigens (e.g., HLA-F, HLA-G), insulin-like growth factors (e.g., IGFBP5, IGFBP7), integrins (e.g., ITGA5, ITGA7, ITGB4), transforming growth factors (e.g., TGFB1, TGFB3), tissue inhibitor of matrix metalloproteinases (e.g., TIMP1, TIMP2, TIMP3), and vascular endothelial growth factors (e.g., VEGFC, VEGF).

As used herein, the term "BRAF sequence" refers to a sequence within a gene which is present in a germ line cell or in a somatic cell of a patient, or specifically in GI tract lesion of a patient, and the presence of which is correlated, positively or negatively, with cancer risk, including progression risk and/or synchronous risk, and recurrence risk. Specifically, the term "BRAF sequence" refers to the V600E mutation that is described by J. Morlan, et al., PLoS ONE 4(2): e4584. doi:10.1371/journal.pone.0004584 (2009)

As used herein the term "correlated" is used to refer to a statistical association between two variables which may be a linear or a non-linear association and which may apply across particular ranges of the variables.

As used herein, the term "premalignant" means tissue that is not yet malignant, but may be capable of becoming malignant. For example, a premalignant esophageal lesion may be histologically identified as metaplastic, hyperplastic or dysplastic. As applied to a lesion of the colorectal mucosa, premalignant lesions include flat intestinal dysplasias and adenomatous polyps, including adenomatous polyps with low grade dysplasia and adenomatous polyps with high grade dysplasia, but not invasive lesions, i.e. adenocarcinoma.

As used herein, the terms "lesion" or "tumor" refer to an area of a tissue that has, or appears to have, undergone a pathological change. For example, in the colon and rectum, polyps are the most commonly observed lesion, but non-polypoid (flat or recessed) lesions are also observed and may be more likely to contain cancerous tissue than polyps, after adjusting for polyp size. As another example, Barrett's Esophagus is characterized clinically as an endoscopically detectable metaplastic lesion of the distal esophagus. The methods disclosed herein can involve use of a tissue sample from a "premalignant lesion," wherein the sample may additionally include histologically normal tissue from the surrounding area.

As used herein, the term "early-stage" colorectal or colon cancer refers to Stage I or Stage II as defined in the UICC, *TNM Classification of Malignant Tumours* (6$^{th}$ Ed. 2002).

As used herein, the term "surveillance program" refers to a set of examinations or procedures used to longitudinally follow up individuals identified in a screening program to have lesions. A "surveillance program" includes strategies for both surveillance interval and surveillance intensity. Examination of the lower gastrointestinal tract may be performed by one or more suitable procedures, e.g., endoscopy (including colonoscopy and sigmoidoscopy), fecal occult blood (FOB) testing, computed tomography (CT) or other imaging procedure, carcinoembryonic antigen testing, and double contrast barium enema. Examination of the upper gastrointestinal tract may be performed by one or more suitable procedures, e.g., endoscopy (gastroscopy, chromoendoscopy, spectroscopy), cytological sampling, and double contrast imaging and CAT scan.

As used herein, the term "surveillance intensity" refers to the exhaustiveness of the cancer surveillance program. The intensity of surveillance should be proportional to the patient's risk of cancer or cancer recurrence. High intensity surveillance may include, for example, examination by colonoscopy rather than sigmoidoscopy. High intensity surveillance may also include, for example, immediate repetition of a completed colonoscopy due to a high likelihood of an undetected malignant lesion.

As used herein, the term "surveillance interval" refers to the length of time between a current examination and a subsequent examination for abnormalities of the gastrointestinal tract.

As used herein, the term "stromal gene" refers to genes that are synthesized predominantly by stromal cells and are involved in stromal response and genes that co-express with stromal group genes. "Stromal cells" are defined herein as connective tissue cells that make up the support structure of biological tissues. Stromal cells include fibroblasts, immune cells, pericytes, endothelial cells, and inflammatory cells. "Stromal response" refers to a desmoplastic response of the host tissues at the site of a primary tumor or invasion. See, e.g., E. Rubin, J. Farber, Pathology, 985-986 (2$^{nd}$ Ed. 1994).

As used herein, the terms "co-expressed gene" or "co-expression" are used to refer to a set of two or more genes, the expression of which is correlated across a set of samples. For example, co-expression may be determined using microarray or polymerase chain reaction (PCR) expression data. Co-expressed genes can be identified by methods known in the art including, e.g., and linear regression analysis (including R$^2$ value, correlation coefficient, p value, slope, and degrees of freedom) and calculation of pairwise correlation coefficients, e.g. Pearson correlation coefficients or Spearman correlation coefficients. Co-expression may optionally include analysis of a pathway-level, weighting, co-expression networks, or gene modules.

The term "expression product" is used herein, in reference to a gene, to refer to the RNA transcription products (transcripts) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

As used herein, the term "expression level" as applied to a gene refers to the normalized level of the expression product of a gene, e.g. the normalized value determined for the RNA expression product of a gene or for the polypeptide expression value of a gene. Expression levels may be normalized with respect to the expression level of one or more reference genes or the expression level may be normalized using global normalization methods. Those skilled in the art will recognize that numerous methods of normalization are known, and can be applied for use in the methods of the present disclosure.

The term "computer-based system", as used herein refers to the hardware, software, and data storage used to analyze information. The minimum hardware of a computer-based system comprises a central processing unit (CPU) and hardware for data input, output, and storage. A skilled artisan can readily appreciate that many of the currently available computer-based system are suitable for use in the present disclosure and may be programmed to perform the specific measurement and/or calculation functions of the present disclosure.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computer" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

The present disclosure provides methods for assessing a patient's cancer risk and/or recurrence risk, which methods comprise assaying, in a biological sample obtained from a lesion of the gastrointestinal (GI) tract of the patient, an expression level of a risk gene, or its expression product. The biological sample can be from a premalignant lesion.

The present disclosure provides risk genes useful in the methods disclosed herein. Risk genes are listed in Tables 4a-8b and 12a-12b wherein increased expression of risk genes listed in Tables 4a, 5a, 6a, 7a, 8a and 12a are positively correlated with increased GI tract cancer risk and/or recurrence risk, and increased expression levels of risk genes listed in Tables 4b, 5b, 6b, 7b, 8b, and 12b are negatively correlated with increased GI tract cancer risk and/or recurrence risk.

The present disclosure also provides a cancer risk/recurrence risk sequence, i.e. V600E mutation of the BRAF gene, which is useful for assessing cancer risk and/or recurrence risk in a patient.

Risk genes analyzed in the methods of the present disclosure include synchronous risk genes, and the expression level of one or more synchronous risk genes can be used to calculate a likelihood that the patient has a concurrent lesion in the GI tract, whether or not the concurrent lesion has been identified.

Risk genes analyzed in the methods of the present disclosure can include progression risk genes, and the expression level of one or more progression risk genes can be used to calculate a likelihood that the patient will develop a malignant lesion of the GI tract within a defined time interval.

Risk genes can be used in the methods of the present disclosure to determine the likelihood that a patient diagnosed with colorectal cancer, after surgery, will have a recurrence of colorectal cancer. The recurrence risk may be a local recurrence, or an anatomically distant metastasis. In a particular embodiment, the colorectal cancer is early stage colorectal cancer.

The methods of the present disclosure can involve generating a report based on the normalized expression level. The report may additionally comprise the expression levels of additional risk genes. The report can include a score indicative of the patient's cancer risk and/or recurrence risk. For example, a score based on the expression level of one or more progression risk genes would indicate the likelihood that the patient's premalignant lesion(s) will develop into a malignant lesion(s), and the physician may therefore decrease the surveillance intervals or recommend intervention for this patient. On the other hand, a score based on synchronous risk gene expression would indicate the likelihood that the patient had an existing malignant lesion, and the physician may therefore increase the surveillance intensity for this patient. The report can include a classification of the patient into a risk subgroup, e.g., low risk, medium risk or high risk. An assessment of cancer risk and/or recurrence risk may facilitate a physician's recommendation regarding a surveillance program or intervention recommendation for the patient.

It is understood that the present disclosure provides methods wherein the expression level of a risk gene is measured in a sample derived from a single lesion and also comprises methods wherein the expression product of a risk gene is measured in a sample derived from more than one lesion. It is further understood that the present disclosure includes methods wherein the measured expression level of a particular risk gene in multiple samples from a single patient is used to determine an aggregate measure of the expression of the risk gene using, e.g., an average or weighted average of the measured expression levels.

It is understood that the present disclosure optionally includes methods wherein cancer risk and/or recurrence risk is assessed using the expression levels of more than one risk gene. Additionally, the present disclosure optionally includes methods wherein gene products are extracted from different regions of lesions. For example, stromal gene products may be extracted from the luminal and tumor-associated stroma, and these expression levels compared as part of generating a risk score.

Risk genes of the present disclosure were identified by correlation of the expression of a risk gene in a biopsy with cancer risk. The present disclosure further provides genes that are co-expressed with risk genes, and co-expressed genes may also be assayed, or assayed as a substitute for, one or more risk genes in the methods disclosed herein. In one or more embodiments, the method comprises measuring the expression levels on one or more comparable risk genes to determine cancer risk and/or recurrence risk for the patient.

Certain risk genes of the present disclosure are members of co-expression clusters, i.e. groups of genes that are generally co-expressed in a range of different situations and for various biological reasons, e.g. because they coordinately regulate a particular biological function(s). It will be appreciated that measuring the expression level of genes that are members of the same co-expression clusters as risk genes will be useful in assessing cancer risk. Examples of genes that are members of co-expression clusters can be found in U.S. provisional patent application No. 61/151,748, which is incorporated herein by reference in its entirety.

The expression level of a risk gene can be used in conjunction with clinical information, e.g. the number, size and location of premalignant lesions to assess the cancer risk of the patient.

Cancer risk can be assessed using cancer risk together with cancer risk sequences (e.g., V600E of BRAF) and/or clinical measures. Recurrence risk can be assessed using recurrence risk sequences and/or clinical measures.

The present disclosure comprises methods wherein the expression product of a risk gene is measured in a sample comprising a biological sample that has, or appears to have, undergone a pathological change, but was not definitively diagnosed as a premalignant lesion at the time the specimen was obtained, but had pathologic characteristics that suggested the sample was a lesion.

The expression product can be is measured as RNA. The RNA can be fragmented RNA. Alternatively or additionally, the expression product that is measured is a polypeptide.

RNA expression products can be measured using quantitative reverse transcription polymerase chain reaction (qRT-PCR), using DNA arrays, and/or using high-throughput transcript sequencing.

The polypeptide expression levels can be measured using, for example, immunohistochemistry, enzyme-linked immunosorbent assay, mass spectrometry, and/or an array-based method.

The premalignant lesion used to assess cancer risk can be a premalignant lesion of the lower gastrointestinal tract, e.g., a lesion of the colon or the rectum. The premalignant lesion of the lower gastrointestinal tract may be, for example, a flat or recessed intestinal dysplasia or an adenomatous polyp, such as an adenomatous polyp with low grade dysplasia or adenomatous polyps with high grade dysplasia.

The premalignant lesion used to assess cancer risk can be a premalignant lesion of the upper gastrointestinal tract. The premalignant lesion of upper gastrointestinal tract may be, for example, an intestinal metaplasia or dysplasia of the distal esophagus, i.e. near the junction of the esophagus and the stomach (Barrett's Esophagus), an intestinal metaplasia or dysplasia of the of the body of the stomach, or a squamous dysplasia of the esophagus.

Risk genes and cancer risk sequences obtained from a lesion in the lower GI tract may be assayed and the results of the assays may be used to assess cancer risk in the entire GI tract, including the upper GI tract. Alternatively or in addition, risk genes and cancer risk sequences obtained from a lesion in the upper GI tract may be assayed and the results of the assays may be used to assess cancer risk in the entire GI tract, including the lower GI tract.

The biological sample can be a tumor cell recovered from a primary tumor of the GI tract, or from sites distant from the original tumor, e.g., circulating tumor cells.

The level of an expression product of a risk gene can be measured in a body fluid obtained from a cancer patient. For example, the body fluid may be urine, blood, or a blood fraction, and the expression product may be soluble in the body fluid.

Exemplary GI Tract Cancer Patients

Patients who can benefit from the methods of the present disclosure include patients who are undergoing screening for GI tract cancer and/or premalignant lesions, patients having or suspected of having a cancer of the GI tract, and patients diagnosed with cancer of the GI tract after surgery who will need surveillance for recurring or metachronous lesions, including cancer patients having a premalignant lesion of the GI tract. GI tract cancers include cancers of the esophagus, stomach, colon, ileum, jejunum, rectum, anus, and of tissues of any connections between these segments. Premalignant lesions of the GI tract are a world-wide medical problem because the individuals who have them are at much higher risk of developing life-threatening cancers than the general population. These lesions generally occur at any anatomic location from the esophagus to the rectum. For example, the two most common lesions seen in the developed world are polypoid dysplastic lesions (polyps) in the colon and metaplastic lesions (Barrett's) in the esophagus.

Barrett's esophagus (BE) is defined clinically as specialized intestinal metaplasia of the distal tubular esophagus. Barrett's esophagus affects 1-5% of the population, however it has been estimated that physicians identify only a minority of the population with the condition. Typically, when a patient is diagnosed with Barrett's esophagus, multiple biopsies are taken from the affected area and histologically examined to determine the presence and degree of dysplasia. In the U.S., when a metaplastic, low-grade dysplasia, or focal high-grade dysplasia lesion is discovered in the esophagus during screening, the patient is followed by repeat endoscopy and no intervention is suggested unless biopsies show high grade nodular dysplasia. The utility of the surveillance guidelines is therefore critically dependent on the accuracy with which clinico-pathologic risk factors predict progression risk.

Colorectal cancer is the second most common cause of cancer-related mortality from in the United States. Colonoscopy is the preferred modality for CRC screening and is recommended for all adults at age 50. (See NCCN Clinical Practice Guidelines in Oncology (2009) version 1 available at www.nccn.org/). Both cancer and premalignant neoplasms can be accurately detected by colonoscopy. In approximately 25% of patients, screened for the first time by colonoscopy, pre-malignant lesions are identified. It would be extremely useful to have prognostic assays that identify patients at significant risk of having a synchronous CRC, or developing CRC after identification and removal of polyp(s), based on lesion tissue taken from the GI tract. Information from such assays would assist patients and physicians in making screening, surveillance, and treatment decisions.

Premalignant lesions are identified based on pathology and anatomic location. For example, squamous dysplasia is located in the esophagus, Barrett's Esophagus in the junction of the esophagus and stomach, intestinal metaplasia in the stomach, and intestinal dysplasia (polypoid, flat) in the colon/rectum. These premalignant lesions may develop into squamous cell cancer (esophagus) or adenocarcinoma (esophagus, stomach, colon/rectum).

Biopsy specimens are classified as containing carcinoma, high-grade dysplasia (HGD), low-grade dysplasia (LGD) or no dysplasia/indefinite for dysplasia, and intestinal metaplasia. Although Barrett's esophagus rarely progresses to adenocarcinoma, optimal management is a matter of debate. Barrett's esophagus and colorectal polyps classified as LGD or indefinite for dysplasia are a particular clinical challenge. The significance of LGD in the GI tract is poorly understood and the optimal interval for follow-up surveillance and biopsy protocol has not been established.

Early detection programs for GI tract lesions have three components: screening to identify asymptomatic individuals in the general population that have the lesions, surveillance to longitudinally follow-up individuals identified as having the lesions by screening, and intervention to remove the lesions when indicated. The goal of these programs is to decrease the mortality rate in the general population from the tumors associated with the premalignant lesions. In order to accomplish this goal, all three components of the program must be efficient; however, it is difficult to develop strategies for all three in a single step. A successful early detection protocol should include reliable tests to identify premalignant changes or curable neoplasms, and a correct histological diagnosis of dysplasia, and proof that surgical resection for high-grade dysplasia will decrease the risk of cancer. Additionally, physicians also require guidance to create an optimal surveillance program after surgery for early stage colorectal cancer.

Currently, physicians rely on clinicopathological variables, such as lesion grade, cellular differentiation, size, number, and other histological features, to predict the prognosis of a patient with GI tract lesions. However, there is not a high degree of concordance among pathologists with respect to staging and characterizing GI tract lesions. Therefore, it would be useful to have a molecular diagnostic that was able to reliably estimate cancer risk based on expression levels in one or more lesions, without reference to interpretation of specific histological features of particular biopsied tissue.

Under the current standard of care, endoscopy is used to screen for cancer in the GI tract. Endoscopy of the upper GI tract, esophagogastroduodenoscopy (EGD), is used to identify morphological changes in the mucosa of the esophagus, stomach and duodenum. Endoscopy of the lower GI tract (colonoscopy) is used to identify morphological changes in the mucosa of the colon and rectum. As an alternative to colonoscopy, sigmoidoscopy is sometimes used for morphological examination of the sigmoid colon and the rectum, but cannot address morphology in regions of the colon beyond the sigmoid colon.

In addition, there are serious risks involved with endoscopy. The incidence of complications, including perforation, respiratory arrest, and myocardial infarction, has been estimated to be 0 to 13 per 10,000 procedures with an associated mortality of 0 to 0.8 per 10,000 procedures.

Under current treatment standards, patients diagnosed with premalignant lesions of the GI tract undergo surgery or biopsy followed by repeat endoscopies at various time intervals (based on histology of lesion). However, given that the rate of progression for those lesions to cancer is low (only 0.5% per year for esophageal and 2% for colorectal), the surveillance program for both of these clinical situations is grossly inefficient.

Tumor progression proceeds through a series of steps with increasingly greater levels of dysplasia and resulting, for some but not all tumors, in transition to a malignant tumor, i.e. cancer. Expression levels of risk genes that can distinguish between these two types of tumors can be measured in premalignant lesions and be utilized to predict progression risk, synchronous risk, and/or recurrence risk.

Clinical Application

The information generated from practice of the methods this invention may be used by patients and physicians to make decisions regarding surveillance and intervention based upon, among other factors, a patient's individual cancer risk. For example, if a premalignant lesion is found in the patient in a screening (routine) sigmoidoscopy, the physician may request the lesion be assayed to determine expression levels of one or more risk genes.

The expression level(s) of one or more risk genes is assayed as described above and a normalized expression level value determined. The risk gene assayed can be selected according to the tissue type of the biopsy based on the disclosure herein and the guidance in the Examples below. If the risk gene assayed is from Table 4a, 5a, 6a, 7a, or 12a, or is a co-expressed gene thereof, then the expression level is positively correlated with increased cancer risk. If the risk gene assayed is from Table 4b, 5b, 6b, 7b, or 12b, or is a co-expressed gene thereof, then the expression level is negatively correlated with increased cancer risk. If the risk gene assayed is from Table 8a, or is a co-expressed gene thereof, then the expression level is positively correlated with increased cancer risk. If the risk gene assayed is from Table 8b, or is a co-expressed gene thereof, then the expression level is negatively correlated with increased cancer risk.

Depending upon the patient's particular cancer risk, the physician may make certain recommendations concerning the frequency, intensity, and/or type of follow-up surveillance. Such recommendations might include, for example, repeating the procedure immediately with colonoscopy if the patient has a high synchronous cancer risk or recommending a repeat sigmoidoscopy in the future if the patient has a high progression risk. A similar process might be followed for patients after surgery for GI tract cancer, such as colorectal cancer.

Methods of Assaying Expression Levels of a Gene Product

Numerous assay methods for measuring an expression level of a gene product are known in the art, including assay methods for measuring an expression level of a nucleic acid gene product (e.g., an mRNA), and assay methods for measuring an expression level of a polypeptide gene product.

Measuring a Level of a Nucleic Acid Gene Product

In general, methods of measuring a level of a nucleic acid gene product (e.g., an mRNA) include methods involving hybridization analysis of polynucleotides, and methods involving amplification of polynucleotides. Commonly used methods known in the art for the quantification of mRNA expression in a sample include northern blotting and in situ hybridization (See for example, Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Expression Methods Based on Hybridization

The level of a target nucleic acid can be measured using a probe that hybridizes to the target nucleic acid. The target nucleic acid could be, for example, a RNA expression product of a response indicator gene associated with response to a VEGF/VEGFR Inhibitor, or a RNA expression product of a reference gene. In some embodiments, the target nucleic acid is first amplified, for example using a polymerase chain reaction (PCR) method.

A number of methods are available for analyzing nucleic acid mixtures for the presence and/or level of a specific nucleic acid. mRNA may be assayed directly or reverse transcribed into cDNA for analysis. The nucleic acid may be amplified by conventional techniques, such as PCR, to provide sufficient amounts for analysis. The use of the PCR is described in Saiki, et al. (1985), *Science* 239:487, and a review of techniques may be found in Sambrook, et al. *Molecular Cloning: A Laboratory Manual*, CSH Press 1989, pp. 14.2-14.33.

In some embodiments, the method involves contacting a sample (e.g., a sample derived from a cancer cell) under stringent hybridization conditions with a nucleic acid probe and detecting binding, if any, of the probe to a nucleic acid in the sample. A variety of nucleic acid hybridization methods are well known to those skilled in the art, and any known method can be used. In some embodiments, the nucleic acid probe will be detectably labeled.

Expression Methods Based on Target Amplification

Methods of amplifying (e.g., by PCR) nucleic acid, methods of performing primers extension, and methods of assessing nucleic acids are generally well known in the art. (See e.g., Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.)

A target mRNA can be amplified by reverse transcribing the mRNA into cDNA, and then performing PCR (reverse transcription-PCR or RT-PCR). Alternatively, a single enzyme may be used for both steps as described in U.S. Pat. No. 5,322,770.

The fluorogenic 5' nuclease assay, known as the TaqMan® assay (Perkin-Elmer), is a powerful and versatile PCR-based detection system for nucleic acid targets. For a detailed description of the TaqMan assay, reagents and conditions for use therein, see, e.g., Holland et al., Proc. Natl. Acad. Sci., U.S.A. (1991) 88:7276-7280; U.S. Pat. Nos. 5,538,848, 5,723,591, and 5,876,930, all incorporated herein by reference in their entireties. Hence, primers and probes derived from regions of a target nucleic acid as described herein can be used in TaqMan analyses to detect a level of target mRNA in a biological sample. Analysis is performed in conjunction with thermal cycling by monitoring the generation of fluorescence signals. (TaqMan is a registered trademark of Roche Molecular Systems.)

The fluorogenic 5' nuclease assay is conveniently performed using, for example, AmpliTaq Gold® DNA polymerase, which has endogenous 5' nuclease activity, to digest an internal oligonucleotide probe labeled with both a fluorescent reporter dye and a quencher (see, Holland et al., Proc Nat Acad Sci USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid. (AmpliTaq Gold is a registered trademark of Roche Molecular Systems.)

The amplification products can be detected in solution or using solid supports. In this method, the TaqMan probe is designed to hybridize to a target sequence within the desired PCR product. The 5' end of the TaqMan probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, head and neck, etc., tumor, or tumor cell lines. If the source of mRNA is a primary tumor, mRNA can be extracted, for example, from frozen or archived paraffin-embedded and fixed (e.g., formalin-fixed) tissue samples or directly from the freshly isolated tissue.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using kits and reagents from commercial manufacturers according to the manufacturer's instructions. For example, total RNA from cells in culture can be isolated using RNeasy® mini-columns (Qiagen GmbH Corp.). Other commercially available RNA isolation kits include MasterPure™ Complete DNA and RNA Purification Kit (EPICENTRE® Biotechnologies, Madison, Wis.), and Paraffin Block RNA Isolation Kit (Ambion, Inc.). Total RNA from tissue samples can be isolated using RNA STAT-60™ (IsoTex Diagnostics, Inc., Friendswood Tex.). RNA prepared from tumor can be isolated, for example, by cesium chloride density gradient centrifugation. (RNeasy is a registered trademark of Qiagen GmbH Corp.; MasterPure is a trademark of EPICENTRE Biotechnologies; RNA STAT-60 is a trademark of Tel-Test Inc.)

As RNA cannot serve as a template for PCR, the first step in gene expression profiling by RT-PCR is the reverse transcription of the RNA template into cDNA, followed by its exponential amplification in a PCR reaction. The two most commonly used reverse transcriptase enzymes are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp® RNA PCR kit (Applied Biosystems Inc., Foster City, Calif.) according to the manufacturer's instructions. The derived cDNA can then be used as a template in a subsequent PCR reaction. (GeneAmp is a registered trademark of Applied Biosystems Inc.)

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data. (TaqMan is a registered mark of Applied Biosystems.)

TaqMan RT-PCR can be performed using commercially available equipment, such as, for example, the ABI PRISM® 7700 Sequence Detection System (Applied Biosystems, Foster City, Calif., USA), or the Lightcycler® (Roche Molecular Biochemicals, Mannheim, Germany). In a preferred embodiment, the 5' nuclease procedure is run on a real-time quantitative PCR device such as the ABI PRISM 7700 Sequence Detection System or 7900 PRISM HTS system. The system consists of a thermocycler, laser, charge-coupled device (CCD), camera and computer. The system amplifies samples in a multi-well (e.g., 96) format on a thermocycler. During amplification, laser-induced fluorescent signal is collected in real-time through fiber optics cables for all 96 wells, and detected at the CCD. The system includes software for running the instrument and for analyzing the data. (ABI PRISM is a registered trademark of Applied Biosystems. Lightcycler is a registered trademark of Roche Diagnostics GmbH LLC.)

5'-Nuclease assay data are initially expressed as $C_t$, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize the effect of sample-to-sample variation, quantitative RT-PCR is usually performed using an internal standard, or one or more reference genes. The ideal internal standard is expressed at a constant level among different tissues, and is unaffected by the experimental treatment. RNAs that can be used to normalize patterns of gene expression include, e.g., mRNAs for the reference genes glyceraldehyde-3-phosphate-dehydrogenase (GAPDH) and β-actin.

A more recent variation of the RT-PCR technique is the real time quantitative PCR, which measures PCR product accumulation through a dual-labeled fluorogenic probe (i.e., TaqMan® probe). Real time PCR is compatible both with quantitative competitive PCR, where internal competitor for each target sequence is used for normalization, and with quantitative comparative PCR using a normalization gene contained within the sample, or a reference gene for RT-PCR. For further details see, e.g., Held et al., *Genome Research* 6:986-994 (1996).

Factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g., about 50 to 70° C. can be used.

For further guidelines for PCR primer and probe design see, e.g., Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. PrimerSelect: Primer and probe design. *Methods Mol. Biol.* 70:520-527 (1997), the entire disclosures of which are hereby expressly incorporated by reference.

Other suitable methods for assaying a level of a nucleic acid gene product include, e.g., microarrays; serial analysis of gene expression (SAGE); MassARRAY® analysis; gene expression by massively parallel signature sequencing (see, e.g., Brenner et al., *Nature Biotechnology* 18:630-634 (2000); and the like. (MassARRAY is a registered trademark of Sequenom, Inc.

Introns

Assays to measure the amount of an RNA gene expression product can be targeted to intron sequences or exon sequences of the primary transcript. The amount of a spliced intron that is measured in human tissue samples is generally indicative of the amount of a corresponding exon (i.e. an exon from the same gene) present in the samples. Polynucleotides that consist of or are complementary to intron sequences can be used, e.g., in hybridization methods or amplification methods to assay the expression level of response indicator genes.

Comparative Levels of Stromal Genes in Different Regions of a Lesion

Clinical development studies in stage II/III colon cancer have demonstrated that stromal genes are correlated with increased risk of recurrence, whereas other gene (e.g., cell cycle genes) are associated with lower risk of recurrence. For example, RNA may be extracted from different regions of GI tract lesions, such as the luminal part of the tumor, and the tumor-associated stroma. It is expected that there will be higher expression levels of the stromal genes (the "stromal gene signature" or SGS) in the tumor-associated stroma and higher expression levels of the cell cycle genes in the luminal part of the tumor. It is therefore likely that the stroma is contributing significantly to the SGS. Thus, the area of stroma within a sample, or multiple samples, could contribute to the variability of the SGS (within and between tumor samples, e.g. sections of paraffin embedded blocks) and therefore the risk score. Similarly, the area of epithelia within the sample analyzed could contribute to the variability of other biomarkers (within and between samples) and therefore the risk score. In addition, some patients may have higher levels of gene expression in their tumor-associated stroma for "informative" genes than others, some have large amounts of stroma but low activity, and still other patients have smaller amounts of stroma but high activity. Therefore, if the area of the tumor-associated stroma and the area of the tumor-luminal regions were taken into account in analyzing cancer risk, the reproducibility of such method might be increased, thus leading to greater accuracy of recurrence free interval prediction.

One could achieve this by capturing percent stroma and percent epithelia and incorporating these values into calculating cancer risk. One skilled in the art would recognize that numerous methods exist to achieve this purpose. For example, percent stroma and percent epithelia would be obtained by examining an H&E slide immediately adjacent to the tissue sections to be analyzed. This could be performed by either a pathologist (to get a gross measurement) or by digital image analysis (to obtain a more precise measurement).

Measuring Levels of a Polypeptide Gene Product

Methods of measuring a level of a polypeptide gene product are known in the art and include antibody-based methods such as enzyme-linked immunoabsorbent assay (ELISA), radioimmunoassay (RIA), protein blot analysis, immunohistochemical analysis, and the like. The measure of a polypeptide gene product may also be measured in vivo in the subject using an antibody that specifically binds a target polypeptide, coupled to a paramagnetic label or other label used for in vivo imaging, and visualizing the distribution of the labeled antibody within the subject using an appropriate in vivo imaging method, such as magnetic resonance imaging. Such methods also include proteomics methods such as mass spectrometric methods and peptide arrays, which are known in the art.

Detecting Risk Sequences (e.g., BRAF Mutation)

Detection of a known mutation may be performed with a PCR assay which consists of a forward and reverse primer. The PCR assay amplifies a region of DNA (or cDNA) carrying the mutation of interest. One primer will be anchored at its 3' end (the anchored primer) on the mutant base. The anchored primer will be shorter than primers used in conventional PCR assays in order to improve selective amplification of the mutant allele. An additional oligonucleotide is added to the assay, the non-extendable blocker, which selectively binds the wild-type allele to prevent its amplification. The assay may be combined with Real-Time detection chemistries (i.e., TaqMan) by adding the appropriate fluorescent probes.

Detection of a mutation may be performed using a DNA sequencing method. Examples of sequencing methods include high-throughput methods that use parallelized sequencing and in vitro amplification (e.g., 454 Life Sciences, Polony sequencing, SOLiD sequencing (Applied Bio systems), bridge PCR (Illumina Genome Analyzer), single-molecule method (Helicos)), microfluidic Sanger sequencing, sequencing by hybridization, nanopore sequencing, microscopy based techniques, etc. Those skilled in the art will recognize that numerous methods exist that may be used to detect BRAF sequences.

Reporting Results

The methods of the present disclosure are suited for the preparation of reports summarizing the predictions resulting from the methods of the present disclosure. A "report," as described herein, is an electronic or tangible document which includes report elements that provide information of interest relating to a likelihood assessment and its results. A subject report includes at least a likelihood assessment, e.g., an indication as to the cancer risk for a subject with a premalignant lesion. A subject report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) test data, where test data can include a normalized level of one or more genes of interest, and 6) other features.

The present disclosure thus provides for methods of creating reports and the reports resulting therefrom. The report may include a summary of the expression levels of the RNA transcripts, or the expression products of such RNA transcripts, for certain genes in the cells obtained from the patient's premalignant lesion. The report can include information relating to the risk sequence status (e.g., BRAF mutation status) of the patient.

In some embodiments, the methods of the present disclosure further include generating a report that provides information regarding the patient's cancer risk. The report may include a prediction that the subject has a quantified cancer risk. That prediction may be in the form of a score or patient stratifier scheme. In some embodiments, the report may further include a recommendation for surveillance program, intervention, or data concerning outcome of a training set of patients, by risk profiles, who received on one or more surveillance programs or intervention.

A report that includes information regarding the patient's cancer risk (the likelihood that a patient having an identified premalignant lesion of the gastrointestinal tract also has a malignant lesion of the gastrointestinal tract or the likelihood that a patient having a premalignant lesion of the gastrointestinal tract will develop a malignant lesion of the gastrointestinal tract within a defined time interval) is provided to a user. For example, the methods disclosed herein can further include a step of generating or outputting a report providing the results of a subject cancer risk assessment, which report can be provided in the form of an electronic medium (e.g., an electronic display on a computer monitor), or in the form of a tangible medium (e.g., a report printed on paper or other tangible medium).

An assessment as to the likelihood is referred to below as a "response likelihood assessment" or, simply, "likelihood assessment." A person or entity who prepares a report ("report generator") will also perform the likelihood assessment. The report generator may also perform one or more of sample gathering, sample processing, and data generation, e.g., the report generator may also perform one or more of: a) sample gathering; b) sample processing; c) measuring a level of a risk gene; d) measuring a level of a reference gene; and e) determining a normalized level of a risk gene. Alternatively, an entity other than the report generator can perform one or more sample gathering, sample processing, and data generation.

For clarity, it should be noted that the term "user," which is used interchangeably with "client," is meant to refer to a person or entity to whom a report is transmitted, and may be the same person or entity who does one or more of the following: a) collects a sample; b) processes a sample; c) provides a sample or a processed sample; and d) generates data (e.g., level of a risk gene; level of a reference gene product(s); normalized level of a risk gene for use in the likelihood assessment. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician (e.g., an oncologist, surgeon, or pathologist), etc.).

In embodiments where the user only executes a portion of the method, the individual who, after computerized data processing according to the methods of the present disclosure, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

Where government regulations or other restrictions apply (e.g., requirements by health, malpractice, or liability insurance), all results, whether generated wholly or partially electronically, are subjected to a quality control routine prior to release to the user.

Manual and Computer-Assisted Methods and Products

The methods and systems described herein can be implemented in numerous ways. In one embodiment of particular interest, the methods involve use of a communications infrastructure, for example the internet. Several embodiments are discussed below. It is also to be understood that the present disclosure may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment. The score can be a numerical score (representative of a numerical value) or a non-numerical score representative of a numerical value or range of numerical values (e.g., "A" representative of a 90=95% likelihood of an outcome).

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a risk gene, level of a reference gene product(s); normalized level of a risk gene; and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present disclosure.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The present disclosure also contemplates a computer-readable storage medium (e.g. CD-ROM, memory key, flash memory card, diskette, etc.) having stored there on a program which, when executed in a computing environment, provides for implementation of algorithms to carry out all or a portion of the results of a response likelihood assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the present disclosure can be packaged with instructions (e.g., for program installation, use, etc.) recorded on a suitable substrate or a web address where such instructions may be obtained. The computer-readable storage medium can also be provided in combination with one or more reagents for carrying out response likelihood assessment (e.g., primers, probes, arrays, or other such kit components).

All aspects of the present disclosure may also be practiced such that a limited number of additional genes that are co-expressed with the disclosed genes, for example as evidenced by high Pearson correlation coefficients, are included in a prognostic or predictive test in addition to and/or in place of disclosed genes.

Having described the invention, the same will be more readily understood through reference to the following Examples, which are provided by way of illustration, and are not intended to limit the invention in any way. All citations throughout the disclosure are hereby expressly incorporated by reference.

Methods of Sample Processing

The following methods were used in processing samples in the Example below.

Global RNA Amplification

In some cases, the amount of RNA that can be extracted from a sample is small and may be insufficient for gene expression analysis. In these cases, it is desirable to amplify the RNA extracted from a sample using a method designed to amplify many of the sequences in the sample, e.g., all polyadenylated sequences, to yield an amplification product that is representative of the species in the unamplified sample, i.e. a global RNA amplification method. Global amplification methods are known in the art. For example, global RNA amplification can be carried out using the methods described in U.S. Ser. No. 11/959,251 (incorporated herein by reference) or SenseAmp™ gene amplification kits in accordance with the manufacturer's (Genisphere, Inc., Hatfield, Pa.) instructions. (SenseAmp is a trademark of Genisphere, Inc.) Alternative methods for global amplification of RNA are described in J. D. Watson, et al., BMC Genomics 9:84 (2008) and R. C. Day, et al., Int J Plant Genomics 61028 (2007), and references cited therein.

Detection of Mutations

Methods of detecting sequence mutations which may be risk sequences are known in the art. In particular, methods for detecting point mutations have such as the point mutation responsible for V660E mutation of the BRAF gene have been described (see e.g., Nollau P and Wagener, Clinical Chemistry 43, 1114-1128 (1997).

Methods of Isolating RNA from Body Fluids

Methods of isolating RNA for expression analysis from blood, plasma and serum (See for example, N B Tsui, et al., 48:1647-53 (2002), and references cited therein) and from urine (see, e.g., R. Boom, et al., J Clin Microbiol. 28:495-503 (1990), and reference cited therein) have been described.

Methods of Data Analysis

Reference Normalization

In order to minimize expression measurement variations due to non-biological variations in samples, e.g., the amount and quality of expression product to be measured, raw expression level data measured for a gene product (e.g., cycle threshold (Ct) measurements obtained by qRT-PCR) may be normalized relative to the mean expression level data obtained for one or more reference genes. In one approach to normalization, a small number of genes are used as reference genes; the genes chosen for reference genes typically show a minimal amount of variation in expression from sample to sample and the expression level of other genes is compared to the relatively stable expression of the reference genes. In the global normalization approach, the expression level of each gene in a sample is compared to an average expression level in the sample of all genes in order to compare the expression of a particular gene to the total amount of material.

Unprocessed data from qRT-PCR is expressed as cycle threshold (Ct), the number of amplification cycles required for the detectable signal to exceed a defined threshold. High $C_t$ is indicative of low expression since more cycles are required to detect the amplification product. Normalization may be carried out such that a one unit increase in normalized expression level of a gene product generally reflects a 2-fold increase in quantity of expression product present in the sample. For further information on normalization techniques applicable to qRT-PCR data from tumor tissue, see, e.g., S. Silva, et al., BMC Cancer 6:200 (2006); J. de Kok, et al., Laboratory Investigation 85:154-159 (2005).

Statistical Analysis

A variety of statistical methods are available that are suitable for comparing the expression level of a gene (or other variable) in two groups and determining the statistical significance of expression level differences that are found. (See e.g., H. Motulsky, *Intuitive Biostatistics*, Oxford University Press, (NY 1995); D. Freedman, R. Pisan, R. Purves, *Statistics, Fourth Edition*, W.W. Norton & Co, (NY 2007)).

Methods for calculating correlation coefficients, particularly the Pearson product-moment correlation coefficient are known in the art. (See e.g., J L Rodgers and W A Nicewander The American Statistician, 42:59-66 (1988); H. Motulsky, *Intuitive Biostatistics*, Oxford University Press, (NY 1995)). Risk genes were assessed using a two sample t test of hypothesis on a gene by gene basis. The cancer and no cancer samples were treated as if selected at random respectively from cancer and no cancer populations. The two sample t test is used to test the hypothesis that the mean gene expression in the cancer population is not different from the mean gene expression in the no cancer population. The test statistic was computed, using a t score, and its significance assessed under the further assumption that the populations from which the gene expression measurements were sampled were normally distributed. Under these assumptions, p-values can be assigned to the t scores. The p-value is the probability of obtaining a t score at least as extreme as the one that was actually observed, assuming that expression values for the cancer and the non-cancer samples are a random selection from two normal distributions with equal mean and variance. If the assumption of normality is relaxed, p-values retain validity if the sample sizes are large. (See, e.g., E. L. Lehmann, J. Romano, *Testing Statistical Hypotheses* (2005)).

Examples 1-3

Global RNA Amplification

Global RNA amplification was carried out for each biopsy sample using the methods described in U.S. Ser. No. 11/959,251 and reagents from SenseAmp.

Expression Analysis

Table 1 shows the sequences of primers and probes used in qRT-PCR to measure RNA expression in each of the samples. Table 2 shows the gene sequences amplified using the primers and probes of Table 1. Tables 1 and 2 also show the Accession Number and the Official ID of each gene listed in the tables as given in the Entrez Gene online database (http://www.ncbi.nlm.nih.gov/Entrez/) by the National Center for Biotechnology Information at the time of the studies. Expression data was normalized using ATP5E, GPX1, PGK1, UBB, VDAC2 and B-actin as reference genes. Data was analyzed using Student's t-test.

Example 1

Risk Genes Based on Gene Expression in Colorectal Polyps

Study Design

Colorectal polyps were obtained from patients undergoing initial screening colonoscopy. Cases were selected based on the availability of sufficient biopsy tissue to provide at least 6×10 µm sections for preparation of RNA and 1 diagnostic H&E slide.

A total of fifty-six (56) polyps were obtained from forty-one (41) patients. These patients were concurrently diagnosed with distant colorectal carcinoma based on the same colonoscopy examination. In this example, analysis included only polyps with low-grade dysplasia from patients for whom low-grade dysplasia was the most advanced dysplasia, i.e. no polyps with cancer and no polyps with high-grade dysplasia were found in the patient.

In addition, sixty (60) polyps were obtained from forty (40) non-cancer patients (patients who were not concurrently diagnosed with colorectal carcinoma).

Table 3 shows the distribution of colorectal polyps analyzed and the patients from whom the polyps were obtained.

TABLE 3

|  | No Cancer Detected | Cancer Detected |
| --- | --- | --- |
| Total Patients | 40 | 41 |
| Patients (One Polyp Analyzed) | 21 | 28 |
| Patients (Two Polyps Analyzed) | 18 | 11 |
| Patients (Three Polyps Analyzed) | 1 | 2 |
| Total Polyps | 60 | 56 |

Risk genes were identified by comparing the expression of each gene in colorectal polyp biopsies from patients with distant metachronous colorectal cancer to the expression of each gene in colorectal polyp biopsies from patients with no cancer. In a first analysis, the expression data from each polyp biopsy was handled as an independent data sample, whether or not the polyp biopsy was the only polyp biopsy obtained from a particular patient. (Tables 4a and 4b.) In a second analysis, when more than one polyp biopsy was obtained from a single individual, the expression data from those polyp biopsies were averaged (herein referred to as "averaged biopsies") in a single data set in order to represent pooled multiple polyp biopsies from the same individual. (Tables 5a and 5b.)

Expression data from averaged biopsies were obtained by averaging the $C_t$ measurements for each gene on an antilog scale, so that, for example, averaged expression of $C_t1$ and $C_t2$ for a gene=log $2[(2^{\wedge}C_t1+2^{\wedge}C_t2)/2]$, wherein $C_t1$ and $C_t2$ are the normalized expression values for the gene in biopsy 1 and biopsy 2 of a averaged biopsy. In the above equation, "log 2" means "log base 2" and "2^x" means "2 to the power x".

Results

Tables 4a and 4b show the risk genes (single biopsy) identified by Student's t-test as significant at p<0.5. Table 4a shows risk genes, the increased expression of which are positively correlated with the likelihood that the patient from whom the colorectal polyp biopsy was obtained had or would develop cancer. Table 4b shows risk genes, the increased expression of which is negatively correlated with the likelihood that the patient from whom the colorectal polyp biopsy was obtained had or would develop cancer.

TABLE 4a

Positively Correlated Risk Genes
(Lower GI Tract - Single Biopsy Analysis)

| Gene | Mean Normalized Expression ($C_t$) | | t-value | p (t-test) |
|---|---|---|---|---|
| | Carcinoma | No Carcinoma | | |
| DUSP6.1 | 12.08 | 11.57 | 5.5259 | 0.0000 |
| RhoB.1 | 11.94 | 11.46 | 5.5067 | 0.0000 |
| DUSP4.1 | 9.18 | 8.10 | 5.2827 | 0.0000 |
| ROCK2.1 | 11.75 | 11.32 | 5.2733 | 0.0000 |
| IMP-1.1 | 1.67 | 1.16 | 4.7696 | 0.0000 |
| PPARG.3 | 1.67 | 1.16 | 4.7696 | 0.0000 |
| EFNB2.1 | 11.08 | 10.77 | 4.4553 | 0.0000 |
| ADAMTS18.1 | 2.26 | 1.35 | 4.2323 | 0.0000 |
| MUC5AC.1 | 9.58 | 7.43 | 4.1507 | 0.0001 |
| KRT14.1 | 1.67 | 1.20 | 4.1265 | 0.0001 |
| CD46 (MCP).1 | 12.42 | 12.15 | 4.0249 | 0.0001 |
| SFRP2.1 | 6.42 | 4.65 | 3.8558 | 0.0002 |
| HNRPD.1 | 14.47 | 14.19 | 3.8219 | 0.0002 |
| ADAMTS12.1 | 8.20 | 7.67 | 3.7360 | 0.0003 |
| P16INK4.3 | 3.14 | 2.24 | 3.6989 | 0.0003 |
| CTGF.1 | 11.73 | 11.32 | 3.6166 | 0.0004 |
| BIK.1 | 10.57 | 10.21 | 3.5974 | 0.0005 |
| EGR1.1 | 11.93 | 11.28 | 3.5443 | 0.0006 |
| PPARD.1 | 11.86 | 11.56 | 3.4796 | 0.0007 |
| VEGF.1 | 12.79 | 12.49 | 3.4641 | 0.0007 |
| MUC6.1 | 3.97 | 2.27 | 3.4427 | 0.0008 |
| FOXP1.1 | 12.75 | 12.48 | 3.4224 | 0.0009 |
| CRCT1.1 | 1.77 | 1.30 | 3.3931 | 0.0009 |
| MADH2.1 | 13.24 | 13.04 | 3.3869 | 0.0010 |
| EGR3.1 | 9.17 | 8.49 | 3.2289 | 0.0016 |
| ITGB4.2 | 13.77 | 13.55 | 3.0386 | 0.0029 |
| CDC42BPA.1 | 12.93 | 12.73 | 2.9579 | 0.0038 |
| PTPRU.1 | 6.50 | 5.83 | 2.9097 | 0.0043 |
| FPGS.1 | 11.49 | 11.29 | 2.8906 | 0.0046 |
| FOS.1 | 11.34 | 10.76 | 2.8014 | 0.0060 |
| COL6A1.1 | 10.74 | 10.37 | 2.7944 | 0.0061 |
| MUC2.1 | 17.54 | 17.12 | 2.7436 | 0.0071 |
| CDX1.1 | 13.45 | 13.24 | 2.7233 | 0.0075 |

TABLE 4a-continued

Positively Correlated Risk Genes
(Lower GI Tract - Single Biopsy Analysis)

| Gene | Mean Normalized Expression ($C_t$) | | t-value | p (t-test) |
|---|---|---|---|---|
| | Carcinoma | No Carcinoma | | |
| EPHA3.1 | 8.40 | 7.96 | 2.7201 | 0.0075 |
| CDH1 intron 2.2 | 10.62 | 10.42 | 2.7147 | 0.0077 |
| CLTB.1 | 12.13 | 11.95 | 2.7097 | 0.0078 |
| TIMP2.1 | 12.45 | 12.24 | 2.6643 | 0.0088 |
| TGFB3.1 | 6.62 | 6.12 | 2.6609 | 0.0089 |
| GTF2IRD1.1 | 10.83 | 10.52 | 2.5980 | 0.0106 |
| RUNX1.2 | 10.94 | 10.69 | 2.5686 | 0.0115 |
| GRO1.2 | 8.97 | 8.46 | 2.5592 | 0.0118 |
| AGR2.1 | 12.82 | 12.43 | 2.4873 | 0.0143 |
| ANXA4.1 | 13.14 | 12.89 | 2.4241 | 0.0169 |
| PAI1.3 | 7.45 | 6.95 | 2.3308 | 0.0215 |
| ITGA7.1 | 8.67 | 8.28 | 2.3228 | 0.0220 |
| CD248.1 | 10.32 | 10.06 | 2.3137 | 0.0225 |
| TNFRSF12A.1 | 10.83 | 10.52 | 2.3089 | 0.0227 |
| FAP.1 | 7.59 | 7.15 | 2.3054 | 0.0229 |
| GJA1.1 | 8.90 | 8.57 | 2.3050 | 0.0230 |
| P14ARF.1 | 7.01 | 6.61 | 2.2327 | 0.0275 |
| KIAA1219.1 | 10.83 | 10.68 | 2.2224 | 0.0282 |
| CRNN.1 | 1.96 | 1.44 | 2.1390 | 0.0345 |
| IL1B.1 | 8.76 | 8.35 | 2.1365 | 0.0348 |
| PLAGL2.1 | 10.19 | 9.96 | 2.1359 | 0.0348 |
| APC.4 | 11.47 | 11.33 | 2.1149 | 0.0366 |
| p21.3 | 13.70 | 13.52 | 2.0729 | 0.0404 |
| Bax.1 | 12.64 | 12.48 | 2.0686 | 0.0408 |
| COL3A1.1 | 12.55 | 12.09 | 2.0645 | 0.0412 |
| COL1A1.1 | 14.45 | 14.24 | 2.0483 | 0.0428 |
| NR4A1.1 | 10.90 | 10.59 | 2.0041 | 0.0474 |
| EPHB4.1 | 11.06 | 10.87 | 1.9851 | 0.0495 |
| SPDEF.1 | 11.91 | 11.66 | 1.9848 | 0.0496 |

TABLE 4b

Negatively Correlated Risk Genes
(Lower GI Tract - Single Biopsy Analysis)

| Gene | Mean Normalized Expression ($C_t$) | | t-value | p (t-test) |
|---|---|---|---|---|
| | Carcinoma | No Carcinoma | | |
| UBB.1 | 15.24 | 15.68 | −5.8869 | 0.0000 |
| GJB2.1 | 9.16 | 9.75 | −5.2482 | 0.0000 |
| PGK1.1 | 11.66 | 12.02 | −5.2449 | 0.0000 |
| LAMA4.1 | 8.66 | 9.19 | −5.1098 | 0.0000 |
| PCNA.2 | 10.42 | 10.94 | −4.9815 | 0.0000 |
| SIR2.2 | 9.43 | 10.05 | −4.4246 | 0.0000 |
| STK4.1 | 9.89 | 10.26 | −4.3986 | 0.0000 |
| HSPE1.1 | 14.37 | 14.72 | −4.2655 | 0.0000 |
| PPP1R14D.1 | 10.98 | 11.43 | −4.2547 | 0.0000 |
| ATP5E.1 | 15.47 | 15.69 | −4.2530 | 0.0000 |
| H2AFJ.1 | 6.77 | 7.24 | −3.9852 | 0.0001 |
| CA12.1 | 13.46 | 13.88 | −3.9695 | 0.0001 |
| NFKBp65.3 | 10.48 | 10.77 | −3.9586 | 0.0001 |
| UQCRC2.1 | 12.74 | 13.03 | −3.9468 | 0.0001 |
| SDC1.3 | 12.71 | 12.96 | −3.9458 | 0.0001 |
| MRP3.1 | 12.26 | 12.56 | −3.8268 | 0.0002 |
| GADD45B.1 | 9.07 | 9.65 | −3.7355 | 0.0003 |
| Grb10.1 | 8.47 | 8.91 | −3.7296 | 0.0003 |
| HSD11B2.1 | 12.70 | 13.18 | −3.6633 | 0.0004 |
| LMNB1.1 | 12.16 | 12.49 | −3.6590 | 0.0004 |
| UCP2.1 | 10.85 | 11.25 | −3.5454 | 0.0006 |
| FOXO3A.1 | 11.56 | 11.86 | −3.4382 | 0.0008 |
| CCNA2.1 | 10.98 | 11.34 | −3.4325 | 0.0008 |
| SLC25A3.2 | 13.63 | 13.81 | −3.3472 | 0.0011 |
| RRM2.1 | 11.82 | 12.37 | −3.3168 | 0.0012 |
| HMGB1.1 | 15.23 | 15.45 | −3.2486 | 0.0015 |
| B-Catenin.3 | 13.70 | 13.93 | −3.2460 | 0.0015 |
| KNTC2.1 | 8.66 | 9.07 | −3.1620 | 0.0020 |
| MMP2.2 | 8.76 | 9.11 | −3.1593 | 0.0020 |

TABLE 4b-continued

Negatively Correlated Risk Genes
(Lower GI Tract - Single Biopsy Analysis)

| Gene | Mean Normalized Expression ($C_t$) Carcinoma | No Carcinoma | t-value | p (t-test) |
|---|---|---|---|---|
| EpCAM.1 | 15.65 | 15.85 | −3.1292 | 0.0022 |
| KCNQ5.1 | 3.53 | 4.28 | −3.0039 | 0.0033 |
| GNAS.1 | 13.70 | 13.86 | −2.9871 | 0.0034 |
| CCNB1.2 | 11.49 | 11.87 | −2.9476 | 0.0039 |
| HSPA1A.1 | 12.02 | 12.36 | −2.9463 | 0.0039 |
| LGALS4.1 | 17.38 | 17.65 | −2.9172 | 0.0042 |
| CES2.2 | 11.14 | 11.59 | −2.9044 | 0.0044 |
| TARBP2.1 | 8.42 | 8.77 | −2.9035 | 0.0044 |
| CSEL1.1 | 10.43 | 10.67 | −2.8324 | 0.0055 |
| STAT5B.2 | 9.60 | 9.80 | −2.8239 | 0.0056 |
| ACSL5.1 | 12.41 | 12.66 | −2.8097 | 0.0058 |
| PTPRD.1 | 8.78 | 9.23 | −2.7698 | 0.0065 |
| RAF1.3 | 12.39 | 12.54 | −2.7677 | 0.0066 |
| ABP1.1 | 13.80 | 14.06 | −2.7660 | 0.0066 |
| CKB.1 | 15.44 | 15.99 | −2.7640 | 0.0067 |
| CKS2.2 | 11.58 | 11.81 | −2.7058 | 0.0079 |
| STAT1.3 | 11.53 | 11.79 | −2.6901 | 0.0082 |
| FABP1.1 | 17.73 | 18.23 | −2.6890 | 0.0082 |
| STC1.1 | 5.69 | 6.42 | −2.5519 | 0.0120 |
| DUSP2.1 | 5.82 | 6.37 | −2.4525 | 0.0157 |
| GPA33.1 | 13.69 | 13.91 | −2.3916 | 0.0184 |
| cMet.2 | 10.79 | 11.04 | −2.3698 | 0.0195 |
| ITGA6.2 | 13.15 | 13.50 | −2.3456 | 0.0207 |
| MADH7.1 | 10.25 | 10.44 | −2.3369 | 0.0212 |
| RRM1.2 | 11.72 | 11.90 | −2.3086 | 0.0228 |
| GGH.1 | 12.68 | 12.98 | −2.2566 | 0.0259 |
| UMPS.2 | 10.72 | 10.85 | −2.2402 | 0.0270 |
| KRT8.3 | 15.10 | 15.36 | −2.2379 | 0.0272 |
| HNRNPA1.1 | 15.43 | 15.57 | −2.2086 | 0.0292 |
| SNAI2.1 | 9.11 | 9.37 | −2.1551 | 0.0332 |
| ENO1.1 | 14.55 | 14.69 | −2.1101 | 0.0370 |
| EIF2C2.1 | 10.47 | 10.58 | −2.0677 | 0.0409 |
| SLC26A2.1 | 13.06 | 13.58 | −2.0648 | 0.0412 |
| EPHB2.1 | 12.40 | 12.60 | −2.0608 | 0.0416 |
| HSPA8.1 | 15.48 | 15.61 | −2.0265 | 0.0450 |
| ALDH3A1.1 | 9.59 | 9.94 | −2.0251 | 0.0452 |
| NME1.3 | 12.13 | 12.32 | −1.9890 | 0.0491 |
| ITGB5.1 | 10.44 | 10.56 | −1.9875 | 0.0492 |

Tables 5a and 5b show risk genes (averaged biopsies) identified by Student's t-test as significant at p<0.5. Table 5a shows risk genes, the increased expression of which are positively correlated with the likelihood that the patient from whom the one or more pooled colorectal polyp biopsies were obtained had or would develop cancer. Table 5b shows risk genes, the increased expression of which is negatively correlated with the likelihood that the patient from whom the one or more pooled colorectal polyp biopsies were obtained had or would develop cancer.

TABLE 5a

Positively Correlated Cancer Risk Genes
(Lower GI Tract - Averaged Biopsies Analysis)

| Gene | Mean Normalized Expression ($C_t$) Carcinoma | No Carcinoma | t-value | p (t-test) |
|---|---|---|---|---|
| ROCK2.1 | 11.78 | 11.33 | 5.1500 | <.0001 |
| RhoB.1 | 11.96 | 11.46 | 5.1129 | <.0001 |
| DUSP6.1 | 12.08 | 11.58 | 4.6694 | <.0001 |
| PPARG.3 | 1.67 | 1.18 | 4.2358 | <.0001 |
| IMP-1.1 | 1.67 | 1.18 | 4.2358 | <.0001 |
| DUSP4.1 | 9.14 | 8.16 | 4.1155 | <.0001 |
| HNRPD.1 | 14.46 | 14.18 | 3.8202 | 0.0003 |
| KRT14.1 | 1.67 | 1.21 | 3.6877 | 0.0004 |
| CD46 (MCP).1 | 12.43 | 12.17 | 3.5364 | 0.0007 |
| FOXP1.1 | 12.78 | 12.48 | 3.4974 | 0.0008 |
| CTGF.1 | 11.77 | 11.32 | 3.4760 | 0.0008 |
| ADAMTS18.1 | 2.27 | 1.41 | 3.4751 | 0.0008 |
| EFNB2.1 | 11.07 | 10.82 | 3.3364 | 0.0013 |
| P16INK4.3 | 3.24 | 2.32 | 3.3254 | 0.0013 |
| VEGF.1 | 12.80 | 12.48 | 3.2591 | 0.0016 |
| EGR3.1 | 9.25 | 8.46 | 3.2471 | 0.0017 |
| PTPRU.1 | 6.65 | 5.97 | 3.2335 | 0.0018 |
| CRCT1.1 | 1.81 | 1.32 | 3.2249 | 0.0018 |
| BIK.1 | 10.55 | 10.20 | 3.2073 | 0.0019 |
| MUC5AC.1 | 9.67 | 7.80 | 3.1365 | 0.0024 |
| ADAMTS12.1 | 8.15 | 7.67 | 2.9513 | 0.0042 |
| EGR1.1 | 11.94 | 11.31 | 2.9399 | 0.0043 |
| MADH2.1 | 13.23 | 13.04 | 2.9138 | 0.0046 |
| RUNX1.2 | 11.00 | 10.71 | 2.8566 | 0.0055 |
| MUC6.1 | 4.24 | 2.54 | 2.7850 | 0.0067 |
| FPGS.1 | 11.49 | 11.28 | 2.7058 | 0.0083 |
| FAP.1 | 7.67 | 7.21 | 2.5881 | 0.0115 |
| SFRP2.1 | 6.47 | 5.12 | 2.5543 | 0.0125 |
| CDH1 intron 2.2 | 10.62 | 10.42 | 2.5118 | 0.0140 |
| CDC42BPA.1 | 12.93 | 12.75 | 2.4541 | 0.0163 |
| PPARD.1 | 11.82 | 11.59 | 2.4489 | 0.0165 |
| COL3A1.1 | 12.57 | 12.29 | 2.4287 | 0.0174 |
| ITGB4.2 | 13.78 | 13.57 | 2.4039 | 0.0185 |
| MUC2.1 | 17.54 | 17.13 | 2.3227 | 0.0227 |
| COL6A1.1 | 10.75 | 10.43 | 2.2947 | 0.0244 |
| GRO1.2 | 9.00 | 8.51 | 2.2223 | 0.0291 |
| GTF2IRD1.1 | 10.85 | 10.54 | 2.2181 | 0.0294 |
| EPHB4.1 | 11.11 | 10.87 | 2.2164 | 0.0295 |
| TIMP2.1 | 12.46 | 12.27 | 2.1737 | 0.0327 |
| EPHA3.1 | 8.40 | 7.99 | 2.1643 | 0.0334 |
| TGFB3.1 | 6.64 | 6.16 | 2.1486 | 0.0347 |
| GJA1.1 | 8.91 | 8.58 | 2.1324 | 0.0360 |
| ITGA7.1 | 8.71 | 8.31 | 2.1160 | 0.0375 |
| AGR2.1 | 12.84 | 12.45 | 2.0840 | 0.0403 |
| Bax.1 | 12.66 | 12.48 | 2.0752 | 0.0412 |
| PLAGL2.1 | 10.20 | 9.96 | 2.0628 | 0.0424 |
| TNFRSF12A.1 | 10.83 | 10.51 | 2.0628 | 0.0424 |
| CRNN.1 | 2.03 | 1.44 | 2.0626 | 0.0424 |
| CDX1.1 | 13.42 | 13.24 | 2.0524 | 0.0434 |
| P14ARF.1 | 7.07 | 6.66 | 2.0142 | 0.0473 |

TABLE 5b

Negatively Correlated Risk Genes
(Lower GI Tract - Averaged Biopsies Analysis)

| Gene | Mean Normalized Expression ($C_t$) Carcinoma | No Carcinoma | t-value | p (t-test) |
|---|---|---|---|---|
| MRP3.1 | 12.26 | 12.61 | −4.2174 | <.0001 |
| SIR2.2 | 9.54 | 10.07 | −4.3760 | <.0001 |
| PCNA.2 | 10.43 | 10.96 | −4.5533 | <.0001 |
| PGK1.1 | 11.66 | 12.01 | −4.6202 | <.0001 |
| LAMA4.1 | 8.67 | 9.24 | −4.8219 | <.0001 |
| GJB2.1 | 9.15 | 9.78 | −4.9063 | <.0001 |
| UBB.1 | 15.25 | 15.67 | −5.0216 | <.0001 |
| CA12.1 | 13.46 | 13.91 | −4.0104 | 0.0001 |
| STK4.1 | 9.92 | 10.27 | −3.9495 | 0.0002 |
| UQCRC2.1 | 12.72 | 13.04 | −3.8253 | 0.0003 |
| ATP5E.1 | 15.48 | 15.68 | −3.6266 | 0.0005 |
| PPP1R14D.1 | 11.00 | 11.45 | −3.6046 | 0.0005 |
| SDC1.3 | 12.73 | 12.96 | −3.5316 | 0.0007 |
| NFKBp65.3 | 10.49 | 10.76 | −3.4673 | 0.0008 |
| HSPE1.1 | 14.39 | 14.71 | −3.4424 | 0.0009 |
| FOXO3A.1 | 11.57 | 11.89 | −3.4276 | 0.0010 |

TABLE 5b-continued

Negatively Correlated Risk Genes
(Lower GI Tract - Averaged Biopsies Analysis)

| Gene | Mean Normalized Expression ($C_i$) | | t-value | p (t-test) |
|---|---|---|---|---|
| | Carcinoma | No Carcinoma | | |
| GADD45B.1 | 9.18 | 9.66 | −3.3908 | 0.0011 |
| HSD11B2.1 | 12.71 | 13.23 | −3.3553 | 0.0012 |
| LMNB1.1 | 12.18 | 12.50 | −3.2355 | 0.0018 |
| Grb10.1 | 8.52 | 8.92 | −3.2340 | 0.0018 |
| UCP2.1 | 10.90 | 11.28 | −3.1283 | 0.0025 |
| EpCAM.1 | 15.65 | 15.87 | −3.0800 | 0.0028 |
| FABP1.1 | 17.68 | 18.28 | −3.0342 | 0.0033 |
| CES2.2 | 11.14 | 11.65 | −2.9725 | 0.0039 |
| STAT1.3 | 11.53 | 11.83 | −2.9547 | 0.0041 |
| GNAS.1 | 13.71 | 13.87 | −2.9283 | 0.0044 |
| LGALS4.1 | 17.37 | 17.67 | −2.9103 | 0.0047 |
| SLC25A3.2 | 13.65 | 13.82 | −2.8302 | 0.0059 |
| H2AFJ.1 | 6.87 | 7.24 | −2.8244 | 0.0060 |
| CCNA2.1 | 11.03 | 11.33 | −2.7923 | 0.0065 |
| HMGB1.1 | 15.25 | 15.46 | −2.7879 | 0.0066 |
| B-Catenin.3 | 13.73 | 13.94 | −2.7763 | 0.0068 |
| KCNQ5.1 | 3.65 | 4.38 | −2.7706 | 0.0070 |
| MMP2.2 | 8.81 | 9.14 | −2.7151 | 0.0081 |
| ABP1.1 | 13.81 | 14.09 | −2.6574 | 0.0095 |
| KNTC2.1 | 8.71 | 9.09 | −2.6531 | 0.0096 |
| RRM2.1 | 11.90 | 12.35 | −2.6325 | 0.0102 |
| STAT5B.2 | 9.62 | 9.81 | −2.6293 | 0.0103 |
| GPA33.1 | 13.70 | 13.94 | −2.5407 | 0.0130 |
| TARBP2.1 | 8.56 | 8.79 | −2.4619 | 0.0160 |
| PTPRD.1 | 8.81 | 9.27 | −2.4567 | 0.0162 |
| CKB.1 | 15.44 | 15.98 | −2.4425 | 0.0168 |
| SLC26A2.1 | 13.03 | 13.69 | −2.4127 | 0.0181 |
| KRT8.3 | 15.11 | 15.42 | −2.3728 | 0.0201 |
| MADH7.1 | 10.28 | 10.46 | −2.3272 | 0.0225 |
| LAMA5.1 | 7.54 | 7.87 | −2.3111 | 0.0234 |
| ENO1.1 | 14.53 | 14.70 | −2.3043 | 0.0238 |
| RRM1.2 | 11.73 | 11.92 | −2.3043 | 0.0238 |
| CA2.1 | 14.03 | 14.67 | −2.2984 | 0.0242 |
| CCNB1.2 | 11.57 | 11.87 | −2.2932 | 0.0245 |
| ACSL5.1 | 12.44 | 12.67 | −2.2577 | 0.0267 |
| RAF1.3 | 12.42 | 12.54 | −2.2146 | 0.0296 |
| HSPA1A.1 | 12.08 | 12.34 | −2.1875 | 0.0316 |
| ITGB5.1 | 10.47 | 10.60 | −2.1156 | 0.0375 |
| ALDH3A1.1 | 9.63 | 10.03 | −2.1064 | 0.0383 |
| DUSP2.1 | 5.80 | 6.37 | −2.0842 | 0.0403 |
| CSEL1.1 | 10.47 | 10.66 | −2.0559 | 0.0431 |
| UMPS.2 | 10.71 | 10.85 | −2.0459 | 0.0440 |
| CTSS.1 | 2.45 | 3.00 | −2.0328 | 0.0454 |
| SNAI2.1 | 9.14 | 9.40 | −2.0209 | 0.0466 |
| ITGA6.2 | 13.17 | 13.52 | −1.9924 | 0.0497 |

Example 2

Risk Genes Based on Gene Expression in Colorectal Polyps

Study Design

This study had two arms: patients who were diagnosed with colon cancer at the time of the colonoscopy (n=78), and patients who were not diagnosed with cancer at the time of the colonoscopy (n=71). Biopsy specimens that exhibited low grade dysplasia (LGD) polyps≤1.0 cm were collected for analysis. Approximately 23% of the patients had more than one eligible polyp. For these patients, RNA from 384 genes was analyzed both individually and pooled in a single sample. Table 14 below shows the distribution of colorectal polyps analyzed and the patients from whom the polyps were obtained.

TABLE 14

| | Cancer | Non-cancer |
|---|---|---|
| Total Patients | 78 | 71 |
| Sample Number | 135 | 108 |
| Patients with multiple polyps | 21 (27%) | 16 (23%) |

Statistical Analysis

Data from Examples 1 and 2 were analyzed to quantify the degree of association of gene expression with the likelihood colorectal cancer. Within each study, gene expression was measured as the reference-gene normalized and compressed $C_p$, using the reference genes UBB, PGK1, ATP5E, B-actin, GPX1, and VDAC2. For each assay gene in each study, the log standardized odds ratio for association of gene expression with synchronous colon cancer was determined using a univariate logistic regression model. For genes that were present in both studies, a meta-analysis estimate of the log standardized odds ratio was computed by combining the estimates from the two studies with weights proportional to the harmonic means of the sample sizes in the cancer and non-cancer groups. These meta-analysis estimates were then analyzed in a standard true discovery rate degree of association (TDRDA) set analysis was used to identify sets of genes among which 80% can be expected to have a standardized odds ratio for association greater than a specified value.

The TDRDA set analysis (meta-analysis) of the combined studies is shown in Tables 12a (genes positively correlated with cancer risk) and 12b (genes negatively correlated with cancer risk). The maximum lower bound (MLB) absolute odds ratio is set to include an 80% TDRDA set, i.e. 80% of the genes can be expected to have absolute standardized odds ratio greater than the specified value. The RM-Corrected Estimate is an estimate of the true absolute odds ratio for each gene, corrected for regression to the mean (RM). The RM-corrected estimates adjust for the "selection bias" inherent in focusing on the genes observed to have the strongest association with clinical outcome; they are an estimate of the odds ratio that would be observed if the genes were included in a future, similar study.

The analysis identified 243 genes for which reference-gene normalized expression is associated with the odds of synchronous cancer, and 41 genes for which the absolute standardized odds ratio for association is greater than 1.2. Estimated standardized odds ratios corrected for regression to the mean ranged up to 2.11.

Example 3

Risk Genes Based on Gene Expression in Barrett's Biopsies

Study Design

Barrett's biopsy specimens were obtained from patients undergoing endoscopic examination after presenting with symptoms consistent with Barrett's Esophagus (BE). Cases were selected based on the availability of sufficient biopsy tissue to provide at least 6×10 μm sections for preparation of RNA and 1 diagnostic H&E slide.

One hundred eleven (111) BE biopsy samples were obtained from 79 patients. For each of these patients, all biopsies obtained upon initial endoscopy were pathologically graded as low grade dysplasia (LGD) (n=25 patients), high grade dysplasia (HGD) (n=33 patients), or cancer (n=21 patients).

Statistical Analysis

Weibull distribution accelerated failure time models were fit separately to the times of the composite event of high grade dysplasia (HGD) or esophageal cancer (EC), and overall survival time, stratifying by study center, and using pseudo-likelihood methods appropriate to the cohort sampling scheme. (See P. L. Prentice, *Biometrika* 73:1-11 (1986).) Fully parametric methods similar to Bryant and Dignam semi-parametric methods (*Biometrics* 60:182-190 (2004), multivariate models, with effects for normalized gene expression, clinicopathologic covariates, and study center, were used for the cumulative incidence function (J B Satagopan, et al., *British Journal of Cancer* 91:1229-1235 (2004)) for HGD/EC, accounting for all-cause mortality as a competing risk. The standardized regression coefficients for normalized gene expression were analyzed using true discovery rate degree of association (TDRDA) set methods. M. Craeger, *Statistics in Medicine* 29:33-45 (2010).

Variability of gene expression and its effect on prognosis for HGD/EC was assessed by fitting a multivariate Weibull distribution accelerated failure time models with effects for clinical and pathology covariates, gene expression from the overall pool and, in some cases, in each successive model, gene expression as determined from a specific location. For example, one could assess gene expression from (1) the upper 1 cm of the esophagus, (2) the middle of the esophagus, (3) the lower 1 cm of the esophagus, (4) the maximum gene expression among the 3 locations, and/or (5) the minimum gene expression among the 3 locations. The difference in the regression parameter estimates for gene expression determined from the overall pool and each of these locations may be computed and its variance determined using the variance-covariance matrix of the parameter estimates. The results were analyzed separately for each location the TDRDA set method and Efron's separate class method (B. Efron, *Annals of Applied Statistics* 2:197-223 (2008)).

Results

In the first analysis, the expression data from each Barrett's biopsy was handled as an independent data sample, whether or not the Barrett's biopsy was the only Barrett's biopsy obtained from a particular patient. Risk genes were identified by comparing the expression of each gene in Barrett's biopsies from patients with cancer to their expression in Barrett's biopsies from patients with no cancer. (Tables 6a and 6b.)

In the second analysis, when more than one Barrett's biopsy was obtained from a single individual, the expression data from those Barrett's biopsies were averaged (herein referred to as "averaged biopsies") in a single data set in order to represent pooled multiple Barrett's biopsies from the same individual. Risk genes were identified by determining the averaged expression of each gene in the Barrett's biopsies available from a patient and comparing the expression in patients with cancer to expression in patients with no cancer. (Tables 7a and 7b.)

Tables 6a and 6b show risk genes (single biopsy) identified by Student's t-test as significant at p<0.5. Table 6a shows risk genes, the increased expression of which is positively correlated with the likelihood that the patient from whom the Barrett's biopsy was obtained had or would develop cancer. Table 6b shows risk genes, the increased expression of which is negatively correlated with the likelihood that the patient from whom the Barrett's biopsy was obtained had or would develop cancer.

TABLE 6a

Positively Correlated Risk Genes
(Upper GI Tract - Single Biopsy Analysis)

| Gene | Mean Normalized Expression ($C_t$) | | t-value | p (t-test) |
|---|---|---|---|---|
| | Carcinoma | No Carcinoma | | |
| NME1.3 | 10.00 | 9.35 | 3.4384 | 0.0014 |
| EGR3.1 | 7.51 | 5.24 | 3.1545 | 0.0030 |
| CALD1.2 | 9.58 | 8.79 | 3.0157 | 0.0044 |
| EVL.1 | 8.34 | 7.49 | 2.9406 | 0.0054 |
| SPARC.1 | 12.16 | 11.36 | 2.8701 | 0.0065 |
| Chk1.2 | 7.68 | 6.77 | 2.6423 | 0.0117 |
| EIF2C2.1 | 8.84 | 8.37 | 2.6013 | 0.0130 |
| MCP1.1 | 8.17 | 7.34 | 2.4780 | 0.0175 |
| CXCL10.1 | 7.38 | 5.76 | 2.4710 | 0.0178 |
| HLA-G.2 | 8.62 | 7.16 | 2.4298 | 0.0197 |
| AP-1 (JUN official).2 | 11.71 | 10.94 | 2.3945 | 0.0214 |
| IFITM1.1 | 8.74 | 7.59 | 2.3872 | 0.0218 |
| HLA-DRA.1 | 12.64 | 12.05 | 2.3841 | 0.0220 |
| S100A4.1 | 9.18 | 8.52 | 2.3838 | 0.0220 |
| IGFBP5.1 | 11.86 | 11.11 | 2.3694 | 0.0227 |
| EGR1.1 | 10.77 | 9.27 | 2.3686 | 0.0228 |
| CD18.2 | 8.80 | 8.07 | 2.3022 | 0.0266 |
| VEGFC.1 | 5.88 | 5.11 | 2.2917 | 0.0273 |
| TP53BP1.2 | 6.92 | 6.21 | 2.2865 | 0.0276 |
| TIMP3.3 | 9.94 | 9.07 | 2.2252 | 0.0318 |
| MCM2.2 | 7.89 | 6.99 | 2.2241 | 0.0318 |
| F3.1 | 9.51 | 9.00 | 2.2127 | 0.0327 |
| BGN.1 | 9.52 | 8.74 | 2.1627 | 0.0366 |
| CCL20.1 | 7.33 | 6.33 | 2.1069 | 0.0414 |
| FOSB.1 | 6.78 | 4.96 | 2.0538 | 0.0466 |
| COL6A3.1 | 10.24 | 9.58 | 2.0528 | 0.0467 |

TABLE 6b

Negatively Correlated Risk Genes
(Upper GI Tract - Single Biopsy Analysis)

| Gene | Mean Normalized Expression ($C_t$) | | t-value | p (t-test) |
|---|---|---|---|---|
| | Carcinoma | No Carcinoma | | |
| BCRP.1 | 5.15 | 6.54 | −2.5738 | 0.0139 |

Tables 7a and 7b show the risk genes (averaged biopsies) identified by Student's t-test as significant at p<0.5. Table 7a shows risk genes, the increased expression of which is positively correlated with the likelihood that the patient from whom the Barrett's biopsy was obtained had or would develop cancer. Table 7b shows risk genes, the increased expression of which is negatively correlated with the likelihood that the patient from whom the Barrett's biopsy was obtained had or would develop cancer.

TABLE 7a

Positively Correlated Risk Genes
(Upper GI Tract - Averaged Biopsies Analysis)

| Gene | Mean Normalized Expression ($C_t$) | | t-value | p (t-test) |
|---|---|---|---|---|
| | Carcinoma | No Carcinoma | | |
| EGR3.1 | 8.03 | 5.40 | 4.3420 | 0.0001 |
| CXCL10.1 | 7.97 | 5.78 | 4.1280 | 0.0002 |
| CCL4.2 | 5.09 | 3.63 | 3.8940 | 0.0003 |
| IL-8.1 | 8.72 | 6.33 | 3.8096 | 0.0004 |
| COL4A1.1 | 8.04 | 7.06 | 3.6099 | 0.0008 |
| GRO1.2 | 7.04 | 5.55 | 3.5716 | 0.0009 |
| IFITM1.1 | 9.21 | 7.63 | 3.5201 | 0.0010 |

TABLE 7a-continued

Positively Correlated Risk Genes
(Upper GI Tract - Averaged Biopsies Analysis)

| Gene | Mean Normalized Expression ($C_t$) Carcinoma | No Carcinoma | t-value | p (t-test) |
|---|---|---|---|---|
| NME1.3 | 9.96 | 9.35 | 3.3901 | 0.0015 |
| CCL20.1 | 7.73 | 6.29 | 3.3507 | 0.0017 |
| ICAM1.1 | 7.47 | 6.59 | 3.2326 | 0.0024 |
| FPGS.1 | 9.65 | 8.92 | 3.1433 | 0.0030 |
| CD18.2 | 8.93 | 8.09 | 3.0523 | 0.0039 |
| TOP2A.4 | 11.52 | 10.63 | 3.0503 | 0.0039 |
| CXCL9.1 | 7.33 | 6.01 | 3.0362 | 0.0041 |
| CXCL2.1 | 9.64 | 8.14 | 2.9779 | 0.0048 |
| INHBA.1 | 7.04 | 5.53 | 2.9690 | 0.0049 |
| CDC25B.1 | 9.98 | 9.15 | 2.9328 | 0.0054 |
| IL1B.1 | 8.74 | 7.11 | 2.8865 | 0.0061 |
| CXCR4.3 | 8.94 | 7.87 | 2.8610 | 0.0065 |
| SPARC.1 | 12.12 | 11.33 | 2.8453 | 0.0068 |
| CD105.1 | 9.27 | 8.40 | 2.8009 | 0.0076 |
| CSEL1.1 | 6.85 | 6.30 | 2.7987 | 0.0077 |
| NRP2.2 | 7.86 | 6.70 | 2.7812 | 0.0080 |
| EIF2C2.1 | 8.88 | 8.38 | 2.7393 | 0.0089 |
| BGN.1 | 9.69 | 8.72 | 2.6918 | 0.0101 |
| HSPA1A.1 | 10.04 | 9.34 | 2.6887 | 0.0102 |
| S100A4.1 | 9.30 | 8.56 | 2.6654 | 0.0108 |
| LILRB3.1 | 6.31 | 5.15 | 2.6290 | 0.0118 |
| LMNB1.1 | 9.44 | 8.98 | 2.6226 | 0.0120 |
| upa.3 | 8.97 | 8.01 | 2.6057 | 0.0125 |
| EGR1.1 | 10.85 | 9.39 | 2.6030 | 0.0126 |
| PAI1.3 | 6.01 | 4.57 | 2.5998 | 0.0127 |
| IGFBP7.1 | 11.01 | 10.49 | 2.5785 | 0.0134 |
| HLA-G.2 | 8.57 | 7.13 | 2.5629 | 0.0140 |
| TNFRSF12A.1 | 9.17 | 8.56 | 2.5567 | 0.0142 |
| ENO1.1 | 12.62 | 12.32 | 2.5458 | 0.0146 |
| C20 orf1.1 | 10.56 | 9.82 | 2.5378 | 0.0149 |
| Chk1.2 | 7.63 | 6.78 | 2.5205 | 0.0155 |
| C13orf18.1 | 6.02 | 4.84 | 2.5041 | 0.0162 |
| STAT1.3 | 9.18 | 8.49 | 2.4813 | 0.0171 |
| BUB1.1 | 8.96 | 8.45 | 2.4567 | 0.0181 |
| THBS1.1 | 8.47 | 7.45 | 2.4357 | 0.0191 |
| CTSB.1 | 12.23 | 11.86 | 2.4246 | 0.0196 |
| Ki-67.2 | 9.54 | 8.82 | 2.4186 | 0.0199 |
| CALD1.2 | 9.47 | 8.81 | 2.4120 | 0.0202 |
| CKS2.2 | 9.40 | 8.87 | 2.4115 | 0.0202 |
| OPN, osteopontin.3 | 6.27 | 4.85 | 2.3750 | 0.0221 |
| STC1.1 | 5.27 | 4.34 | 2.3733 | 0.0222 |
| IGFBP5.1 | 11.86 | 11.15 | 2.3527 | 0.0233 |
| P16INK4.3 | 5.20 | 4.11 | 2.3195 | 0.0252 |
| STK4.1 | 7.87 | 7.11 | 2.3069 | 0.0259 |
| EVL.1 | 8.20 | 7.53 | 2.2934 | 0.0268 |
| CD248.1 | 9.93 | 8.79 | 2.2889 | 0.0271 |
| TGFBI.1 | 6.53 | 5.76 | 2.2728 | 0.0281 |
| UCP2.1 | 8.54 | 7.89 | 2.2723 | 0.0281 |
| BEST1.1 | 5.29 | 4.21 | 2.2596 | 0.0290 |
| HLA-F.1 | 11.75 | 11.24 | 2.2484 | 0.0297 |
| ECGF1_gen1.1 | 9.54 | 8.95 | 2.2473 | 0.0298 |
| COX2.2 | 7.43 | 6.08 | 2.2198 | 0.0318 |
| IL8RB.1 | 7.39 | 6.18 | 2.1849 | 0.0344 |
| DUSP2.1 | 4.61 | 3.73 | 2.1777 | 0.0350 |
| MCM2.2 | 7.80 | 7.05 | 2.1737 | 0.0353 |
| COL6A3.1 | 10.23 | 9.58 | 2.1680 | 0.0357 |
| ITGA5.1 | 7.67 | 6.91 | 2.1496 | 0.0373 |
| PKHD1.1 | 6.04 | 5.05 | 2.1300 | 0.0389 |
| TIMP1.1 | 11.85 | 11.05 | 2.1293 | 0.0390 |
| MCP1.1 | 8.21 | 7.38 | 2.1097 | 0.0407 |
| TP53BP1.2 | 6.80 | 6.23 | 2.1010 | 0.0415 |
| COL12A1.1 | 8.66 | 8.00 | 2.0871 | 0.0428 |
| GPX1.2 | 11.48 | 11.22 | 2.0857 | 0.0430 |
| CXCL5.1 | 6.71 | 5.04 | 2.0720 | 0.0443 |
| F3.1 | 9.44 | 9.01 | 2.0619 | 0.0453 |
| VIP.1 | 4.52 | 3.58 | 2.0600 | 0.0455 |
| cMYC.3 | 10.04 | 9.56 | 2.0490 | 0.0466 |
| IFI30.1 | 10.62 | 9.73 | 2.0479 | 0.0467 |
| C20ORF126.1 | 5.32 | 4.90 | 2.0473 | 0.0468 |
| UBE2C.1 | 6.74 | 6.07 | 2.0376 | 0.0478 |
| BLR1.1 | 5.19 | 4.14 | 2.0347 | 0.0481 |
| CTGF.1 | 9.94 | 9.00 | 2.0333 | 0.0482 |
| CD31.3 | 10.57 | 10.06 | 2.0212 | 0.0495 |

TABLE 7b

Negatively Correlated Risk Genes
(Upper GI Tract - Single Biopsy Analysis)

| Gene | Mean Normalized Expression ($C_t$) Carcinoma | No Carcinoma | t-value | p (t-test) |
|---|---|---|---|---|
| FABP1.1 | 10.56 | 12.18 | -2.0271 | 0.0489 |
| SDC1.3 | 10.57 | 11.11 | -2.2152 | 0.0321 |
| CES2.2 | 8.96 | 9.62 | -2.2249 | 0.0314 |
| BCRP.1 | 5.36 | 6.54 | -2.7728 | 0.0082 |

Genes that were identified as risk genes in both the upper GI tract and the lower GI tract are shown in Tables 8a and 8b. Table 8a shows risk genes, the increased expression of which was positively correlated with the likelihood that the patient from whom the biopsy was obtained had or would develop cancer. Table 8b shows risk genes, the increased expression of which was negatively correlated with the likelihood that the patient from whom the biopsy was obtained had or would develop cancer.

TABLE 8a

Positively Correlated Risk Genes
(Upper and Lower GI Tract)

AP-1
BLR1
BUB1
C13ORF18
C20ORF126
CCL20
CD105
CD18
CD248
CD31
CDC25B
Chk1
cMYC
COL12A1
COL4A1
COL6A3
COX2
CSEL1
CTGF
CTSB
CXCL2
CXCR4
ECGF1_GEN1
EGR1
EGR3
EIF2C2
EPGS
EVL
F3
FOSB
FPGS
GRO1

TABLE 8a-continued

Positively Correlated Risk Genes
(Upper and Lower GI Tract)

HLA-DRA
ICAM1
IFITM1
IGFBP5
IGFBP7
IL1B
IL-8
IL8RB
ITGA5
Ki-67
LILRB3
MCM2
MCP1
NRP2
ONHBA
OPN
P16INK4
PAI1
S100A4
SPARC
THBS1
TIMP1
TIMP3
TNFRSF12A
TOP2A
TP53
TP53BP1
UPA
VEGFC
VIP

TABLE 8b

Negatively Correlated Risk Genes
(Upper and Lower GI Tract)

BCRP
CES2
FABP1
SDC1

Many of these genes are in the stromal response and early response pathways.

Example 4

Co-Expressed Genes

The risk genes disclosed herein were identified based on comparison of expression data in patients with cancer and patients with no cancer. Additional risk genes were found by identifying genes that are strongly co-expressed with the cancer genes disclosed in Tables 4a-7b, and 12a and b. For example, Table 9 shows the Pearson pairwise correlation coefficients for the co-expression of certain genes that are strongly co-expressed with particular genes in Tables 4a-7b in Barrett's Esophagus Biopsies. Table 10 shows the Pearson pairwise correlation coefficients (in parentheses after the gene name) for the co-expression of certain genes with a risk gene disclosed herein in colon polyps. "Est" is the estimated effect (i.e., the difference in average cycle threshold (Ct) between cancer and non-cancer). Table 13 shows the Spearman pairwise correlation coefficients for the co-expression of certain genes that are strongly co-expressed with particular genes in Tables 12a and 12b.

Example 5

BRAF Mutations

Colorectal polyp biopsies were obtained from patients as described in Example 1 above. Each sample was tested for the presence or absence of the V600E (Samowitz W S et al. (2005) Cancer Research 65, 6063-6070) mutation in the BRAF (v-raf murine sarcoma viral oncogene homolog B1) gene. This mutation is accessioned as Mutation id 476 in the Catalogue Of Somatic Mutations In Cancer (COSMIC) database maintained by the Wellcome Trust Sanger Institute. This database can be accessed on line at www.sanger.ac.uk/genetics/CGP/cosmic/.

The V600E mutation was assayed as previously described by Morlan and colleagues (J. Morlan, et al., PLoS ONE 4(2): e4584. Doi:10.1371/journal.pone.0004584 (2009)) by qRT-PCR using forward primers specific for the mutant and wild type alleles as indicated.

```
Mutant Allele (V600E)(SEQ ID NO: 1)
TATTTCTTCATGAAGACCTCACAGTAAAAATAGGTGATTTTGGTCTA

GCTACAGAGAAATCTCGATGGAGTGGGTCATAAAGAAGTACTTCTGG

AGTGTCATTTTTATCCACTAAAACCAGATCGATGTCTCTTTAGAGCT

ACCTCACCCAG

Wild Type Allele (SEQ ID NO: 2)
TATTTCTTCATGAAGACCTCACAGTAAAAATAGGTGATTTTGGTCTA

GCTACAGTGAAATCTCGATGGAGTGGGTCATAAAGAAGTACTTCTGG

AGTGTCATTTTTATCCACTAAAACCAGATCGATGTCACTTTAGAGCT

ACCTCACCCAG
```

The mutation was found in a higher proportion of polyp biopsies from patients with cancer than from patients with no cancer (Table 11).

Lengthy table referenced here

US08765383-20140701-T00001

Please refer to the end of the specification for access instructions.

Lengthy table referenced here

US08765383-20140701-T00002

Please refer to the end of the specification for access instructions.

Lengthy table referenced here

US08765383-20140701-T00003

Please refer to the end of the specification for access instructions.

Lengthy table referenced here

US08765383-20140701-T00004

Please refer to the end of the specification for access instructions.

Lengthy table referenced here

US08765383-20140701-T00005

Please refer to the end of the specification for access instructions.

Lengthy table referenced here

US08765383-20140701-T00006

Please refer to the end of the specification for access instructions.

Lengthy table referenced here

US08765383-20140701-T00007

Please refer to the end of the specification for access instructions.

Lengthy table referenced here

US08765383-20140701-T00008

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08765383B2). An electronic copy of the table will also be available from the USPTO upon request and payment of the fee set forth in 37 CFR 1.19(b)(3).

We claim:

1. A method for determining cancer risk for a human patient, comprising:
   analyzing a sequence of BRAF in a tissue sample obtained from a premalignant lesion from the lower gastrointestinal (GI) tract of the patient to detect a V600E mutation;
   measuring a level of an RNA transcript of DUSP6, or its expression product, in the tissue sample;
   normalizing the level of the RNA transcript of DUSP6, or its expression product, against an expression level of at least one reference gene, to obtain a normalized expression level of DUSP6,
   comparing the normalized expression level of DUSP6 from the patient to the normalized expression level of DUSP6 in a population with no cancer; and
   determining that the patient has an increased cancer risk if the normalized expression level of DUSP6 from the patient is increased, or that the patient has a decreased cancer risk if the normalized expression level of DUSP6 from the patient is decreased.

2. The method of claim 1, wherein the premalignant lesion comprises a colorectal polyp with low grade dysplasia.

3. The method of claim 2, wherein said cancer risk is a synchronous risk.

4. The method of claim 2, wherein said cancer risk is a progression risk.

5. The method of claim 1, wherein said measuring step is conducted using quantitative polymerase chain reaction.

6. The method of claim 1, wherein the measuring step quantifies an RNA transcript of DUSP6.

7. The method of claim 1, wherein the measuring step quantifies a polypeptide level of DUSP6.

8. The method of claim 1, further comprising using the normalized expression level of DUSP6 to generate a score indicative of the cancer risk for the patient.

9. The method of claim 8, wherein the score provides information concerning a likelihood that the patient has a co-existent malignant lesion of the lower GI tract.

10. The method of claim 8, wherein the score provides information concerning a likelihood that the patient will develop a malignant lesion in the lower GI tract.

11. The method of claim 1, wherein the premalignant lesion comprises a colorectal polyp.

12. The method of claim 1, wherein the tissue sample is obtained from a biopsy.

13. The method of claim 1, wherein the cancer risk is colorectal cancer risk.

14. A method for determining cancer risk for a human patient, comprising:
   extracting RNA from a tissue sample obtained from a premalignant lesion from the lower gastrointestinal (GI) tract of the patient;
   analyzing a sequence of BRAF from the tissue sample to detect a V600E mutation;
   reverse transcribing an RNA transcript of DUSP6 to produce a cDNA of DUSP6;
   amplifying the cDNA of DUSP6;
   producing an amplicon of the RNA transcript of DUSP6;
   assaying a level of the amplicon of the RNA transcript of DUSP6;
   normalizing the amplicon level of the RNA transcript of DUSP6 against an amplicon level of at least one reference RNA transcript in the tissue sample to provide a normalized amplicon level of DUSP6, comparing the normalized amplicon level of DUSP6 from the patient to the normalized amplicon level of DUSP6 in a population with no cancer; and determining that the patient has an increased cancer risk if the normalized amplicon level of DUSP6 from the patient is increased, or that the patient has a decreased cancer risk if the normalized amplicon level of DUSP6 from the patient is decreased.

15. The method of claim 14, wherein the premalignant lesion comprises a colorectal polyp with low grade dysplasia.

16. The method of claim 14, wherein the premalignant lesion comprises a colorectal polyp.

17. The method of claim 14, wherein the amplifying step is performed by polymerase chain reaction.

18. The method of claim 14, wherein the cancer risk is colorectal cancer risk.

* * * * *

UNITED STATES PATENT AND TRADEMARK OFFICE
CERTIFICATE OF CORRECTION

PATENT NO. : 8,765,383 B2  
APPLICATION NO. : 12/755368  
DATED : July 1, 2014  
INVENTOR(S) : Cowens et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 426 days.

Signed and Sealed this
Fourth Day of August, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,765,383 B2 | Page 1 of 1 |
| APPLICATION NO. | : 12/755368 | |
| DATED | : July 1, 2014 | |
| INVENTOR(S) | : Cowens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 484 days.

Signed and Sealed this
Twelfth Day of July, 2016

Michelle K. Lee
*Director of the United States Patent and Trademark Office*

```
                         SEQUENCE LISTING

<160> NUMBER OF SEQ ID NOS: 1538

<210> SEQ ID NO 1
<211> LENGTH: 152
<212> TYPE: DNA
<213> ORGANISM: Artificial Sequence
<220> FEATURE:
<223> OTHER INFORMATION: Synthetic oligonucleotide

<400> SEQUENCE: 1
tatttcttca tgaagacctc acagtaaaaa taggtgattt tggtctagct acagagaaat        60
ctcgatggag tgggtcataa agaagtactt ctggagtgtc atttttatcc actaaaacca       120
gatcgatgtc tctttagagc tacctcaccc ag                                    152

<210> SEQ ID NO 2
<211> LENGTH: 152
<212> TYPE: DNA
<213> ORGANISM: Artificial Sequence
<220> FEATURE:
<223> OTHER INFORMATION: Synthetic oligonucleotide

<400> SEQUENCE: 2
tatttcttca tgaagacctc acagtaaaaa taggtgattt tggtctagct acagtgaaat        60
ctcgatggag tgggtcataa agaagtactt ctggagtgtc atttttatcc actaaaacca       120
gatcgatgtc actttagagc tacctcaccc ag                                    152
```

```
<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
atattcctca aggtggccg                                               19

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
tgctggcaag gtaccatct                                               19

<210> SEQ ID NO 5
<211> LENGTH: 24
<212> TYPE: DNA
<213> ORGANISM: Artificial Sequence
<220> FEATURE:
<223> OTHER INFORMATION: Synthetic probe

<400> SEQUENCE: 5
aggtctcagc atccacccca ctct                                         24

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
ctcagaggac attcccaaca                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
ggtcctctgg gaagaagttg                                              20

<210> SEQ ID NO 8
<211> LENGTH: 24
<212> TYPE: DNA
<213> ORGANISM: Artificial Sequence
<220> FEATURE:
<223> OTHER INFORMATION: Synthetic probe

<400> SEQUENCE: 8
acctgggaac tccgtgggct tcct                                         24

<210> SEQ ID NO 9
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 9
tttgccgaga aggagttgtt                                               20

<210> SEQ ID NO 10
<211> LENGTH: 18
<212> TYPE: DNA
<213> ORGANISM: Artificial Sequence
<220> FEATURE:
<223> OTHER INFORMATION: Synthetic primer

<400> SEQUENCE: 10
gagccgctgg gaagagat                                                 18

<210> SEQ ID NO 11
<211> LENGTH: 24
<212> TYPE: DNA
<213> ORGANISM: Artificial Sequence
<220> FEATURE:
<223> OTHER INFORMATION: Synthetic probe

<400> SEQUENCE: 11
ttccttatcc acctgggctg caat                                          24

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
gaagccccca ttcactagaa                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
gaacagcagc aggaaattca                                               20

<210> SEQ ID NO 14
<211> LENGTH: 21
<212> TYPE: DNA
<213> ORGANISM: Artificial Sequence
<220> FEATURE:
<223> OTHER INFORMATION: Synthetic probe

<400> SEQUENCE: 14
actgagagat gcggccccct c                                             21

<210> SEQ ID NO 15
<211> LENGTH: 18
<212> TYPE: DNA
<213> ORGANISM: Artificial Sequence
<220> FEATURE:
<223> OTHER INFORMATION: Synthetic primer

<400> SEQUENCE: 15
aaggagccac accacctg                                                 18

<210> SEQ ID NO 16
<211> LENGTH: 22

```
<212> TYPE: DNA
<213> ORGANISM: Artificial Sequence
<220> FEATURE:
<223> OTHER INFORMATION: Synthetic primer

<400> SEQUENCE: 16
gtccctgtta tggaaacact gg                                          22

<210> SEQ ID NO 17
<211> LENGTH: 24
<212> TYPE: DNA
<213> ORGANISM: Artificial Sequence
<220> FEATURE:
<223> OTHER INFORMATION: Synthetic probe

<400> SEQUENCE: 17
ctccagccct gacttctgct ctgg                                        24

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
ggacaggtgc aagctcatct g                                           21

<210> SEQ ID NO 19
<211> LENGTH: 21
<212> TYPE: DNA
<213> ORGANISM: Artificial Sequence
<220> FEATURE:
<223> OTHER INFORMATION: Synthetic primer

<400> SEQUENCE: 19
atctacaacc ttgggctgca a                                           21

<210> SEQ ID NO 20
<211> LENGTH: 28
<212> TYPE: DNA
<213> ORGANISM: Artificial Sequence
<220> FEATURE:
<223> OTHER INFORMATION: Synthetic probe

<400> SEQUENCE: 20
caagccaaag gcattggcta cttcttcg                                    28

<210> SEQ ID NO 21
<211> LENGTH: 19
<212> TYPE: DNA
<213> ORGANISM: Artificial Sequence
<220> FEATURE:
<223> OTHER INFORMATION: Synthetic primer

<400> SEQUENCE: 21
ggagaagggt ggagtgcag                                              19

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
```

```
cagggtcagg tctctggatg                                                   20

<210> SEQ ID NO 23
<211> LENGTH: 24
<212> TYPE: DNA
<213> ORGANISM: Artificial Sequence
<220> FEATURE:
<223> OTHER INFORMATION: Synthetic probe

<400> SEQUENCE: 23
cgcacagtca gaatccatct gggt                                              24

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
aggctttcaa cggctacaac                                                   20

<210> SEQ ID NO 25
<211> LENGTH: 19
<212> TYPE: DNA
<213> ORGANISM: Artificial Sequence
<220> FEATURE:
<223> OTHER INFORMATION: Synthetic primer

<400> SEQUENCE: 25
agacacgccg gagtacttg                                                    19

<210> SEQ ID NO 26
<211> LENGTH: 23
<212> TYPE: DNA
<213> ORGANISM: Artificial Sequence
<220> FEATURE:
<223> OTHER INFORMATION: Synthetic probe

<400> SEQUENCE: 26
acagcaccaa ccggctcact ctc                                               23

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
ttatccggtg gtcctcattc                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
gcgaggtaac tggaggaaac                                                   20

<210> SEQ ID NO 29
<211> LENGTH: 24
<212> TYPE: DNA
<213> ORGANISM: Artificial Sequence
```

```
<220> FEATURE:
<223> OTHER INFORMATION: Synthetic probe

<400> SEQUENCE: 29
cagctcctgg atttcgatgc ttcg                                          24

<210> SEQ ID NO 30
<211> LENGTH: 19
<212> TYPE: DNA
<213> ORGANISM: Artificial Sequence
<220> FEATURE:
<223> OTHER INFORMATION: Synthetic primer

<400> SEQUENCE: 30
caagtggatt gccatggag                                                19

<210> SEQ ID NO 31
<211> LENGTH: 19
<212> TYPE: DNA
<213> ORGANISM: Artificial Sequence
<220> FEATURE:
<223> OTHER INFORMATION: Synthetic primer

<400> SEQUENCE: 31
aacccggtac cgtaaccct                                                19

<210> SEQ ID NO 32
<211> LENGTH: 24
<212> TYPE: DNA
<213> ORGANISM: Artificial Sequence
<220> FEATURE:
<223> OTHER INFORMATION: Synthetic probe

<400> SEQUENCE: 32
ctcagtgcac agtgacttgt ggcc                                          24

<210> SEQ ID NO 33
<211> LENGTH: 22
<212> TYPE: DNA
<213> ORGANISM: Artificial Sequence
<220> FEATURE:
<223> OTHER INFORMATION: Synthetic primer

<400> SEQUENCE: 33
agccaacatg tgactaattg ga                                            22

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
tctgatctcc atctgcctca                                               20

<210> SEQ ID NO 35
<211> LENGTH: 24
<212> TYPE: DNA
<213> ORGANISM: Artificial Sequence
<220> FEATURE:
<223> OTHER INFORMATION: Synthetic probe

<400> SEQUENCE: 35
caacacgtca ccacccttty ctct                                          24
```

```
<210> SEQ ID NO 36
<211> LENGTH: 19
<212> TYPE: DNA
<213> ORGANISM: Artificial Sequence
<220> FEATURE:
<223> OTHER INFORMATION: Synthetic primer

<400> SEQUENCE: 36
gcggcataga gaccgactt                                                19

<210> SEQ ID NO 37
<211> LENGTH: 19
<212> TYPE: DNA
<213> ORGANISM: Artificial Sequence
<220> FEATURE:
<223> OTHER INFORMATION: Synthetic primer

<400> SEQUENCE: 37
acatcttgtg ggaaaggca                                                19

<210> SEQ ID NO 38
<211> LENGTH: 24
<212> TYPE: DNA
<213> ORGANISM: Artificial Sequence
<220> FEATURE:
<223> OTHER INFORMATION: Synthetic probe

<400> SEQUENCE: 38
caggctagcc aaacggtcca actc                                          24

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
tagagagccc ctgacaatcc                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
ggttggtctt ggaaagagga                                               20

<210> SEQ ID NO 41
<211> LENGTH: 25
<212> TYPE: DNA
<213> ORGANISM: Artificial Sequence
<220> FEATURE:
<223> OTHER INFORMATION: Synthetic probe

<400> SEQUENCE: 41
tggctctagc tcctgatgaa gcctc                                         25

<210> SEQ ID NO 42
<211> LENGTH: 25
<212> TYPE: DNA
<213> ORGANISM: Artificial Sequence
<220> FEATURE:
<223> OTHER INFORMATION: Synthetic primer
```

```
<400> SEQUENCE: 42
ttgtctctgc cttggactat ctaca                                    25

<210> SEQ ID NO 43
<211> LENGTH: 24
<212> TYPE: DNA
<213> ORGANISM: Artificial Sequence
<220> FEATURE:
<223> OTHER INFORMATION: Synthetic primer

<400> SEQUENCE: 43
ccagcattag attctccaac ttga                                     24

<210> SEQ ID NO 44
<211> LENGTH: 23
<212> TYPE: DNA
<213> ORGANISM: Artificial Sequence
<220> FEATURE:
<223> OTHER INFORMATION: Synthetic probe

<400> SEQUENCE: 44
tcacggtaca caatctttcc gga                                      23

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
gtgaggcctc tgatgaatga                                          20

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
ctcagtgctg ggtcatcttg                                          20

<210> SEQ ID NO 47
<211> LENGTH: 24
<212> TYPE: DNA
<213> ORGANISM: Artificial Sequence
<220> FEATURE:
<223> OTHER INFORMATION: Synthetic probe

<400> SEQUENCE: 47
aaggcctgaa ggtcagatac cccc                                     24

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
ctccaggtgt acctccaacc                                          20

<210> SEQ ID NO 49
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
gagaaggctg ggagactctg                                              20

<210> SEQ ID NO 50
<211> LENGTH: 24
<212> TYPE: DNA
<213> ORGANISM: Artificial Sequence
<220> FEATURE:
<223> OTHER INFORMATION: Synthetic probe

<400> SEQUENCE: 50
agccttctcc cacagctgcc taca                                         24

<210> SEQ ID NO 51
<211> LENGTH: 22
<212> TYPE: DNA
<213> ORGANISM: Artificial Sequence
<220> FEATURE:
<223> OTHER INFORMATION: Synthetic primer

<400> SEQUENCE: 51
gcccctatcc taccttcaat cc                                           22

<210> SEQ ID NO 52
<211> LENGTH: 24
<212> TYPE: DNA
<213> ORGANISM: Artificial Sequence
<220> FEATURE:
<223> OTHER INFORMATION: Synthetic primer

<400> SEQUENCE: 52
cctttaacca ttatggcctt atgc                                         24

<210> SEQ ID NO 53
<211> LENGTH: 19
<212> TYPE: DNA
<213> ORGANISM: Artificial Sequence
<220> FEATURE:
<223> OTHER INFORMATION: Synthetic probe

<400> SEQUENCE: 53
tcctcggatg tcgctgcct                                               19

<210> SEQ ID NO 54
<211> LENGTH: 19
<212> TYPE: DNA
<213> ORGANISM: Artificial Sequence
<220> FEATURE:
<223> OTHER INFORMATION: Synthetic primer

<400> SEQUENCE: 54
tgggagggat gaaggaaat                                               19

<210> SEQ ID NO 55
<211> LENGTH: 19
<212> TYPE: DNA
<213> ORGANISM: Artificial Sequence
<220> FEATURE:
<223> OTHER INFORMATION: Synthetic primer

<400> SEQUENCE: 55
```
ctcatacagg tcctgggca                                                19

<210> SEQ ID NO 56
<211> LENGTH: 24
<212> TYPE: DNA
<213> ORGANISM: Artificial Sequence
<220> FEATURE:
<223> OTHER INFORMATION: Synthetic probe

<400> SEQUENCE: 56
tgtctcacga gagcatcgtc caga                                          24

<210> SEQ ID NO 57
<211> LENGTH: 20
<212> TYPE: DNA
<213> ORGANISM: Artificial Sequence
<220> FEATURE:
<223> OTHER INFORMATION: Synthetic primer

<400> SEQUENCE: 57
gactgcaaag atggaaacga                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic primer

<400> SEQUENCE: 58
tagccataag gtccgctctc                                               20

<210> SEQ ID NO 59
<211> LENGTH: 24
<212> TYPE: DNA
<213> ORGANISM: Artificial Sequence
<220> FEATURE:
<223> OTHER INFORMATION: Synthetic probe

<400> SEQUENCE: 59
ctatgacgat gccctcaacg cctc                                          24

<210> SEQ ID NO 60
<211> LENGTH: 20
<212> TYPE: DNA
<213> ORGANISM: Artificial Sequence
<220> FEATURE:
<223> OTHER INFORMATION: Synthetic primer

<400> SEQUENCE: 60
ggacagcagg aatgtgtttc                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic primer

<400> SEQUENCE: 61
acccactcga tttgtttctg                                               20

<210> SEQ ID NO 62
<211> LENGTH: 22
<212> TYPE: DNA

```
<213> ORGANISM: Artificial Sequence
<220> FEATURE:
<223> OTHER INFORMATION: Synthetic probe

<400> SEQUENCE: 62
cattggctcc ccgtgacctg ta                                            22

<210> SEQ ID NO 63
<211> LENGTH: 22
<212> TYPE: DNA
<213> ORGANISM: Artificial Sequence
<220> FEATURE:
<223> OTHER INFORMATION: Synthetic primer

<400> SEQUENCE: 63
ccaccttgga ccaaagtaaa gc                                            22

<210> SEQ ID NO 64
<211> LENGTH: 21
<212> TYPE: DNA
<213> ORGANISM: Artificial Sequence
<220> FEATURE:
<223> OTHER INFORMATION: Synthetic primer

<400> SEQUENCE: 64
tctcagcgtc acccggtagg a                                             21

<210> SEQ ID NO 65
<211> LENGTH: 22
<212> TYPE: DNA
<213> ORGANISM: Artificial Sequence
<220> FEATURE:
<223> OTHER INFORMATION: Synthetic probe

<400> SEQUENCE: 65
ctccccaaca cgctgaaacc cg                                            22

<210> SEQ ID NO 66
<211> LENGTH: 27
<212> TYPE: DNA
<213> ORGANISM: Artificial Sequence
<220> FEATURE:
<223> OTHER INFORMATION: Synthetic primer

<400> SEQUENCE: 66
tgtgagtgaa atgccttcta gtagtga                                       27

<210> SEQ ID NO 67
<211> LENGTH: 27
<212> TYPE: DNA
<213> ORGANISM: Artificial Sequence
<220> FEATURE:
<223> OTHER INFORMATION: Synthetic primer

<400> SEQUENCE: 67
ttgtggttcg ttatcatact cttctga                                       27

<210> SEQ ID NO 68
<211> LENGTH: 23
<212> TYPE: DNA
<213> ORGANISM: Artificial Sequence
<220> FEATURE:
<223> OTHER INFORMATION: Synthetic probe

<400> SEQUENCE: 68
ccgtcctcgg gagccgacta tga                                           23
```

<210> SEQ ID NO 69
<211> LENGTH: 19
<212> TYPE: DNA
<213> ORGANISM: Artificial Sequence
<220> FEATURE:
<223> OTHER INFORMATION: Synthetic primer

<400> SEQUENCE: 69
cgcctcatcg agatcaagt                                        19

<210> SEQ ID NO 70
<211> LENGTH: 20
<212> TYPE: DNA
<213> ORGANISM: Artificial Sequence
<220> FEATURE:
<223> OTHER INFORMATION: Synthetic primer

<400> SEQUENCE: 70
ggtcacggac acagattcac                                       20

<210> SEQ ID NO 71
<211> LENGTH: 23
<212> TYPE: DNA
<213> ORGANISM: Artificial Sequence
<220> FEATURE:
<223> OTHER INFORMATION: Synthetic probe

<400> SEQUENCE: 71
ctgcgagtgg accagtccat cct                                   23

<210> SEQ ID NO 72
<211> LENGTH: 18
<212> TYPE: DNA
<213> ORGANISM: Artificial Sequence
<220> FEATURE:
<223> OTHER INFORMATION: Synthetic primer

<400> SEQUENCE: 72
ccgctttcgc tacagcat                                         18

<210> SEQ ID NO 73
<211> LENGTH: 21
<212> TYPE: DNA
<213> ORGANISM: Artificial Sequence
<220> FEATURE:
<223> OTHER INFORMATION: Synthetic primer

<400> SEQUENCE: 73
tgggagtatc ggatgtagct g                                     21

<210> SEQ ID NO 74
<211> LENGTH: 24
<212> TYPE: DNA
<213> ORGANISM: Artificial Sequence
<220> FEATURE:
<223> OTHER INFORMATION: Synthetic probe

<400> SEQUENCE: 74
tccagcctgt ctccagtagg ccac                                  24

<210> SEQ ID NO 75
<211> LENGTH: 20
<212> TYPE: DNA
<213> ORGANISM: Artificial Sequence
<220> FEATURE:

<223> OTHER INFORMATION: Synthetic primer

<400> SEQUENCE: 75
ggctatgtct ttgcaccagc                                           20

<210> SEQ ID NO 76
<211> LENGTH: 18
<212> TYPE: DNA
<213> ORGANISM: Artificial Sequence
<220> FEATURE:
<223> OTHER INFORMATION: Synthetic primer

<400> SEQUENCE: 76
atccgtcagc gcatcact                                             18

<210> SEQ ID NO 77
<211> LENGTH: 24
<212> TYPE: DNA
<213> ORGANISM: Artificial Sequence
<220> FEATURE:
<223> OTHER INFORMATION: Synthetic probe

<400> SEQUENCE: 77
accagcgcca acgacagtga gata                                      24

<210> SEQ ID NO 78
<211> LENGTH: 21
<212> TYPE: DNA
<213> ORGANISM: Artificial Sequence
<220> FEATURE:
<223> OTHER INFORMATION: Synthetic primer

<400> SEQUENCE: 78
cagcagatgt ggatcagcaa g                                         21

<210> SEQ ID NO 79
<211> LENGTH: 18
<212> TYPE: DNA
<213> ORGANISM: Artificial Sequence
<220> FEATURE:
<223> OTHER INFORMATION: Synthetic primer

<400> SEQUENCE: 79
gcatttgcgg tggacgat                                             18

<210> SEQ ID NO 80
<211> LENGTH: 23
<212> TYPE: DNA
<213> ORGANISM: Artificial Sequence
<220> FEATURE:
<223> OTHER INFORMATION: Synthetic probe

<400> SEQUENCE: 80
aggagtatga cgagtccggc ccc                                       23

<210> SEQ ID NO 81
<211> LENGTH: 22
<212> TYPE: DNA
<213> ORGANISM: Artificial Sequence
<220> FEATURE:
<223> OTHER INFORMATION: Synthetic primer

<400> SEQUENCE: 81
ggctcttgtg cgtactgtcc tt                                        22

<210> SEQ ID NO 82
<211> LENGTH: 23
<212> TYPE: DNA
<213> ORGANISM: Artificial Sequence
<220> FEATURE:
<223> OTHER INFORMATION: Synthetic primer

<400> SEQUENCE: 82
tcagatgacg aagagcacag atg                                    23

<210> SEQ ID NO 83
<211> LENGTH: 29
<212> TYPE: DNA
<213> ORGANISM: Artificial Sequence
<220> FEATURE:
<223> OTHER INFORMATION: Synthetic probe

<400> SEQUENCE: 83
aggctcagtg atgtcttccc tgtcaccag                              29

<210> SEQ ID NO 84
<211> LENGTH: 18
<212> TYPE: DNA
<213> ORGANISM: Artificial Sequence
<220> FEATURE:
<223> OTHER INFORMATION: Synthetic primer

<400> SEQUENCE: 84
ccgccgtgga cacagact                                          18

<210> SEQ ID NO 85
<211> LENGTH: 21
<212> TYPE: DNA
<213> ORGANISM: Artificial Sequence
<220> FEATURE:
<223> OTHER INFORMATION: Synthetic primer

<400> SEQUENCE: 85
ttgccgtcag aaaacatgtc a                                      21

<210> SEQ ID NO 86
<211> LENGTH: 25
<212> TYPE: DNA
<213> ORGANISM: Artificial Sequence
<220> FEATURE:
<223> OTHER INFORMATION: Synthetic probe

<400> SEQUENCE: 86
tgccactcgg aaaaagacct ctcgg                                  25

<210> SEQ ID NO 87
<211> LENGTH: 20
<212> TYPE: DNA
<213> ORGANISM: Artificial Sequence
<220> FEATURE:
<223> OTHER INFORMATION: Synthetic primer

<400> SEQUENCE: 87
ccccgagaca acggagataa                                        20

<210> SEQ ID NO 88
<211> LENGTH: 19
<212> TYPE: DNA
<213> ORGANISM: Artificial Sequence
<220> FEATURE:
<223> OTHER INFORMATION: Synthetic primer

```
<400> SEQUENCE: 88
ctcgggtttg gcctctttc                                              19

<210> SEQ ID NO 89
<211> LENGTH: 23
<212> TYPE: DNA
<213> ORGANISM: Artificial Sequence
<220> FEATURE:
<223> OTHER INFORMATION: Synthetic probe

<400> SEQUENCE: 89
ctttccgttg gcatccgcaa cag                                         23

<210> SEQ ID NO 90
<211> LENGTH: 25
<212> TYPE: DNA
<213> ORGANISM: Artificial Sequence
<220> FEATURE:
<223> OTHER INFORMATION: Synthetic primer

<400> SEQUENCE: 90
cagatggacc tagtacccac tgaga                                       25

<210> SEQ ID NO 91
<211> LENGTH: 24
<212> TYPE: DNA
<213> ORGANISM: Artificial Sequence
<220> FEATURE:
<223> OTHER INFORMATION: Synthetic primer

<400> SEQUENCE: 91
cctatgattt aagggcattt ttcc                                        24

<210> SEQ ID NO 92
<211> LENGTH: 22
<212> TYPE: DNA
<213> ORGANISM: Artificial Sequence
<220> FEATURE:
<223> OTHER INFORMATION: Synthetic probe

<400> SEQUENCE: 92
ttccacgccg aaggacagcg at                                          22

<210> SEQ ID NO 93
<211> LENGTH: 26
<212> TYPE: DNA
<213> ORGANISM: Artificial Sequence
<220> FEATURE:
<223> OTHER INFORMATION: Synthetic primer

<400> SEQUENCE: 93
tgtactggcg aagaatattt ggtaaa                                      26

<210> SEQ ID NO 94
<211> LENGTH: 20
<212> TYPE: DNA
<213> ORGANISM: Artificial Sequence
<220> FEATURE:
<223> OTHER INFORMATION: Synthetic primer

<400> SEQUENCE: 94
gccacgtgat tcttccacaa                                             20

<210> SEQ ID NO 95
<211> LENGTH: 24
```

```
<212> TYPE: DNA
<213> ORGANISM: Artificial Sequence
<220> FEATURE:
<223> OTHER INFORMATION: Synthetic probe

<400> SEQUENCE: 95
cagggcatcg atctctcacc ctgg                                          24

<210> SEQ ID NO 96
<211> LENGTH: 19
<212> TYPE: DNA
<213> ORGANISM: Artificial Sequence
<220> FEATURE:
<223> OTHER INFORMATION: Synthetic primer

<400> SEQUENCE: 96
gcctgcagtc ccatgatca                                                19

<210> SEQ ID NO 97
<211> LENGTH: 20
<212> TYPE: DNA
<213> ORGANISM: Artificial Sequence
<220> FEATURE:
<223> OTHER INFORMATION: Synthetic primer

<400> SEQUENCE: 97
ttccctcttg ggccacagta                                               20

<210> SEQ ID NO 98
<211> LENGTH: 25
<212> TYPE: DNA
<213> ORGANISM: Artificial Sequence
<220> FEATURE:
<223> OTHER INFORMATION: Synthetic probe

<400> SEQUENCE: 98
tcccagggca aactcaagga ccaaa                                         25

<210> SEQ ID NO 99
<211> LENGTH: 18
<212> TYPE: DNA
<213> ORGANISM: Artificial Sequence
<220> FEATURE:
<223> OTHER INFORMATION: Synthetic primer

<400> SEQUENCE: 99
gagctccgca aggatgac                                                 18

<210> SEQ ID NO 100
<211> LENGTH: 20
<212> TYPE: DNA
<213> ORGANISM: Artificial Sequence
<220> FEATURE:
<223> OTHER INFORMATION: Synthetic primer

<400> SEQUENCE: 100
cttgttgttc accaggacga                                               20

<210> SEQ ID NO 101
<211> LENGTH: 24
<212> TYPE: DNA
<213> ORGANISM: Artificial Sequence
<220> FEATURE:
<223> OTHER INFORMATION: Synthetic probe

<400> SEQUENCE: 101
```

```
caagggtctc cagcacctct acgc                                              24

<210> SEQ ID NO 102
<211> LENGTH: 23
<212> TYPE: DNA
<213> ORGANISM: Artificial Sequence
<220> FEATURE:
<223> OTHER INFORMATION: Synthetic primer

<400> SEQUENCE: 102
attcctatgg ctctgcaatt gtc                                               23

<210> SEQ ID NO 103
<211> LENGTH: 21
<212> TYPE: DNA
<213> ORGANISM: Artificial Sequence
<220> FEATURE:
<223> OTHER INFORMATION: Synthetic primer

<400> SEQUENCE: 103
ggcaggagtg aatggctctt c                                                 21

<210> SEQ ID NO 104
<211> LENGTH: 23
<212> TYPE: DNA
<213> ORGANISM: Artificial Sequence
<220> FEATURE:
<223> OTHER INFORMATION: Synthetic probe

<400> SEQUENCE: 104
ccggttaact gtggcctgtg ccc                                               23

<210> SEQ ID NO 105
<211> LENGTH: 20
<212> TYPE: DNA
<213> ORGANISM: Artificial Sequence
<220> FEATURE:
<223> OTHER INFORMATION: Synthetic primer

<400> SEQUENCE: 105
cctgcaaaag ggaacaagag                                                   20

<210> SEQ ID NO 106
<211> LENGTH: 20
<212> TYPE: DNA
<213> ORGANISM: Artificial Sequence
<220> FEATURE:
<223> OTHER INFORMATION: Synthetic primer

<400> SEQUENCE: 106
cgtggttgac tctgatctcg                                                   20

<210> SEQ ID NO 107
<211> LENGTH: 21
<212> TYPE: DNA
<213> ORGANISM: Artificial Sequence
<220> FEATURE:
<223> OTHER INFORMATION: Synthetic probe

<400> SEQUENCE: 107
cttcgcctcc agatggctcc c                                                 21

<210> SEQ ID NO 108
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 108
gaccaagcag gaagctcaga                                                   20

<210> SEQ ID NO 109
<211> LENGTH: 18
<212> TYPE: DNA
<213> ORGANISM: Artificial Sequence
<220> FEATURE:
<223> OTHER INFORMATION: Synthetic primer

<400> SEQUENCE: 109
agcgctgttt cggtcaga                                                     18

<210> SEQ ID NO 110
<211> LENGTH: 24
<212> TYPE: DNA
<213> ORGANISM: Artificial Sequence
<220> FEATURE:
<223> OTHER INFORMATION: Synthetic probe

<400> SEQUENCE: 110
ccaggggcag ctacctgaac tcaa                                              24

<210> SEQ ID NO 111
<211> LENGTH: 20
<212> TYPE: DNA
<213> ORGANISM: Artificial Sequence
<220> FEATURE:
<223> OTHER INFORMATION: Synthetic primer

<400> SEQUENCE: 111
ctggacggag tagctccaag                                                   20

<210> SEQ ID NO 112
<211> LENGTH: 20
<212> TYPE: DNA
<213> ORGANISM: Artificial Sequence
<220> FEATURE:
<223> OTHER INFORMATION: Synthetic primer

<400> SEQUENCE: 112
ggtatcttgt ggtgtctgcg                                                   20

<210> SEQ ID NO 113
<211> LENGTH: 24
<212> TYPE: DNA
<213> ORGANISM: Artificial Sequence
<220> FEATURE:
<223> OTHER INFORMATION: Synthetic probe

<400> SEQUENCE: 113
ctctcactgt gacagcccac ctcg                                              24

<210> SEQ ID NO 114
<211> LENGTH: 27
<212> TYPE: DNA
<213> ORGANISM: Artificial Sequence
<220> FEATURE:
<223> OTHER INFORMATION: Synthetic primer

<400> SEQUENCE: 114
tatttcttca tgaagacctc acagtaa                                           27
```

<210> SEQ ID NO 115
<211> LENGTH: 21
<212> TYPE: DNA
<213> ORGANISM: Artificial Sequence
<220> FEATURE:
<223> OTHER INFORMATION: Synthetic primer

<400> SEQUENCE: 115
acccactcca tcgagatttc a                                              21

<210> SEQ ID NO 116
<211> LENGTH: 18
<212> TYPE: DNA
<213> ORGANISM: Artificial Sequence
<220> FEATURE:
<223> OTHER INFORMATION: Synthetic probe

<400> SEQUENCE: 116
tagctagacc aaaatcac                                                  18

<210> SEQ ID NO 117
<211> LENGTH: 27
<212> TYPE: DNA
<213> ORGANISM: Artificial Sequence
<220> FEATURE:
<223> OTHER INFORMATION: Synthetic primer

<400> SEQUENCE: 117
tatttcttca tgaagacctc acagtaa                                        27

<210> SEQ ID NO 118
<211> LENGTH: 22
<212> TYPE: DNA
<213> ORGANISM: Artificial Sequence
<220> FEATURE:
<223> OTHER INFORMATION: Synthetic primer

<400> SEQUENCE: 118
gacccactcc atcgagattt ct                                             22

<210> SEQ ID NO 119
<211> LENGTH: 18
<212> TYPE: DNA
<213> ORGANISM: Artificial Sequence
<220> FEATURE:
<223> OTHER INFORMATION: Synthetic probe

<400> SEQUENCE: 119
tagctagacc aaaatcac                                                  18

<210> SEQ ID NO 120
<211> LENGTH: 20
<212> TYPE: DNA
<213> ORGANISM: Artificial Sequence
<220> FEATURE:
<223> OTHER INFORMATION: Synthetic primer

<400> SEQUENCE: 120
tcagggggct agaaatctgt                                                20

<210> SEQ ID NO 121
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 121
ccattccagt tgatctgtgg                                          20

<210> SEQ ID NO 122
<211> LENGTH: 23
<212> TYPE: DNA
<213> ORGANISM: Artificial Sequence
<220> FEATURE:
<223> OTHER INFORMATION: Synthetic probe

<400> SEQUENCE: 122
ctatgggccc ttcaccaaca tgc                                      23

<210> SEQ ID NO 123
<211> LENGTH: 18
<212> TYPE: DNA
<213> ORGANISM: Artificial Sequence
<220> FEATURE:
<223> OTHER INFORMATION: Synthetic primer

<400> SEQUENCE: 123
gctacgaatg gcacgacc                                            18

<210> SEQ ID NO 124
<211> LENGTH: 18
<212> TYPE: DNA
<213> ORGANISM: Artificial Sequence
<220> FEATURE:
<223> OTHER INFORMATION: Synthetic primer

<400> SEQUENCE: 124
tcccaagctt ccatgcac                                            18

<210> SEQ ID NO 125
<211> LENGTH: 24
<212> TYPE: DNA
<213> ORGANISM: Artificial Sequence
<220> FEATURE:
<223> OTHER INFORMATION: Synthetic probe

<400> SEQUENCE: 125
ctcgagcttg gcagtctcca gttg                                     24

<210> SEQ ID NO 126
<211> LENGTH: 21
<212> TYPE: DNA
<213> ORGANISM: Artificial Sequence
<220> FEATURE:
<223> OTHER INFORMATION: Synthetic primer

<400> SEQUENCE: 126
ccgaggttaa tccagcacgt a                                        21

<210> SEQ ID NO 127
<211> LENGTH: 21
<212> TYPE: DNA
<213> ORGANISM: Artificial Sequence
<220> FEATURE:
<223> OTHER INFORMATION: Synthetic primer

<400> SEQUENCE: 127
aagacatggc gctctcagtt c                                        21

<210> SEQ ID NO 128
```

```
<211> LENGTH: 23
<212> TYPE: DNA
<213> ORGANISM: Artificial Sequence
<220> FEATURE:
<223> OTHER INFORMATION: Synthetic probe

<400> SEQUENCE: 128
tgctgggagc ctacacttgg ccc                                          23

<210> SEQ ID NO 129
<211> LENGTH: 24
<212> TYPE: DNA
<213> ORGANISM: Artificial Sequence
<220> FEATURE:
<223> OTHER INFORMATION: Synthetic primer

<400> SEQUENCE: 129
aactcagact tggaaatgcc ttct                                         24

<210> SEQ ID NO 130
<211> LENGTH: 27
<212> TYPE: DNA
<213> ORGANISM: Artificial Sequence
<220> FEATURE:
<223> OTHER INFORMATION: Synthetic primer

<400> SEQUENCE: 130
ctggtctcta tgaaatggtg ttgtaac                                      27

<210> SEQ ID NO 131
<211> LENGTH: 26
<212> TYPE: DNA
<213> ORGANISM: Artificial Sequence
<220> FEATURE:
<223> OTHER INFORMATION: Synthetic probe

<400> SEQUENCE: 131
aacttccacc cccctcattg gtcaca                                       26

<210> SEQ ID NO 132
<211> LENGTH: 22
<212> TYPE: DNA
<213> ORGANISM: Artificial Sequence
<220> FEATURE:
<223> OTHER INFORMATION: Synthetic primer

<400> SEQUENCE: 132
tcctcaacag aggtacacat gg                                           22

<210> SEQ ID NO 133
<211> LENGTH: 18
<212> TYPE: DNA
<213> ORGANISM: Artificial Sequence
<220> FEATURE:
<223> OTHER INFORMATION: Synthetic primer

<400> SEQUENCE: 133
atcccagggc ttgtgggc                                                18

<210> SEQ ID NO 134
<211> LENGTH: 24
<212> TYPE: DNA
<213> ORGANISM: Artificial Sequence
<220> FEATURE:
<223> OTHER INFORMATION: Synthetic probe

<400> SEQUENCE: 134
```

```
acacccgatg agagtatcct gggc                                      24
```

<210> SEQ ID NO 135
<211> LENGTH: 20
<212> TYPE: DNA
<213> ORGANISM: Artificial Sequence
<220> FEATURE:
<223> OTHER INFORMATION: Synthetic primer

<400> SEQUENCE: 135

```
tcagctgtga gctgcggata                                           20
```

<210> SEQ ID NO 136
<211> LENGTH: 24
<212> TYPE: DNA
<213> ORGANISM: Artificial Sequence
<220> FEATURE:
<223> OTHER INFORMATION: Synthetic primer

<400> SEQUENCE: 136

```
acggtcctag gtttgaggtt aaga                                      24
```

<210> SEQ ID NO 137
<211> LENGTH: 19
<212> TYPE: DNA
<213> ORGANISM: Artificial Sequence
<220> FEATURE:
<223> OTHER INFORMATION: Synthetic probe

<400> SEQUENCE: 137

```
caggtcccat tgccgggcg                                            19
```

<210> SEQ ID NO 138
<211> LENGTH: 20
<212> TYPE: DNA
<213> ORGANISM: Artificial Sequence
<220> FEATURE:
<223> OTHER INFORMATION: Synthetic primer

<400> SEQUENCE: 138

```
ccagcactgc tcgttactgt                                           20
```

<210> SEQ ID NO 139
<211> LENGTH: 21
<212> TYPE: DNA
<213> ORGANISM: Artificial Sequence
<220> FEATURE:
<223> OTHER INFORMATION: Synthetic primer

<400> SEQUENCE: 139

```
ttgacttcac ggcagttcat a                                         21
```

<210> SEQ ID NO 140
<211> LENGTH: 23
<212> TYPE: DNA
<213> ORGANISM: Artificial Sequence
<220> FEATURE:
<223> OTHER INFORMATION: Synthetic probe

<400> SEQUENCE: 140

```
tgggacctca gaccactgaa ggc                                       23
```

<210> SEQ ID NO 141
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 141
aggacaacga taaccgatca                                              20

<210> SEQ ID NO 142
<211> LENGTH: 20
<212> TYPE: DNA
<213> ORGANISM: Artificial Sequence
<220> FEATURE:
<223> OTHER INFORMATION: Synthetic primer

<400> SEQUENCE: 142
cccagtgaaa atggaactga                                              20

<210> SEQ ID NO 143
<211> LENGTH: 26
<212> TYPE: DNA
<213> ORGANISM: Artificial Sequence
<220> FEATURE:
<223> OTHER INFORMATION: Synthetic probe

<400> SEQUENCE: 143
tggtcctttc tctgacagct acaggc                                       26

<210> SEQ ID NO 144
<211> LENGTH: 20
<212> TYPE: DNA
<213> ORGANISM: Artificial Sequence
<220> FEATURE:
<223> OTHER INFORMATION: Synthetic primer

<400> SEQUENCE: 144
ctctctgaag gtgtcctggc                                              20

<210> SEQ ID NO 145
<211> LENGTH: 19
<212> TYPE: DNA
<213> ORGANISM: Artificial Sequence
<220> FEATURE:
<223> OTHER INFORMATION: Synthetic primer

<400> SEQUENCE: 145
acaggaactg aggggtgct                                               19

<210> SEQ ID NO 146
<211> LENGTH: 24
<212> TYPE: DNA
<213> ORGANISM: Artificial Sequence
<220> FEATURE:
<223> OTHER INFORMATION: Synthetic probe

<400> SEQUENCE: 146
agacaccagt gcttctccag ggct                                         24

<210> SEQ ID NO 147
<211> LENGTH: 22
<212> TYPE: DNA
<213> ORGANISM: Artificial Sequence
<220> FEATURE:
<223> OTHER INFORMATION: Synthetic primer

<400> SEQUENCE: 147
caacgtggag tttgatgact ct                                           22
```

<210> SEQ ID NO 148
<211> LENGTH: 19
<212> TYPE: DNA
<213> ORGANISM: Artificial Sequence
<220> FEATURE:
<223> OTHER INFORMATION: Synthetic primer

<400> SEQUENCE: 148
ctgtaagtgc catccaggg                                                   19

<210> SEQ ID NO 149
<211> LENGTH: 24
<212> TYPE: DNA
<213> ORGANISM: Artificial Sequence
<220> FEATURE:
<223> OTHER INFORMATION: Synthetic probe

<400> SEQUENCE: 149
cctcccttga gcactgcttt gtcc                                             24

<210> SEQ ID NO 150
<211> LENGTH: 20
<212> TYPE: DNA
<213> ORGANISM: Artificial Sequence
<220> FEATURE:
<223> OTHER INFORMATION: Synthetic primer

<400> SEQUENCE: 150
atcctagccc tggtttttgg                                                  20

<210> SEQ ID NO 151
<211> LENGTH: 20
<212> TYPE: DNA
<213> ORGANISM: Artificial Sequence
<220> FEATURE:
<223> OTHER INFORMATION: Synthetic primer

<400> SEQUENCE: 151
ctgccttctc atctgcacaa                                                  20

<210> SEQ ID NO 152
<211> LENGTH: 20
<212> TYPE: DNA
<213> ORGANISM: Artificial Sequence
<220> FEATURE:
<223> OTHER INFORMATION: Synthetic probe

<400> SEQUENCE: 152
tttgctgtca ccagcgtcgc                                                  20

<210> SEQ ID NO 153
<211> LENGTH: 20
<212> TYPE: DNA
<213> ORGANISM: Artificial Sequence
<220> FEATURE:
<223> OTHER INFORMATION: Synthetic primer

<400> SEQUENCE: 153
gaaggccaag aaccgagtca                                                  20

<210> SEQ ID NO 154
<211> LENGTH: 24
<212> TYPE: DNA
<213> ORGANISM: Artificial Sequence
<220> FEATURE:

<223> OTHER INFORMATION: Synthetic primer

<400> SEQUENCE: 154
tccccagtta gttcaaaagt caca                                    24

<210> SEQ ID NO 155
<211> LENGTH: 27
<212> TYPE: DNA
<213> ORGANISM: Artificial Sequence
<220> FEATURE:
<223> OTHER INFORMATION: Synthetic probe

<400> SEQUENCE: 155
ttatattcca gtttaaggcc aatcctc                                 27

<210> SEQ ID NO 156
<211> LENGTH: 26
<212> TYPE: DNA
<213> ORGANISM: Artificial Sequence
<220> FEATURE:
<223> OTHER INFORMATION: Synthetic primer

<400> SEQUENCE: 156
cactaaggtt tgagacagtt ccagaa                                  26

<210> SEQ ID NO 157
<211> LENGTH: 23
<212> TYPE: DNA
<213> ORGANISM: Artificial Sequence
<220> FEATURE:
<223> OTHER INFORMATION: Synthetic primer

<400> SEQUENCE: 157
gcgaattagc cctctacaac tga                                     23

<210> SEQ ID NO 158
<211> LENGTH: 26
<212> TYPE: DNA
<213> ORGANISM: Artificial Sequence
<220> FEATURE:
<223> OTHER INFORMATION: Synthetic probe

<400> SEQUENCE: 158
aacccaagct caagacgcag gacgag                                  26

<210> SEQ ID NO 159
<211> LENGTH: 20
<212> TYPE: DNA
<213> ORGANISM: Artificial Sequence
<220> FEATURE:
<223> OTHER INFORMATION: Synthetic primer

<400> SEQUENCE: 159
atgcaaagca ctgtggaaac                                         20

<210> SEQ ID NO 160
<211> LENGTH: 20
<212> TYPE: DNA
<213> ORGANISM: Artificial Sequence
<220> FEATURE:
<223> OTHER INFORMATION: Synthetic primer

<400> SEQUENCE: 160
tccaaactgc aacaagaagg                                         20

```
<210> SEQ ID NO 161
<211> LENGTH: 26
<212> TYPE: DNA
<213> ORGANISM: Artificial Sequence
<220> FEATURE:
<223> OTHER INFORMATION: Synthetic probe

<400> SEQUENCE: 161
tccatttcag aatcagagcc ctgttg                                          26

<210> SEQ ID NO 162
<211> LENGTH: 23
<212> TYPE: DNA
<213> ORGANISM: Artificial Sequence
<220> FEATURE:
<223> OTHER INFORMATION: Synthetic primer

<400> SEQUENCE: 162
ccatgtgctg taccaagagt ttg                                             23

<210> SEQ ID NO 163
<211> LENGTH: 18
<212> TYPE: DNA
<213> ORGANISM: Artificial Sequence
<220> FEATURE:
<223> OTHER INFORMATION: Synthetic primer

<400> SEQUENCE: 163
cgccgcagag gtggagta                                                   18

<210> SEQ ID NO 164
<211> LENGTH: 26
<212> TYPE: DNA
<213> ORGANISM: Artificial Sequence
<220> FEATURE:
<223> OTHER INFORMATION: Synthetic probe

<400> SEQUENCE: 164
cagcactgac atcaaagcag ccagga                                          26

<210> SEQ ID NO 165
<211> LENGTH: 23
<212> TYPE: DNA
<213> ORGANISM: Artificial Sequence
<220> FEATURE:
<223> OTHER INFORMATION: Synthetic primer

<400> SEQUENCE: 165
gggtccagga gtacgtgtat gac                                             23

<210> SEQ ID NO 166
<211> LENGTH: 23
<212> TYPE: DNA
<213> ORGANISM: Artificial Sequence
<220> FEATURE:
<223> OTHER INFORMATION: Synthetic primer

<400> SEQUENCE: 166
ccttccctga agacttcctg tct                                             23

<210> SEQ ID NO 167
<211> LENGTH: 18
<212> TYPE: DNA
<213> ORGANISM: Artificial Sequence
<220> FEATURE:
<223> OTHER INFORMATION: Synthetic probe
```

```
<400> SEQUENCE: 167
actgaactga gctgctca                                                 18

<210> SEQ ID NO 168
<211> LENGTH: 20
<212> TYPE: DNA
<213> ORGANISM: Artificial Sequence
<220> FEATURE:
<223> OTHER INFORMATION: Synthetic primer

<400> SEQUENCE: 168
aggttctgag ctctggcttt                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic primer

<400> SEQUENCE: 169
atgctgactt ccttcctggt                                               20

<210> SEQ ID NO 170
<211> LENGTH: 22
<212> TYPE: DNA
<213> ORGANISM: Artificial Sequence
<220> FEATURE:
<223> OTHER INFORMATION: Synthetic probe

<400> SEQUENCE: 170
acagagccct ggcaaagcca ag                                            22

<210> SEQ ID NO 171
<211> LENGTH: 25
<212> TYPE: DNA
<213> ORGANISM: Artificial Sequence
<220> FEATURE:
<223> OTHER INFORMATION: Synthetic primer

<400> SEQUENCE: 171
ccatacctca agtatttgcc atcag                                         25

<210> SEQ ID NO 172
<211> LENGTH: 22
<212> TYPE: DNA
<213> ORGANISM: Artificial Sequence
<220> FEATURE:
<223> OTHER INFORMATION: Synthetic primer

<400> SEQUENCE: 172
agctttgtcc cgtgactgtg ta                                            22

<210> SEQ ID NO 173
<211> LENGTH: 29
<212> TYPE: DNA
<213> ORGANISM: Artificial Sequence
<220> FEATURE:
<223> OTHER INFORMATION: Synthetic primer

<400> SEQUENCE: 173
attgctggag ctgcctttca tttagcact                                     29

<210> SEQ ID NO 174
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 174
ttcaggttgt tgcaggagac                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic primer

<400> SEQUENCE: 175
catcttcttg ggcacacaat                                              20

<210> SEQ ID NO 176
<211> LENGTH: 27
<212> TYPE: DNA
<213> ORGANISM: Artificial Sequence
<220> FEATURE:
<223> OTHER INFORMATION: Synthetic primer

<400> SEQUENCE: 176
tgtctccatt attgatcggt tcatgca                                      27

<210> SEQ ID NO 177
<211> LENGTH: 21
<212> TYPE: DNA
<213> ORGANISM: Artificial Sequence
<220> FEATURE:
<223> OTHER INFORMATION: Synthetic primer

<400> SEQUENCE: 177
gcatgttcgt ggcctctaag a                                            21

<210> SEQ ID NO 178
<211> LENGTH: 22
<212> TYPE: DNA
<213> ORGANISM: Artificial Sequence
<220> FEATURE:
<223> OTHER INFORMATION: Synthetic primer

<400> SEQUENCE: 178
cggtgtagat gcacagcttc tc                                           22

<210> SEQ ID NO 179
<211> LENGTH: 23
<212> TYPE: DNA
<213> ORGANISM: Artificial Sequence
<220> FEATURE:
<223> OTHER INFORMATION: Synthetic probe

<400> SEQUENCE: 179
aaggagacca tccccctgac ggc                                          23

<210> SEQ ID NO 180
<211> LENGTH: 19
<212> TYPE: DNA
<213> ORGANISM: Artificial Sequence
<220> FEATURE:
<223> OTHER INFORMATION: Synthetic primer

<400> SEQUENCE: 180
```
ctcgggaatc ctgaaaacc                                           19

<210> SEQ ID NO 181
<211> LENGTH: 20
<212> TYPE: DNA
<213> ORGANISM: Artificial Sequence
<220> FEATURE:
<223> OTHER INFORMATION: Synthetic primer

<400> SEQUENCE: 181
gactctcact gccctatgcc                                          20

<210> SEQ ID NO 182
<211> LENGTH: 24
<212> TYPE: DNA
<213> ORGANISM: Artificial Sequence
<220> FEATURE:
<223> OTHER INFORMATION: Synthetic probe

<400> SEQUENCE: 182
tcttctcgtt tcgacaccga agca                                     24

<210> SEQ ID NO 183
<211> LENGTH: 18
<212> TYPE: DNA
<213> ORGANISM: Artificial Sequence
<220> FEATURE:
<223> OTHER INFORMATION: Synthetic primer

<400> SEQUENCE: 183
cagactgaat gggggtgg                                            18

<210> SEQ ID NO 184
<211> LENGTH: 20
<212> TYPE: DNA
<213> ORGANISM: Artificial Sequence
<220> FEATURE:
<223> OTHER INFORMATION: Synthetic primer

<400> SEQUENCE: 184
ctggtttgtc tggagaaggc                                          20

<210> SEQ ID NO 185
<211> LENGTH: 25
<212> TYPE: DNA
<213> ORGANISM: Artificial Sequence
<220> FEATURE:
<223> OTHER INFORMATION: Synthetic probe

<400> SEQUENCE: 185
tggaataagt acctaaggcg ccccc                                    25

<210> SEQ ID NO 186
<211> LENGTH: 20
<212> TYPE: DNA
<213> ORGANISM: Artificial Sequence
<220> FEATURE:
<223> OTHER INFORMATION: Synthetic primer

<400> SEQUENCE: 186
cgatgtctgt gaacccaagt                                          20

<210> SEQ ID NO 187
<211> LENGTH: 20
<212> TYPE: DNA
<213> ORGANISM: Artificial Sequence
<220> FEATURE:
<223> OTHER INFORMATION: Synthetic primer

<400> SEQUENCE: 187
agtagctcaa gccccaacat                                                20

<210> SEQ ID NO 188
<211> LENGTH: 24
<212> TYPE: DNA
<213> ORGANISM: Artificial Sequence
<220> FEATURE:
<223> OTHER INFORMATION: Synthetic probe

<400> SEQUENCE: 188
agactgtctc ggagcccatc aggt                                           24

<210> SEQ ID NO 189
<211> LENGTH: 20
<212> TYPE: DNA
<213> ORGANISM: Artificial Sequence
<220> FEATURE:
<223> OTHER INFORMATION: Synthetic primer

<400> SEQUENCE: 189
ggatgacatg cactcagctc                                                20

<210> SEQ ID NO 190
<211> LENGTH: 20
<212> TYPE: DNA
<213> ORGANISM: Artificial Sequence
<220> FEATURE:
<223> OTHER INFORMATION: Synthetic primer

<400> SEQUENCE: 190
cctgacattt cccttgtcct                                                20

<210> SEQ ID NO 191
<211> LENGTH: 21
<212> TYPE: DNA
<213> ORGANISM: Artificial Sequence
<220> FEATURE:
<223> OTHER INFORMATION: Synthetic probe

<400> SEQUENCE: 191
ctcccatccc agtggagcca a                                              21

<210> SEQ ID NO 192
<211> LENGTH: 24
<212> TYPE: DNA
<213> ORGANISM: Artificial Sequence
<220> FEATURE:
<223> OTHER INFORMATION: Synthetic primer

<400> SEQUENCE: 192
gcaggtgtca gcaagtatga tcag                                           24

<210> SEQ ID NO 193
<211> LENGTH: 20
<212> TYPE: DNA
<213> ORGANISM: Artificial Sequence
<220> FEATURE:
<223> OTHER INFORMATION: Synthetic primer

<400> SEQUENCE: 193
tttttccgct gtggtgatga                                                20

```
<210> SEQ ID NO 194
<211> LENGTH: 27
<212> TYPE: DNA
<213> ORGANISM: Artificial Sequence
<220> FEATURE:
<223> OTHER INFORMATION: Synthetic probe

<400> SEQUENCE: 194
cgacaggata ttgaccaccg cctcatt                                            27

<210> SEQ ID NO 195
<211> LENGTH: 20
<212> TYPE: DNA
<213> ORGANISM: Artificial Sequence
<220> FEATURE:
<223> OTHER INFORMATION: Synthetic primer

<400> SEQUENCE: 195
cgtcaggacc caccatgtct                                                    20

<210> SEQ ID NO 196
<211> LENGTH: 24
<212> TYPE: DNA
<213> ORGANISM: Artificial Sequence
<220> FEATURE:
<223> OTHER INFORMATION: Synthetic primer

<400> SEQUENCE: 196
ggttaattgg tgacatcctc aaga                                               24

<210> SEQ ID NO 197
<211> LENGTH: 20
<212> TYPE: DNA
<213> ORGANISM: Artificial Sequence
<220> FEATURE:
<223> OTHER INFORMATION: Synthetic probe

<400> SEQUENCE: 197
cgcggccgag acatggcttg                                                    20

<210> SEQ ID NO 198
<211> LENGTH: 18
<212> TYPE: DNA
<213> ORGANISM: Artificial Sequence
<220> FEATURE:
<223> OTHER INFORMATION: Synthetic primer

<400> SEQUENCE: 198
ccagctaccc cctcaagc                                                      18

<210> SEQ ID NO 199
<211> LENGTH: 19
<212> TYPE: DNA
<213> ORGANISM: Artificial Sequence
<220> FEATURE:
<223> OTHER INFORMATION: Synthetic primer

<400> SEQUENCE: 199
ataatgggaa gctgggtgg                                                     19

<210> SEQ ID NO 200
<211> LENGTH: 24
<212> TYPE: DNA
<213> ORGANISM: Artificial Sequence
<220> FEATURE:
<223> OTHER INFORMATION: Synthetic probe
```

```
<400> SEQUENCE: 200
agatgccctt gtcctcagaa ccca                                              24

<210> SEQ ID NO 201
<211> LENGTH: 25
<212> TYPE: DNA
<213> ORGANISM: Artificial Sequence
<220> FEATURE:
<223> OTHER INFORMATION: Synthetic primer

<400> SEQUENCE: 201
tgtatttcaa gacctctgtg cactt                                             25

<210> SEQ ID NO 202
<211> LENGTH: 23
<212> TYPE: DNA
<213> ORGANISM: Artificial Sequence
<220> FEATURE:
<223> OTHER INFORMATION: Synthetic primer

<400> SEQUENCE: 202
ttagcctgag gaattgctgt gtt                                               23

<210> SEQ ID NO 203
<211> LENGTH: 25
<212> TYPE: DNA
<213> ORGANISM: Artificial Sequence
<220> FEATURE:
<223> OTHER INFORMATION: Synthetic probe

<400> SEQUENCE: 203
tttatgaacc tgccctgctc ccaca                                             25

<210> SEQ ID NO 204
<211> LENGTH: 20
<212> TYPE: DNA
<213> ORGANISM: Artificial Sequence
<220> FEATURE:
<223> OTHER INFORMATION: Synthetic primer

<400> SEQUENCE: 204
agatgaagtg gaaggcgctt                                                   20

<210> SEQ ID NO 205
<211> LENGTH: 21
<212> TYPE: DNA
<213> ORGANISM: Artificial Sequence
<220> FEATURE:
<223> OTHER INFORMATION: Synthetic primer

<400> SEQUENCE: 205
tgcctctgta atcggcaact g                                                 21

<210> SEQ ID NO 206
<211> LENGTH: 18
<212> TYPE: DNA
<213> ORGANISM: Artificial Sequence
<220> FEATURE:
<223> OTHER INFORMATION: Synthetic probe

<400> SEQUENCE: 206
caccgcggcc atcctgca                                                     18

<210> SEQ ID NO 207
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 207
ctcataccag ccatccaatg                                              20

<210> SEQ ID NO 208
<211> LENGTH: 21
<212> TYPE: DNA
<213> ORGANISM: Artificial Sequence
<220> FEATURE:
<223> OTHER INFORMATION: Synthetic primer

<400> SEQUENCE: 208
ttgggttgaa gaaatcagtc c                                            21

<210> SEQ ID NO 209
<211> LENGTH: 24
<212> TYPE: DNA
<213> ORGANISM: Artificial Sequence
<220> FEATURE:
<223> OTHER INFORMATION: Synthetic probe

<400> SEQUENCE: 209
caccaagccc agaggacagt tcct                                         24

<210> SEQ ID NO 210
<211> LENGTH: 21
<212> TYPE: DNA
<213> ORGANISM: Artificial Sequence
<220> FEATURE:
<223> OTHER INFORMATION: Synthetic primer

<400> SEQUENCE: 210
gtcccttagc caagcagttt c                                            21

<210> SEQ ID NO 211
<211> LENGTH: 19
<212> TYPE: DNA
<213> ORGANISM: Artificial Sequence
<220> FEATURE:
<223> OTHER INFORMATION: Synthetic primer

<400> SEQUENCE: 211
aaatgcagtg gcagtccct                                               19

<210> SEQ ID NO 212
<211> LENGTH: 24
<212> TYPE: DNA
<213> ORGANISM: Artificial Sequence
<220> FEATURE:
<223> OTHER INFORMATION: Synthetic probe

<400> SEQUENCE: 212
cttttcgcct gctggcttct ttga                                         24

<210> SEQ ID NO 213
<211> LENGTH: 18
<212> TYPE: DNA
<213> ORGANISM: Artificial Sequence
<220> FEATURE:
<223> OTHER INFORMATION: Synthetic primer

<400> SEQUENCE: 213
```

```
tggttcccag ccctgtgt                                                      18

<210> SEQ ID NO 214
<211> LENGTH: 19
<212> TYPE: DNA
<213> ORGANISM: Artificial Sequence
<220> FEATURE:
<223> OTHER INFORMATION: Synthetic primer

<400> SEQUENCE: 214
ctcctccacc ctgggttgt                                                     19

<210> SEQ ID NO 215
<211> LENGTH: 28
<212> TYPE: DNA
<213> ORGANISM: Artificial Sequence
<220> FEATURE:
<223> OTHER INFORMATION: Synthetic probe

<400> SEQUENCE: 215
ctccaagccc agattcagat tcgagtca                                           28

<210> SEQ ID NO 216
<211> LENGTH: 20
<212> TYPE: DNA
<213> ORGANISM: Artificial Sequence
<220> FEATURE:
<223> OTHER INFORMATION: Synthetic primer

<400> SEQUENCE: 216
gtgcaggctc aggtgaagtg                                                    20

<210> SEQ ID NO 217
<211> LENGTH: 20
<212> TYPE: DNA
<213> ORGANISM: Artificial Sequence
<220> FEATURE:
<223> OTHER INFORMATION: Synthetic primer

<400> SEQUENCE: 217
gacctcaggg cgattcatga                                                    20

<210> SEQ ID NO 218
<211> LENGTH: 30
<212> TYPE: DNA
<213> ORGANISM: Artificial Sequence
<220> FEATURE:
<223> OTHER INFORMATION: Synthetic probe

<400> SEQUENCE: 218
tcagcttcta caactggaca gacaacgctg                                         30

<210> SEQ ID NO 219
<211> LENGTH: 20
<212> TYPE: DNA
<213> ORGANISM: Artificial Sequence
<220> FEATURE:
<223> OTHER INFORMATION: Synthetic primer

<400> SEQUENCE: 219
agggtgaggt gcttgagtct                                                    20

<210> SEQ ID NO 220
<211> LENGTH: 19
<212> TYPE: DNA
```

```
<213> ORGANISM: Artificial Sequence
<220> FEATURE:
<223> OTHER INFORMATION: Synthetic primer

<400> SEQUENCE: 220
gggcacagta tcccaggta                                                    19

<210> SEQ ID NO 221
<211> LENGTH: 26
<212> TYPE: DNA
<213> ORGANISM: Artificial Sequence
<220> FEATURE:
<223> OTHER INFORMATION: Synthetic probe

<400> SEQUENCE: 221
ccaacggcaa gggaacaagt acttct                                            26

<210> SEQ ID NO 222
<211> LENGTH: 21
<212> TYPE: DNA
<213> ORGANISM: Artificial Sequence
<220> FEATURE:
<223> OTHER INFORMATION: Synthetic primer

<400> SEQUENCE: 222
tggattggag ttctgggaat g                                                 21

<210> SEQ ID NO 223
<211> LENGTH: 22
<212> TYPE: DNA
<213> ORGANISM: Artificial Sequence
<220> FEATURE:
<223> OTHER INFORMATION: Synthetic primer

<400> SEQUENCE: 223
gcttgcactc cacaggtaca ca                                                22

<210> SEQ ID NO 224
<211> LENGTH: 23
<212> TYPE: DNA
<213> ORGANISM: Artificial Sequence
<220> FEATURE:
<223> OTHER INFORMATION: Synthetic probe

<400> SEQUENCE: 224
actggccgtg gcactggaca aca                                               23

<210> SEQ ID NO 225
<211> LENGTH: 21
<212> TYPE: DNA
<213> ORGANISM: Artificial Sequence
<220> FEATURE:
<223> OTHER INFORMATION: Synthetic primer

<400> SEQUENCE: 225
aaacgagcag tttgccatca g                                                 21

<210> SEQ ID NO 226
<211> LENGTH: 20
<212> TYPE: DNA
<213> ORGANISM: Artificial Sequence
<220> FEATURE:
<223> OTHER INFORMATION: Synthetic primer

<400> SEQUENCE: 226
gttggtgatg ttccgaagca                                                   20
```

<210> SEQ ID NO 227
<211> LENGTH: 24
<212> TYPE: DNA
<213> ORGANISM: Artificial Sequence
<220> FEATURE:
<223> OTHER INFORMATION: Synthetic probe

<400> SEQUENCE: 227
cctcaccggc atagactgga agcg                                           24

<210> SEQ ID NO 228
<211> LENGTH: 20
<212> TYPE: DNA
<213> ORGANISM: Artificial Sequence
<220> FEATURE:
<223> OTHER INFORMATION: Synthetic primer

<400> SEQUENCE: 228
gagctgaaag acgcacactg                                                20

<210> SEQ ID NO 229
<211> LENGTH: 18
<212> TYPE: DNA
<213> ORGANISM: Artificial Sequence
<220> FEATURE:
<223> OTHER INFORMATION: Synthetic primer

<400> SEQUENCE: 229
gccgctcatt gatctcca                                                  18

<210> SEQ ID NO 230
<211> LENGTH: 24
<212> TYPE: DNA
<213> ORGANISM: Artificial Sequence
<220> FEATURE:
<223> OTHER INFORMATION: Synthetic probe

<400> SEQUENCE: 230
aattcctgca tggccagttt cctc                                           24

<210> SEQ ID NO 231
<211> LENGTH: 25
<212> TYPE: DNA
<213> ORGANISM: Artificial Sequence
<220> FEATURE:
<223> OTHER INFORMATION: Synthetic primer

<400> SEQUENCE: 231
gctacctcta ggaagccttc tctga                                          25

<210> SEQ ID NO 232
<211> LENGTH: 24
<212> TYPE: DNA
<213> ORGANISM: Artificial Sequence
<220> FEATURE:
<223> OTHER INFORMATION: Synthetic primer

<400> SEQUENCE: 232
caaagggaag gagtaggacg tatc                                           24

<210> SEQ ID NO 233
<211> LENGTH: 23
<212> TYPE: DNA
<213> ORGANISM: Artificial Sequence
<220> FEATURE:

<223> OTHER INFORMATION: Synthetic probe

<400> SEQUENCE: 233
cctcatcccc aaggcctgtg tcg                                            23

<210> SEQ ID NO 234
<211> LENGTH: 21
<212> TYPE: DNA
<213> ORGANISM: Artificial Sequence
<220> FEATURE:
<223> OTHER INFORMATION: Synthetic primer

<400> SEQUENCE: 234
tgagtgtccc ccggtatctt c                                              21

<210> SEQ ID NO 235
<211> LENGTH: 21
<212> TYPE: DNA
<213> ORGANISM: Artificial Sequence
<220> FEATURE:
<223> OTHER INFORMATION: Synthetic primer

<400> SEQUENCE: 235
cagccgcttt cagattttca t                                              21

<210> SEQ ID NO 236
<211> LENGTH: 27
<212> TYPE: DNA
<213> ORGANISM: Artificial Sequence
<220> FEATURE:
<223> OTHER INFORMATION: Synthetic probe

<400> SEQUENCE: 236
tgccaatccc gatgaaattg gaaattt                                        27

<210> SEQ ID NO 237
<211> LENGTH: 18
<212> TYPE: DNA
<213> ORGANISM: Artificial Sequence
<220> FEATURE:
<223> OTHER INFORMATION: Synthetic primer

<400> SEQUENCE: 237
gtcggcagaa gcaggact                                                  18

<210> SEQ ID NO 238
<211> LENGTH: 18
<212> TYPE: DNA
<213> ORGANISM: Artificial Sequence
<220> FEATURE:
<223> OTHER INFORMATION: Synthetic primer

<400> SEQUENCE: 238
ctactcatgg gcgggatg                                                  18

<210> SEQ ID NO 239
<211> LENGTH: 24
<212> TYPE: DNA
<213> ORGANISM: Artificial Sequence
<220> FEATURE:
<223> OTHER INFORMATION: Synthetic probe

<400> SEQUENCE: 239
ccttctgccc atagtgatca gcga                                           24

```
<210> SEQ ID NO 240
<211> LENGTH: 18
<212> TYPE: DNA
<213> ORGANISM: Artificial Sequence
<220> FEATURE:
<223> OTHER INFORMATION: Synthetic primer

<400> SEQUENCE: 240
acccatgtac cgtcctcg                                                 18

<210> SEQ ID NO 241
<211> LENGTH: 19
<212> TYPE: DNA
<213> ORGANISM: Artificial Sequence
<220> FEATURE:
<223> OTHER INFORMATION: Synthetic primer

<400> SEQUENCE: 241
ccgccttcag gttctcaat                                                19

<210> SEQ ID NO 242
<211> LENGTH: 24
<212> TYPE: DNA
<213> ORGANISM: Artificial Sequence
<220> FEATURE:
<223> OTHER INFORMATION: Synthetic probe

<400> SEQUENCE: 242
ccaacccaga tgaaatcggc aact                                          24

<210> SEQ ID NO 243
<211> LENGTH: 20
<212> TYPE: DNA
<213> ORGANISM: Artificial Sequence
<220> FEATURE:
<223> OTHER INFORMATION: Synthetic primer

<400> SEQUENCE: 243
gagctgaagg aggtggttgt                                               20

<210> SEQ ID NO 244
<211> LENGTH: 20
<212> TYPE: DNA
<213> ORGANISM: Artificial Sequence
<220> FEATURE:
<223> OTHER INFORMATION: Synthetic primer

<400> SEQUENCE: 244
ccaggtcctg ctcacagtaa                                               20

<210> SEQ ID NO 245
<211> LENGTH: 24
<212> TYPE: DNA
<213> ORGANISM: Artificial Sequence
<220> FEATURE:
<223> OTHER INFORMATION: Synthetic probe

<400> SEQUENCE: 245
ccatcaccag gaagatgctc tcca                                          24

<210> SEQ ID NO 246
<211> LENGTH: 18
<212> TYPE: DNA
<213> ORGANISM: Artificial Sequence
<220> FEATURE:
<223> OTHER INFORMATION: Synthetic primer
```

<400> SEQUENCE: 246
agcaacacca gcctcctg                                                 18

<210> SEQ ID NO 247
<211> LENGTH: 20
<212> TYPE: DNA
<213> ORGANISM: Artificial Sequence
<220> FEATURE:
<223> OTHER INFORMATION: Synthetic primer

<400> SEQUENCE: 247
gggctatggc agaaactcct                                               20

<210> SEQ ID NO 248
<211> LENGTH: 24
<212> TYPE: DNA
<213> ORGANISM: Artificial Sequence
<220> FEATURE:
<223> OTHER INFORMATION: Synthetic probe

<400> SEQUENCE: 248
cacctcctct ccaatgcctg tgaa                                          24

<210> SEQ ID NO 249
<211> LENGTH: 18
<212> TYPE: DNA
<213> ORGANISM: Artificial Sequence
<220> FEATURE:
<223> OTHER INFORMATION: Synthetic primer

<400> SEQUENCE: 249
gggcaggcaa ggtttaca                                                 18

<210> SEQ ID NO 250
<211> LENGTH: 22
<212> TYPE: DNA
<213> ORGANISM: Artificial Sequence
<220> FEATURE:
<223> OTHER INFORMATION: Synthetic primer

<400> SEQUENCE: 250
gtctttggtc agtccagctt tc                                            22

<210> SEQ ID NO 251
<211> LENGTH: 24
<212> TYPE: DNA
<213> ORGANISM: Artificial Sequence
<220> FEATURE:
<223> OTHER INFORMATION: Synthetic probe

<400> SEQUENCE: 251
atcttagctg cctttggctt ccgc                                          24

<210> SEQ ID NO 252
<211> LENGTH: 22
<212> TYPE: DNA
<213> ORGANISM: Artificial Sequence
<220> FEATURE:
<223> OTHER INFORMATION: Synthetic primer

<400> SEQUENCE: 252
acttgcctgt tcagagcact ca                                            22

<210> SEQ ID NO 253
<211> LENGTH: 22

```
<212> TYPE: DNA
<213> ORGANISM: Artificial Sequence
<220> FEATURE:
<223> OTHER INFORMATION: Synthetic primer

<400> SEQUENCE: 253
tggcaaatcc gaattagagt ga                                              22

<210> SEQ ID NO 254
<211> LENGTH: 23
<212> TYPE: DNA
<213> ORGANISM: Artificial Sequence
<220> FEATURE:
<223> OTHER INFORMATION: Synthetic probe

<400> SEQUENCE: 254
tccttcccac ccccagtcct gtc                                             23

<210> SEQ ID NO 255
<211> LENGTH: 20
<212> TYPE: DNA
<213> ORGANISM: Artificial Sequence
<220> FEATURE:
<223> OTHER INFORMATION: Synthetic primer

<400> SEQUENCE: 255
ggcctcaata ggaccacagt                                                 20

<210> SEQ ID NO 256
<211> LENGTH: 20
<212> TYPE: DNA
<213> ORGANISM: Artificial Sequence
<220> FEATURE:
<223> OTHER INFORMATION: Synthetic primer

<400> SEQUENCE: 256
gttgttgctg gtgatgaagg                                                 20

<210> SEQ ID NO 257
<211> LENGTH: 24
<212> TYPE: DNA
<213> ORGANISM: Artificial Sequence
<220> FEATURE:
<223> OTHER INFORMATION: Synthetic probe

<400> SEQUENCE: 257
tcacagtcta tgcagagcca ccca                                            24

<210> SEQ ID NO 258
<211> LENGTH: 20
<212> TYPE: DNA
<213> ORGANISM: Artificial Sequence
<220> FEATURE:
<223> OTHER INFORMATION: Synthetic primer

<400> SEQUENCE: 258
actttgcgag aaatgggaac                                                 20

<210> SEQ ID NO 259
<211> LENGTH: 20
<212> TYPE: DNA
<213> ORGANISM: Artificial Sequence
<220> FEATURE:
<223> OTHER INFORMATION: Synthetic primer

<400> SEQUENCE: 259
```
caggtattgc tcctcctggt                                                         20

<210> SEQ ID NO 260
<211> LENGTH: 22
<212> TYPE: DNA
<213> ORGANISM: Artificial Sequence
<220> FEATURE:
<223> OTHER INFORMATION: Synthetic probe

<400> SEQUENCE: 260
agtgtggcag accctcgcca tt                                                      22

<210> SEQ ID NO 261
<211> LENGTH: 18
<212> TYPE: DNA
<213> ORGANISM: Artificial Sequence
<220> FEATURE:
<223> OTHER INFORMATION: Synthetic primer

<400> SEQUENCE: 261
ccaccatagg cagaggca                                                           18

<210> SEQ ID NO 262
<211> LENGTH: 20
<212> TYPE: DNA
<213> ORGANISM: Artificial Sequence
<220> FEATURE:
<223> OTHER INFORMATION: Synthetic primer

<400> SEQUENCE: 262
agtcgtcgag tgctagggac                                                         20

<210> SEQ ID NO 263
<211> LENGTH: 24
<212> TYPE: DNA
<213> ORGANISM: Artificial Sequence
<220> FEATURE:
<223> OTHER INFORMATION: Synthetic probe

<400> SEQUENCE: 263
acaccctact ccctgtgcct ccag                                                    24

<210> SEQ ID NO 264
<211> LENGTH: 26
<212> TYPE: DNA
<213> ORGANISM: Artificial Sequence
<220> FEATURE:
<223> OTHER INFORMATION: Synthetic primer

<400> SEQUENCE: 264
gataaattgg tacaagggat cagctt                                                  26

<210> SEQ ID NO 265
<211> LENGTH: 24
<212> TYPE: DNA
<213> ORGANISM: Artificial Sequence
<220> FEATURE:
<223> OTHER INFORMATION: Synthetic primer

<400> SEQUENCE: 265
gggtgccaag taactgacta ttca                                                    24

<210> SEQ ID NO 266
<211> LENGTH: 26
<212> TYPE: DNA
<213> ORGANISM: Artificial Sequence
<220> FEATURE:
<223> OTHER INFORMATION: Synthetic probe

<400> SEQUENCE: 266
ccagcccaca tgtcctgatc atatgc                                              26

<210> SEQ ID NO 267
<211> LENGTH: 19
<212> TYPE: DNA
<213> ORGANISM: Artificial Sequence
<220> FEATURE:
<223> OTHER INFORMATION: Synthetic primer

<400> SEQUENCE: 267
gtgggagcct ttgaaatcc                                                      19

<210> SEQ ID NO 268
<211> LENGTH: 20
<212> TYPE: DNA
<213> ORGANISM: Artificial Sequence
<220> FEATURE:
<223> OTHER INFORMATION: Synthetic primer

<400> SEQUENCE: 268
tggcttccag gtcactctgt                                                     20

<210> SEQ ID NO 269
<211> LENGTH: 24
<212> TYPE: DNA
<213> ORGANISM: Artificial Sequence
<220> FEATURE:
<223> OTHER INFORMATION: Synthetic probe

<400> SEQUENCE: 269
tctaggcctg gtccattctg ctcc                                                24

<210> SEQ ID NO 270
<211> LENGTH: 18
<212> TYPE: DNA
<213> ORGANISM: Artificial Sequence
<220> FEATURE:
<223> OTHER INFORMATION: Synthetic primer

<400> SEQUENCE: 270
catgcacccc tgatgttc                                                       18

<210> SEQ ID NO 271
<211> LENGTH: 20
<212> TYPE: DNA
<213> ORGANISM: Artificial Sequence
<220> FEATURE:
<223> OTHER INFORMATION: Synthetic primer

<400> SEQUENCE: 271
ctaccaaggg tgacggaagt                                                     20

<210> SEQ ID NO 272
<211> LENGTH: 24
<212> TYPE: DNA
<213> ORGANISM: Artificial Sequence
<220> FEATURE:
<223> OTHER INFORMATION: Synthetic probe

<400> SEQUENCE: 272
tctacagcaa ggctaagggc tcgc                                                24

```
<210> SEQ ID NO 273
<211> LENGTH: 20
<212> TYPE: DNA
<213> ORGANISM: Artificial Sequence
<220> FEATURE:
<223> OTHER INFORMATION: Synthetic primer

<400> SEQUENCE: 273
ggctggacgt ggttttgtct                                            20

<210> SEQ ID NO 274
<211> LENGTH: 20
<212> TYPE: DNA
<213> ORGANISM: Artificial Sequence
<220> FEATURE:
<223> OTHER INFORMATION: Synthetic primer

<400> SEQUENCE: 274
cgctgcagaa aatgaaacga                                            20

<210> SEQ ID NO 275
<211> LENGTH: 18
<212> TYPE: DNA
<213> ORGANISM: Artificial Sequence
<220> FEATURE:
<223> OTHER INFORMATION: Synthetic probe

<400> SEQUENCE: 275
ctgcgcccgc tcttcgcg                                              18

<210> SEQ ID NO 276
<211> LENGTH: 18
<212> TYPE: DNA
<213> ORGANISM: Artificial Sequence
<220> FEATURE:
<223> OTHER INFORMATION: Synthetic primer

<400> SEQUENCE: 276
acgagtgggg ctggttct                                              18

<210> SEQ ID NO 277
<211> LENGTH: 19
<212> TYPE: DNA
<213> ORGANISM: Artificial Sequence
<220> FEATURE:
<223> OTHER INFORMATION: Synthetic primer

<400> SEQUENCE: 277
gttggcctcc tgaaacaca                                             19

<210> SEQ ID NO 278
<211> LENGTH: 24
<212> TYPE: DNA
<213> ORGANISM: Artificial Sequence
<220> FEATURE:
<223> OTHER INFORMATION: Synthetic probe

<400> SEQUENCE: 278
tccattgact gtggtcccca tgtc                                       24

<210> SEQ ID NO 279
<211> LENGTH: 23
<212> TYPE: DNA
<213> ORGANISM: Artificial Sequence
<220> FEATURE:
<223> OTHER INFORMATION: Synthetic primer
```

<400> SEQUENCE: 279
ccccaggata cctaccacta cct                                          23

<210> SEQ ID NO 280
<211> LENGTH: 18
<212> TYPE: DNA
<213> ORGANISM: Artificial Sequence
<220> FEATURE:
<223> OTHER INFORMATION: Synthetic primer

<400> SEQUENCE: 280
tgcgggactt gggaaaga                                                18

<210> SEQ ID NO 281
<211> LENGTH: 20
<212> TYPE: DNA
<213> ORGANISM: Artificial Sequence
<220> FEATURE:
<223> OTHER INFORMATION: Synthetic probe

<400> SEQUENCE: 281
cccttcagcc tgccccaccg                                              20

<210> SEQ ID NO 282
<211> LENGTH: 22
<212> TYPE: DNA
<213> ORGANISM: Artificial Sequence
<220> FEATURE:
<223> OTHER INFORMATION: Synthetic primer

<400> SEQUENCE: 282
gacatttcca gtcctgcagt ca                                           22

<210> SEQ ID NO 283
<211> LENGTH: 20
<212> TYPE: DNA
<213> ORGANISM: Artificial Sequence
<220> FEATURE:
<223> OTHER INFORMATION: Synthetic primer

<400> SEQUENCE: 283
ctccgatcgc acacatttgt                                              20

<210> SEQ ID NO 284
<211> LENGTH: 23
<212> TYPE: DNA
<213> ORGANISM: Artificial Sequence
<220> FEATURE:
<223> OTHER INFORMATION: Synthetic probe

<400> SEQUENCE: 284
tgcctctctg ccccaccctt tgt                                          23

<210> SEQ ID NO 285
<211> LENGTH: 21
<212> TYPE: DNA
<213> ORGANISM: Artificial Sequence
<220> FEATURE:
<223> OTHER INFORMATION: Synthetic primer

<400> SEQUENCE: 285
tccctccact cggaaggact a                                            21

<210> SEQ ID NO 286

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 286
cggttgttgc tgatctgtct ca                                    22

<210> SEQ ID NO 287
<211> LENGTH: 27
<212> TYPE: DNA
<213> ORGANISM: Artificial Sequence
<220> FEATURE:
<223> OTHER INFORMATION: Synthetic probe

<400> SEQUENCE: 287
tctgacactg tccaacttga ccctctt                               27

<210> SEQ ID NO 288
<211> LENGTH: 20
<212> TYPE: DNA
<213> ORGANISM: Artificial Sequence
<220> FEATURE:
<223> OTHER INFORMATION: Synthetic primer

<400> SEQUENCE: 288
cgaggctttg gttatgtggt                                       20

<210> SEQ ID NO 289
<211> LENGTH: 19
<212> TYPE: DNA
<213> ORGANISM: Artificial Sequence
<220> FEATURE:
<223> OTHER INFORMATION: Synthetic primer

<400> SEQUENCE: 289
cagcactgtc agcatccag                                        19

<210> SEQ ID NO 290
<211> LENGTH: 24
<212> TYPE: DNA
<213> ORGANISM: Artificial Sequence
<220> FEATURE:
<223> OTHER INFORMATION: Synthetic probe

<400> SEQUENCE: 290
ccttccggcc ctacggtaaa atga                                  24

<210> SEQ ID NO 291
<211> LENGTH: 18
<212> TYPE: DNA
<213> ORGANISM: Artificial Sequence
<220> FEATURE:
<223> OTHER INFORMATION: Synthetic primer

<400> SEQUENCE: 291
tacctctccc tgttgccg                                         18

<210> SEQ ID NO 292
<211> LENGTH: 18
<212> TYPE: DNA
<213> ORGANISM: Artificial Sequence
<220> FEATURE:
<223> OTHER INFORMATION: Synthetic primer

<400> SEQUENCE: 292
```
ctactccgca tccttggc                                                  18

<210> SEQ ID NO 293
<211> LENGTH: 24
<212> TYPE: DNA
<213> ORGANISM: Artificial Sequence
<220> FEATURE:
<223> OTHER INFORMATION: Synthetic probe

<400> SEQUENCE: 293
tctcttcatg ccgctgtaag ctcg                                           24

<210> SEQ ID NO 294
<211> LENGTH: 18
<212> TYPE: DNA
<213> ORGANISM: Artificial Sequence
<220> FEATURE:
<223> OTHER INFORMATION: Synthetic primer

<400> SEQUENCE: 294
gtggccatcc agctgacc                                                  18

<210> SEQ ID NO 295
<211> LENGTH: 23
<212> TYPE: DNA
<213> ORGANISM: Artificial Sequence
<220> FEATURE:
<223> OTHER INFORMATION: Synthetic primer

<400> SEQUENCE: 295
cagtggtagg tgatgttctg gga                                            23

<210> SEQ ID NO 296
<211> LENGTH: 21
<212> TYPE: DNA
<213> ORGANISM: Artificial Sequence
<220> FEATURE:
<223> OTHER INFORMATION: Synthetic probe

<400> SEQUENCE: 296
tcctgcgcct gatgtccacc g                                              21

<210> SEQ ID NO 297
<211> LENGTH: 24
<212> TYPE: DNA
<213> ORGANISM: Artificial Sequence
<220> FEATURE:
<223> OTHER INFORMATION: Synthetic primer

<400> SEQUENCE: 297
cagccaagaa ctggtatagg agct                                           24

<210> SEQ ID NO 298
<211> LENGTH: 19
<212> TYPE: DNA
<213> ORGANISM: Artificial Sequence
<220> FEATURE:
<223> OTHER INFORMATION: Synthetic primer

<400> SEQUENCE: 298
aaactggctg ccagcattg                                                 19

<210> SEQ ID NO 299
<211> LENGTH: 30
<212> TYPE: DNA

<213> ORGANISM: Artificial Sequence
<220> FEATURE:
<223> OTHER INFORMATION: Synthetic probe

<400> SEQUENCE: 299
tctcctagcc agacgtgttt cttgtccttg                                    30

<210> SEQ ID NO 300
<211> LENGTH: 19
<212> TYPE: DNA
<213> ORGANISM: Artificial Sequence
<220> FEATURE:
<223> OTHER INFORMATION: Synthetic primer

<400> SEQUENCE: 300
ggaggttctg gacctgctg                                                19

<210> SEQ ID NO 301
<211> LENGTH: 18
<212> TYPE: DNA
<213> ORGANISM: Artificial Sequence
<220> FEATURE:
<223> OTHER INFORMATION: Synthetic primer

<400> SEQUENCE: 301
accaggactg ccacgttc                                                 18

<210> SEQ ID NO 302
<211> LENGTH: 24
<212> TYPE: DNA
<213> ORGANISM: Artificial Sequence
<220> FEATURE:
<223> OTHER INFORMATION: Synthetic probe

<400> SEQUENCE: 302
ctcctggtcc ccaaggtgtc aaag                                          24

<210> SEQ ID NO 303
<211> LENGTH: 18
<212> TYPE: DNA
<213> ORGANISM: Artificial Sequence
<220> FEATURE:
<223> OTHER INFORMATION: Synthetic primer

<400> SEQUENCE: 303
acaaaggcct cccaggat                                                 18

<210> SEQ ID NO 304
<211> LENGTH: 20
<212> TYPE: DNA
<213> ORGANISM: Artificial Sequence
<220> FEATURE:
<223> OTHER INFORMATION: Synthetic primer

<400> SEQUENCE: 304
gagtcccagg aagacctgct                                               20

<210> SEQ ID NO 305
<211> LENGTH: 24
<212> TYPE: DNA
<213> ORGANISM: Artificial Sequence
<220> FEATURE:
<223> OTHER INFORMATION: Synthetic probe

<400> SEQUENCE: 305
ctcctttgac accagggatg ccat                                          24

<210> SEQ ID NO 306
<211> LENGTH: 18
<212> TYPE: DNA
<213> ORGANISM: Artificial Sequence
<220> FEATURE:
<223> OTHER INFORMATION: Synthetic primer

<400> SEQUENCE: 306
ggtcgaggaa cccaaggt                                              18

<210> SEQ ID NO 307
<211> LENGTH: 19
<212> TYPE: DNA
<213> ORGANISM: Artificial Sequence
<220> FEATURE:
<223> OTHER INFORMATION: Synthetic primer

<400> SEQUENCE: 307
gcctggaggt ccaactctg                                             19

<210> SEQ ID NO 308
<211> LENGTH: 24
<212> TYPE: DNA
<213> ORGANISM: Artificial Sequence
<220> FEATURE:
<223> OTHER INFORMATION: Synthetic probe

<400> SEQUENCE: 308
ccaggaaatc ctgtagcacc aggc                                       24

<210> SEQ ID NO 309
<211> LENGTH: 19
<212> TYPE: DNA
<213> ORGANISM: Artificial Sequence
<220> FEATURE:
<223> OTHER INFORMATION: Synthetic primer

<400> SEQUENCE: 309
ggagaccctg gtgaagctg                                             19

<210> SEQ ID NO 310
<211> LENGTH: 18
<212> TYPE: DNA
<213> ORGANISM: Artificial Sequence
<220> FEATURE:
<223> OTHER INFORMATION: Synthetic primer

<400> SEQUENCE: 310
tctccaggga caccaacg                                              18

<210> SEQ ID NO 311
<211> LENGTH: 24
<212> TYPE: DNA
<213> ORGANISM: Artificial Sequence
<220> FEATURE:
<223> OTHER INFORMATION: Synthetic probe

<400> SEQUENCE: 311
cttctcttcc ctgatcaccc tgcg                                       24

<210> SEQ ID NO 312
<211> LENGTH: 21
<212> TYPE: DNA
<213> ORGANISM: Artificial Sequence
<220> FEATURE:

```
<223> OTHER INFORMATION: Synthetic primer

<400> SEQUENCE: 312
gagagcaagc gagacattct g                                           21

<210> SEQ ID NO 313
<211> LENGTH: 18
<212> TYPE: DNA
<213> ORGANISM: Artificial Sequence
<220> FEATURE:
<223> OTHER INFORMATION: Synthetic primer

<400> SEQUENCE: 313
aacagggaac tggcccac                                               18

<210> SEQ ID NO 314
<211> LENGTH: 24
<212> TYPE: DNA
<213> ORGANISM: Artificial Sequence
<220> FEATURE:
<223> OTHER INFORMATION: Synthetic probe

<400> SEQUENCE: 314
cctctttgac ggctcagcca atct                                        24

<210> SEQ ID NO 315
<211> LENGTH: 22
<212> TYPE: DNA
<213> ORGANISM: Artificial Sequence
<220> FEATURE:
<223> OTHER INFORMATION: Synthetic primer

<400> SEQUENCE: 315
gaatcattca ccaggcaaat tg                                          22

<210> SEQ ID NO 316
<211> LENGTH: 20
<212> TYPE: DNA
<213> ORGANISM: Artificial Sequence
<220> FEATURE:
<223> OTHER INFORMATION: Synthetic primer

<400> SEQUENCE: 316
ctgtactgcg ggtggaacat                                             20

<210> SEQ ID NO 317
<211> LENGTH: 22
<212> TYPE: DNA
<213> ORGANISM: Artificial Sequence
<220> FEATURE:
<223> OTHER INFORMATION: Synthetic probe

<400> SEQUENCE: 317
cctaccacca gcaaccctgc ca                                          22

<210> SEQ ID NO 318
<211> LENGTH: 20
<212> TYPE: DNA
<213> ORGANISM: Artificial Sequence
<220> FEATURE:
<223> OTHER INFORMATION: Synthetic primer

<400> SEQUENCE: 318
cttcaaggtt ggggaggagt                                             20
```

```
<210> SEQ ID NO 319
<211> LENGTH: 20
<212> TYPE: DNA
<213> ORGANISM: Artificial Sequence
<220> FEATURE:
<223> OTHER INFORMATION: Synthetic primer

<400> SEQUENCE: 319
ttcaccaggc tcttacaggg                                              20

<210> SEQ ID NO 320
<211> LENGTH: 24
<212> TYPE: DNA
<213> ORGANISM: Artificial Sequence
<220> FEATURE:
<223> OTHER INFORMATION: Synthetic probe

<400> SEQUENCE: 320
ctcccatcca cagtctgctc ctca                                         24

<210> SEQ ID NO 321
<211> LENGTH: 20
<212> TYPE: DNA
<213> ORGANISM: Artificial Sequence
<220> FEATURE:
<223> OTHER INFORMATION: Synthetic primer

<400> SEQUENCE: 321
agggtctggt ttgtcgtgag                                              20

<210> SEQ ID NO 322
<211> LENGTH: 18
<212> TYPE: DNA
<213> ORGANISM: Artificial Sequence
<220> FEATURE:
<223> OTHER INFORMATION: Synthetic primer

<400> SEQUENCE: 322
aaagcctttg gcggaaac                                                18

<210> SEQ ID NO 323
<211> LENGTH: 24
<212> TYPE: DNA
<213> ORGANISM: Artificial Sequence
<220> FEATURE:
<223> OTHER INFORMATION: Synthetic probe

<400> SEQUENCE: 323
ctccgcgatg tcctctcaac agag                                         24

<210> SEQ ID NO 324
<211> LENGTH: 18
<212> TYPE: DNA
<213> ORGANISM: Artificial Sequence
<220> FEATURE:
<223> OTHER INFORMATION: Synthetic primer

<400> SEQUENCE: 324
gggtctgtgc cccatgac                                                18

<210> SEQ ID NO 325
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 325
tgaccgtgcc agcatttaca                                              20

<210> SEQ ID NO 326
<211> LENGTH: 25
<212> TYPE: DNA
<213> ORGANISM: Artificial Sequence
<220> FEATURE:
<223> OTHER INFORMATION: Synthetic probe

<400> SEQUENCE: 326
cctggctgcc caagaagtgt tccct                                        25

<210> SEQ ID NO 327
<211> LENGTH: 18
<212> TYPE: DNA
<213> ORGANISM: Artificial Sequence
<220> FEATURE:
<223> OTHER INFORMATION: Synthetic primer

<400> SEQUENCE: 327
caccagcacc cagacaca                                                18

<210> SEQ ID NO 328
<211> LENGTH: 18
<212> TYPE: DNA
<213> ORGANISM: Artificial Sequence
<220> FEATURE:
<223> OTHER INFORMATION: Synthetic primer

<400> SEQUENCE: 328
tctggctcct gccttgac                                                18

<210> SEQ ID NO 329
<211> LENGTH: 24
<212> TYPE: DNA
<213> ORGANISM: Artificial Sequence
<220> FEATURE:
<223> OTHER INFORMATION: Synthetic probe

<400> SEQUENCE: 329
tcagtccctc tgttctggcc attg                                         24

<210> SEQ ID NO 330
<211> LENGTH: 20
<212> TYPE: DNA
<213> ORGANISM: Artificial Sequence
<220> FEATURE:
<223> OTHER INFORMATION: Synthetic primer

<400> SEQUENCE: 330
gatgtgattg aggtgcatgg                                              20

<210> SEQ ID NO 331
<211> LENGTH: 21
<212> TYPE: DNA
<213> ORGANISM: Artificial Sequence
<220> FEATURE:
<223> OTHER INFORMATION: Synthetic primer

<400> SEQUENCE: 331
gaactccctg gagatgaaac c                                            21

<210> SEQ ID NO 332
<211> LENGTH: 24
```

```
<212> TYPE: DNA
<213> ORGANISM: Artificial Sequence
<220> FEATURE:
<223> OTHER INFORMATION: Synthetic probe

<400> SEQUENCE: 332
tgttcatcct ggcgctcttc atgt                                           24

<210> SEQ ID NO 333
<211> LENGTH: 20
<212> TYPE: DNA
<213> ORGANISM: Artificial Sequence
<220> FEATURE:
<223> OTHER INFORMATION: Synthetic primer

<400> SEQUENCE: 333
ttacgcagct catgctcttg                                                20

<210> SEQ ID NO 334
<211> LENGTH: 22
<212> TYPE: DNA
<213> ORGANISM: Artificial Sequence
<220> FEATURE:
<223> OTHER INFORMATION: Synthetic primer

<400> SEQUENCE: 334
gcagctgtaa agagagtggc at                                             22

<210> SEQ ID NO 335
<211> LENGTH: 24
<212> TYPE: DNA
<213> ORGANISM: Artificial Sequence
<220> FEATURE:
<223> OTHER INFORMATION: Synthetic probe

<400> SEQUENCE: 335
acggctcttt actatgcgag ggcc                                           24

<210> SEQ ID NO 336
<211> LENGTH: 18
<212> TYPE: DNA
<213> ORGANISM: Artificial Sequence
<220> FEATURE:
<223> OTHER INFORMATION: Synthetic primer

<400> SEQUENCE: 336
tgcagcggct gattgaca                                                  18

<210> SEQ ID NO 337
<211> LENGTH: 25
<212> TYPE: DNA
<213> ORGANISM: Artificial Sequence
<220> FEATURE:
<223> OTHER INFORMATION: Synthetic primer

<400> SEQUENCE: 337
caactgttcc tggtctacaa actca                                          25

<210> SEQ ID NO 338
<211> LENGTH: 28
<212> TYPE: DNA
<213> ORGANISM: Artificial Sequence
<220> FEATURE:
<223> OTHER INFORMATION: Synthetic probe

<400> SEQUENCE: 338
```

```
tcagatggag acctcgtgcc aaattaca                                              28

<210> SEQ ID NO 339
<211> LENGTH: 19
<212> TYPE: DNA
<213> ORGANISM: Artificial Sequence
<220> FEATURE:
<223> OTHER INFORMATION: Synthetic primer

<400> SEQUENCE: 339
gagttcaagt gccctgacg                                                        19

<210> SEQ ID NO 340
<211> LENGTH: 20
<212> TYPE: DNA
<213> ORGANISM: Artificial Sequence
<220> FEATURE:
<223> OTHER INFORMATION: Synthetic primer

<400> SEQUENCE: 340
agttgtaatg gcaggcacag                                                       20

<210> SEQ ID NO 341
<211> LENGTH: 28
<212> TYPE: DNA
<213> ORGANISM: Artificial Sequence
<220> FEATURE:
<223> OTHER INFORMATION: Synthetic probe

<400> SEQUENCE: 341
aacatcatgt tcttcttcat gacctcgc                                              28

<210> SEQ ID NO 342
<211> LENGTH: 20
<212> TYPE: DNA
<213> ORGANISM: Artificial Sequence
<220> FEATURE:
<223> OTHER INFORMATION: Synthetic primer

<400> SEQUENCE: 342
tggctcactt cggctaaaat                                                       20

<210> SEQ ID NO 343
<211> LENGTH: 21
<212> TYPE: DNA
<213> ORGANISM: Artificial Sequence
<220> FEATURE:
<223> OTHER INFORMATION: Synthetic primer

<400> SEQUENCE: 343
tcagctccat tgaatgtgaa a                                                     21

<210> SEQ ID NO 344
<211> LENGTH: 24
<212> TYPE: DNA
<213> ORGANISM: Artificial Sequence
<220> FEATURE:
<223> OTHER INFORMATION: Synthetic probe

<400> SEQUENCE: 344
caacgctgac agcatgcatt tctg                                                  24

<210> SEQ ID NO 345
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 345
ggccgagatc tacaaaaacg                                                   20

<210> SEQ ID NO 346
<211> LENGTH: 20
<212> TYPE: DNA
<213> ORGANISM: Artificial Sequence
<220> FEATURE:
<223> OTHER INFORMATION: Synthetic primer

<400> SEQUENCE: 346
gcaggaagtc cgaatacaca                                                   20

<210> SEQ ID NO 347
<211> LENGTH: 21
<212> TYPE: DNA
<213> ORGANISM: Artificial Sequence
<220> FEATURE:
<223> OTHER INFORMATION: Synthetic probe

<400> SEQUENCE: 347
ccccgtggag ggagctttct c                                                 21

<210> SEQ ID NO 348
<211> LENGTH: 20
<212> TYPE: DNA
<213> ORGANISM: Artificial Sequence
<220> FEATURE:
<223> OTHER INFORMATION: Synthetic primer

<400> SEQUENCE: 348
tgacaacatg atggctcaga                                                   20

<210> SEQ ID NO 349
<211> LENGTH: 20
<212> TYPE: DNA
<213> ORGANISM: Artificial Sequence
<220> FEATURE:
<223> OTHER INFORMATION: Synthetic primer

<400> SEQUENCE: 349
gcaccacctt ctgggttact                                                   20

<210> SEQ ID NO 350
<211> LENGTH: 24
<212> TYPE: DNA
<213> ORGANISM: Artificial Sequence
<220> FEATURE:
<223> OTHER INFORMATION: Synthetic probe

<400> SEQUENCE: 350
aaaacatcgg caagtccacc aggt                                              24

<210> SEQ ID NO 351
<211> LENGTH: 22
<212> TYPE: DNA
<213> ORGANISM: Artificial Sequence
<220> FEATURE:
<223> OTHER INFORMATION: Synthetic primer

<400> SEQUENCE: 351
tgacaacggc tttccagtac at                                                22
```

-continued

<210> SEQ ID NO 352
<211> LENGTH: 22
<212> TYPE: DNA
<213> ORGANISM: Artificial Sequence
<220> FEATURE:
<223> OTHER INFORMATION: Synthetic primer

<400> SEQUENCE: 352
tccatggctt tgtagggata gg                                            22

<210> SEQ ID NO 353
<211> LENGTH: 28
<212> TYPE: DNA
<213> ORGANISM: Artificial Sequence
<220> FEATURE:
<223> OTHER INFORMATION: Synthetic probe

<400> SEQUENCE: 353
tgataacaag ggcatcgact cagacgct                                      28

<210> SEQ ID NO 354
<211> LENGTH: 19
<212> TYPE: DNA
<213> ORGANISM: Artificial Sequence
<220> FEATURE:
<223> OTHER INFORMATION: Synthetic primer

<400> SEQUENCE: 354
ggagcaaaat cgatgcagt                                                19

<210> SEQ ID NO 355
<211> LENGTH: 20
<212> TYPE: DNA
<213> ORGANISM: Artificial Sequence
<220> FEATURE:
<223> OTHER INFORMATION: Synthetic primer

<400> SEQUENCE: 355
tagggaagtg atgggagagg                                               20

<210> SEQ ID NO 356
<211> LENGTH: 24
<212> TYPE: DNA
<213> ORGANISM: Artificial Sequence
<220> FEATURE:
<223> OTHER INFORMATION: Synthetic probe

<400> SEQUENCE: 356
tctgtgtggt ccatccttgg aagc                                          24

<210> SEQ ID NO 357
<211> LENGTH: 21
<212> TYPE: DNA
<213> ORGANISM: Artificial Sequence
<220> FEATURE:
<223> OTHER INFORMATION: Synthetic primer

<400> SEQUENCE: 357
cttccccatg ttcaaaagag g                                             21

<210> SEQ ID NO 358
<211> LENGTH: 22
<212> TYPE: DNA
<213> ORGANISM: Artificial Sequence
<220> FEATURE:
<223> OTHER INFORMATION: Synthetic primer

<400> SEQUENCE: 358
gaggctttct caatatctgc ca                                22

<210> SEQ ID NO 359
<211> LENGTH: 24
<212> TYPE: DNA
<213> ORGANISM: Artificial Sequence
<220> FEATURE:
<223> OTHER INFORMATION: Synthetic probe

<400> SEQUENCE: 359
tcactgcttt taccccaggg ccta                              24

<210> SEQ ID NO 360
<211> LENGTH: 19
<212> TYPE: DNA
<213> ORGANISM: Artificial Sequence
<220> FEATURE:
<223> OTHER INFORMATION: Synthetic primer

<400> SEQUENCE: 360
gagctacaga tgcccatgc                                    19

<210> SEQ ID NO 361
<211> LENGTH: 20
<212> TYPE: DNA
<213> ORGANISM: Artificial Sequence
<220> FEATURE:
<223> OTHER INFORMATION: Synthetic primer

<400> SEQUENCE: 361
tttgagatgc ttgacgttgg                                   20

<210> SEQ ID NO 362
<211> LENGTH: 24
<212> TYPE: DNA
<213> ORGANISM: Artificial Sequence
<220> FEATURE:
<223> OTHER INFORMATION: Synthetic probe

<400> SEQUENCE: 362
ttcttcgaaa gccatgttgc caga                              24

<210> SEQ ID NO 363
<211> LENGTH: 18
<212> TYPE: DNA
<213> ORGANISM: Artificial Sequence
<220> FEATURE:
<223> OTHER INFORMATION: Synthetic primer

<400> SEQUENCE: 363
tgcgcccttt cctctgta                                     18

<210> SEQ ID NO 364
<211> LENGTH: 19
<212> TYPE: DNA
<213> ORGANISM: Artificial Sequence
<220> FEATURE:
<223> OTHER INFORMATION: Synthetic primer

<400> SEQUENCE: 364
caatgcggca tatactggg                                    19

<210> SEQ ID NO 365

```
<211> LENGTH: 24
<212> TYPE: DNA
<213> ORGANISM: Artificial Sequence
<220> FEATURE:
<223> OTHER INFORMATION: Synthetic probe

<400> SEQUENCE: 365 taccctttaag aacgccccct ccac                                      24

<210> SEQ ID NO 366
<211> LENGTH: 22
<212> TYPE: DNA
<213> ORGANISM: Artificial Sequence
<220> FEATURE:
<223> OTHER INFORMATION: Synthetic primer

<400> SEQUENCE: 366
aagaatgggc agaaagcttg tc                                         22

<210> SEQ ID NO 367
<211> LENGTH: 25
<212> TYPE: DNA
<213> ORGANISM: Artificial Sequence
<220> FEATURE:
<223> OTHER INFORMATION: Synthetic primer

<400> SEQUENCE: 367
catttttcag catcttttcg atgat                                      25

<210> SEQ ID NO 368
<211> LENGTH: 19
<212> TYPE: DNA
<213> ORGANISM: Artificial Sequence
<220> FEATURE:
<223> OTHER INFORMATION: Synthetic probe

<400> SEQUENCE: 368
caaccccgca tcgcccatg                                             19

<210> SEQ ID NO 369
<211> LENGTH: 20
<212> TYPE: DNA
<213> ORGANISM: Artificial Sequence
<220> FEATURE:
<223> OTHER INFORMATION: Synthetic primer

<400> SEQUENCE: 369
aagaaggcca gcatttatgg                                            20

<210> SEQ ID NO 370
<211> LENGTH: 19
<212> TYPE: DNA
<213> ORGANISM: Artificial Sequence
<220> FEATURE:
<223> OTHER INFORMATION: Synthetic primer

<400> SEQUENCE: 370
gtgagtgggg agggaactt                                             19

<210> SEQ ID NO 371
<211> LENGTH: 26
<212> TYPE: DNA
<213> ORGANISM: Artificial Sequence
<220> FEATURE:
<223> OTHER INFORMATION: Synthetic probe

<400> SEQUENCE: 371
```
ccccagcgtg gccaccttat atataa                                              26

<210> SEQ ID NO 372
<211> LENGTH: 21
<212> TYPE: DNA
<213> ORGANISM: Artificial Sequence
<220> FEATURE:
<223> OTHER INFORMATION: Synthetic primer

<400> SEQUENCE: 372
accagaccat tgtctcagag c                                                   21

<210> SEQ ID NO 373
<211> LENGTH: 21
<212> TYPE: DNA
<213> ORGANISM: Artificial Sequence
<220> FEATURE:
<223> OTHER INFORMATION: Synthetic primer

<400> SEQUENCE: 373
gttaccagag gctagccaac a                                                   21

<210> SEQ ID NO 374
<211> LENGTH: 24
<212> TYPE: DNA
<213> ORGANISM: Artificial Sequence
<220> FEATURE:
<223> OTHER INFORMATION: Synthetic probe

<400> SEQUENCE: 374
tgctggctct ttcctggcta ctcc                                                24

<210> SEQ ID NO 375
<211> LENGTH: 19
<212> TYPE: DNA
<213> ORGANISM: Artificial Sequence
<220> FEATURE:
<223> OTHER INFORMATION: Synthetic primer

<400> SEQUENCE: 375
gtctttggct ctggcctct                                                      19

<210> SEQ ID NO 376
<211> LENGTH: 20
<212> TYPE: DNA
<213> ORGANISM: Artificial Sequence
<220> FEATURE:
<223> OTHER INFORMATION: Synthetic primer

<400> SEQUENCE: 376
ggctcctgcg tagaagttga                                                     20

<210> SEQ ID NO 377
<211> LENGTH: 24
<212> TYPE: DNA
<213> ORGANISM: Artificial Sequence
<220> FEATURE:
<223> OTHER INFORMATION: Synthetic probe

<400> SEQUENCE: 377
aaagtggcag gtgccctctt caac                                                24

<210> SEQ ID NO 378
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 378
tgaccgcttc taccccaatg                                                20

<210> SEQ ID NO 379
<211> LENGTH: 22
<212> TYPE: DNA
<213> ORGANISM: Artificial Sequence
<220> FEATURE:
<223> OTHER INFORMATION: Synthetic primer

<400> SEQUENCE: 379
aggataaggc caaccatgat gt                                             22

<210> SEQ ID NO 380
<211> LENGTH: 28
<212> TYPE: DNA
<213> ORGANISM: Artificial Sequence
<220> FEATURE:
<223> OTHER INFORMATION: Synthetic probe

<400> SEQUENCE: 380
ctgaaactgg aacacaacca cccacaag                                       28

<210> SEQ ID NO 381
<211> LENGTH: 22
<212> TYPE: DNA
<213> ORGANISM: Artificial Sequence
<220> FEATURE:
<223> OTHER INFORMATION: Synthetic primer

<400> SEQUENCE: 381
ccagctttgt gcctgtcact at                                             22

<210> SEQ ID NO 382
<211> LENGTH: 20
<212> TYPE: DNA
<213> ORGANISM: Artificial Sequence
<220> FEATURE:
<223> OTHER INFORMATION: Synthetic primer

<400> SEQUENCE: 382
gggaatgtgg tagcccaaga                                                20

<210> SEQ ID NO 383
<211> LENGTH: 25
<212> TYPE: DNA
<213> ORGANISM: Artificial Sequence
<220> FEATURE:
<223> OTHER INFORMATION: Synthetic probe

<400> SEQUENCE: 383
ctcatgccac cactgccaac acctc                                          25

<210> SEQ ID NO 384
<211> LENGTH: 20
<212> TYPE: DNA
<213> ORGANISM: Artificial Sequence
<220> FEATURE:
<223> OTHER INFORMATION: Synthetic primer

<400> SEQUENCE: 384
tgctcattct tgaggagcat                                                20
```

```
<210> SEQ ID NO 385
<211> LENGTH: 20
<212> TYPE: DNA
<213> ORGANISM: Artificial Sequence
<220> FEATURE:
<223> OTHER INFORMATION: Synthetic primer

<400> SEQUENCE: 385
gtggctgcat tagtgtccat                                              20

<210> SEQ ID NO 386
<211> LENGTH: 24
<212> TYPE: DNA
<213> ORGANISM: Artificial Sequence
<220> FEATURE:
<223> OTHER INFORMATION: Synthetic probe

<400> SEQUENCE: 386
cagcaccctt ggcagtttcg aaat                                         24

<210> SEQ ID NO 387
<211> LENGTH: 20
<212> TYPE: DNA
<213> ORGANISM: Artificial Sequence
<220> FEATURE:
<223> OTHER INFORMATION: Synthetic primer

<400> SEQUENCE: 387
tccaattcca gcatcactgt                                              20

<210> SEQ ID NO 388
<211> LENGTH: 20
<212> TYPE: DNA
<213> ORGANISM: Artificial Sequence
<220> FEATURE:
<223> OTHER INFORMATION: Synthetic primer

<400> SEQUENCE: 388
ggcagtgaag gcgataaagt                                              20

<210> SEQ ID NO 389
<211> LENGTH: 25
<212> TYPE: DNA
<213> ORGANISM: Artificial Sequence
<220> FEATURE:
<223> OTHER INFORMATION: Synthetic probe

<400> SEQUENCE: 389
agaaaagctg tttgtctccc cagca                                        25

<210> SEQ ID NO 390
<211> LENGTH: 20
<212> TYPE: DNA
<213> ORGANISM: Artificial Sequence
<220> FEATURE:
<223> OTHER INFORMATION: Synthetic primer

<400> SEQUENCE: 390
gattcagacg aggatgagcc                                              20

<210> SEQ ID NO 391
<211> LENGTH: 20
<212> TYPE: DNA
<213> ORGANISM: Artificial Sequence
<220> FEATURE:
```

<223> OTHER INFORMATION: Synthetic primer

<400> SEQUENCE: 391
cacctcttgc tgtccctttg                                           20

<210> SEQ ID NO 392
<211> LENGTH: 24
<212> TYPE: DNA
<213> ORGANISM: Artificial Sequence
<220> FEATURE:
<223> OTHER INFORMATION: Synthetic probe

<400> SEQUENCE: 392
aaagtccatt tgccactgat ggca                                      24

<210> SEQ ID NO 393
<211> LENGTH: 20
<212> TYPE: DNA
<213> ORGANISM: Artificial Sequence
<220> FEATURE:
<223> OTHER INFORMATION: Synthetic primer

<400> SEQUENCE: 393
agacatcagc tcctggttca                                           20

<210> SEQ ID NO 394
<211> LENGTH: 20
<212> TYPE: DNA
<213> ORGANISM: Artificial Sequence
<220> FEATURE:
<223> OTHER INFORMATION: Synthetic primer

<400> SEQUENCE: 394
gacaaacacc cttcctccag                                           20

<210> SEQ ID NO 395
<211> LENGTH: 26
<212> TYPE: DNA
<213> ORGANISM: Artificial Sequence
<220> FEATURE:
<223> OTHER INFORMATION: Synthetic probe

<400> SEQUENCE: 395
cgaggccatt gacttcatag actcca                                    26

<210> SEQ ID NO 396
<211> LENGTH: 20
<212> TYPE: DNA
<213> ORGANISM: Artificial Sequence
<220> FEATURE:
<223> OTHER INFORMATION: Synthetic primer

<400> SEQUENCE: 396
tatccctgtg gaggacaacc                                           20

<210> SEQ ID NO 397
<211> LENGTH: 20
<212> TYPE: DNA
<213> ORGANISM: Artificial Sequence
<220> FEATURE:
<223> OTHER INFORMATION: Synthetic primer

<400> SEQUENCE: 397
cacccagtca atgaagccta                                           20

```
<210> SEQ ID NO 398
<211> LENGTH: 24
<212> TYPE: DNA
<213> ORGANISM: Artificial Sequence
<220> FEATURE:
<223> OTHER INFORMATION: Synthetic probe

<400> SEQUENCE: 398
cctcctggaa ccaggcactg atct                                           24

<210> SEQ ID NO 399
<211> LENGTH: 18
<212> TYPE: DNA
<213> ORGANISM: Artificial Sequence
<220> FEATURE:
<223> OTHER INFORMATION: Synthetic primer

<400> SEQUENCE: 399
tggtgacgat ggaggagc                                                  18

<210> SEQ ID NO 400
<211> LENGTH: 18
<212> TYPE: DNA
<213> ORGANISM: Artificial Sequence
<220> FEATURE:
<223> OTHER INFORMATION: Synthetic primer

<400> SEQUENCE: 400
ctcgtcccgg ttcatcag                                                  18

<210> SEQ ID NO 401
<211> LENGTH: 24
<212> TYPE: DNA
<213> ORGANISM: Artificial Sequence
<220> FEATURE:
<223> OTHER INFORMATION: Synthetic probe

<400> SEQUENCE: 401
ttgagcacac tgcagtccat ctcc                                           24

<210> SEQ ID NO 402
<211> LENGTH: 18
<212> TYPE: DNA
<213> ORGANISM: Artificial Sequence
<220> FEATURE:
<223> OTHER INFORMATION: Synthetic primer

<400> SEQUENCE: 402
catgcaggga ctgggatt                                                  18

<210> SEQ ID NO 403
<211> LENGTH: 21
<212> TYPE: DNA
<213> ORGANISM: Artificial Sequence
<220> FEATURE:
<223> OTHER INFORMATION: Synthetic primer

<400> SEQUENCE: 403
tgctcctacc ctatcatttg g                                              21

<210> SEQ ID NO 404
<211> LENGTH: 24
<212> TYPE: DNA
<213> ORGANISM: Artificial Sequence
<220> FEATURE:
<223> OTHER INFORMATION: Synthetic probe
```

```
<400> SEQUENCE: 404
tctaccctat gcgcctggaa gtcc                                          24

<210> SEQ ID NO 405
<211> LENGTH: 20
<212> TYPE: DNA
<213> ORGANISM: Artificial Sequence
<220> FEATURE:
<223> OTHER INFORMATION: Synthetic primer

<400> SEQUENCE: 405
actccctcta cccttgagca                                               20

<210> SEQ ID NO 406
<211> LENGTH: 20
<212> TYPE: DNA
<213> ORGANISM: Artificial Sequence
<220> FEATURE:
<223> OTHER INFORMATION: Synthetic primer

<400> SEQUENCE: 406
caggcctcag ttccttcagt                                               20

<210> SEQ ID NO 407
<211> LENGTH: 24
<212> TYPE: DNA
<213> ORGANISM: Artificial Sequence
<220> FEATURE:
<223> OTHER INFORMATION: Synthetic probe

<400> SEQUENCE: 407
cagaagaaca gctcagggac ccct                                          24

<210> SEQ ID NO 408
<211> LENGTH: 19
<212> TYPE: DNA
<213> ORGANISM: Artificial Sequence
<220> FEATURE:
<223> OTHER INFORMATION: Synthetic primer

<400> SEQUENCE: 408
accacctcct ttccagacg                                                19

<210> SEQ ID NO 409
<211> LENGTH: 18
<212> TYPE: DNA
<213> ORGANISM: Artificial Sequence
<220> FEATURE:
<223> OTHER INFORMATION: Synthetic primer

<400> SEQUENCE: 409
aggttgggag ctgcctgt                                                 18

<210> SEQ ID NO 410
<211> LENGTH: 24
<212> TYPE: DNA
<213> ORGANISM: Artificial Sequence
<220> FEATURE:
<223> OTHER INFORMATION: Synthetic probe

<400> SEQUENCE: 410
ataccgcaca tgcagcaacc agtc                                          24

<210> SEQ ID NO 411
<211> LENGTH: 23
```

```
<212> TYPE: DNA
<213> ORGANISM: Artificial Sequence
<220> FEATURE:
<223> OTHER INFORMATION: Synthetic primer

<400> SEQUENCE: 411
tgacattatc atcccgctaa gga                                           23

<210> SEQ ID NO 412
<211> LENGTH: 21
<212> TYPE: DNA
<213> ORGANISM: Artificial Sequence
<220> FEATURE:
<223> OTHER INFORMATION: Synthetic primer

<400> SEQUENCE: 412
gtagtccccg ctgaccttct c                                             21

<210> SEQ ID NO 413
<211> LENGTH: 24
<212> TYPE: DNA
<213> ORGANISM: Artificial Sequence
<220> FEATURE:
<223> OTHER INFORMATION: Synthetic probe

<400> SEQUENCE: 413
cggacagcgt cttctgccct cact                                          24

<210> SEQ ID NO 414
<211> LENGTH: 20
<212> TYPE: DNA
<213> ORGANISM: Artificial Sequence
<220> FEATURE:
<223> OTHER INFORMATION: Synthetic primer

<400> SEQUENCE: 414
tgtcgatgga cttccagaac                                               20

<210> SEQ ID NO 415
<211> LENGTH: 19
<212> TYPE: DNA
<213> ORGANISM: Artificial Sequence
<220> FEATURE:
<223> OTHER INFORMATION: Synthetic primer

<400> SEQUENCE: 415
attgggacag cttggatca                                                19

<210> SEQ ID NO 416
<211> LENGTH: 18
<212> TYPE: DNA
<213> ORGANISM: Artificial Sequence
<220> FEATURE:
<223> OTHER INFORMATION: Synthetic probe

<400> SEQUENCE: 416
cacctgggca gctgccaa                                                 18

<210> SEQ ID NO 417
<211> LENGTH: 19
<212> TYPE: DNA
<213> ORGANISM: Artificial Sequence
<220> FEATURE:
<223> OTHER INFORMATION: Synthetic primer

<400> SEQUENCE: 417
```
gtccccgctg cagatctct                                                   19

<210> SEQ ID NO 418
<211> LENGTH: 24
<212> TYPE: DNA
<213> ORGANISM: Artificial Sequence
<220> FEATURE:
<223> OTHER INFORMATION: Synthetic primer

<400> SEQUENCE: 418
ctccagctta gggtagttgt ccat                                             24

<210> SEQ ID NO 419
<211> LENGTH: 23
<212> TYPE: DNA
<213> ORGANISM: Artificial Sequence
<220> FEATURE:
<223> OTHER INFORMATION: Synthetic probe

<400> SEQUENCE: 419
cggatccttt cctcactcgc cca                                              23

<210> SEQ ID NO 420
<211> LENGTH: 20
<212> TYPE: DNA
<213> ORGANISM: Artificial Sequence
<220> FEATURE:
<223> OTHER INFORMATION: Synthetic primer

<400> SEQUENCE: 420
ccatgtggat gaatgaggtg                                                  20

<210> SEQ ID NO 421
<211> LENGTH: 20
<212> TYPE: DNA
<213> ORGANISM: Artificial Sequence
<220> FEATURE:
<223> OTHER INFORMATION: Synthetic primer

<400> SEQUENCE: 421
tgcctgagaa gaggtgaggt                                                  20

<210> SEQ ID NO 422
<211> LENGTH: 24
<212> TYPE: DNA
<213> ORGANISM: Artificial Sequence
<220> FEATURE:
<223> OTHER INFORMATION: Synthetic probe

<400> SEQUENCE: 422
acccagtctc accttctccc cacc                                             24

<210> SEQ ID NO 423
<211> LENGTH: 18
<212> TYPE: DNA
<213> ORGANISM: Artificial Sequence
<220> FEATURE:
<223> OTHER INFORMATION: Synthetic primer

<400> SEQUENCE: 423
gcactgtggg cagatgaa                                                    18

<210> SEQ ID NO 424
<211> LENGTH: 18
<212> TYPE: DNA
<213> ORGANISM: Artificial Sequence

```
<220> FEATURE:
<223> OTHER INFORMATION: Synthetic primer

<400> SEQUENCE: 424
atgtttggtg actggcgg                                                       18

<210> SEQ ID NO 425
<211> LENGTH: 24
<212> TYPE: DNA
<213> ORGANISM: Artificial Sequence
<220> FEATURE:
<223> OTHER INFORMATION: Synthetic probe

<400> SEQUENCE: 425
cgggtcacat tgcagacacg gtac                                                24

<210> SEQ ID NO 426
<211> LENGTH: 25
<212> TYPE: DNA
<213> ORGANISM: Artificial Sequence
<220> FEATURE:
<223> OTHER INFORMATION: Synthetic primer

<400> SEQUENCE: 426
gctagtactt tgatgctccc ttgat                                               25

<210> SEQ ID NO 427
<211> LENGTH: 20
<212> TYPE: DNA
<213> ORGANISM: Artificial Sequence
<220> FEATURE:
<223> OTHER INFORMATION: Synthetic primer

<400> SEQUENCE: 427
gaacagctgg aggccaagtc                                                     20

<210> SEQ ID NO 428
<211> LENGTH: 22
<212> TYPE: DNA
<213> ORGANISM: Artificial Sequence
<220> FEATURE:
<223> OTHER INFORMATION: Synthetic probe

<400> SEQUENCE: 428
ccagagagcc tccctgcagc ca                                                  22

<210> SEQ ID NO 429
<211> LENGTH: 20
<212> TYPE: DNA
<213> ORGANISM: Artificial Sequence
<220> FEATURE:
<223> OTHER INFORMATION: Synthetic primer

<400> SEQUENCE: 429
caaggccgtg aacgagaagt                                                     20

<210> SEQ ID NO 430
<211> LENGTH: 18
<212> TYPE: DNA
<213> ORGANISM: Artificial Sequence
<220> FEATURE:
<223> OTHER INFORMATION: Synthetic primer

<400> SEQUENCE: 430
cggtcacgga gccaatct                                                       18
```

<210> SEQ ID NO 431
<211> LENGTH: 26
<212> TYPE: DNA
<213> ORGANISM: Artificial Sequence
<220> FEATURE:
<223> OTHER INFORMATION: Synthetic probe

<400> SEQUENCE: 431
ctgcaactgc ctcctgctca aagtca                                          26

<210> SEQ ID NO 432
<211> LENGTH: 21
<212> TYPE: DNA
<213> ORGANISM: Artificial Sequence
<220> FEATURE:
<223> OTHER INFORMATION: Synthetic primer

<400> SEQUENCE: 432
aagccttgga gggtttcatt g                                               21

<210> SEQ ID NO 433
<211> LENGTH: 25
<212> TYPE: DNA
<213> ORGANISM: Artificial Sequence
<220> FEATURE:
<223> OTHER INFORMATION: Synthetic primer

<400> SEQUENCE: 433
tgctgatgtt ttctgacaga aagat                                           25

<210> SEQ ID NO 434
<211> LENGTH: 23
<212> TYPE: DNA
<213> ORGANISM: Artificial Sequence
<220> FEATURE:
<223> OTHER INFORMATION: Synthetic probe

<400> SEQUENCE: 434
tgtcgccatc ttgggtcacc acg                                             23

<210> SEQ ID NO 435
<211> LENGTH: 20
<212> TYPE: DNA
<213> ORGANISM: Artificial Sequence
<220> FEATURE:
<223> OTHER INFORMATION: Synthetic primer

<400> SEQUENCE: 435
gggccctcca gaacaatgat                                                 20

<210> SEQ ID NO 436
<211> LENGTH: 21
<212> TYPE: DNA
<213> ORGANISM: Artificial Sequence
<220> FEATURE:
<223> OTHER INFORMATION: Synthetic primer

<400> SEQUENCE: 436
tgcactgctt ggccttaaag a                                               21

<210> SEQ ID NO 437
<211> LENGTH: 25
<212> TYPE: DNA
<213> ORGANISM: Artificial Sequence
<220> FEATURE:
<223> OTHER INFORMATION: Synthetic probe

```
<400> SEQUENCE: 437
ccgctctcat cgcagtcagg atcat                                              25

<210> SEQ ID NO 438
<211> LENGTH: 20
<212> TYPE: DNA
<213> ORGANISM: Artificial Sequence
<220> FEATURE:
<223> OTHER INFORMATION: Synthetic primer

<400> SEQUENCE: 438
gcggtcagca tcacaactaa                                                    20

<210> SEQ ID NO 439
<211> LENGTH: 20
<212> TYPE: DNA
<213> ORGANISM: Artificial Sequence
<220> FEATURE:
<223> OTHER INFORMATION: Synthetic primer

<400> SEQUENCE: 439
tctggaggtc cgatctttct                                                    20

<210> SEQ ID NO 440
<211> LENGTH: 24
<212> TYPE: DNA
<213> ORGANISM: Artificial Sequence
<220> FEATURE:
<223> OTHER INFORMATION: Synthetic probe

<400> SEQUENCE: 440
tgctccatca cctgtcctga cgat                                               24

<210> SEQ ID NO 441
<211> LENGTH: 18
<212> TYPE: DNA
<213> ORGANISM: Artificial Sequence
<220> FEATURE:
<223> OTHER INFORMATION: Synthetic primer

<400> SEQUENCE: 441
caaccaggca gctccatc                                                      18

<210> SEQ ID NO 442
<211> LENGTH: 19
<212> TYPE: DNA
<213> ORGANISM: Artificial Sequence
<220> FEATURE:
<223> OTHER INFORMATION: Synthetic primer

<400> SEQUENCE: 442
gtaatgctgt ccacggtgc                                                     19

<210> SEQ ID NO 443
<211> LENGTH: 24
<212> TYPE: DNA
<213> ORGANISM: Artificial Sequence
<220> FEATURE:
<223> OTHER INFORMATION: Synthetic probe

<400> SEQUENCE: 443
cacctgatgc atgatggaca ctgc                                               24

<210> SEQ ID NO 444
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 444
tgaacggggt atcctcctta                                          20

<210> SEQ ID NO 445
<211> LENGTH: 20
<212> TYPE: DNA
<213> ORGANISM: Artificial Sequence
<220> FEATURE:
<223> OTHER INFORMATION: Synthetic primer

<400> SEQUENCE: 445
aggtacctct cggtcagtgg                                          20

<210> SEQ ID NO 446
<211> LENGTH: 24
<212> TYPE: DNA
<213> ORGANISM: Artificial Sequence
<220> FEATURE:
<223> OTHER INFORMATION: Synthetic probe

<400> SEQUENCE: 446
cgtcccattt gagcctgtca atgt                                     24

<210> SEQ ID NO 447
<211> LENGTH: 18
<212> TYPE: DNA
<213> ORGANISM: Artificial Sequence
<220> FEATURE:
<223> OTHER INFORMATION: Synthetic primer

<400> SEQUENCE: 447
actggtcctc catcggct                                            18

<210> SEQ ID NO 448
<211> LENGTH: 21
<212> TYPE: DNA
<213> ORGANISM: Artificial Sequence
<220> FEATURE:
<223> OTHER INFORMATION: Synthetic primer

<400> SEQUENCE: 448
ccagtgtagc atgagtgctg a                                        21

<210> SEQ ID NO 449
<211> LENGTH: 24
<212> TYPE: DNA
<213> ORGANISM: Artificial Sequence
<220> FEATURE:
<223> OTHER INFORMATION: Synthetic probe

<400> SEQUENCE: 449
ccttgcacct caaaccaaag ctcc                                     24

<210> SEQ ID NO 450
<211> LENGTH: 18
<212> TYPE: DNA
<213> ORGANISM: Artificial Sequence
<220> FEATURE:
<223> OTHER INFORMATION: Synthetic primer

<400> SEQUENCE: 450
```

```
gccaaaggca aggagacc                                              18

<210> SEQ ID NO 451
<211> LENGTH: 21
<212> TYPE: DNA
<213> ORGANISM: Artificial Sequence
<220> FEATURE:
<223> OTHER INFORMATION: Synthetic primer

<400> SEQUENCE: 451
tcaccctcag agtctccctc t                                          21

<210> SEQ ID NO 452
<211> LENGTH: 24
<212> TYPE: DNA
<213> ORGANISM: Artificial Sequence
<220> FEATURE:
<223> OTHER INFORMATION: Synthetic probe

<400> SEQUENCE: 452
ctctggcctc atgtctgact ccca                                       24

<210> SEQ ID NO 453
<211> LENGTH: 28
<212> TYPE: DNA
<213> ORGANISM: Artificial Sequence
<220> FEATURE:
<223> OTHER INFORMATION: Synthetic primer

<400> SEQUENCE: 453
ataacaaagt gtagctctga catgaatg                                   28

<210> SEQ ID NO 454
<211> LENGTH: 24
<212> TYPE: DNA
<213> ORGANISM: Artificial Sequence
<220> FEATURE:
<223> OTHER INFORMATION: Synthetic primer

<400> SEQUENCE: 454
cacacctgca gtagttttga ctca                                       24

<210> SEQ ID NO 455
<211> LENGTH: 30
<212> TYPE: DNA
<213> ORGANISM: Artificial Sequence
<220> FEATURE:
<223> OTHER INFORMATION: Synthetic probe

<400> SEQUENCE: 455
ttgtttgcat ggacagtgca tctatctggt                                 30

<210> SEQ ID NO 456
<211> LENGTH: 18
<212> TYPE: DNA
<213> ORGANISM: Artificial Sequence
<220> FEATURE:
<223> OTHER INFORMATION: Synthetic primer

<400> SEQUENCE: 456 accccagac cggatcag                                               18

<210> SEQ ID NO 457
<211> LENGTH: 23
<212> TYPE: DNA
```

```
<213> ORGANISM: Artificial Sequence
<220> FEATURE:
<223> OTHER INFORMATION: Synthetic primer

<400> SEQUENCE: 457
tgtagggcag acttcctcaa aca                                          23

<210> SEQ ID NO 458
<211> LENGTH: 23
<212> TYPE: DNA
<213> ORGANISM: Artificial Sequence
<220> FEATURE:
<223> OTHER INFORMATION: Synthetic probe

<400> SEQUENCE: 458
ctggccctca tgtcccttc acg                                           23

<210> SEQ ID NO 459
<211> LENGTH: 20
<212> TYPE: DNA
<213> ORGANISM: Artificial Sequence
<220> FEATURE:
<223> OTHER INFORMATION: Synthetic primer

<400> SEQUENCE: 459
cagcagcgtc aggaatctct                                              20

<210> SEQ ID NO 460
<211> LENGTH: 19
<212> TYPE: DNA
<213> ORGANISM: Artificial Sequence
<220> FEATURE:
<223> OTHER INFORMATION: Synthetic primer

<400> SEQUENCE: 460
atgtcctggt gggaggatg                                               19

<210> SEQ ID NO 461
<211> LENGTH: 24
<212> TYPE: DNA
<213> ORGANISM: Artificial Sequence
<220> FEATURE:
<223> OTHER INFORMATION: Synthetic probe

<400> SEQUENCE: 461
ccctgtggcc gaggttcttc tttc                                         24

<210> SEQ ID NO 462
<211> LENGTH: 20
<212> TYPE: DNA
<213> ORGANISM: Artificial Sequence
<220> FEATURE:
<223> OTHER INFORMATION: Synthetic primer

<400> SEQUENCE: 462
tgcaggccag actcagtatt                                              20

<210> SEQ ID NO 463
<211> LENGTH: 20
<212> TYPE: DNA
<213> ORGANISM: Artificial Sequence
<220> FEATURE:
<223> OTHER INFORMATION: Synthetic primer

<400> SEQUENCE: 463
tagggctgtc ctgtctgtga                                              20
```

```
<210> SEQ ID NO 464
<211> LENGTH: 24
<212> TYPE: DNA
<213> ORGANISM: Artificial Sequence
<220> FEATURE:
<223> OTHER INFORMATION: Synthetic probe

<400> SEQUENCE: 464
cagccagccg tctacacagc ctac                                              24

<210> SEQ ID NO 465
<211> LENGTH: 23
<212> TYPE: DNA
<213> ORGANISM: Artificial Sequence
<220> FEATURE:
<223> OTHER INFORMATION: Synthetic primer

<400> SEQUENCE: 465
gtgaaggatg tgaagcagac gta                                               23

<210> SEQ ID NO 466
<211> LENGTH: 20
<212> TYPE: DNA
<213> ORGANISM: Artificial Sequence
<220> FEATURE:
<223> OTHER INFORMATION: Synthetic primer

<400> SEQUENCE: 466
aaccggtgct ctccacattc                                                   20

<210> SEQ ID NO 467
<211> LENGTH: 21
<212> TYPE: DNA
<213> ORGANISM: Artificial Sequence
<220> FEATURE:
<223> OTHER INFORMATION: Synthetic probe

<400> SEQUENCE: 467
tggcacgggt cttctcctac c                                                 21

<210> SEQ ID NO 468
<211> LENGTH: 20
<212> TYPE: DNA
<213> ORGANISM: Artificial Sequence
<220> FEATURE:
<223> OTHER INFORMATION: Synthetic primer

<400> SEQUENCE: 468
gggtccaaag tgatccaaaa                                                   20

<210> SEQ ID NO 469
<211> LENGTH: 19
<212> TYPE: DNA
<213> ORGANISM: Artificial Sequence
<220> FEATURE:
<223> OTHER INFORMATION: Synthetic primer

<400> SEQUENCE: 469
ccctgtcatt gtctccagc                                                    19

<210> SEQ ID NO 470
<211> LENGTH: 24
<212> TYPE: DNA
<213> ORGANISM: Artificial Sequence
<220> FEATURE:
```

<223> OTHER INFORMATION: Synthetic probe

<400> SEQUENCE: 470
acattcctcc cccaccgtga attc                                          24

<210> SEQ ID NO 471
<211> LENGTH: 19
<212> TYPE: DNA
<213> ORGANISM: Artificial Sequence
<220> FEATURE:
<223> OTHER INFORMATION: Synthetic primer

<400> SEQUENCE: 471
gctttgccac caggaaagt                                                19

<210> SEQ ID NO 472
<211> LENGTH: 20
<212> TYPE: DNA
<213> ORGANISM: Artificial Sequence
<220> FEATURE:
<223> OTHER INFORMATION: Synthetic primer

<400> SEQUENCE: 472
catccccatt cacactgatg                                               20

<210> SEQ ID NO 473
<211> LENGTH: 24
<212> TYPE: DNA
<213> ORGANISM: Artificial Sequence
<220> FEATURE:
<223> OTHER INFORMATION: Synthetic probe

<400> SEQUENCE: 473
ctggcatggc caaacctaac atga                                          24

<210> SEQ ID NO 474
<211> LENGTH: 18
<212> TYPE: DNA
<213> ORGANISM: Artificial Sequence
<220> FEATURE:
<223> OTHER INFORMATION: Synthetic primer

<400> SEQUENCE: 474
gccccaggtc tcctgaca                                                 18

<210> SEQ ID NO 475
<211> LENGTH: 20
<212> TYPE: DNA
<213> ORGANISM: Artificial Sequence
<220> FEATURE:
<223> OTHER INFORMATION: Synthetic primer

<400> SEQUENCE: 475
gaaccggagg caaacactgt                                               20

<210> SEQ ID NO 476
<211> LENGTH: 23
<212> TYPE: DNA
<213> ORGANISM: Artificial Sequence
<220> FEATURE:
<223> OTHER INFORMATION: Synthetic probe

<400> SEQUENCE: 476
cttagcccgc agcctggaac aca                                           23

```
<210> SEQ ID NO 477
<211> LENGTH: 18
<212> TYPE: DNA
<213> ORGANISM: Artificial Sequence
<220> FEATURE:
<223> OTHER INFORMATION: Synthetic primer

<400> SEQUENCE: 477
ctgaccagaa ccacggct                                                       18

<210> SEQ ID NO 478
<211> LENGTH: 18
<212> TYPE: DNA
<213> ORGANISM: Artificial Sequence
<220> FEATURE:
<223> OTHER INFORMATION: Synthetic primer

<400> SEQUENCE: 478
ggaagtgggt catgtggg                                                       18

<210> SEQ ID NO 479
<211> LENGTH: 24
<212> TYPE: DNA
<213> ORGANISM: Artificial Sequence
<220> FEATURE:
<223> OTHER INFORMATION: Synthetic probe

<400> SEQUENCE: 479
cggcctgtcc acgaaccact tata                                                24

<210> SEQ ID NO 480
<211> LENGTH: 21
<212> TYPE: DNA
<213> ORGANISM: Artificial Sequence
<220> FEATURE:
<223> OTHER INFORMATION: Synthetic primer

<400> SEQUENCE: 480
ggattgctca acaaccatgc t                                                   21

<210> SEQ ID NO 481
<211> LENGTH: 24
<212> TYPE: DNA
<213> ORGANISM: Artificial Sequence
<220> FEATURE:
<223> OTHER INFORMATION: Synthetic primer

<400> SEQUENCE: 481
ggcattaaca cttttggacg ataa                                                24

<210> SEQ ID NO 482
<211> LENGTH: 30
<212> TYPE: DNA
<213> ORGANISM: Artificial Sequence
<220> FEATURE:
<223> OTHER INFORMATION: Synthetic probe

<400> SEQUENCE: 482
tctggaccct cctacctctg gttcttacgt                                          30

<210> SEQ ID NO 483
<211> LENGTH: 24
<212> TYPE: DNA
<213> ORGANISM: Artificial Sequence
<220> FEATURE:
<223> OTHER INFORMATION: Synthetic primer
```

```
<400> SEQUENCE: 483
gcactttggg attctttcca ttat                                          24

<210> SEQ ID NO 484
<211> LENGTH: 24
<212> TYPE: DNA
<213> ORGANISM: Artificial Sequence
<220> FEATURE:
<223> OTHER INFORMATION: Synthetic primer

<400> SEQUENCE: 484
gcatgtaaga agaccctcac tgaa                                          24

<210> SEQ ID NO 485
<211> LENGTH: 29
<212> TYPE: DNA
<213> ORGANISM: Artificial Sequence
<220> FEATURE:
<223> OTHER INFORMATION: Synthetic probe

<400> SEQUENCE: 485
acaacattct cggtgcctgt aacaaagaa                                     29

<210> SEQ ID NO 486
<211> LENGTH: 18
<212> TYPE: DNA
<213> ORGANISM: Artificial Sequence
<220> FEATURE:
<223> OTHER INFORMATION: Synthetic primer

<400> SEQUENCE: 486
gcctcttcct gttcgacg                                                 18

<210> SEQ ID NO 487
<211> LENGTH: 18
<212> TYPE: DNA
<213> ORGANISM: Artificial Sequence
<220> FEATURE:
<223> OTHER INFORMATION: Synthetic primer

<400> SEQUENCE: 487
gctttgcccg gtagctct                                                 18

<210> SEQ ID NO 488
<211> LENGTH: 24
<212> TYPE: DNA
<213> ORGANISM: Artificial Sequence
<220> FEATURE:
<223> OTHER INFORMATION: Synthetic probe

<400> SEQUENCE: 488
tcgcccacct acgtactggc ctac                                          24

<210> SEQ ID NO 489
<211> LENGTH: 20
<212> TYPE: DNA
<213> ORGANISM: Artificial Sequence
<220> FEATURE:
<223> OTHER INFORMATION: Synthetic primer

<400> SEQUENCE: 489
caacctcacc acctttgatg                                               20

<210> SEQ ID NO 490
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 490
gcgggaagag agctcataga                                          20

<210> SEQ ID NO 491
<211> LENGTH: 21
<212> TYPE: DNA
<213> ORGANISM: Artificial Sequence
<220> FEATURE:
<223> OTHER INFORMATION: Synthetic probe

<400> SEQUENCE: 491
cgtggtgcca ccacctctcc t                                        21

<210> SEQ ID NO 492
<211> LENGTH: 21
<212> TYPE: DNA
<213> ORGANISM: Artificial Sequence
<220> FEATURE:
<223> OTHER INFORMATION: Synthetic primer

<400> SEQUENCE: 492
cgagcccttt gatgacttcc t                                        21

<210> SEQ ID NO 493
<211> LENGTH: 18
<212> TYPE: DNA
<213> ORGANISM: Artificial Sequence
<220> FEATURE:
<223> OTHER INFORMATION: Synthetic primer

<400> SEQUENCE: 493
ggagcgggct gtctcaga                                            18

<210> SEQ ID NO 494
<211> LENGTH: 22
<212> TYPE: DNA
<213> ORGANISM: Artificial Sequence
<220> FEATURE:
<223> OTHER INFORMATION: Synthetic probe

<400> SEQUENCE: 494
tcccagcatc atccaggccc ag                                       22

<210> SEQ ID NO 495
<211> LENGTH: 20
<212> TYPE: DNA
<213> ORGANISM: Artificial Sequence
<220> FEATURE:
<223> OTHER INFORMATION: Synthetic primer

<400> SEQUENCE: 495
gaagaggaga agcgaagggt                                          20

<210> SEQ ID NO 496
<211> LENGTH: 18
<212> TYPE: DNA
<213> ORGANISM: Artificial Sequence
<220> FEATURE:
<223> OTHER INFORMATION: Synthetic primer

<400> SEQUENCE: 496
```

```
ccggttcctg catttagc                                           18
```

<210> SEQ ID NO 497
<211> LENGTH: 24
<212> TYPE: DNA
<213> ORGANISM: Artificial Sequence
<220> FEATURE:
<223> OTHER INFORMATION: Synthetic probe

<400> SEQUENCE: 497

```
cgccgggaac gaaataaact agca                                    24
```

<210> SEQ ID NO 498
<211> LENGTH: 20
<212> TYPE: DNA
<213> ORGANISM: Artificial Sequence
<220> FEATURE:
<223> OTHER INFORMATION: Synthetic primer

<400> SEQUENCE: 498

```
catccaagtg gagggaaact                                         20
```

<210> SEQ ID NO 499
<211> LENGTH: 20
<212> TYPE: DNA
<213> ORGANISM: Artificial Sequence
<220> FEATURE:
<223> OTHER INFORMATION: Synthetic primer

<400> SEQUENCE: 499

```
tctcctcacg catcatatcc                                         20
```

<210> SEQ ID NO 500
<211> LENGTH: 28
<212> TYPE: DNA
<213> ORGANISM: Artificial Sequence
<220> FEATURE:
<223> OTHER INFORMATION: Synthetic probe

<400> SEQUENCE: 500

```
aaacaaaaac acccagtact gtggctca                                28
```

<210> SEQ ID NO 501
<211> LENGTH: 20
<212> TYPE: DNA
<213> ORGANISM: Artificial Sequence
<220> FEATURE:
<223> OTHER INFORMATION: Synthetic primer

<400> SEQUENCE: 501

```
tgaagtccag gacgatgatg                                         20
```

<210> SEQ ID NO 502
<211> LENGTH: 20
<212> TYPE: DNA
<213> ORGANISM: Artificial Sequence
<220> FEATURE:
<223> OTHER INFORMATION: Synthetic primer

<400> SEQUENCE: 502

```
acggcttgct tactgaaggt                                         20
```

<210> SEQ ID NO 503
<211> LENGTH: 24
<212> TYPE: DNA
<213> ORGANISM: Artificial Sequence

```
<220> FEATURE:
<223> OTHER INFORMATION: Synthetic probe

<400> SEQUENCE: 503
ctctacagca gctcagccag cctg                                              24

<210> SEQ ID NO 504
<211> LENGTH: 19
<212> TYPE: DNA
<213> ORGANISM: Artificial Sequence
<220> FEATURE:
<223> OTHER INFORMATION: Synthetic primer

<400> SEQUENCE: 504
cgacagagct tgtgcacct                                                    19

<210> SEQ ID NO 505
<211> LENGTH: 19
<212> TYPE: DNA
<213> ORGANISM: Artificial Sequence
<220> FEATURE:
<223> OTHER INFORMATION: Synthetic primer

<400> SEQUENCE: 505
ggtcgtccat tggaatcct                                                    19

<210> SEQ ID NO 506
<211> LENGTH: 24
<212> TYPE: DNA
<213> ORGANISM: Artificial Sequence
<220> FEATURE:
<223> OTHER INFORMATION: Synthetic probe

<400> SEQUENCE: 506
cagaccaagc ctttgcccag aatt                                              24

<210> SEQ ID NO 507
<211> LENGTH: 18
<212> TYPE: DNA
<213> ORGANISM: Artificial Sequence
<220> FEATURE:
<223> OTHER INFORMATION: Synthetic primer

<400> SEQUENCE: 507
cagccctgcc agtttgac                                                     18

<210> SEQ ID NO 508
<211> LENGTH: 19
<212> TYPE: DNA
<213> ORGANISM: Artificial Sequence
<220> FEATURE:
<223> OTHER INFORMATION: Synthetic primer

<400> SEQUENCE: 508
gttgcctgtg gatgacacc                                                    19

<210> SEQ ID NO 509
<211> LENGTH: 24
<212> TYPE: DNA
<213> ORGANISM: Artificial Sequence
<220> FEATURE:
<223> OTHER INFORMATION: Synthetic probe

<400> SEQUENCE: 509
atgccgtctt ctgccctaac ctga                                              24
```

```
<210> SEQ ID NO 510
<211> LENGTH: 23
<212> TYPE: DNA
<213> ORGANISM: Artificial Sequence
<220> FEATURE:
<223> OTHER INFORMATION: Synthetic primer

<400> SEQUENCE: 510
gtaagtcgga tgagcctgtc tgt                                          23

<210> SEQ ID NO 511
<211> LENGTH: 21
<212> TYPE: DNA
<213> ORGANISM: Artificial Sequence
<220> FEATURE:
<223> OTHER INFORMATION: Synthetic primer

<400> SEQUENCE: 511
cagcttcctt catggcacac t                                            21

<210> SEQ ID NO 512
<211> LENGTH: 26
<212> TYPE: DNA
<213> ORGANISM: Artificial Sequence
<220> FEATURE:
<223> OTHER INFORMATION: Synthetic probe

<400> SEQUENCE: 512
ccagtgacaa tgccacttat gccagc                                       26

<210> SEQ ID NO 513
<211> LENGTH: 20
<212> TYPE: DNA
<213> ORGANISM: Artificial Sequence
<220> FEATURE:
<223> OTHER INFORMATION: Synthetic primer

<400> SEQUENCE: 513
accctcgaca agaccacact                                              20

<210> SEQ ID NO 514
<211> LENGTH: 20
<212> TYPE: DNA
<213> ORGANISM: Artificial Sequence
<220> FEATURE:
<223> OTHER INFORMATION: Synthetic primer

<400> SEQUENCE: 514
tgggagttca tgggtacaga                                              20

<210> SEQ ID NO 515
<211> LENGTH: 24
<212> TYPE: DNA
<213> ORGANISM: Artificial Sequence
<220> FEATURE:
<223> OTHER INFORMATION: Synthetic probe

<400> SEQUENCE: 515
aacttcagcc ccagctccca agtc                                         24

<210> SEQ ID NO 516
<211> LENGTH: 18
<212> TYPE: DNA
<213> ORGANISM: Artificial Sequence
<220> FEATURE:
<223> OTHER INFORMATION: Synthetic primer
```

```
<400> SEQUENCE: 516
gctcacagga cggctacc                                              18

<210> SEQ ID NO 517
<211> LENGTH: 18
<212> TYPE: DNA
<213> ORGANISM: Artificial Sequence
<220> FEATURE:
<223> OTHER INFORMATION: Synthetic primer

<400> SEQUENCE: 517
taggcgtttc tggcatgg                                              18

<210> SEQ ID NO 518
<211> LENGTH: 24
<212> TYPE: DNA
<213> ORGANISM: Artificial Sequence
<220> FEATURE:
<223> OTHER INFORMATION: Synthetic probe

<400> SEQUENCE: 518
atccgcaatg gcttctacac cacc                                       24

<210> SEQ ID NO 519
<211> LENGTH: 18
<212> TYPE: DNA
<213> ORGANISM: Artificial Sequence
<220> FEATURE:
<223> OTHER INFORMATION: Synthetic primer

<400> SEQUENCE: 519
agcaccaatc ccgagaac                                              18

<210> SEQ ID NO 520
<211> LENGTH: 20
<212> TYPE: DNA
<213> ORGANISM: Artificial Sequence
<220> FEATURE:
<223> OTHER INFORMATION: Synthetic primer

<400> SEQUENCE: 520
gcgagactga cgcctatgta                                            20

<210> SEQ ID NO 521
<211> LENGTH: 26
<212> TYPE: DNA
<213> ORGANISM: Artificial Sequence
<220> FEATURE:
<223> OTHER INFORMATION: Synthetic probe

<400> SEQUENCE: 521
agcccatctt gacccgaata cttgag                                     26

<210> SEQ ID NO 522
<211> LENGTH: 19
<212> TYPE: DNA
<213> ORGANISM: Artificial Sequence
<220> FEATURE:
<223> OTHER INFORMATION: Synthetic primer

<400> SEQUENCE: 522
gcatgggaac catcaacca                                             19

<210> SEQ ID NO 523
```

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 523
tgaggagttt gccttgattc g                                           21

<210> SEQ ID NO 524
<211> LENGTH: 30
<212> TYPE: DNA
<213> ORGANISM: Artificial Sequence
<220> FEATURE:
<223> OTHER INFORMATION: Synthetic probe

<400> SEQUENCE: 524
ccatggacca acttcactat gtgacagagc                                  30

<210> SEQ ID NO 525
<211> LENGTH: 21
<212> TYPE: DNA
<213> ORGANISM: Artificial Sequence
<220> FEATURE:
<223> OTHER INFORMATION: Synthetic primer

<400> SEQUENCE: 525
cgctccagac ctatgatgac t                                           21

<210> SEQ ID NO 526
<211> LENGTH: 20
<212> TYPE: DNA
<213> ORGANISM: Artificial Sequence
<220> FEATURE:
<223> OTHER INFORMATION: Synthetic primer

<400> SEQUENCE: 526
acagtggaag gaccaggact                                             20

<210> SEQ ID NO 527
<211> LENGTH: 24
<212> TYPE: DNA
<213> ORGANISM: Artificial Sequence
<220> FEATURE:
<223> OTHER INFORMATION: Synthetic probe

<400> SEQUENCE: 527
tgttagccaa agactgccac tgca                                        24

<210> SEQ ID NO 528
<211> LENGTH: 18
<212> TYPE: DNA
<213> ORGANISM: Artificial Sequence
<220> FEATURE:
<223> OTHER INFORMATION: Synthetic primer

<400> SEQUENCE: 528
ctgggcctgc tactctgc                                               18

<210> SEQ ID NO 529
<211> LENGTH: 18
<212> TYPE: DNA
<213> ORGANISM: Artificial Sequence
<220> FEATURE:
<223> OTHER INFORMATION: Synthetic primer

<400> SEQUENCE: 529
```
cgatgatggg cttcttgg                                          18

<210> SEQ ID NO 530
<211> LENGTH: 24
<212> TYPE: DNA
<213> ORGANISM: Artificial Sequence
<220> FEATURE:
<223> OTHER INFORMATION: Synthetic probe

<400> SEQUENCE: 530
agcctcgagc tgtctagacc ccac                                   24

<210> SEQ ID NO 531
<211> LENGTH: 19
<212> TYPE: DNA
<213> ORGANISM: Artificial Sequence
<220> FEATURE:
<223> OTHER INFORMATION: Synthetic primer

<400> SEQUENCE: 531
gttcactggg ggtgtatgg                                         19

<210> SEQ ID NO 532
<211> LENGTH: 23
<212> TYPE: DNA
<213> ORGANISM: Artificial Sequence
<220> FEATURE:
<223> OTHER INFORMATION: Synthetic primer

<400> SEQUENCE: 532
aaataccaac atgcacctct ctt                                    23

<210> SEQ ID NO 533
<211> LENGTH: 24
<212> TYPE: DNA
<213> ORGANISM: Artificial Sequence
<220> FEATURE:
<223> OTHER INFORMATION: Synthetic probe

<400> SEQUENCE: 533
atcccctccc tctccaccca tcta                                   24

<210> SEQ ID NO 534
<211> LENGTH: 20
<212> TYPE: DNA
<213> ORGANISM: Artificial Sequence
<220> FEATURE:
<223> OTHER INFORMATION: Synthetic primer

<400> SEQUENCE: 534
tgtcatgtac gacggcttct                                        20

<210> SEQ ID NO 535
<211> LENGTH: 20
<212> TYPE: DNA
<213> ORGANISM: Artificial Sequence
<220> FEATURE:
<223> OTHER INFORMATION: Synthetic primer

<400> SEQUENCE: 535
agtccacagt gttgggacaa                                        20

<210> SEQ ID NO 536
<211> LENGTH: 21
<212> TYPE: DNA

```
<213> ORGANISM: Artificial Sequence
<220> FEATURE:
<223> OTHER INFORMATION: Synthetic probe

<400> SEQUENCE: 536
aggcgttgca cttcaccagc c                                              21

<210> SEQ ID NO 537
<211> LENGTH: 21
<212> TYPE: DNA
<213> ORGANISM: Artificial Sequence
<220> FEATURE:
<223> OTHER INFORMATION: Synthetic primer

<400> SEQUENCE: 537
gaacgtgcct gactttgact t                                              21

<210> SEQ ID NO 538
<211> LENGTH: 20
<212> TYPE: DNA
<213> ORGANISM: Artificial Sequence
<220> FEATURE:
<223> OTHER INFORMATION: Synthetic primer

<400> SEQUENCE: 538
actccttcat cctcccacag                                                20

<210> SEQ ID NO 539
<211> LENGTH: 24
<212> TYPE: DNA
<213> ORGANISM: Artificial Sequence
<220> FEATURE:
<223> OTHER INFORMATION: Synthetic probe

<400> SEQUENCE: 539
cctcccgaat tctatgagca tgcc                                           24

<210> SEQ ID NO 540
<211> LENGTH: 20
<212> TYPE: DNA
<213> ORGANISM: Artificial Sequence
<220> FEATURE:
<223> OTHER INFORMATION: Synthetic primer

<400> SEQUENCE: 540
accactagca tctcccaagc                                                20

<210> SEQ ID NO 541
<211> LENGTH: 20
<212> TYPE: DNA
<213> ORGANISM: Artificial Sequence
<220> FEATURE:
<223> OTHER INFORMATION: Synthetic primer

<400> SEQUENCE: 541
accctgtcca tacaggcttc                                                20

<210> SEQ ID NO 542
<211> LENGTH: 28
<212> TYPE: DNA
<213> ORGANISM: Artificial Sequence
<220> FEATURE:
<223> OTHER INFORMATION: Synthetic probe

<400> SEQUENCE: 542
catctttagc tgctccacag ctttcctg                                       28
```

```
<210> SEQ ID NO 543
<211> LENGTH: 20
<212> TYPE: DNA
<213> ORGANISM: Artificial Sequence
<220> FEATURE:
<223> OTHER INFORMATION: Synthetic primer

<400> SEQUENCE: 543
ccacagacac atcgggttac                                                    20

<210> SEQ ID NO 544
<211> LENGTH: 20
<212> TYPE: DNA
<213> ORGANISM: Artificial Sequence
<220> FEATURE:
<223> OTHER INFORMATION: Synthetic primer

<400> SEQUENCE: 544
caccgtgatg ttgcagaact                                                    20

<210> SEQ ID NO 545
<211> LENGTH: 24
<212> TYPE: DNA
<213> ORGANISM: Artificial Sequence
<220> FEATURE:
<223> OTHER INFORMATION: Synthetic probe

<400> SEQUENCE: 545
tcccctcctc attgctggag gtac                                               24

<210> SEQ ID NO 546
<211> LENGTH: 18
<212> TYPE: DNA
<213> ORGANISM: Artificial Sequence
<220> FEATURE:
<223> OTHER INFORMATION: Synthetic primer

<400> SEQUENCE: 546
gcttatgacc gaccccaa                                                      18

<210> SEQ ID NO 547
<211> LENGTH: 20
<212> TYPE: DNA
<213> ORGANISM: Artificial Sequence
<220> FEATURE:
<223> OTHER INFORMATION: Synthetic primer

<400> SEQUENCE: 547
aaagttccag gcaacatcgt                                                    20

<210> SEQ ID NO 548
<211> LENGTH: 24
<212> TYPE: DNA
<213> ORGANISM: Artificial Sequence
<220> FEATURE:
<223> OTHER INFORMATION: Synthetic probe

<400> SEQUENCE: 548
ctcatcacct ggtctccggt gtgt                                               24

<210> SEQ ID NO 549
<211> LENGTH: 24
<212> TYPE: DNA
<213> ORGANISM: Artificial Sequence
<220> FEATURE:
```

```
<223> OTHER INFORMATION: Synthetic primer

<400> SEQUENCE: 549
cacacagatc tcctactcca tcca                                          24

<210> SEQ ID NO 550
<211> LENGTH: 21
<212> TYPE: DNA
<213> ORGANISM: Artificial Sequence
<220> FEATURE:
<223> OTHER INFORMATION: Synthetic primer

<400> SEQUENCE: 550
ggtccagcag tgtctcctga a                                             21

<210> SEQ ID NO 551
<211> LENGTH: 26
<212> TYPE: DNA
<213> ORGANISM: Artificial Sequence
<220> FEATURE:
<223> OTHER INFORMATION: Synthetic probe

<400> SEQUENCE: 551
catgctgcat cctaaggctc ctcagg                                        26

<210> SEQ ID NO 552
<211> LENGTH: 22
<212> TYPE: DNA
<213> ORGANISM: Artificial Sequence
<220> FEATURE:
<223> OTHER INFORMATION: Synthetic primer

<400> SEQUENCE: 552
gctctaggtc caattgttct gc                                            22

<210> SEQ ID NO 553
<211> LENGTH: 18
<212> TYPE: DNA
<213> ORGANISM: Artificial Sequence
<220> FEATURE:
<223> OTHER INFORMATION: Synthetic primer

<400> SEQUENCE: 553
tggaggcagt gggagatg                                                 18

<210> SEQ ID NO 554
<211> LENGTH: 24
<212> TYPE: DNA
<213> ORGANISM: Artificial Sequence
<220> FEATURE:
<223> OTHER INFORMATION: Synthetic probe

<400> SEQUENCE: 554
actgatacct caaccttggg gcca                                          24

<210> SEQ ID NO 555
<211> LENGTH: 18
<212> TYPE: DNA
<213> ORGANISM: Artificial Sequence
<220> FEATURE:
<223> OTHER INFORMATION: Synthetic primer

<400> SEQUENCE: 555
atctctgcgc ctttctgg                                                 18
```

```
<210> SEQ ID NO 556
<211> LENGTH: 20
<212> TYPE: DNA
<213> ORGANISM: Artificial Sequence
<220> FEATURE:
<223> OTHER INFORMATION: Synthetic primer

<400> SEQUENCE: 556
cactgcagtt tgcactgtga                                               20

<210> SEQ ID NO 557
<211> LENGTH: 23
<212> TYPE: DNA
<213> ORGANISM: Artificial Sequence
<220> FEATURE:
<223> OTHER INFORMATION: Synthetic probe

<400> SEQUENCE: 557
cacaaatcta ccgccagctt gcc                                           23

<210> SEQ ID NO 558
<211> LENGTH: 23
<212> TYPE: DNA
<213> ORGANISM: Artificial Sequence
<220> FEATURE:
<223> OTHER INFORMATION: Synthetic primer

<400> SEQUENCE: 558
cgaaaagatg ctgaacagtg aca                                           23

<210> SEQ ID NO 559
<211> LENGTH: 20
<212> TYPE: DNA
<213> ORGANISM: Artificial Sequence
<220> FEATURE:
<223> OTHER INFORMATION: Synthetic primer

<400> SEQUENCE: 559
tcaggaacag ccaccagtga                                               20

<210> SEQ ID NO 560
<211> LENGTH: 28
<212> TYPE: DNA
<213> ORGANISM: Artificial Sequence
<220> FEATURE:
<223> OTHER INFORMATION: Synthetic probe

<400> SEQUENCE: 560
cttcctcctc ccttctggtc agttggat                                      28

<210> SEQ ID NO 561
<211> LENGTH: 18
<212> TYPE: DNA
<213> ORGANISM: Artificial Sequence
<220> FEATURE:
<223> OTHER INFORMATION: Synthetic primer

<400> SEQUENCE: 561
gctggaactc cgcgttca                                                 18

<210> SEQ ID NO 562
<211> LENGTH: 22
<212> TYPE: DNA
<213> ORGANISM: Artificial Sequence
<220> FEATURE:
<223> OTHER INFORMATION: Synthetic primer
```

<400> SEQUENCE: 562
cgctgagcac atggagtcta ag                                    22

<210> SEQ ID NO 563
<211> LENGTH: 25
<212> TYPE: DNA
<213> ORGANISM: Artificial Sequence
<220> FEATURE:
<223> OTHER INFORMATION: Synthetic probe

<400> SEQUENCE: 563
cgcaaagacg agatcatcac cagcc                                 25

<210> SEQ ID NO 564
<211> LENGTH: 21
<212> TYPE: DNA
<213> ORGANISM: Artificial Sequence
<220> FEATURE:
<223> OTHER INFORMATION: Synthetic primer

<400> SEQUENCE: 564
tggaagaccg attcagatga g                                     21

<210> SEQ ID NO 565
<211> LENGTH: 18
<212> TYPE: DNA
<213> ORGANISM: Artificial Sequence
<220> FEATURE:
<223> OTHER INFORMATION: Synthetic primer

<400> SEQUENCE: 565
caccccaaca actccagc                                         18

<210> SEQ ID NO 566
<211> LENGTH: 24
<212> TYPE: DNA
<213> ORGANISM: Artificial Sequence
<220> FEATURE:
<223> OTHER INFORMATION: Synthetic probe

<400> SEQUENCE: 566
aggaattcac tcaggctccg tgct                                  24

<210> SEQ ID NO 567
<211> LENGTH: 20
<212> TYPE: DNA
<213> ORGANISM: Artificial Sequence
<220> FEATURE:
<223> OTHER INFORMATION: Synthetic primer

<400> SEQUENCE: 567
cttctcccat gttgccattt                                       20

<210> SEQ ID NO 568
<211> LENGTH: 21
<212> TYPE: DNA
<213> ORGANISM: Artificial Sequence
<220> FEATURE:
<223> OTHER INFORMATION: Synthetic primer

<400> SEQUENCE: 568
ttgcctccta acagaggtgt g                                     21

<210> SEQ ID NO 569
<211> LENGTH: 24

```
<212> TYPE: DNA
<213> ORGANISM: Artificial Sequence
<220> FEATURE:
<223> OTHER INFORMATION: Synthetic probe

<400> SEQUENCE: 569
acggcctgac ctttgtacac ctca                                      24

<210> SEQ ID NO 570
<211> LENGTH: 19
<212> TYPE: DNA
<213> ORGANISM: Artificial Sequence
<220> FEATURE:
<223> OTHER INFORMATION: Synthetic primer

<400> SEQUENCE: 570
aacagttgcc tggggtagc                                            19

<210> SEQ ID NO 571
<211> LENGTH: 18
<212> TYPE: DNA
<213> ORGANISM: Artificial Sequence
<220> FEATURE:
<223> OTHER INFORMATION: Synthetic primer

<400> SEQUENCE: 571
ccatggcctc tggaatca                                             18

<210> SEQ ID NO 572
<211> LENGTH: 24
<212> TYPE: DNA
<213> ORGANISM: Artificial Sequence
<220> FEATURE:
<223> OTHER INFORMATION: Synthetic probe

<400> SEQUENCE: 572
acacaactct gtccagccca cagc                                      24

<210> SEQ ID NO 573
<211> LENGTH: 20
<212> TYPE: DNA
<213> ORGANISM: Artificial Sequence
<220> FEATURE:
<223> OTHER INFORMATION: Synthetic primer

<400> SEQUENCE: 573
gacgatttgc cagctttgag                                           20

<210> SEQ ID NO 574
<211> LENGTH: 18
<212> TYPE: DNA
<213> ORGANISM: Artificial Sequence
<220> FEATURE:
<223> OTHER INFORMATION: Synthetic primer

<400> SEQUENCE: 574
tccaggttgg ctttgtcc                                             18

<210> SEQ ID NO 575
<211> LENGTH: 24
<212> TYPE: DNA
<213> ORGANISM: Artificial Sequence
<220> FEATURE:
<223> OTHER INFORMATION: Synthetic probe

<400> SEQUENCE: 575
```
tcaaggtgca ttggccaaca tagc                                          24

<210> SEQ ID NO 576
<211> LENGTH: 18
<212> TYPE: DNA
<213> ORGANISM: Artificial Sequence
<220> FEATURE:
<223> OTHER INFORMATION: Synthetic primer

<400> SEQUENCE: 576
aagaggggcc gcagtatt                                                 18

<210> SEQ ID NO 577
<211> LENGTH: 19
<212> TYPE: DNA
<213> ORGANISM: Artificial Sequence
<220> FEATURE:
<223> OTHER INFORMATION: Synthetic primer

<400> SEQUENCE: 577
ctcggtcagt ctgtgcgtt                                                19

<210> SEQ ID NO 578
<211> LENGTH: 24
<212> TYPE: DNA
<213> ORGANISM: Artificial Sequence
<220> FEATURE:
<223> OTHER INFORMATION: Synthetic probe

<400> SEQUENCE: 578
cttggcgtac cctgtggtcc actc                                          24

<210> SEQ ID NO 579
<211> LENGTH: 19
<212> TYPE: DNA
<213> ORGANISM: Artificial Sequence
<220> FEATURE:
<223> OTHER INFORMATION: Synthetic primer

<400> SEQUENCE: 579
cctgcgcggc tactacaac                                                19

<210> SEQ ID NO 580
<211> LENGTH: 19
<212> TYPE: DNA
<213> ORGANISM: Artificial Sequence
<220> FEATURE:
<223> OTHER INFORMATION: Synthetic primer

<400> SEQUENCE: 580
caggtcgcag ccaatcatc                                                19

<210> SEQ ID NO 581
<211> LENGTH: 25
<212> TYPE: DNA
<213> ORGANISM: Artificial Sequence
<220> FEATURE:
<223> OTHER INFORMATION: Synthetic probe

<400> SEQUENCE: 581
cgaggccagt tctcacaccc tccag                                         25

<210> SEQ ID NO 582
<211> LENGTH: 19
<212> TYPE: DNA
<213> ORGANISM: Artificial Sequence

```
<220> FEATURE:
<223> OTHER INFORMATION: Synthetic primer

<400> SEQUENCE: 582
tggcctgtcc attggtgat                                              19

<210> SEQ ID NO 583
<211> LENGTH: 22
<212> TYPE: DNA
<213> ORGANISM: Artificial Sequence
<220> FEATURE:
<223> OTHER INFORMATION: Synthetic primer

<400> SEQUENCE: 583
gcttgtcatc tgcagcagtg tt                                          22

<210> SEQ ID NO 584
<211> LENGTH: 28
<212> TYPE: DNA
<213> ORGANISM: Artificial Sequence
<220> FEATURE:
<223> OTHER INFORMATION: Synthetic probe

<400> SEQUENCE: 584
ttccacatct ctcccagttt cttcgcaa                                    28

<210> SEQ ID NO 585
<211> LENGTH: 20
<212> TYPE: DNA
<213> ORGANISM: Artificial Sequence
<220> FEATURE:
<223> OTHER INFORMATION: Synthetic primer

<400> SEQUENCE: 585
aatggccaca actgtgaagt                                             20

<210> SEQ ID NO 586
<211> LENGTH: 20
<212> TYPE: DNA
<213> ORGANISM: Artificial Sequence
<220> FEATURE:
<223> OTHER INFORMATION: Synthetic primer

<400> SEQUENCE: 586
acctctttgg ctggatgaag                                             20

<210> SEQ ID NO 587
<211> LENGTH: 24
<212> TYPE: DNA
<213> ORGANISM: Artificial Sequence
<220> FEATURE:
<223> OTHER INFORMATION: Synthetic probe

<400> SEQUENCE: 587
agccatctct tgctttgaca gggc                                        24

<210> SEQ ID NO 588
<211> LENGTH: 20
<212> TYPE: DNA
<213> ORGANISM: Artificial Sequence
<220> FEATURE:
<223> OTHER INFORMATION: Synthetic primer

<400> SEQUENCE: 588
gccagtaaga acgaggagga                                             20
```

<210> SEQ ID NO 589
<211> LENGTH: 19
<212> TYPE: DNA
<213> ORGANISM: Artificial Sequence
<220> FEATURE:
<223> OTHER INFORMATION: Synthetic primer

<400> SEQUENCE: 589
cgtcgctgct tcagagtgt                                                    19

<210> SEQ ID NO 590
<211> LENGTH: 24
<212> TYPE: DNA
<213> ORGANISM: Artificial Sequence
<220> FEATURE:
<223> OTHER INFORMATION: Synthetic probe

<400> SEQUENCE: 590
aaggccattc aaactcctcc ccac                                              24

<210> SEQ ID NO 591
<211> LENGTH: 20
<212> TYPE: DNA
<213> ORGANISM: Artificial Sequence
<220> FEATURE:
<223> OTHER INFORMATION: Synthetic primer

<400> SEQUENCE: 591
cagcctcaag ttcggttttc                                                   20

<210> SEQ ID NO 592
<211> LENGTH: 18
<212> TYPE: DNA
<213> ORGANISM: Artificial Sequence
<220> FEATURE:
<223> OTHER INFORMATION: Synthetic primer

<400> SEQUENCE: 592
gttggaagca aacgcaca                                                     18

<210> SEQ ID NO 593
<211> LENGTH: 24
<212> TYPE: DNA
<213> ORGANISM: Artificial Sequence
<220> FEATURE:
<223> OTHER INFORMATION: Synthetic probe

<400> SEQUENCE: 593
accggagcct tcccagaaca aact                                              24

<210> SEQ ID NO 594
<211> LENGTH: 18
<212> TYPE: DNA
<213> ORGANISM: Artificial Sequence
<220> FEATURE:
<223> OTHER INFORMATION: Synthetic primer

<400> SEQUENCE: 594
ccaacctgcc tcaagagc                                                     18

<210> SEQ ID NO 595
<211> LENGTH: 18
<212> TYPE: DNA
<213> ORGANISM: Artificial Sequence
<220> FEATURE:
<223> OTHER INFORMATION: Synthetic primer

```
<400> SEQUENCE: 595
ggaactgccc atgcaagt                                                   18

<210> SEQ ID NO 596
<211> LENGTH: 24
<212> TYPE: DNA
<213> ORGANISM: Artificial Sequence
<220> FEATURE:
<223> OTHER INFORMATION: Synthetic probe

<400> SEQUENCE: 596
ctgcaggcct acggcaagga ctac                                            24

<210> SEQ ID NO 597
<211> LENGTH: 19
<212> TYPE: DNA
<213> ORGANISM: Artificial Sequence
<220> FEATURE:
<223> OTHER INFORMATION: Synthetic primer

<400> SEQUENCE: 597
ctgctgcgac agtccacta                                                  19

<210> SEQ ID NO 598
<211> LENGTH: 18
<212> TYPE: DNA
<213> ORGANISM: Artificial Sequence
<220> FEATURE:
<223> OTHER INFORMATION: Synthetic primer

<400> SEQUENCE: 598
caggttcgct ctgggaag                                                   18

<210> SEQ ID NO 599
<211> LENGTH: 24
<212> TYPE: DNA
<213> ORGANISM: Artificial Sequence
<220> FEATURE:
<223> OTHER INFORMATION: Synthetic probe

<400> SEQUENCE: 599
agagtgactc ccgttgtccc aagg                                            24

<210> SEQ ID NO 600
<211> LENGTH: 19
<212> TYPE: DNA
<213> ORGANISM: Artificial Sequence
<220> FEATURE:
<223> OTHER INFORMATION: Synthetic primer

<400> SEQUENCE: 600
cctccctctg gtggtgctt                                                  19

<210> SEQ ID NO 601
<211> LENGTH: 26
<212> TYPE: DNA
<213> ORGANISM: Artificial Sequence
<220> FEATURE:
<223> OTHER INFORMATION: Synthetic primer

<400> SEQUENCE: 601
gctacatcta cacttggttg gcttaa                                          26

<210> SEQ ID NO 602
```

```
<211> LENGTH: 26
<212> TYPE: DNA
<213> ORGANISM: Artificial Sequence
<220> FEATURE:
<223> OTHER INFORMATION: Synthetic probe

<400> SEQUENCE: 602
ctcagggccc accattgaag aggttg                                          26

<210> SEQ ID NO 603
<211> LENGTH: 20
<212> TYPE: DNA
<213> ORGANISM: Artificial Sequence
<220> FEATURE:
<223> OTHER INFORMATION: Synthetic primer

<400> SEQUENCE: 603
gcaagcaaca gtagtcgctg                                                 20

<210> SEQ ID NO 604
<211> LENGTH: 21
<212> TYPE: DNA
<213> ORGANISM: Artificial Sequence
<220> FEATURE:
<223> OTHER INFORMATION: Synthetic primer

<400> SEQUENCE: 604
ccaactttca cgctaactgg t                                               21

<210> SEQ ID NO 605
<211> LENGTH: 25
<212> TYPE: DNA
<213> ORGANISM: Artificial Sequence
<220> FEATURE:
<223> OTHER INFORMATION: Synthetic probe

<400> SEQUENCE: 605
tctccaccct ttcctttaga acccg                                           25

<210> SEQ ID NO 606
<211> LENGTH: 24
<212> TYPE: DNA
<213> ORGANISM: Artificial Sequence
<220> FEATURE:
<223> OTHER INFORMATION: Synthetic primer

<400> SEQUENCE: 606
gcagacagtg accatctaca gctt                                            24

<210> SEQ ID NO 607
<211> LENGTH: 22
<212> TYPE: DNA
<213> ORGANISM: Artificial Sequence
<220> FEATURE:
<223> OTHER INFORMATION: Synthetic primer

<400> SEQUENCE: 607
cttctgagac ctctggcttc gt                                              22

<210> SEQ ID NO 608
<211> LENGTH: 20
<212> TYPE: DNA
<213> ORGANISM: Artificial Sequence
<220> FEATURE:
<223> OTHER INFORMATION: Synthetic probe

<400> SEQUENCE: 608
```
ccggcgccca acgtgattct                                              20

<210> SEQ ID NO 609
<211> LENGTH: 20
<212> TYPE: DNA
<213> ORGANISM: Artificial Sequence
<220> FEATURE:
<223> OTHER INFORMATION: Synthetic primer

<400> SEQUENCE: 609
atcccatgaa gcccagatac                                              20

<210> SEQ ID NO 610
<211> LENGTH: 20
<212> TYPE: DNA
<213> ORGANISM: Artificial Sequence
<220> FEATURE:
<223> OTHER INFORMATION: Synthetic primer

<400> SEQUENCE: 610
gcaccattct tagtggagca                                              20

<210> SEQ ID NO 611
<211> LENGTH: 27
<212> TYPE: DNA
<213> ORGANISM: Artificial Sequence
<220> FEATURE:
<223> OTHER INFORMATION: Synthetic probe

<400> SEQUENCE: 611
aaaattccac cccatgatca agaatcc                                      27

<210> SEQ ID NO 612
<211> LENGTH: 20
<212> TYPE: DNA
<213> ORGANISM: Artificial Sequence
<220> FEATURE:
<223> OTHER INFORMATION: Synthetic primer

<400> SEQUENCE: 612
cacgcagaaa accacacttc                                              20

<210> SEQ ID NO 613
<211> LENGTH: 20
<212> TYPE: DNA
<213> ORGANISM: Artificial Sequence
<220> FEATURE:
<223> OTHER INFORMATION: Synthetic primer

<400> SEQUENCE: 613
catgttcctc cttgtgcatc                                              20

<210> SEQ ID NO 614
<211> LENGTH: 24
<212> TYPE: DNA
<213> ORGANISM: Artificial Sequence
<220> FEATURE:
<223> OTHER INFORMATION: Synthetic probe

<400> SEQUENCE: 614
caacacttcc ttccccaaag ccag                                         24

<210> SEQ ID NO 615
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 615
ctgagaacca tcccggtaac                                              20

<210> SEQ ID NO 616
<211> LENGTH: 22
<212> TYPE: DNA
<213> ORGANISM: Artificial Sequence
<220> FEATURE:
<223> OTHER INFORMATION: Synthetic primer

<400> SEQUENCE: 616
tgttgacagg agagaaggtt tg                                           22

<210> SEQ ID NO 617
<211> LENGTH: 23
<212> TYPE: DNA
<213> ORGANISM: Artificial Sequence
<220> FEATURE:
<223> OTHER INFORMATION: Synthetic probe

<400> SEQUENCE: 617
atcaccgctg gtcaccatga acc                                          23

<210> SEQ ID NO 618
<211> LENGTH: 19
<212> TYPE: DNA
<213> ORGANISM: Artificial Sequence
<220> FEATURE:
<223> OTHER INFORMATION: Synthetic primer

<400> SEQUENCE: 618
ccgtgcttcc ggacaactt                                               19

<210> SEQ ID NO 619
<211> LENGTH: 20
<212> TYPE: DNA
<213> ORGANISM: Artificial Sequence
<220> FEATURE:
<223> OTHER INFORMATION: Synthetic primer

<400> SEQUENCE: 619
tggactgctt ccaggtgtca                                              20

<210> SEQ ID NO 620
<211> LENGTH: 24
<212> TYPE: DNA
<213> ORGANISM: Artificial Sequence
<220> FEATURE:
<223> OTHER INFORMATION: Synthetic probe

<400> SEQUENCE: 620 tacccgtgg gcaagttctt ccaa                                          24

<210> SEQ ID NO 621
<211> LENGTH: 18
<212> TYPE: DNA
<213> ORGANISM: Artificial Sequence
<220> FEATURE:
<223> OTHER INFORMATION: Synthetic primer

<400> SEQUENCE: 621
acatcccaac gcatgctc                                                18
```

<210> SEQ ID NO 622
<211> LENGTH: 18
<212> TYPE: DNA
<213> ORGANISM: Artificial Sequence
<220> FEATURE:
<223> OTHER INFORMATION: Synthetic primer

<400> SEQUENCE: 622
ccacgccctt gtttcaga                                                 18

<210> SEQ ID NO 623
<211> LENGTH: 24
<212> TYPE: DNA
<213> ORGANISM: Artificial Sequence
<220> FEATURE:
<223> OTHER INFORMATION: Synthetic probe

<400> SEQUENCE: 623
acaccacaga aggctgtgag ctcc                                          24

<210> SEQ ID NO 624
<211> LENGTH: 22
<212> TYPE: DNA
<213> ORGANISM: Artificial Sequence
<220> FEATURE:
<223> OTHER INFORMATION: Synthetic primer

<400> SEQUENCE: 624
tggacaagta cgggatgaag ct                                            22

<210> SEQ ID NO 625
<211> LENGTH: 21
<212> TYPE: DNA
<213> ORGANISM: Artificial Sequence
<220> FEATURE:
<223> OTHER INFORMATION: Synthetic primer

<400> SEQUENCE: 625
cgaaggtgtg gcactgaaag t                                             21

<210> SEQ ID NO 626
<211> LENGTH: 24
<212> TYPE: DNA
<213> ORGANISM: Artificial Sequence
<220> FEATURE:
<223> OTHER INFORMATION: Synthetic probe

<400> SEQUENCE: 626
cccgtcaacg tactccatgc ctgg                                          24

<210> SEQ ID NO 627
<211> LENGTH: 23
<212> TYPE: DNA
<213> ORGANISM: Artificial Sequence
<220> FEATURE:
<223> OTHER INFORMATION: Synthetic primer

<400> SEQUENCE: 627
gggtcactat ggagttcaaa gga                                           23

<210> SEQ ID NO 628
<211> LENGTH: 19
<212> TYPE: DNA
<213> ORGANISM: Artificial Sequence
<220> FEATURE:

<223> OTHER INFORMATION: Synthetic primer

<400> SEQUENCE: 628
gggtctgaat ggccaggtt                                        19

<210> SEQ ID NO 629
<211> LENGTH: 23
<212> TYPE: DNA
<213> ORGANISM: Artificial Sequence
<220> FEATURE:
<223> OTHER INFORMATION: Synthetic probe

<400> SEQUENCE: 629
cccggtcacc aggcaggagt tct                                   23

<210> SEQ ID NO 630
<211> LENGTH: 21
<212> TYPE: DNA
<213> ORGANISM: Artificial Sequence
<220> FEATURE:
<223> OTHER INFORMATION: Synthetic primer

<400> SEQUENCE: 630
aaacatgctg gcagttattg a                                     21

<210> SEQ ID NO 631
<211> LENGTH: 20
<212> TYPE: DNA
<213> ORGANISM: Artificial Sequence
<220> FEATURE:
<223> OTHER INFORMATION: Synthetic primer

<400> SEQUENCE: 631
tggcacagtc tcactgttga                                       20

<210> SEQ ID NO 632
<211> LENGTH: 23
<212> TYPE: DNA
<213> ORGANISM: Artificial Sequence
<220> FEATURE:
<223> OTHER INFORMATION: Synthetic probe

<400> SEQUENCE: 632
aattcagggc ctgcatcagc tca                                   23

<210> SEQ ID NO 633
<211> LENGTH: 26
<212> TYPE: DNA
<213> ORGANISM: Artificial Sequence
<220> FEATURE:
<223> OTHER INFORMATION: Synthetic primer

<400> SEQUENCE: 633
aaggaaccat ctcactgtgt gtaaac                                26

<210> SEQ ID NO 634
<211> LENGTH: 20
<212> TYPE: DNA
<213> ORGANISM: Artificial Sequence
<220> FEATURE:
<223> OTHER INFORMATION: Synthetic primer

<400> SEQUENCE: 634
atcaggaagg ctgccaagag                                       20

```
<210> SEQ ID NO 635
<211> LENGTH: 22
<212> TYPE: DNA
<213> ORGANISM: Artificial Sequence
<220> FEATURE:
<223> OTHER INFORMATION: Synthetic probe

<400> SEQUENCE: 635
tgacttccaa gctggccgtg gc                                          22

<210> SEQ ID NO 636
<211> LENGTH: 20
<212> TYPE: DNA
<213> ORGANISM: Artificial Sequence
<220> FEATURE:
<223> OTHER INFORMATION: Synthetic primer

<400> SEQUENCE: 636
ggcgctgtca tcgatttctt                                             20

<210> SEQ ID NO 637
<211> LENGTH: 25
<212> TYPE: DNA
<213> ORGANISM: Artificial Sequence
<220> FEATURE:
<223> OTHER INFORMATION: Synthetic primer

<400> SEQUENCE: 637
tggagcttat taaaggcatt cttca                                       25

<210> SEQ ID NO 638
<211> LENGTH: 22
<212> TYPE: DNA
<213> ORGANISM: Artificial Sequence
<220> FEATURE:
<223> OTHER INFORMATION: Synthetic probe

<400> SEQUENCE: 638
ctgctccacg gccttgctct tg                                          22

<210> SEQ ID NO 639
<211> LENGTH: 20
<212> TYPE: DNA
<213> ORGANISM: Artificial Sequence
<220> FEATURE:
<223> OTHER INFORMATION: Synthetic primer

<400> SEQUENCE: 639
agctgaggaa gatgctggtt                                             20

<210> SEQ ID NO 640
<211> LENGTH: 20
<212> TYPE: DNA
<213> ORGANISM: Artificial Sequence
<220> FEATURE:
<223> OTHER INFORMATION: Synthetic primer

<400> SEQUENCE: 640
ggaaagaagg tgctcaggtc                                             20

<210> SEQ ID NO 641
<211> LENGTH: 24
<212> TYPE: DNA
<213> ORGANISM: Artificial Sequence
<220> FEATURE:
<223> OTHER INFORMATION: Synthetic probe
```

```
<400> SEQUENCE: 641
tgcccacaga ccttccagga gaat                                      24

<210> SEQ ID NO 642
<211> LENGTH: 20
<212> TYPE: DNA
<213> ORGANISM: Artificial Sequence
<220> FEATURE:
<223> OTHER INFORMATION: Synthetic primer

<400> SEQUENCE: 642
cctgaacctt ccaaagatgg                                           20

<210> SEQ ID NO 643
<211> LENGTH: 20
<212> TYPE: DNA
<213> ORGANISM: Artificial Sequence
<220> FEATURE:
<223> OTHER INFORMATION: Synthetic primer

<400> SEQUENCE: 643
accaggcaag tctcctcatt                                           20

<210> SEQ ID NO 644
<211> LENGTH: 27
<212> TYPE: DNA
<213> ORGANISM: Artificial Sequence
<220> FEATURE:
<223> OTHER INFORMATION: Synthetic probe

<400> SEQUENCE: 644
ccagattgga agcatccatc tttttca                                   27

<210> SEQ ID NO 645
<211> LENGTH: 20
<212> TYPE: DNA
<213> ORGANISM: Artificial Sequence
<220> FEATURE:
<223> OTHER INFORMATION: Synthetic primer

<400> SEQUENCE: 645
ccgctccgtc actgatgtct                                           20

<210> SEQ ID NO 646
<211> LENGTH: 21
<212> TYPE: DNA
<213> ORGANISM: Artificial Sequence
<220> FEATURE:
<223> OTHER INFORMATION: Synthetic primer

<400> SEQUENCE: 646
gcaaggtcag ggcaaagagt a                                         21

<210> SEQ ID NO 647
<211> LENGTH: 24
<212> TYPE: DNA
<213> ORGANISM: Artificial Sequence
<220> FEATURE:
<223> OTHER INFORMATION: Synthetic probe

<400> SEQUENCE: 647
cctgctgaac ctagccttgg ccga                                      24

<210> SEQ ID NO 648
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 648
agccatcact ctcagtgcag                                              20

<210> SEQ ID NO 649
<211> LENGTH: 20
<212> TYPE: DNA
<213> ORGANISM: Artificial Sequence
<220> FEATURE:
<223> OTHER INFORMATION: Synthetic primer

<400> SEQUENCE: 649
actgcagagt cagggtctcc                                              20

<210> SEQ ID NO 650
<211> LENGTH: 22
<212> TYPE: DNA
<213> ORGANISM: Artificial Sequence
<220> FEATURE:
<223> OTHER INFORMATION: Synthetic probe

<400> SEQUENCE: 650
caggtcctat cgtggccct ga                                            22

<210> SEQ ID NO 651
<211> LENGTH: 19
<212> TYPE: DNA
<213> ORGANISM: Artificial Sequence
<220> FEATURE:
<223> OTHER INFORMATION: Synthetic primer

<400> SEQUENCE: 651
gaaagtgttt gcggagcac                                               19

<210> SEQ ID NO 652
<211> LENGTH: 18
<212> TYPE: DNA
<213> ORGANISM: Artificial Sequence
<220> FEATURE:
<223> OTHER INFORMATION: Synthetic primer

<400> SEQUENCE: 652
gaaggcgtag ccggattt                                                18

<210> SEQ ID NO 653
<211> LENGTH: 24
<212> TYPE: DNA
<213> ORGANISM: Artificial Sequence
<220> FEATURE:
<223> OTHER INFORMATION: Synthetic probe

<400> SEQUENCE: 653
ctcctacagc ggccagttct tggt                                         24

<210> SEQ ID NO 654
<211> LENGTH: 19
<212> TYPE: DNA
<213> ORGANISM: Artificial Sequence
<220> FEATURE:
<223> OTHER INFORMATION: Synthetic primer

<400> SEQUENCE: 654
```

```
gtgcccgagc catatagca                                              19

<210> SEQ ID NO 655
<211> LENGTH: 23
<212> TYPE: DNA
<213> ORGANISM: Artificial Sequence
<220> FEATURE:
<223> OTHER INFORMATION: Synthetic primer

<400> SEQUENCE: 655
cggtagtggt tgatgactgt tga                                         23

<210> SEQ ID NO 656
<211> LENGTH: 25
<212> TYPE: DNA
<213> ORGANISM: Artificial Sequence
<220> FEATURE:
<223> OTHER INFORMATION: Synthetic probe

<400> SEQUENCE: 656
acgtccgggt cctcactgtc cttcc                                       25

<210> SEQ ID NO 657
<211> LENGTH: 20
<212> TYPE: DNA
<213> ORGANISM: Artificial Sequence
<220> FEATURE:
<223> OTHER INFORMATION: Synthetic primer

<400> SEQUENCE: 657
ccatgatcct cactctgctg                                             20

<210> SEQ ID NO 658
<211> LENGTH: 20
<212> TYPE: DNA
<213> ORGANISM: Artificial Sequence
<220> FEATURE:
<223> OTHER INFORMATION: Synthetic primer

<400> SEQUENCE: 658
gaagctttgt agccggtgat                                             20

<210> SEQ ID NO 659
<211> LENGTH: 24
<212> TYPE: DNA
<213> ORGANISM: Artificial Sequence
<220> FEATURE:
<223> OTHER INFORMATION: Synthetic probe

<400> SEQUENCE: 659
cactccagac ctcgcttagc atgg                                        24

<210> SEQ ID NO 660
<211> LENGTH: 21
<212> TYPE: DNA
<213> ORGANISM: Artificial Sequence
<220> FEATURE:
<223> OTHER INFORMATION: Synthetic primer

<400> SEQUENCE: 660
caacgcttca gtgatcaatc c                                           21

<210> SEQ ID NO 661
<211> LENGTH: 18
<212> TYPE: DNA
<213> ORGANISM: Artificial Sequence
```

```
<220> FEATURE:
<223> OTHER INFORMATION: Synthetic primer

<400> SEQUENCE: 661
gtctggccgg gattcttt                                              18

<210> SEQ ID NO 662
<211> LENGTH: 24
<212> TYPE: DNA
<213> ORGANISM: Artificial Sequence
<220> FEATURE:
<223> OTHER INFORMATION: Synthetic probe

<400> SEQUENCE: 662
cgatcctgca tctgtaaatc gccc                                       24

<210> SEQ ID NO 663
<211> LENGTH: 20
<212> TYPE: DNA
<213> ORGANISM: Artificial Sequence
<220> FEATURE:
<223> OTHER INFORMATION: Synthetic primer

<400> SEQUENCE: 663
aggccagccc tacattatca                                            20

<210> SEQ ID NO 664
<211> LENGTH: 20
<212> TYPE: DNA
<213> ORGANISM: Artificial Sequence
<220> FEATURE:
<223> OTHER INFORMATION: Synthetic primer

<400> SEQUENCE: 664
gtcttctcca cagtccagca                                            20

<210> SEQ ID NO 665
<211> LENGTH: 24
<212> TYPE: DNA
<213> ORGANISM: Artificial Sequence
<220> FEATURE:
<223> OTHER INFORMATION: Synthetic probe

<400> SEQUENCE: 665
tctgagcctt gtcctctatc cggc                                       24

<210> SEQ ID NO 666
<211> LENGTH: 20
<212> TYPE: DNA
<213> ORGANISM: Artificial Sequence
<220> FEATURE:
<223> OTHER INFORMATION: Synthetic primer

<400> SEQUENCE: 666
cagtgacaaa cagcccttcc                                            20

<210> SEQ ID NO 667
<211> LENGTH: 19
<212> TYPE: DNA
<213> ORGANISM: Artificial Sequence
<220> FEATURE:
<223> OTHER INFORMATION: Synthetic primer

<400> SEQUENCE: 667
gtttagcctc atgggcgtc                                             19
```

```
<210> SEQ ID NO 668
<211> LENGTH: 24
<212> TYPE: DNA
<213> ORGANISM: Artificial Sequence
<220> FEATURE:
<223> OTHER INFORMATION: Synthetic probe

<400> SEQUENCE: 668
tcgccatctt ttgtgggatt cctt                                          24

<210> SEQ ID NO 669
<211> LENGTH: 22
<212> TYPE: DNA
<213> ORGANISM: Artificial Sequence
<220> FEATURE:
<223> OTHER INFORMATION: Synthetic primer

<400> SEQUENCE: 669
gatatgattg gtcgctgctt tg                                            22

<210> SEQ ID NO 670
<211> LENGTH: 21
<212> TYPE: DNA
<213> ORGANISM: Artificial Sequence
<220> FEATURE:
<223> OTHER INFORMATION: Synthetic primer

<400> SEQUENCE: 670
agaacttcca ttccccacca t                                             21

<210> SEQ ID NO 671
<211> LENGTH: 21
<212> TYPE: DNA
<213> ORGANISM: Artificial Sequence
<220> FEATURE:
<223> OTHER INFORMATION: Synthetic probe

<400> SEQUENCE: 671
cagccaggac ctggccatcc g                                             21

<210> SEQ ID NO 672
<211> LENGTH: 21
<212> TYPE: DNA
<213> ORGANISM: Artificial Sequence
<220> FEATURE:
<223> OTHER INFORMATION: Synthetic primer

<400> SEQUENCE: 672
actcggactg cacaagctat t                                             21

<210> SEQ ID NO 673
<211> LENGTH: 20
<212> TYPE: DNA
<213> ORGANISM: Artificial Sequence
<220> FEATURE:
<223> OTHER INFORMATION: Synthetic primer

<400> SEQUENCE: 673
tgccatcacc attgaaatct                                               20

<210> SEQ ID NO 674
<211> LENGTH: 24
<212> TYPE: DNA
<213> ORGANISM: Artificial Sequence
<220> FEATURE:
<223> OTHER INFORMATION: Synthetic probe
```

-continued

```
<400> SEQUENCE: 674
ccgacagcca cagaataacc caaa                                              24

<210> SEQ ID NO 675
<211> LENGTH: 20
<212> TYPE: DNA
<213> ORGANISM: Artificial Sequence
<220> FEATURE:
<223> OTHER INFORMATION: Synthetic primer

<400> SEQUENCE: 675
tcagaattgg atttggctca                                                   20

<210> SEQ ID NO 676
<211> LENGTH: 20
<212> TYPE: DNA
<213> ORGANISM: Artificial Sequence
<220> FEATURE:
<223> OTHER INFORMATION: Synthetic primer

<400> SEQUENCE: 676
cctgagctta gctggtgttg                                                   20

<210> SEQ ID NO 677
<211> LENGTH: 30
<212> TYPE: DNA
<213> ORGANISM: Artificial Sequence
<220> FEATURE:
<223> OTHER INFORMATION: Synthetic probe

<400> SEQUENCE: 677
tgctaatgta aggcatcaca gtcttttcca                                        30

<210> SEQ ID NO 678
<211> LENGTH: 19
<212> TYPE: DNA
<213> ORGANISM: Artificial Sequence
<220> FEATURE:
<223> OTHER INFORMATION: Synthetic primer

<400> SEQUENCE: 678
accggggagc cctacatga                                                    19

<210> SEQ ID NO 679
<211> LENGTH: 27
<212> TYPE: DNA
<213> ORGANISM: Artificial Sequence
<220> FEATURE:
<223> OTHER INFORMATION: Synthetic primer

<400> SEQUENCE: 679
ccttaagctc tttcactgac tcaatct                                           27

<210> SEQ ID NO 680
<211> LENGTH: 28
<212> TYPE: DNA
<213> ORGANISM: Artificial Sequence
<220> FEATURE:
<223> OTHER INFORMATION: Synthetic probe

<400> SEQUENCE: 680
aaatacctgc aaccgttact gccgtgac                                          28

<210> SEQ ID NO 681
```

```
<211> LENGTH: 18
<212> TYPE: DNA
<213> ORGANISM: Artificial Sequence
<220> FEATURE:
<223> OTHER INFORMATION: Synthetic primer

<400> SEQUENCE: 681
caaggtgccc tcagtgga                                              18

<210> SEQ ID NO 682
<211> LENGTH: 19
<212> TYPE: DNA
<213> ORGANISM: Artificial Sequence
<220> FEATURE:
<223> OTHER INFORMATION: Synthetic primer

<400> SEQUENCE: 682
gcgcacacct tcatctcat                                             19

<210> SEQ ID NO 683
<211> LENGTH: 24
<212> TYPE: DNA
<213> ORGANISM: Artificial Sequence
<220> FEATURE:
<223> OTHER INFORMATION: Synthetic probe

<400> SEQUENCE: 683
caccaacctg tacccgtatt gcga                                       24

<210> SEQ ID NO 684
<211> LENGTH: 20
<212> TYPE: DNA
<213> ORGANISM: Artificial Sequence
<220> FEATURE:
<223> OTHER INFORMATION: Synthetic primer

<400> SEQUENCE: 684
tcgtgaaaga tgaccaggag                                            20

<210> SEQ ID NO 685
<211> LENGTH: 20
<212> TYPE: DNA
<213> ORGANISM: Artificial Sequence
<220> FEATURE:
<223> OTHER INFORMATION: Synthetic primer

<400> SEQUENCE: 685
ggtgaacatc atgacgcagt                                            20

<210> SEQ ID NO 686
<211> LENGTH: 27
<212> TYPE: DNA
<213> ORGANISM: Artificial Sequence
<220> FEATURE:
<223> OTHER INFORMATION: Synthetic probe

<400> SEQUENCE: 686
tgctatgttt ctacaaaacc gccaagg                                    27

<210> SEQ ID NO 687
<211> LENGTH: 20
<212> TYPE: DNA
<213> ORGANISM: Artificial Sequence
<220> FEATURE:
<223> OTHER INFORMATION: Synthetic primer

<400> SEQUENCE: 687
```
gcaagaggaa aagcacatga                                               20

<210> SEQ ID NO 688
<211> LENGTH: 20
<212> TYPE: DNA
<213> ORGANISM: Artificial Sequence
<220> FEATURE:
<223> OTHER INFORMATION: Synthetic primer

<400> SEQUENCE: 688
ccttctgctg ttgctcacat                                               20

<210> SEQ ID NO 689
<211> LENGTH: 24
<212> TYPE: DNA
<213> ORGANISM: Artificial Sequence
<220> FEATURE:
<223> OTHER INFORMATION: Synthetic probe

<400> SEQUENCE: 689
tgctcaggca gtccctttac agca                                          24

<210> SEQ ID NO 690
<211> LENGTH: 20
<212> TYPE: DNA
<213> ORGANISM: Artificial Sequence
<220> FEATURE:
<223> OTHER INFORMATION: Synthetic primer

<400> SEQUENCE: 690
acaacgtctt gggaagatcc                                               20

<210> SEQ ID NO 691
<211> LENGTH: 20
<212> TYPE: DNA
<213> ORGANISM: Artificial Sequence
<220> FEATURE:
<223> OTHER INFORMATION: Synthetic primer

<400> SEQUENCE: 691
cagcagctct gtcacacaaa                                               20

<210> SEQ ID NO 692
<211> LENGTH: 24
<212> TYPE: DNA
<213> ORGANISM: Artificial Sequence
<220> FEATURE:
<223> OTHER INFORMATION: Synthetic probe

<400> SEQUENCE: 692
tgaacagaaa tggccatgca cgtt                                          24

<210> SEQ ID NO 693
<211> LENGTH: 20
<212> TYPE: DNA
<213> ORGANISM: Artificial Sequence
<220> FEATURE:
<223> OTHER INFORMATION: Synthetic primer

<400> SEQUENCE: 693
gtcaaaatgg ggagggacta                                               20

<210> SEQ ID NO 694
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 694
caggaccacc acagagtgag                                                   20

<210> SEQ ID NO 695
<211> LENGTH: 29
<212> TYPE: DNA
<213> ORGANISM: Artificial Sequence
<220> FEATURE:
<223> OTHER INFORMATION: Synthetic probe

<400> SEQUENCE: 695
tgtatcttgt tgagctatcc aaactgccc                                         29

<210> SEQ ID NO 696
<211> LENGTH: 20
<212> TYPE: DNA
<213> ORGANISM: Artificial Sequence
<220> FEATURE:
<223> OTHER INFORMATION: Synthetic primer

<400> SEQUENCE: 696
acgcgcttag ccctactatg                                                   20

<210> SEQ ID NO 697
<211> LENGTH: 20
<212> TYPE: DNA
<213> ORGANISM: Artificial Sequence
<220> FEATURE:
<223> OTHER INFORMATION: Synthetic primer

<400> SEQUENCE: 697
ctgagccatc gctttgacta                                                   20

<210> SEQ ID NO 698
<211> LENGTH: 24
<212> TYPE: DNA
<213> ORGANISM: Artificial Sequence
<220> FEATURE:
<223> OTHER INFORMATION: Synthetic probe

<400> SEQUENCE: 698
acagtcaagc aacacaggtg ccaa                                              24

<210> SEQ ID NO 699
<211> LENGTH: 20
<212> TYPE: DNA
<213> ORGANISM: Artificial Sequence
<220> FEATURE:
<223> OTHER INFORMATION: Synthetic primer

<400> SEQUENCE: 699
gaggacgaag gcctctacac                                                   20

<210> SEQ ID NO 700
<211> LENGTH: 20
<212> TYPE: DNA
<213> ORGANISM: Artificial Sequence
<220> FEATURE:
<223> OTHER INFORMATION: Synthetic primer

<400> SEQUENCE: 700
aaaaatgcct ccacttttgc                                                   20
```

```
<210> SEQ ID NO 701
<211> LENGTH: 24
<212> TYPE: DNA
<213> ORGANISM: Artificial Sequence
<220> FEATURE:
<223> OTHER INFORMATION: Synthetic probe

<400> SEQUENCE: 701
caggcatgca gtgttcttgg ctgt                                              24

<210> SEQ ID NO 702
<211> LENGTH: 19
<212> TYPE: DNA
<213> ORGANISM: Artificial Sequence
<220> FEATURE:
<223> OTHER INFORMATION: Synthetic primer

<400> SEQUENCE: 702
cggactttgg gtgcgactt                                                    19

<210> SEQ ID NO 703
<211> LENGTH: 24
<212> TYPE: DNA
<213> ORGANISM: Artificial Sequence
<220> FEATURE:
<223> OTHER INFORMATION: Synthetic primer

<400> SEQUENCE: 703
ttacaactct tccactggga cgat                                              24

<210> SEQ ID NO 704
<211> LENGTH: 23
<212> TYPE: DNA
<213> ORGANISM: Artificial Sequence
<220> FEATURE:
<223> OTHER INFORMATION: Synthetic probe

<400> SEQUENCE: 704
ccacttgtcg aaccaccgct cgt                                               23

<210> SEQ ID NO 705
<211> LENGTH: 24
<212> TYPE: DNA
<213> ORGANISM: Artificial Sequence
<220> FEATURE:
<223> OTHER INFORMATION: Synthetic primer

<400> SEQUENCE: 705
tgcaaaggta aaagtgatgg ttga                                              24

<210> SEQ ID NO 706
<211> LENGTH: 27
<212> TYPE: DNA
<213> ORGANISM: Artificial Sequence
<220> FEATURE:
<223> OTHER INFORMATION: Synthetic primer

<400> SEQUENCE: 706
ataaacaatg taggtgcaca cagaact                                           27

<210> SEQ ID NO 707
<211> LENGTH: 22
<212> TYPE: DNA
<213> ORGANISM: Artificial Sequence
<220> FEATURE:
```

<223> OTHER INFORMATION: Synthetic probe

<400> SEQUENCE: 707
tggctcgctt ccggtctcct ga                                             22

<210> SEQ ID NO 708
<211> LENGTH: 20
<212> TYPE: DNA
<213> ORGANISM: Artificial Sequence
<220> FEATURE:
<223> OTHER INFORMATION: Synthetic primer

<400> SEQUENCE: 708
atgtgccagt gagcttgagt                                                20

<210> SEQ ID NO 709
<211> LENGTH: 20
<212> TYPE: DNA
<213> ORGANISM: Artificial Sequence
<220> FEATURE:
<223> OTHER INFORMATION: Synthetic primer

<400> SEQUENCE: 709
tgagcccctg gttaacagta                                                20

<210> SEQ ID NO 710
<211> LENGTH: 24
<212> TYPE: DNA
<213> ORGANISM: Artificial Sequence
<220> FEATURE:
<223> OTHER INFORMATION: Synthetic probe

<400> SEQUENCE: 710
ccttggagaa acacaagcac ctgc                                           24

<210> SEQ ID NO 711
<211> LENGTH: 20
<212> TYPE: DNA
<213> ORGANISM: Artificial Sequence
<220> FEATURE:
<223> OTHER INFORMATION: Synthetic primer

<400> SEQUENCE: 711
ggcctgctga gatcaaagac                                                20

<210> SEQ ID NO 712
<211> LENGTH: 20
<212> TYPE: DNA
<213> ORGANISM: Artificial Sequence
<220> FEATURE:
<223> OTHER INFORMATION: Synthetic primer

<400> SEQUENCE: 712
gtccactgtg gctgtgagaa                                                20

<210> SEQ ID NO 713
<211> LENGTH: 26
<212> TYPE: DNA
<213> ORGANISM: Artificial Sequence
<220> FEATURE:
<223> OTHER INFORMATION: Synthetic probe

<400> SEQUENCE: 713
tgttcctcag gtcctcaatg gtcttg                                         26

```
<210> SEQ ID NO 714
<211> LENGTH: 20
<212> TYPE: DNA
<213> ORGANISM: Artificial Sequence
<220> FEATURE:
<223> OTHER INFORMATION: Synthetic primer

<400> SEQUENCE: 714
agagatcgag gctctcaagg                                                   20

<210> SEQ ID NO 715
<211> LENGTH: 20
<212> TYPE: DNA
<213> ORGANISM: Artificial Sequence
<220> FEATURE:
<223> OTHER INFORMATION: Synthetic primer

<400> SEQUENCE: 715
ggccttttac ttcctcttcg                                                   20

<210> SEQ ID NO 716
<211> LENGTH: 27
<212> TYPE: DNA
<213> ORGANISM: Artificial Sequence
<220> FEATURE:
<223> OTHER INFORMATION: Synthetic probe

<400> SEQUENCE: 716
tggttcttct tcatgaagag cagctcc                                           27

<210> SEQ ID NO 717
<211> LENGTH: 22
<212> TYPE: DNA
<213> ORGANISM: Artificial Sequence
<220> FEATURE:
<223> OTHER INFORMATION: Synthetic primer

<400> SEQUENCE: 717
aggttcaact aacggagctg ag                                                22

<210> SEQ ID NO 718
<211> LENGTH: 20
<212> TYPE: DNA
<213> ORGANISM: Artificial Sequence
<220> FEATURE:
<223> OTHER INFORMATION: Synthetic primer

<400> SEQUENCE: 718
gctgagatgg gactggagtt                                                   20

<210> SEQ ID NO 719
<211> LENGTH: 24
<212> TYPE: DNA
<213> ORGANISM: Artificial Sequence
<220> FEATURE:
<223> OTHER INFORMATION: Synthetic probe

<400> SEQUENCE: 719
cgcacctccc agagccttga gata                                              24

<210> SEQ ID NO 720
<211> LENGTH: 19
<212> TYPE: DNA
<213> ORGANISM: Artificial Sequence
<220> FEATURE:
<223> OTHER INFORMATION: Synthetic primer
```

```
<400> SEQUENCE: 720
agaacgagct gtgtctccg                                              19

<210> SEQ ID NO 721
<211> LENGTH: 18
<212> TYPE: DNA
<213> ORGANISM: Artificial Sequence
<220> FEATURE:
<223> OTHER INFORMATION: Synthetic primer

<400> SEQUENCE: 721
tcatccagga ctttccgc                                               18

<210> SEQ ID NO 722
<211> LENGTH: 24
<212> TYPE: DNA
<213> ORGANISM: Artificial Sequence
<220> FEATURE:
<223> OTHER INFORMATION: Synthetic probe

<400> SEQUENCE: 722
cattgatgtc agcctccacg ctct                                        24

<210> SEQ ID NO 723
<211> LENGTH: 20
<212> TYPE: DNA
<213> ORGANISM: Artificial Sequence
<220> FEATURE:
<223> OTHER INFORMATION: Synthetic primer

<400> SEQUENCE: 723
ctctgcctct tggagtttgg                                             20

<210> SEQ ID NO 724
<211> LENGTH: 20
<212> TYPE: DNA
<213> ORGANISM: Artificial Sequence
<220> FEATURE:
<223> OTHER INFORMATION: Synthetic primer

<400> SEQUENCE: 724
agctgacatc cttcccattc                                             20

<210> SEQ ID NO 725
<211> LENGTH: 26
<212> TYPE: DNA
<213> ORGANISM: Artificial Sequence
<220> FEATURE:
<223> OTHER INFORMATION: Synthetic probe

<400> SEQUENCE: 725
tcaccaggcc caaatcaaga agtagc                                      26

<210> SEQ ID NO 726
<211> LENGTH: 20
<212> TYPE: DNA
<213> ORGANISM: Artificial Sequence
<220> FEATURE:
<223> OTHER INFORMATION: Synthetic primer

<400> SEQUENCE: 726
tcagtggaga aggagttgga                                             20

<210> SEQ ID NO 727
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 727
tgccatatcc agaggaaaca                                                    20

<210> SEQ ID NO 728
<211> LENGTH: 28
<212> TYPE: DNA
<213> ORGANISM: Artificial Sequence
<220> FEATURE:
<223> OTHER INFORMATION: Synthetic probe

<400> SEQUENCE: 728
ccagtcaaca tctctgttgt cacaagca                                           28

<210> SEQ ID NO 729
<211> LENGTH: 26
<212> TYPE: DNA
<213> ORGANISM: Artificial Sequence
<220> FEATURE:
<223> OTHER INFORMATION: Synthetic primer

<400> SEQUENCE: 729
tcaaagtcag gtacgaagat gaaatt                                             26

<210> SEQ ID NO 730
<211> LENGTH: 22
<212> TYPE: DNA
<213> ORGANISM: Artificial Sequence
<220> FEATURE:
<223> OTHER INFORMATION: Synthetic primer

<400> SEQUENCE: 730
acgtcctttt tcagggctac aa                                                 22

<210> SEQ ID NO 731
<211> LENGTH: 26
<212> TYPE: DNA
<213> ORGANISM: Artificial Sequence
<220> FEATURE:
<223> OTHER INFORMATION: Synthetic probe

<400> SEQUENCE: 731
ttcattctca gcagctgtgc gcttgt                                             26

<210> SEQ ID NO 732
<211> LENGTH: 27
<212> TYPE: DNA
<213> ORGANISM: Artificial Sequence
<220> FEATURE:
<223> OTHER INFORMATION: Synthetic primer

<400> SEQUENCE: 732
ggatgaagct tacatgaaca aggtaga                                            27

<210> SEQ ID NO 733
<211> LENGTH: 25
<212> TYPE: DNA
<213> ORGANISM: Artificial Sequence
<220> FEATURE:
<223> OTHER INFORMATION: Synthetic primer

<400> SEQUENCE: 733
```

```
catatagctg cctgaggaag ttgat                                           25

<210> SEQ ID NO 734
<211> LENGTH: 21
<212> TYPE: DNA
<213> ORGANISM: Artificial Sequence
<220> FEATURE:
<223> OTHER INFORMATION: Synthetic probe

<400> SEQUENCE: 734
cgtcggtcag cccttccagg c                                               21

<210> SEQ ID NO 735
<211> LENGTH: 20
<212> TYPE: DNA
<213> ORGANISM: Artificial Sequence
<220> FEATURE:
<223> OTHER INFORMATION: Synthetic primer

<400> SEQUENCE: 735
cagatgaggc acatggagac                                                 20

<210> SEQ ID NO 736
<211> LENGTH: 20
<212> TYPE: DNA
<213> ORGANISM: Artificial Sequence
<220> FEATURE:
<223> OTHER INFORMATION: Synthetic primer

<400> SEQUENCE: 736
ttgaaatggc agaacggtag                                                 20

<210> SEQ ID NO 737
<211> LENGTH: 24
<212> TYPE: DNA
<213> ORGANISM: Artificial Sequence
<220> FEATURE:
<223> OTHER INFORMATION: Synthetic probe

<400> SEQUENCE: 737
ctgattcctc aggtccttgg cctg                                            24

<210> SEQ ID NO 738
<211> LENGTH: 19
<212> TYPE: DNA
<213> ORGANISM: Artificial Sequence
<220> FEATURE:
<223> OTHER INFORMATION: Synthetic primer

<400> SEQUENCE: 738
gatgcactgc ggttagcag                                                  19

<210> SEQ ID NO 739
<211> LENGTH: 20
<212> TYPE: DNA
<213> ORGANISM: Artificial Sequence
<220> FEATURE:
<223> OTHER INFORMATION: Synthetic primer

<400> SEQUENCE: 739
cagaggatac gctcagcacc                                                 20

<210> SEQ ID NO 740
<211> LENGTH: 24
<212> TYPE: DNA
<213> ORGANISM: Artificial Sequence
```

```
<220> FEATURE:
<223> OTHER INFORMATION: Synthetic probe

<400> SEQUENCE: 740
ctctccatcg aggaaggcaa atcc                                          24

<210> SEQ ID NO 741
<211> LENGTH: 18
<212> TYPE: DNA
<213> ORGANISM: Artificial Sequence
<220> FEATURE:
<223> OTHER INFORMATION: Synthetic primer

<400> SEQUENCE: 741
ctcctggcca acagcact                                                 18

<210> SEQ ID NO 742
<211> LENGTH: 18
<212> TYPE: DNA
<213> ORGANISM: Artificial Sequence
<220> FEATURE:
<223> OTHER INFORMATION: Synthetic primer

<400> SEQUENCE: 742
acacaaggcc cagcctct                                                 18

<210> SEQ ID NO 743
<211> LENGTH: 24
<212> TYPE: DNA
<213> ORGANISM: Artificial Sequence
<220> FEATURE:
<223> OTHER INFORMATION: Synthetic probe

<400> SEQUENCE: 743
ctgttcctgg agcatggcct cttc                                          24

<210> SEQ ID NO 744
<211> LENGTH: 21
<212> TYPE: DNA
<213> ORGANISM: Artificial Sequence
<220> FEATURE:
<223> OTHER INFORMATION: Synthetic primer

<400> SEQUENCE: 744
actcaagcgg aaattgaagc a                                             21

<210> SEQ ID NO 745
<211> LENGTH: 21
<212> TYPE: DNA
<213> ORGANISM: Artificial Sequence
<220> FEATURE:
<223> OTHER INFORMATION: Synthetic primer

<400> SEQUENCE: 745
actccctgaa gccgagacac t                                             21

<210> SEQ ID NO 746
<211> LENGTH: 28
<212> TYPE: DNA
<213> ORGANISM: Artificial Sequence
<220> FEATURE:
<223> OTHER INFORMATION: Synthetic probe

<400> SEQUENCE: 746
aggtcttatc agcacagtct ccgcctcc                                      28
```

```
<210> SEQ ID NO 747
<211> LENGTH: 19
<212> TYPE: DNA
<213> ORGANISM: Artificial Sequence
<220> FEATURE:
<223> OTHER INFORMATION: Synthetic primer

<400> SEQUENCE: 747
atttggtccc ggacagttc                                              19

<210> SEQ ID NO 748
<211> LENGTH: 20
<212> TYPE: DNA
<213> ORGANISM: Artificial Sequence
<220> FEATURE:
<223> OTHER INFORMATION: Synthetic primer

<400> SEQUENCE: 748
ccattggcgt aaaccttgaa                                             20

<210> SEQ ID NO 749
<211> LENGTH: 24
<212> TYPE: DNA
<213> ORGANISM: Artificial Sequence
<220> FEATURE:
<223> OTHER INFORMATION: Synthetic probe

<400> SEQUENCE: 749
caagccacag cgaatggaca gatc                                        24

<210> SEQ ID NO 750
<211> LENGTH: 21
<212> TYPE: DNA
<213> ORGANISM: Artificial Sequence
<220> FEATURE:
<223> OTHER INFORMATION: Synthetic primer

<400> SEQUENCE: 750
cacctggtct gggaagatac c                                           21

<210> SEQ ID NO 751
<211> LENGTH: 19
<212> TYPE: DNA
<213> ORGANISM: Artificial Sequence
<220> FEATURE:
<223> OTHER INFORMATION: Synthetic primer

<400> SEQUENCE: 751
aagagcagca ggacgaagg                                              19

<210> SEQ ID NO 752
<211> LENGTH: 24
<212> TYPE: DNA
<213> ORGANISM: Artificial Sequence
<220> FEATURE:
<223> OTHER INFORMATION: Synthetic probe

<400> SEQUENCE: 752
accgagaccc caatcaaaac ctcc                                        24

<210> SEQ ID NO 753
<211> LENGTH: 19
<212> TYPE: DNA
<213> ORGANISM: Artificial Sequence
<220> FEATURE:
<223> OTHER INFORMATION: Synthetic primer
```

<400> SEQUENCE: 753
tgcaaacgct ggtgtcaca                                          19

<210> SEQ ID NO 754
<211> LENGTH: 21
<212> TYPE: DNA
<213> ORGANISM: Artificial Sequence
<220> FEATURE:
<223> OTHER INFORMATION: Synthetic primer

<400> SEQUENCE: 754
ccccacgagt tctggttctt c                                       21

<210> SEQ ID NO 755
<211> LENGTH: 22
<212> TYPE: DNA
<213> ORGANISM: Artificial Sequence
<220> FEATURE:
<223> OTHER INFORMATION: Synthetic probe

<400> SEQUENCE: 755 cagccccca actgacctca tc                                       22

<210> SEQ ID NO 756
<211> LENGTH: 18
<212> TYPE: DNA
<213> ORGANISM: Artificial Sequence
<220> FEATURE:
<223> OTHER INFORMATION: Synthetic primer

<400> SEQUENCE: 756
ccaatgggag aacaacgg                                           18

<210> SEQ ID NO 757
<211> LENGTH: 19
<212> TYPE: DNA
<213> ORGANISM: Artificial Sequence
<220> FEATURE:
<223> OTHER INFORMATION: Synthetic primer

<400> SEQUENCE: 757
cgctgaggct ggtactgtg                                          19

<210> SEQ ID NO 758
<211> LENGTH: 24
<212> TYPE: DNA
<213> ORGANISM: Artificial Sequence
<220> FEATURE:
<223> OTHER INFORMATION: Synthetic probe

<400> SEQUENCE: 758
caggctcagc aagctgaaca cctg                                    24

<210> SEQ ID NO 759
<211> LENGTH: 19
<212> TYPE: DNA
<213> ORGANISM: Artificial Sequence
<220> FEATURE:
<223> OTHER INFORMATION: Synthetic primer

<400> SEQUENCE: 759
tcagcgggct cttaaacaa                                          19

<210> SEQ ID NO 760

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 760
aagacaggag ttgaccacgc                                              20

<210> SEQ ID NO 761
<211> LENGTH: 24
<212> TYPE: DNA
<213> ORGANISM: Artificial Sequence
<220> FEATURE:
<223> OTHER INFORMATION: Synthetic probe

<400> SEQUENCE: 761
cagctgtccc cgcagtaaag aagc                                         24

<210> SEQ ID NO 762
<211> LENGTH: 18
<212> TYPE: DNA
<213> ORGANISM: Artificial Sequence
<220> FEATURE:
<223> OTHER INFORMATION: Synthetic primer

<400> SEQUENCE: 762
ccgggagcag ggaatcac                                                18

<210> SEQ ID NO 763
<211> LENGTH: 20
<212> TYPE: DNA
<213> ORGANISM: Artificial Sequence
<220> FEATURE:
<223> OTHER INFORMATION: Synthetic primer

<400> SEQUENCE: 763
atgctgttga tgccgaatga                                              20

<210> SEQ ID NO 764
<211> LENGTH: 19
<212> TYPE: DNA
<213> ORGANISM: Artificial Sequence
<220> FEATURE:
<223> OTHER INFORMATION: Synthetic probe

<400> SEQUENCE: 764
cggccacgat ttcggcgct                                               19

<210> SEQ ID NO 765
<211> LENGTH: 23
<212> TYPE: DNA
<213> ORGANISM: Artificial Sequence
<220> FEATURE:
<223> OTHER INFORMATION: Synthetic primer

<400> SEQUENCE: 765
gctgcctttg gtaagaacat gtc                                          23

<210> SEQ ID NO 766
<211> LENGTH: 23
<212> TYPE: DNA
<213> ORGANISM: Artificial Sequence
<220> FEATURE:
<223> OTHER INFORMATION: Synthetic primer

<400> SEQUENCE: 766
```

```
atcccagcag tctcttcaca act                                            23

<210> SEQ ID NO 767
<211> LENGTH: 22
<212> TYPE: DNA
<213> ORGANISM: Artificial Sequence
<220> FEATURE:
<223> OTHER INFORMATION: Synthetic probe

<400> SEQUENCE: 767
tccatcttgc cattcacgcc gc                                             22

<210> SEQ ID NO 768
<211> LENGTH: 22
<212> TYPE: DNA
<213> ORGANISM: Artificial Sequence
<220> FEATURE:
<223> OTHER INFORMATION: Synthetic primer

<400> SEQUENCE: 768
ggacattact ggcctgttca ca                                             22

<210> SEQ ID NO 769
<211> LENGTH: 23
<212> TYPE: DNA
<213> ORGANISM: Artificial Sequence
<220> FEATURE:
<223> OTHER INFORMATION: Synthetic primer

<400> SEQUENCE: 769
accaatactc aggagcagga tga                                            23

<210> SEQ ID NO 770
<211> LENGTH: 23
<212> TYPE: DNA
<213> ORGANISM: Artificial Sequence
<220> FEATURE:
<223> OTHER INFORMATION: Synthetic probe

<400> SEQUENCE: 770
tgcattccag cctcccattt cca                                            23

<210> SEQ ID NO 771
<211> LENGTH: 20
<212> TYPE: DNA
<213> ORGANISM: Artificial Sequence
<220> FEATURE:
<223> OTHER INFORMATION: Synthetic primer

<400> SEQUENCE: 771
tccatcaagg ctttcgacta                                                20

<210> SEQ ID NO 772
<211> LENGTH: 20
<212> TYPE: DNA
<213> ORGANISM: Artificial Sequence
<220> FEATURE:
<223> OTHER INFORMATION: Synthetic primer

<400> SEQUENCE: 772
ctgctgcata aactcgtggt                                                20

<210> SEQ ID NO 773
<211> LENGTH: 22
<212> TYPE: DNA
```

```
<213> ORGANISM: Artificial Sequence
<220> FEATURE:
<223> OTHER INFORMATION: Synthetic probe

<400> SEQUENCE: 773
ctgcaggctg tacgccttct cg                                          22

<210> SEQ ID NO 774
<211> LENGTH: 19
<212> TYPE: DNA
<213> ORGANISM: Artificial Sequence
<220> FEATURE:
<223> OTHER INFORMATION: Synthetic primer

<400> SEQUENCE: 774
gttgggagct tgctgtgtc                                              19

<210> SEQ ID NO 775
<211> LENGTH: 20
<212> TYPE: DNA
<213> ORGANISM: Artificial Sequence
<220> FEATURE:
<223> OTHER INFORMATION: Synthetic primer

<400> SEQUENCE: 775
cacaaacagg aggtgaccct                                             20

<210> SEQ ID NO 776
<211> LENGTH: 24
<212> TYPE: DNA
<213> ORGANISM: Artificial Sequence
<220> FEATURE:
<223> OTHER INFORMATION: Synthetic probe

<400> SEQUENCE: 776
acctccaact gctgtgctgt ctgc                                        24

<210> SEQ ID NO 777
<211> LENGTH: 18
<212> TYPE: DNA
<213> ORGANISM: Artificial Sequence
<220> FEATURE:
<223> OTHER INFORMATION: Synthetic primer

<400> SEQUENCE: 777
attcggcagc ctcgttct                                               18

<210> SEQ ID NO 778
<211> LENGTH: 20
<212> TYPE: DNA
<213> ORGANISM: Artificial Sequence
<220> FEATURE:
<223> OTHER INFORMATION: Synthetic primer

<400> SEQUENCE: 778
agatgctgaa ggcatggaga                                             20

<210> SEQ ID NO 779
<211> LENGTH: 23
<212> TYPE: DNA
<213> ORGANISM: Artificial Sequence
<220> FEATURE:
<223> OTHER INFORMATION: Synthetic probe

<400> SEQUENCE: 779
cttcatcgcc acgctgctct aca                                         23
```

<210> SEQ ID NO 780
<211> LENGTH: 18
<212> TYPE: DNA
<213> ORGANISM: Artificial Sequence
<220> FEATURE:
<223> OTHER INFORMATION: Synthetic primer

<400> SEQUENCE: 780
cggaccacca ggtcagag                                                    18

<210> SEQ ID NO 781
<211> LENGTH: 20
<212> TYPE: DNA
<213> ORGANISM: Artificial Sequence
<220> FEATURE:
<223> OTHER INFORMATION: Synthetic primer

<400> SEQUENCE: 781 cagggggtagt gggtgttgag                                                  20

<210> SEQ ID NO 782
<211> LENGTH: 24
<212> TYPE: DNA
<213> ORGANISM: Artificial Sequence
<220> FEATURE:
<223> OTHER INFORMATION: Synthetic probe

<400> SEQUENCE: 782
ccactcttcc ctgctctgcg aatt                                              24

<210> SEQ ID NO 783
<211> LENGTH: 21
<212> TYPE: DNA
<213> ORGANISM: Artificial Sequence
<220> FEATURE:
<223> OTHER INFORMATION: Synthetic primer

<400> SEQUENCE: 783
gacttttgcc cgctaccttt c                                                 21

<210> SEQ ID NO 784
<211> LENGTH: 26
<212> TYPE: DNA
<213> ORGANISM: Artificial Sequence
<220> FEATURE:
<223> OTHER INFORMATION: Synthetic primer

<400> SEQUENCE: 784
gccactaact gcttcagtat gaagag                                            26

<210> SEQ ID NO 785
<211> LENGTH: 24
<212> TYPE: DNA
<213> ORGANISM: Artificial Sequence
<220> FEATURE:
<223> OTHER INFORMATION: Synthetic probe

<400> SEQUENCE: 785
acagctcatt gttgtcacgc cgga                                              24

<210> SEQ ID NO 786
<211> LENGTH: 19
<212> TYPE: DNA
<213> ORGANISM: Artificial Sequence
<220> FEATURE:

```
<223> OTHER INFORMATION: Synthetic primer

<400> SEQUENCE: 786
cgctcagcca gatgcaatc                                              19

<210> SEQ ID NO 787
<211> LENGTH: 25
<212> TYPE: DNA
<213> ORGANISM: Artificial Sequence
<220> FEATURE:
<223> OTHER INFORMATION: Synthetic primer

<400> SEQUENCE: 787
gcactgagat cttcctattg gtgaa                                       25

<210> SEQ ID NO 788
<211> LENGTH: 21
<212> TYPE: DNA
<213> ORGANISM: Artificial Sequence
<220> FEATURE:
<223> OTHER INFORMATION: Synthetic probe

<400> SEQUENCE: 788
tgccccagtc acctgctgtt a                                           21

<210> SEQ ID NO 789
<211> LENGTH: 19
<212> TYPE: DNA
<213> ORGANISM: Artificial Sequence
<220> FEATURE:
<223> OTHER INFORMATION: Synthetic primer

<400> SEQUENCE: 789
ctacagggac gccatcgaa                                              19

<210> SEQ ID NO 790
<211> LENGTH: 23
<212> TYPE: DNA
<213> ORGANISM: Artificial Sequence
<220> FEATURE:
<223> OTHER INFORMATION: Synthetic primer

<400> SEQUENCE: 790
atccaaccaa tcacctgaat gtt                                         23

<210> SEQ ID NO 791
<211> LENGTH: 23
<212> TYPE: DNA
<213> ORGANISM: Artificial Sequence
<220> FEATURE:
<223> OTHER INFORMATION: Synthetic probe

<400> SEQUENCE: 791
cttacaccag catcaagatc cgg                                         23

<210> SEQ ID NO 792
<211> LENGTH: 20
<212> TYPE: DNA
<213> ORGANISM: Artificial Sequence
<220> FEATURE:
<223> OTHER INFORMATION: Synthetic primer

<400> SEQUENCE: 792
ccatgatgga gaggcagaca                                             20
```

```
<210> SEQ ID NO 793
<211> LENGTH: 21
<212> TYPE: DNA
<213> ORGANISM: Artificial Sequence
<220> FEATURE:
<223> OTHER INFORMATION: Synthetic primer

<400> SEQUENCE: 793
ggagtccgtc cttaccgtca a                                         21

<210> SEQ ID NO 794
<211> LENGTH: 24
<212> TYPE: DNA
<213> ORGANISM: Artificial Sequence
<220> FEATURE:
<223> OTHER INFORMATION: Synthetic probe

<400> SEQUENCE: 794
ctgggagcat ggcgatggat accc                                      24

<210> SEQ ID NO 795
<211> LENGTH: 22
<212> TYPE: DNA
<213> ORGANISM: Artificial Sequence
<220> FEATURE:
<223> OTHER INFORMATION: Synthetic primer

<400> SEQUENCE: 795
tcatcctggc gatctacttc ct                                        22

<210> SEQ ID NO 796
<211> LENGTH: 20
<212> TYPE: DNA
<213> ORGANISM: Artificial Sequence
<220> FEATURE:
<223> OTHER INFORMATION: Synthetic primer

<400> SEQUENCE: 796
ccgttgagtg gaatcagcaa                                           20

<210> SEQ ID NO 797
<211> LENGTH: 26
<212> TYPE: DNA
<213> ORGANISM: Artificial Sequence
<220> FEATURE:
<223> OTHER INFORMATION: Synthetic probe

<400> SEQUENCE: 797
tctgtcctgg ctggagtcgc tttcat                                    26

<210> SEQ ID NO 798
<211> LENGTH: 20
<212> TYPE: DNA
<213> ORGANISM: Artificial Sequence
<220> FEATURE:
<223> OTHER INFORMATION: Synthetic primer

<400> SEQUENCE: 798
gatgcagaat tgaggcagac                                           20

<210> SEQ ID NO 799
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 799
tcttggcaag tcggttaaga                                              20

<210> SEQ ID NO 800
<211> LENGTH: 29
<212> TYPE: DNA
<213> ORGANISM: Artificial Sequence
<220> FEATURE:
<223> OTHER INFORMATION: Synthetic probe

<400> SEQUENCE: 800
caagaagatt tacttcgtcg attcccaga                                    29

<210> SEQ ID NO 801
<211> LENGTH: 19
<212> TYPE: DNA
<213> ORGANISM: Artificial Sequence
<220> FEATURE:
<223> OTHER INFORMATION: Synthetic primer

<400> SEQUENCE: 801
cccgctccca gatgtaaag                                               19

<210> SEQ ID NO 802
<211> LENGTH: 19
<212> TYPE: DNA
<213> ORGANISM: Artificial Sequence
<220> FEATURE:
<223> OTHER INFORMATION: Synthetic primer

<400> SEQUENCE: 802
ggtcacggtc agggttgta                                               19

<210> SEQ ID NO 803
<211> LENGTH: 24
<212> TYPE: DNA
<213> ORGANISM: Artificial Sequence
<220> FEATURE:
<223> OTHER INFORMATION: Synthetic probe

<400> SEQUENCE: 803
acgcgacttc cacaaacctg gatt                                         24

<210> SEQ ID NO 804
<211> LENGTH: 20
<212> TYPE: DNA
<213> ORGANISM: Artificial Sequence
<220> FEATURE:
<223> OTHER INFORMATION: Synthetic primer

<400> SEQUENCE: 804
ctatgagcca tgtgggaacc                                              20

<210> SEQ ID NO 805
<211> LENGTH: 18
<212> TYPE: DNA
<213> ORGANISM: Artificial Sequence
<220> FEATURE:
<223> OTHER INFORMATION: Synthetic primer

<400> SEQUENCE: 805
atgttggagt ggatgccg                                                18

<210> SEQ ID NO 806
<211> LENGTH: 24
```

```
<212> TYPE: DNA
<213> ORGANISM: Artificial Sequence
<220> FEATURE:
<223> OTHER INFORMATION: Synthetic probe

<400> SEQUENCE: 806
agcttcgaga cctgcaggac catc                                           24

<210> SEQ ID NO 807
<211> LENGTH: 20
<212> TYPE: DNA
<213> ORGANISM: Artificial Sequence
<220> FEATURE:
<223> OTHER INFORMATION: Synthetic primer

<400> SEQUENCE: 807
agtgtgcctg cgtctacaac                                                20

<210> SEQ ID NO 808
<211> LENGTH: 20
<212> TYPE: DNA
<213> ORGANISM: Artificial Sequence
<220> FEATURE:
<223> OTHER INFORMATION: Synthetic primer

<400> SEQUENCE: 808
agttggtgca gtctgtggag                                                20

<210> SEQ ID NO 809
<211> LENGTH: 21
<212> TYPE: DNA
<213> ORGANISM: Artificial Sequence
<220> FEATURE:
<223> OTHER INFORMATION: Synthetic probe

<400> SEQUENCE: 809
ctatgcccca ggggccacct a                                              21

<210> SEQ ID NO 810
<211> LENGTH: 19
<212> TYPE: DNA
<213> ORGANISM: Artificial Sequence
<220> FEATURE:
<223> OTHER INFORMATION: Synthetic primer

<400> SEQUENCE: 810
tgcccttgca ctgtcctaa                                                 19

<210> SEQ ID NO 811
<211> LENGTH: 18
<212> TYPE: DNA
<213> ORGANISM: Artificial Sequence
<220> FEATURE:
<223> OTHER INFORMATION: Synthetic primer

<400> SEQUENCE: 811
cagccacact catccacg                                                  18

<210> SEQ ID NO 812
<211> LENGTH: 24
<212> TYPE: DNA
<213> ORGANISM: Artificial Sequence
<220> FEATURE:
<223> OTHER INFORMATION: Synthetic probe

<400> SEQUENCE: 812
```
tcagccatcc tgcacaccta cacc                                            24

<210> SEQ ID NO 813
<211> LENGTH: 18
<212> TYPE: DNA
<213> ORGANISM: Artificial Sequence
<220> FEATURE:
<223> OTHER INFORMATION: Synthetic primer

<400> SEQUENCE: 813
caccttcggg tgcttctg                                                   18

<210> SEQ ID NO 814
<211> LENGTH: 19
<212> TYPE: DNA
<213> ORGANISM: Artificial Sequence
<220> FEATURE:
<223> OTHER INFORMATION: Synthetic primer

<400> SEQUENCE: 814
acgcaggtgt ggttattgg                                                  19

<210> SEQ ID NO 815
<211> LENGTH: 25
<212> TYPE: DNA
<213> ORGANISM: Artificial Sequence
<220> FEATURE:
<223> OTHER INFORMATION: Synthetic probe

<400> SEQUENCE: 815
aggtcattca ggaccgtacc ttccg                                           25

<210> SEQ ID NO 816
<211> LENGTH: 18
<212> TYPE: DNA
<213> ORGANISM: Artificial Sequence
<220> FEATURE:
<223> OTHER INFORMATION: Synthetic primer

<400> SEQUENCE: 816
gccgagatcg ccaagatg                                                   18

<210> SEQ ID NO 817
<211> LENGTH: 27
<212> TYPE: DNA
<213> ORGANISM: Artificial Sequence
<220> FEATURE:
<223> OTHER INFORMATION: Synthetic primer

<400> SEQUENCE: 817
cttttgatgg tagagttcca gtgattc                                         27

<210> SEQ ID NO 818
<211> LENGTH: 24
<212> TYPE: DNA
<213> ORGANISM: Artificial Sequence
<220> FEATURE:
<223> OTHER INFORMATION: Synthetic probe

<400> SEQUENCE: 818
cagcattgtc tgtcctccct ggca                                            24

<210> SEQ ID NO 819
<211> LENGTH: 19
<212> TYPE: DNA
<213> ORGANISM: Artificial Sequence

```
<220> FEATURE:
<223> OTHER INFORMATION: Synthetic primer

<400> SEQUENCE: 819
atgaaagtgc gcaaacagg                                                19

<210> SEQ ID NO 820
<211> LENGTH: 19
<212> TYPE: DNA
<213> ORGANISM: Artificial Sequence
<220> FEATURE:
<223> OTHER INFORMATION: Synthetic primer

<400> SEQUENCE: 820
agtgcctcag tgatgccag                                                19

<210> SEQ ID NO 821
<211> LENGTH: 23
<212> TYPE: DNA
<213> ORGANISM: Artificial Sequence
<220> FEATURE:
<223> OTHER INFORMATION: Synthetic probe

<400> SEQUENCE: 821
ctccgagaca tgccacgttt cct                                           23

<210> SEQ ID NO 822
<211> LENGTH: 19
<212> TYPE: DNA
<213> ORGANISM: Artificial Sequence
<220> FEATURE:
<223> OTHER INFORMATION: Synthetic primer

<400> SEQUENCE: 822
ctgccgggat ggcttctat                                                19

<210> SEQ ID NO 823
<211> LENGTH: 22
<212> TYPE: DNA
<213> ORGANISM: Artificial Sequence
<220> FEATURE:
<223> OTHER INFORMATION: Synthetic primer

<400> SEQUENCE: 823
ccaggttctg gaaactgtgg at                                            22

<210> SEQ ID NO 824
<211> LENGTH: 21
<212> TYPE: DNA
<213> ORGANISM: Artificial Sequence
<220> FEATURE:
<223> OTHER INFORMATION: Synthetic probe

<400> SEQUENCE: 824
ctgagctctg cccggaccgc t                                             21

<210> SEQ ID NO 825
<211> LENGTH: 20
<212> TYPE: DNA
<213> ORGANISM: Artificial Sequence
<220> FEATURE:
<223> OTHER INFORMATION: Synthetic primer

<400> SEQUENCE: 825
gagagagtga gcgaaccctg                                               20
```

```
<210> SEQ ID NO 826
<211> LENGTH: 18
<212> TYPE: DNA
<213> ORGANISM: Artificial Sequence
<220> FEATURE:
<223> OTHER INFORMATION: Synthetic primer

<400> SEQUENCE: 826
cgtcgcactg gagctctt                                                   18

<210> SEQ ID NO 827
<211> LENGTH: 24
<212> TYPE: DNA
<213> ORGANISM: Artificial Sequence
<220> FEATURE:
<223> OTHER INFORMATION: Synthetic probe

<400> SEQUENCE: 827
ccaggctcca agaagcagct gaag                                            24

<210> SEQ ID NO 828
<211> LENGTH: 19
<212> TYPE: DNA
<213> ORGANISM: Artificial Sequence
<220> FEATURE:
<223> OTHER INFORMATION: Synthetic primer

<400> SEQUENCE: 828
ccaaccctgc agactccaa                                                  19

<210> SEQ ID NO 829
<211> LENGTH: 28
<212> TYPE: DNA
<213> ORGANISM: Artificial Sequence
<220> FEATURE:
<223> OTHER INFORMATION: Synthetic primer

<400> SEQUENCE: 829
atgtataatg ttcctgccaa cttgtatg                                        28

<210> SEQ ID NO 830
<211> LENGTH: 25
<212> TYPE: DNA
<213> ORGANISM: Artificial Sequence
<220> FEATURE:
<223> OTHER INFORMATION: Synthetic probe

<400> SEQUENCE: 830
cctgggacca tccgtggaga cttct                                           25

<210> SEQ ID NO 831
<211> LENGTH: 21
<212> TYPE: DNA
<213> ORGANISM: Artificial Sequence
<220> FEATURE:
<223> OTHER INFORMATION: Synthetic primer

<400> SEQUENCE: 831
cacagcttgc ttgtcgatgt c                                               21

<210> SEQ ID NO 832
<211> LENGTH: 18
<212> TYPE: DNA
<213> ORGANISM: Artificial Sequence
<220> FEATURE:
<223> OTHER INFORMATION: Synthetic primer
```

```
<400> SEQUENCE: 832
atgccggtcg gtgatgag                                          18

<210> SEQ ID NO 833
<211> LENGTH: 21
<212> TYPE: DNA
<213> ORGANISM: Artificial Sequence
<220> FEATURE:
<223> OTHER INFORMATION: Synthetic probe

<400> SEQUENCE: 833
ccttcgcctg cctctctgcc c                                      21

<210> SEQ ID NO 834
<211> LENGTH: 20
<212> TYPE: DNA
<213> ORGANISM: Artificial Sequence
<220> FEATURE:
<223> OTHER INFORMATION: Synthetic primer

<400> SEQUENCE: 834
ctacagccta aacggcaagg                                        20

<210> SEQ ID NO 835
<211> LENGTH: 20
<212> TYPE: DNA
<213> ORGANISM: Artificial Sequence
<220> FEATURE:
<223> OTHER INFORMATION: Synthetic primer

<400> SEQUENCE: 835
gttcccttcg aacagctttg                                        20

<210> SEQ ID NO 836
<211> LENGTH: 20
<212> TYPE: DNA
<213> ORGANISM: Artificial Sequence
<220> FEATURE:
<223> OTHER INFORMATION: Synthetic probe

<400> SEQUENCE: 836
aggaccccag gacccagcag                                        20

<210> SEQ ID NO 837
<211> LENGTH: 23
<212> TYPE: DNA
<213> ORGANISM: Artificial Sequence
<220> FEATURE:
<223> OTHER INFORMATION: Synthetic primer

<400> SEQUENCE: 837
caaccgaagt tttcactcca gtt                                    23

<210> SEQ ID NO 838
<211> LENGTH: 25
<212> TYPE: DNA
<213> ORGANISM: Artificial Sequence
<220> FEATURE:
<223> OTHER INFORMATION: Synthetic primer

<400> SEQUENCE: 838
cctcagtcca taaaccacac tatca                                  25

<210> SEQ ID NO 839
```

```
<211> LENGTH: 28
<212> TYPE: DNA
<213> ORGANISM: Artificial Sequence
<220> FEATURE:
<223> OTHER INFORMATION: Synthetic probe

<400> SEQUENCE: 839
tccccacagt agacacatat gatggccg                                          28

<210> SEQ ID NO 840
<211> LENGTH: 19
<212> TYPE: DNA
<213> ORGANISM: Artificial Sequence
<220> FEATURE:
<223> OTHER INFORMATION: Synthetic primer

<400> SEQUENCE: 840
ccctcgtgct gatgctact                                                    19

<210> SEQ ID NO 841
<211> LENGTH: 22
<212> TYPE: DNA
<213> ORGANISM: Artificial Sequence
<220> FEATURE:
<223> OTHER INFORMATION: Synthetic primer

<400> SEQUENCE: 841
catcatgacc tggtcttcta gg                                                22

<210> SEQ ID NO 842
<211> LENGTH: 22
<212> TYPE: DNA
<213> ORGANISM: Artificial Sequence
<220> FEATURE:
<223> OTHER INFORMATION: Synthetic probe

<400> SEQUENCE: 842
ctgccctaga cgctggctcc tc                                                22

<210> SEQ ID NO 843
<211> LENGTH: 19
<212> TYPE: DNA
<213> ORGANISM: Artificial Sequence
<220> FEATURE:
<223> OTHER INFORMATION: Synthetic primer

<400> SEQUENCE: 843
ggtccctcca gaggatttg                                                    19

<210> SEQ ID NO 844
<211> LENGTH: 19
<212> TYPE: DNA
<213> ORGANISM: Artificial Sequence
<220> FEATURE:
<223> OTHER INFORMATION: Synthetic primer

<400> SEQUENCE: 844
cagcccctcc tctttcttc                                                    19

<210> SEQ ID NO 845
<211> LENGTH: 21
<212> TYPE: DNA
<213> ORGANISM: Artificial Sequence
<220> FEATURE:
<223> OTHER INFORMATION: Synthetic probe

<400> SEQUENCE: 845
```
aagagccccc tccgaccctg t                                21

<210> SEQ ID NO 846
<211> LENGTH: 21
<212> TYPE: DNA
<213> ORGANISM: Artificial Sequence
<220> FEATURE:
<223> OTHER INFORMATION: Synthetic primer

<400> SEQUENCE: 846
tggagactct cagggtcgaa a                                21

<210> SEQ ID NO 847
<211> LENGTH: 22
<212> TYPE: DNA
<213> ORGANISM: Artificial Sequence
<220> FEATURE:
<223> OTHER INFORMATION: Synthetic primer

<400> SEQUENCE: 847
ggcgtttgga gtggtagaaa tc                               22

<210> SEQ ID NO 848
<211> LENGTH: 20
<212> TYPE: DNA
<213> ORGANISM: Artificial Sequence
<220> FEATURE:
<223> OTHER INFORMATION: Synthetic probe

<400> SEQUENCE: 848
cggcggcaga ccagcatgac                                  20

<210> SEQ ID NO 849
<211> LENGTH: 20
<212> TYPE: DNA
<213> ORGANISM: Artificial Sequence
<220> FEATURE:
<223> OTHER INFORMATION: Synthetic primer

<400> SEQUENCE: 849
ctttgaaccc ttgcttgcaa                                  20

<210> SEQ ID NO 850
<211> LENGTH: 18
<212> TYPE: DNA
<213> ORGANISM: Artificial Sequence
<220> FEATURE:
<223> OTHER INFORMATION: Synthetic primer

<400> SEQUENCE: 850
cccgggacaa agcaaatg                                    18

<210> SEQ ID NO 851
<211> LENGTH: 25
<212> TYPE: DNA
<213> ORGANISM: Artificial Sequence
<220> FEATURE:
<223> OTHER INFORMATION: Synthetic probe

<400> SEQUENCE: 851
aagtcctggg tgcttctgac gcaca                            25

<210> SEQ ID NO 852
<211> LENGTH: 19
<212> TYPE: DNA

```
<213> ORGANISM: Artificial Sequence
<220> FEATURE:
<223> OTHER INFORMATION: Synthetic primer

<400> SEQUENCE: 852
ccgcaacgtg gttttctca                                                    19

<210> SEQ ID NO 853
<211> LENGTH: 21
<212> TYPE: DNA
<213> ORGANISM: Artificial Sequence
<220> FEATURE:
<223> OTHER INFORMATION: Synthetic primer

<400> SEQUENCE: 853
tgctgggttt ctcctcctgt t                                                 21

<210> SEQ ID NO 854
<211> LENGTH: 22
<212> TYPE: DNA
<213> ORGANISM: Artificial Sequence
<220> FEATURE:
<223> OTHER INFORMATION: Synthetic probe

<400> SEQUENCE: 854
ctcggtgttg gccatgctcc ag                                                22

<210> SEQ ID NO 855
<211> LENGTH: 22
<212> TYPE: DNA
<213> ORGANISM: Artificial Sequence
<220> FEATURE:
<223> OTHER INFORMATION: Synthetic primer

<400> SEQUENCE: 855
gaaggtgttg gaggcactca ag                                                22

<210> SEQ ID NO 856
<211> LENGTH: 21
<212> TYPE: DNA
<213> ORGANISM: Artificial Sequence
<220> FEATURE:
<223> OTHER INFORMATION: Synthetic primer

<400> SEQUENCE: 856
ggtttacacc gctggagcta a                                                 21

<210> SEQ ID NO 857
<211> LENGTH: 24
<212> TYPE: DNA
<213> ORGANISM: Artificial Sequence
<220> FEATURE:
<223> OTHER INFORMATION: Synthetic probe

<400> SEQUENCE: 857
atcccagcag gcctcgttga tgag                                              24

<210> SEQ ID NO 858
<211> LENGTH: 28
<212> TYPE: DNA
<213> ORGANISM: Artificial Sequence
<220> FEATURE:
<223> OTHER INFORMATION: Synthetic primer

<400> SEQUENCE: 858
agttactaaa aaataccacg aggtcctt                                          28
```

<210> SEQ ID NO 859
<211> LENGTH: 21
<212> TYPE: DNA
<213> ORGANISM: Artificial Sequence
<220> FEATURE:
<223> OTHER INFORMATION: Synthetic primer

<400> SEQUENCE: 859
gtcggtgagt gatttgtgca a                                        21

<210> SEQ ID NO 860
<211> LENGTH: 27
<212> TYPE: DNA
<213> ORGANISM: Artificial Sequence
<220> FEATURE:
<223> OTHER INFORMATION: Synthetic probe

<400> SEQUENCE: 860
ccctgacacc ggtctttggt ctcaact                                  27

<210> SEQ ID NO 861
<211> LENGTH: 20
<212> TYPE: DNA
<213> ORGANISM: Artificial Sequence
<220> FEATURE:
<223> OTHER INFORMATION: Synthetic primer

<400> SEQUENCE: 861
ccagctctcc ttccagctac                                          20

<210> SEQ ID NO 862
<211> LENGTH: 20
<212> TYPE: DNA
<213> ORGANISM: Artificial Sequence
<220> FEATURE:
<223> OTHER INFORMATION: Synthetic primer

<400> SEQUENCE: 862
gggtggctct cacttagctc                                          20

<210> SEQ ID NO 863
<211> LENGTH: 23
<212> TYPE: DNA
<213> ORGANISM: Artificial Sequence
<220> FEATURE:
<223> OTHER INFORMATION: Synthetic probe

<400> SEQUENCE: 863
tcaatgtccc tgtccgagtg ctg                                      23

<210> SEQ ID NO 864
<211> LENGTH: 24
<212> TYPE: DNA
<213> ORGANISM: Artificial Sequence
<220> FEATURE:
<223> OTHER INFORMATION: Synthetic primer

<400> SEQUENCE: 864
agagccagtt gctgtagaac tcaa                                     24

<210> SEQ ID NO 865
<211> LENGTH: 21
<212> TYPE: DNA
<213> ORGANISM: Artificial Sequence
<220> FEATURE:

<223> OTHER INFORMATION: Synthetic primer

<400> SEQUENCE: 865
ctgggcctac acagtccttc a                                               21

<210> SEQ ID NO 866
<211> LENGTH: 27
<212> TYPE: DNA
<213> ORGANISM: Artificial Sequence
<220> FEATURE:
<223> OTHER INFORMATION: Synthetic probe

<400> SEQUENCE: 866
tctctgctgg gcaaggatgt tctgttc                                         27

<210> SEQ ID NO 867
<211> LENGTH: 20
<212> TYPE: DNA
<213> ORGANISM: Artificial Sequence
<220> FEATURE:
<223> OTHER INFORMATION: Synthetic primer

<400> SEQUENCE: 867
gtgattgaag agcatgccaa                                                 20

<210> SEQ ID NO 868
<211> LENGTH: 18
<212> TYPE: DNA
<213> ORGANISM: Artificial Sequence
<220> FEATURE:
<223> OTHER INFORMATION: Synthetic primer

<400> SEQUENCE: 868
gtcctgcgtg ggaatagc                                                   18

<210> SEQ ID NO 869
<211> LENGTH: 24
<212> TYPE: DNA
<213> ORGANISM: Artificial Sequence
<220> FEATURE:
<223> OTHER INFORMATION: Synthetic probe

<400> SEQUENCE: 869
tcctgcttct cgggatacag acca                                            24

<210> SEQ ID NO 870
<211> LENGTH: 20
<212> TYPE: DNA
<213> ORGANISM: Artificial Sequence
<220> FEATURE:
<223> OTHER INFORMATION: Synthetic primer

<400> SEQUENCE: 870
ctccaccaag agcttcacct                                                 20

<210> SEQ ID NO 871
<211> LENGTH: 20
<212> TYPE: DNA
<213> ORGANISM: Artificial Sequence
<220> FEATURE:
<223> OTHER INFORMATION: Synthetic primer

<400> SEQUENCE: 871
ggtgctgaga acatggactg                                                 20

<210> SEQ ID NO 872
<211> LENGTH: 23
<212> TYPE: DNA
<213> ORGANISM: Artificial Sequence
<220> FEATURE:
<223> OTHER INFORMATION: Synthetic probe

<400> SEQUENCE: 872
cttcaactcc atgagcccgc tgt                                            23

<210> SEQ ID NO 873
<211> LENGTH: 20
<212> TYPE: DNA
<213> ORGANISM: Artificial Sequence
<220> FEATURE:
<223> OTHER INFORMATION: Synthetic primer

<400> SEQUENCE: 873
gatggtccag gactcacagc                                                20

<210> SEQ ID NO 874
<211> LENGTH: 18
<212> TYPE: DNA
<213> ORGANISM: Artificial Sequence
<220> FEATURE:
<223> OTHER INFORMATION: Synthetic primer

<400> SEQUENCE: 874
ccactgtgac gttgtcgc                                                  18

<210> SEQ ID NO 875
<211> LENGTH: 24
<212> TYPE: DNA
<213> ORGANISM: Artificial Sequence
<220> FEATURE:
<223> OTHER INFORMATION: Synthetic probe

<400> SEQUENCE: 875
cttgtggcag cctttcagga aacc                                           24

<210> SEQ ID NO 876
<211> LENGTH: 20
<212> TYPE: DNA
<213> ORGANISM: Artificial Sequence
<220> FEATURE:
<223> OTHER INFORMATION: Synthetic primer

<400> SEQUENCE: 876
gagcgcggtg aagagattgt                                                20

<210> SEQ ID NO 877
<211> LENGTH: 19
<212> TYPE: DNA
<213> ORGANISM: Artificial Sequence
<220> FEATURE:
<223> OTHER INFORMATION: Synthetic primer

<400> SEQUENCE: 877
cgctccacac aggctctca                                                 19

<210> SEQ ID NO 878
<211> LENGTH: 26
<212> TYPE: DNA
<213> ORGANISM: Artificial Sequence
<220> FEATURE:
<223> OTHER INFORMATION: Synthetic probe -continued

```
<400> SEQUENCE: 878
cacagcctcc aacgcagctt tcagaa                                          26

<210> SEQ ID NO 879
<211> LENGTH: 20
<212> TYPE: DNA
<213> ORGANISM: Artificial Sequence
<220> FEATURE:
<223> OTHER INFORMATION: Synthetic primer

<400> SEQUENCE: 879
cccatggatg ctcctctgaa                                                 20

<210> SEQ ID NO 880
<211> LENGTH: 20
<212> TYPE: DNA
<213> ORGANISM: Artificial Sequence
<220> FEATURE:
<223> OTHER INFORMATION: Synthetic primer

<400> SEQUENCE: 880
ccggtggcta ccagacattg                                                 20

<210> SEQ ID NO 881
<211> LENGTH: 22
<212> TYPE: DNA
<213> ORGANISM: Artificial Sequence
<220> FEATURE:
<223> OTHER INFORMATION: Synthetic probe

<400> SEQUENCE: 881
cattgactgc cgaggcccca tg                                              22

<210> SEQ ID NO 882
<211> LENGTH: 18
<212> TYPE: DNA
<213> ORGANISM: Artificial Sequence
<220> FEATURE:
<223> OTHER INFORMATION: Synthetic primer

<400> SEQUENCE: 882
gtggcccaat taggcttg                                                   18

<210> SEQ ID NO 883
<211> LENGTH: 18
<212> TYPE: DNA
<213> ORGANISM: Artificial Sequence
<220> FEATURE:
<223> OTHER INFORMATION: Synthetic primer

<400> SEQUENCE: 883
tcacaggtgc cagcaaag                                                   18

<210> SEQ ID NO 884
<211> LENGTH: 24
<212> TYPE: DNA
<213> ORGANISM: Artificial Sequence
<220> FEATURE:
<223> OTHER INFORMATION: Synthetic probe

<400> SEQUENCE: 884
ttctccatct ggcctcagag caga                                            24

<210> SEQ ID NO 885
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 885
ctcactgagt tcgccaagag                                          20

<210> SEQ ID NO 886
<211> LENGTH: 20
<212> TYPE: DNA
<213> ORGANISM: Artificial Sequence
<220> FEATURE:
<223> OTHER INFORMATION: Synthetic primer

<400> SEQUENCE: 886
agggtaacct ggtcgttgag                                          20

<210> SEQ ID NO 887
<211> LENGTH: 22
<212> TYPE: DNA
<213> ORGANISM: Artificial Sequence
<220> FEATURE:
<223> OTHER INFORMATION: Synthetic probe

<400> SEQUENCE: 887
ccccagcttc agcagcctct tc                                       22

<210> SEQ ID NO 888
<211> LENGTH: 21
<212> TYPE: DNA
<213> ORGANISM: Artificial Sequence
<220> FEATURE:
<223> OTHER INFORMATION: Synthetic primer

<400> SEQUENCE: 888
tgactttatg gagcccaagt t                                        21

<210> SEQ ID NO 889
<211> LENGTH: 20
<212> TYPE: DNA
<213> ORGANISM: Artificial Sequence
<220> FEATURE:
<223> OTHER INFORMATION: Synthetic primer

<400> SEQUENCE: 889
gccaagtcgc tgtcatctaa                                          20

<210> SEQ ID NO 890
<211> LENGTH: 25
<212> TYPE: DNA
<213> ORGANISM: Artificial Sequence
<220> FEATURE:
<223> OTHER INFORMATION: Synthetic probe

<400> SEQUENCE: 890
ttccagtgca ttgaacttca cagca                                    25

<210> SEQ ID NO 891
<211> LENGTH: 24
<212> TYPE: DNA
<213> ORGANISM: Artificial Sequence
<220> FEATURE:
<223> OTHER INFORMATION: Synthetic primer

<400> SEQUENCE: 891
```

```
ccaatacttc catgctgtct tcaa                                          24
```

<210> SEQ ID NO 892
<211> LENGTH: 20
<212> TYPE: DNA
<213> ORGANISM: Artificial Sequence
<220> FEATURE:
<223> OTHER INFORMATION: Synthetic primer

<400> SEQUENCE: 892

```
acatgggttc tccccatctg                                               20
```

<210> SEQ ID NO 893
<211> LENGTH: 23
<212> TYPE: DNA
<213> ORGANISM: Artificial Sequence
<220> FEATURE:
<223> OTHER INFORMATION: Synthetic probe

<400> SEQUENCE: 893

```
ccctgcttcc tgcacatctc cca                                           23
```

<210> SEQ ID NO 894
<211> LENGTH: 19
<212> TYPE: DNA
<213> ORGANISM: Artificial Sequence
<220> FEATURE:
<223> OTHER INFORMATION: Synthetic primer

<400> SEQUENCE: 894

```
gccctcccag tgtgcaaat                                                19
```

<210> SEQ ID NO 895
<211> LENGTH: 25
<212> TYPE: DNA
<213> ORGANISM: Artificial Sequence
<220> FEATURE:
<223> OTHER INFORMATION: Synthetic primer

<400> SEQUENCE: 895

```
cgtcgatggt attaggatag aagca                                         25
```

<210> SEQ ID NO 896
<211> LENGTH: 23
<212> TYPE: DNA
<213> ORGANISM: Artificial Sequence
<220> FEATURE:
<223> OTHER INFORMATION: Synthetic probe

<400> SEQUENCE: 896

```
tgctgtttcg acgacaccgt tcg                                           23
```

<210> SEQ ID NO 897
<211> LENGTH: 25
<212> TYPE: DNA
<213> ORGANISM: Artificial Sequence
<220> FEATURE:
<223> OTHER INFORMATION: Synthetic primer

<400> SEQUENCE: 897

```
tggctaagtg aagatgacaa tcatg                                         25
```

<210> SEQ ID NO 898
<211> LENGTH: 25
<212> TYPE: DNA
<213> ORGANISM: Artificial Sequence

```
<220> FEATURE:
<223> OTHER INFORMATION: Synthetic primer

<400> SEQUENCE: 898
tgcacatatc attacaccag ttcgt                                              25

<210> SEQ ID NO 899
<211> LENGTH: 29
<212> TYPE: DNA
<213> ORGANISM: Artificial Sequence
<220> FEATURE:
<223> OTHER INFORMATION: Synthetic probe

<400> SEQUENCE: 899
cctttccagc tttacagtga attgctgca                                          29

<210> SEQ ID NO 900
<211> LENGTH: 19
<212> TYPE: DNA
<213> ORGANISM: Artificial Sequence
<220> FEATURE:
<223> OTHER INFORMATION: Synthetic primer

<400> SEQUENCE: 900
gctcatacga gcaaagggc                                                     19

<210> SEQ ID NO 901
<211> LENGTH: 19
<212> TYPE: DNA
<213> ORGANISM: Artificial Sequence
<220> FEATURE:
<223> OTHER INFORMATION: Synthetic primer

<400> SEQUENCE: 901
tgatccacag gcagtgtcc                                                     19

<210> SEQ ID NO 902
<211> LENGTH: 24
<212> TYPE: DNA
<213> ORGANISM: Artificial Sequence
<220> FEATURE:
<223> OTHER INFORMATION: Synthetic probe

<400> SEQUENCE: 902
cgggccatat agtcccagtg tcca                                               24

<210> SEQ ID NO 903
<211> LENGTH: 20
<212> TYPE: DNA
<213> ORGANISM: Artificial Sequence
<220> FEATURE:
<223> OTHER INFORMATION: Synthetic primer

<400> SEQUENCE: 903
tggtctacga ttacgggtgc                                                    20

<210> SEQ ID NO 904
<211> LENGTH: 18
<212> TYPE: DNA
<213> ORGANISM: Artificial Sequence
<220> FEATURE:
<223> OTHER INFORMATION: Synthetic primer

<400> SEQUENCE: 904
aggcggagtt ggactggt                                                      18
```

<210> SEQ ID NO 905
<211> LENGTH: 24
<212> TYPE: DNA
<213> ORGANISM: Artificial Sequence
<220> FEATURE:
<223> OTHER INFORMATION: Synthetic probe

<400> SEQUENCE: 905
ctccatcgtc atgctcaacc agct                                          24

<210> SEQ ID NO 906
<211> LENGTH: 20
<212> TYPE: DNA
<213> ORGANISM: Artificial Sequence
<220> FEATURE:
<223> OTHER INFORMATION: Synthetic primer

<400> SEQUENCE: 906
cgtcgtatgc gagagtctgt                                               20

<210> SEQ ID NO 907
<211> LENGTH: 20
<212> TYPE: DNA
<213> ORGANISM: Artificial Sequence
<220> FEATURE:
<223> OTHER INFORMATION: Synthetic primer

<400> SEQUENCE: 907
tgaaggcgtg aggtgtagaa                                               20

<210> SEQ ID NO 908
<211> LENGTH: 26
<212> TYPE: DNA
<213> ORGANISM: Artificial Sequence
<220> FEATURE:
<223> OTHER INFORMATION: Synthetic probe

<400> SEQUENCE: 908
tccaggatgc ctgttagttc tcagca                                        26

<210> SEQ ID NO 909
<211> LENGTH: 19
<212> TYPE: DNA
<213> ORGANISM: Artificial Sequence
<220> FEATURE:
<223> OTHER INFORMATION: Synthetic primer

<400> SEQUENCE: 909
tgctaactcc tgcacagcc                                                19

<210> SEQ ID NO 910
<211> LENGTH: 20
<212> TYPE: DNA
<213> ORGANISM: Artificial Sequence
<220> FEATURE:
<223> OTHER INFORMATION: Synthetic primer

<400> SEQUENCE: 910
tgctaggttt cccctctgaa                                               20

<210> SEQ ID NO 911
<211> LENGTH: 25
<212> TYPE: DNA
<213> ORGANISM: Artificial Sequence
<220> FEATURE:
<223> OTHER INFORMATION: Synthetic probe

```
<400> SEQUENCE: 911
tcctcttcct ttctgctagc ctggc                                              25

<210> SEQ ID NO 912
<211> LENGTH: 19
<212> TYPE: DNA
<213> ORGANISM: Artificial Sequence
<220> FEATURE:
<223> OTHER INFORMATION: Synthetic primer

<400> SEQUENCE: 912
gcctgtgcag ttcttgtgc                                                     19

<210> SEQ ID NO 913
<211> LENGTH: 18
<212> TYPE: DNA
<213> ORGANISM: Artificial Sequence
<220> FEATURE:
<223> OTHER INFORMATION: Synthetic primer

<400> SEQUENCE: 913
ggaagggcag accctcac                                                      18

<210> SEQ ID NO 914
<211> LENGTH: 24
<212> TYPE: DNA
<213> ORGANISM: Artificial Sequence
<220> FEATURE:
<223> OTHER INFORMATION: Synthetic probe

<400> SEQUENCE: 914
aacatcagcg tggcctacag gctc                                               24

<210> SEQ ID NO 915
<211> LENGTH: 21
<212> TYPE: DNA
<213> ORGANISM: Artificial Sequence
<220> FEATURE:
<223> OTHER INFORMATION: Synthetic primer

<400> SEQUENCE: 915
aagcatgaac aggacttgac c                                                  21

<210> SEQ ID NO 916
<211> LENGTH: 18
<212> TYPE: DNA
<213> ORGANISM: Artificial Sequence
<220> FEATURE:
<223> OTHER INFORMATION: Synthetic primer

<400> SEQUENCE: 916
cctccccaag tcagttgc                                                      18

<210> SEQ ID NO 917
<211> LENGTH: 24
<212> TYPE: DNA
<213> ORGANISM: Artificial Sequence
<220> FEATURE:
<223> OTHER INFORMATION: Synthetic probe

<400> SEQUENCE: 917
ctttccaacc cctggggaag acat                                               24

<210> SEQ ID NO 918
```

```
<211> LENGTH: 23
<212> TYPE: DNA
<213> ORGANISM: Artificial Sequence
<220> FEATURE:
<223> OTHER INFORMATION: Synthetic primer

<400> SEQUENCE: 918
tcaacatcac agagggagat tca                                              23

<210> SEQ ID NO 919
<211> LENGTH: 21
<212> TYPE: DNA
<213> ORGANISM: Artificial Sequence
<220> FEATURE:
<223> OTHER INFORMATION: Synthetic primer

<400> SEQUENCE: 919
ggtggagtct tcgacctggt t                                                21

<210> SEQ ID NO 920
<211> LENGTH: 24
<212> TYPE: DNA
<213> ORGANISM: Artificial Sequence
<220> FEATURE:
<223> OTHER INFORMATION: Synthetic probe

<400> SEQUENCE: 920
ccagtccctg ggaccctctc gatc                                             24

<210> SEQ ID NO 921
<211> LENGTH: 18
<212> TYPE: DNA
<213> ORGANISM: Artificial Sequence
<220> FEATURE:
<223> OTHER INFORMATION: Synthetic primer

<400> SEQUENCE: 921
gatccgagac cctcgctc                                                    18

<210> SEQ ID NO 922
<211> LENGTH: 21
<212> TYPE: DNA
<213> ORGANISM: Artificial Sequence
<220> FEATURE:
<223> OTHER INFORMATION: Synthetic primer

<400> SEQUENCE: 922
aggaccaagg aatttaagcc a                                                21

<210> SEQ ID NO 923
<211> LENGTH: 23
<212> TYPE: DNA
<213> ORGANISM: Artificial Sequence
<220> FEATURE:
<223> OTHER INFORMATION: Synthetic probe

<400> SEQUENCE: 923
cccatcaacg tggagagctt gct                                              23

<210> SEQ ID NO 924
<211> LENGTH: 20
<212> TYPE: DNA
<213> ORGANISM: Artificial Sequence
<220> FEATURE:
<223> OTHER INFORMATION: Synthetic primer

<400> SEQUENCE: 924
```
gggctactgg cagctacatt                                              20

<210> SEQ ID NO 925
<211> LENGTH: 20
<212> TYPE: DNA
<213> ORGANISM: Artificial Sequence
<220> FEATURE:
<223> OTHER INFORMATION: Synthetic primer

<400> SEQUENCE: 925
ctctcagcat cggtacaagg                                              20

<210> SEQ ID NO 926
<211> LENGTH: 25
<212> TYPE: DNA
<213> ORGANISM: Artificial Sequence
<220> FEATURE:
<223> OTHER INFORMATION: Synthetic probe

<400> SEQUENCE: 926
cattggaatt gccattagtc ccagc                                        25

<210> SEQ ID NO 927
<211> LENGTH: 20
<212> TYPE: DNA
<213> ORGANISM: Artificial Sequence
<220> FEATURE:
<223> OTHER INFORMATION: Synthetic primer

<400> SEQUENCE: 927
cagcgggatt aaacagtcct                                              20

<210> SEQ ID NO 928
<211> LENGTH: 20
<212> TYPE: DNA
<213> ORGANISM: Artificial Sequence
<220> FEATURE:
<223> OTHER INFORMATION: Synthetic primer

<400> SEQUENCE: 928
atctgcgttg aagcagtgag                                              20

<210> SEQ ID NO 929
<211> LENGTH: 25
<212> TYPE: DNA
<213> ORGANISM: Artificial Sequence
<220> FEATURE:
<223> OTHER INFORMATION: Synthetic probe

<400> SEQUENCE: 929
ccagcacagc cagttaaaag atgca                                        25

<210> SEQ ID NO 930
<211> LENGTH: 20
<212> TYPE: DNA
<213> ORGANISM: Artificial Sequence
<220> FEATURE:
<223> OTHER INFORMATION: Synthetic primer

<400> SEQUENCE: 930
aacagagaca ttgccaacca                                              20

<210> SEQ ID NO 931
<211> LENGTH: 21
<212> TYPE: DNA

```
<213> ORGANISM: Artificial Sequence
<220> FEATURE:
<223> OTHER INFORMATION: Synthetic primer

<400> SEQUENCE: 931
gtgatttgcc caggaaagtt t                                              21

<210> SEQ ID NO 932
<211> LENGTH: 24
<212> TYPE: DNA
<213> ORGANISM: Artificial Sequence
<220> FEATURE:
<223> OTHER INFORMATION: Synthetic probe

<400> SEQUENCE: 932
ttggatctgc ttgctgtcca aacc                                           24

<210> SEQ ID NO 933
<211> LENGTH: 18
<212> TYPE: DNA
<213> ORGANISM: Artificial Sequence
<220> FEATURE:
<223> OTHER INFORMATION: Synthetic primer

<400> SEQUENCE: 933
cagcgtgagc tcctccac                                                  18

<210> SEQ ID NO 934
<211> LENGTH: 18
<212> TYPE: DNA
<213> ORGANISM: Artificial Sequence
<220> FEATURE:
<223> OTHER INFORMATION: Synthetic primer

<400> SEQUENCE: 934
atgctgggcg aggtactg                                                  18

<210> SEQ ID NO 935
<211> LENGTH: 24
<212> TYPE: DNA
<213> ORGANISM: Artificial Sequence
<220> FEATURE:
<223> OTHER INFORMATION: Synthetic probe

<400> SEQUENCE: 935
aagactggcc aaacagaacc ctgc                                           24

<210> SEQ ID NO 936
<211> LENGTH: 19
<212> TYPE: DNA
<213> ORGANISM: Artificial Sequence
<220> FEATURE:
<223> OTHER INFORMATION: Synthetic primer

<400> SEQUENCE: 936
tgggcgaggg aagagtttc                                                 19

<210> SEQ ID NO 937
<211> LENGTH: 19
<212> TYPE: DNA
<213> ORGANISM: Artificial Sequence
<220> FEATURE:
<223> OTHER INFORMATION: Synthetic primer

<400> SEQUENCE: 937
ccttgatggc tcggtggta                                                 19
```

```
<210> SEQ ID NO 938
<211> LENGTH: 27
<212> TYPE: DNA
<213> ORGANISM: Artificial Sequence
<220> FEATURE:
<223> OTHER INFORMATION: Synthetic probe

<400> SEQUENCE: 938
ccctgaccat cactgtgttc accaacc                                              27

<210> SEQ ID NO 939
<211> LENGTH: 21
<212> TYPE: DNA
<213> ORGANISM: Artificial Sequence
<220> FEATURE:
<223> OTHER INFORMATION: Synthetic primer

<400> SEQUENCE: 939
tggctgtgct ggtcactacc t                                                    21

<210> SEQ ID NO 940
<211> LENGTH: 22
<212> TYPE: DNA
<213> ORGANISM: Artificial Sequence
<220> FEATURE:
<223> OTHER INFORMATION: Synthetic primer

<400> SEQUENCE: 940
tcccccttac tcagcttgaa ct                                                   22

<210> SEQ ID NO 941
<211> LENGTH: 27
<212> TYPE: DNA
<213> ORGANISM: Artificial Sequence
<220> FEATURE:
<223> OTHER INFORMATION: Synthetic probe

<400> SEQUENCE: 941
cacaagtact cctgccaaga gggcgac                                              27

<210> SEQ ID NO 942
<211> LENGTH: 18
<212> TYPE: DNA
<213> ORGANISM: Artificial Sequence
<220> FEATURE:
<223> OTHER INFORMATION: Synthetic primer

<400> SEQUENCE: 942
gactgctgtc atggcgtg                                                        18

<210> SEQ ID NO 943
<211> LENGTH: 22
<212> TYPE: DNA
<213> ORGANISM: Artificial Sequence
<220> FEATURE:
<223> OTHER INFORMATION: Synthetic primer

<400> SEQUENCE: 943
cgagtacttg tggaaggtgg ac                                                   22

<210> SEQ ID NO 944
<211> LENGTH: 24
<212> TYPE: DNA
<213> ORGANISM: Artificial Sequence
<220> FEATURE:
```

<223> OTHER INFORMATION: Synthetic probe

<400> SEQUENCE: 944
atcacatcca gggccttctc caga				24

<210> SEQ ID NO 945
<211> LENGTH: 21
<212> TYPE: DNA
<213> ORGANISM: Artificial Sequence
<220> FEATURE:
<223> OTHER INFORMATION: Synthetic primer

<400> SEQUENCE: 945
cctgctgacg atgatgaagg a				21

<210> SEQ ID NO 946
<211> LENGTH: 21
<212> TYPE: DNA
<213> ORGANISM: Artificial Sequence
<220> FEATURE:
<223> OTHER INFORMATION: Synthetic primer

<400> SEQUENCE: 946
gcgaggtaat ttgtgccctt t				21

<210> SEQ ID NO 947
<211> LENGTH: 28
<212> TYPE: DNA
<213> ORGANISM: Artificial Sequence
<220> FEATURE:
<223> OTHER INFORMATION: Synthetic probe

<400> SEQUENCE: 947
ttccccaact tccttagtgc ctgtgaca				28

<210> SEQ ID NO 948
<211> LENGTH: 22
<212> TYPE: DNA
<213> ORGANISM: Artificial Sequence
<220> FEATURE:
<223> OTHER INFORMATION: Synthetic primer

<400> SEQUENCE: 948
actccctgat aaagggaat tt				22

<210> SEQ ID NO 949
<211> LENGTH: 21
<212> TYPE: DNA
<213> ORGANISM: Artificial Sequence
<220> FEATURE:
<223> OTHER INFORMATION: Synthetic primer

<400> SEQUENCE: 949
tgaggacact cggtctctag c				21

<210> SEQ ID NO 950
<211> LENGTH: 24
<212> TYPE: DNA
<213> ORGANISM: Artificial Sequence
<220> FEATURE:
<223> OTHER INFORMATION: Synthetic probe

<400> SEQUENCE: 950
catgccgtct acagggatga cctg				24

```
<210> SEQ ID NO 951
<211> LENGTH: 19
<212> TYPE: DNA
<213> ORGANISM: Artificial Sequence
<220> FEATURE:
<223> OTHER INFORMATION: Synthetic primer

<400> SEQUENCE: 951
caccctgcct ctacccaac                                                   19

<210> SEQ ID NO 952
<211> LENGTH: 18
<212> TYPE: DNA
<213> ORGANISM: Artificial Sequence
<220> FEATURE:
<223> OTHER INFORMATION: Synthetic primer

<400> SEQUENCE: 952
ctagccccac agccaaga                                                    18

<210> SEQ ID NO 953
<211> LENGTH: 23
<212> TYPE: DNA
<213> ORGANISM: Artificial Sequence
<220> FEATURE:
<223> OTHER INFORMATION: Synthetic probe

<400> SEQUENCE: 953
cccggggcct gttatgtcaa act                                              23

<210> SEQ ID NO 954
<211> LENGTH: 20
<212> TYPE: DNA
<213> ORGANISM: Artificial Sequence
<220> FEATURE:
<223> OTHER INFORMATION: Synthetic primer

<400> SEQUENCE: 954
gaaattgacg aggggtgtct                                                  20

<210> SEQ ID NO 955
<211> LENGTH: 20
<212> TYPE: DNA
<213> ORGANISM: Artificial Sequence
<220> FEATURE:
<223> OTHER INFORMATION: Synthetic primer

<400> SEQUENCE: 955
aggagctaac ggagaacctg                                                  20

<210> SEQ ID NO 956
<211> LENGTH: 22
<212> TYPE: DNA
<213> ORGANISM: Artificial Sequence
<220> FEATURE:
<223> OTHER INFORMATION: Synthetic probe

<400> SEQUENCE: 956
ctctgagcgc ctccatccaa gg                                               22

<210> SEQ ID NO 957
<211> LENGTH: 19
<212> TYPE: DNA
<213> ORGANISM: Artificial Sequence
<220> FEATURE:
<223> OTHER INFORMATION: Synthetic primer
```

```
<400> SEQUENCE: 957
ggtaccagcc tcgacacaa                                              19

<210> SEQ ID NO 958
<211> LENGTH: 21
<212> TYPE: DNA
<213> ORGANISM: Artificial Sequence
<220> FEATURE:
<223> OTHER INFORMATION: Synthetic primer

<400> SEQUENCE: 958
ccatctcgta agacattggg a                                           21

<210> SEQ ID NO 959
<211> LENGTH: 24
<212> TYPE: DNA
<213> ORGANISM: Artificial Sequence
<220> FEATURE:
<223> OTHER INFORMATION: Synthetic probe

<400> SEQUENCE: 959
tgcccactca gtgctgatca tgac                                        24

<210> SEQ ID NO 960
<211> LENGTH: 19
<212> TYPE: DNA
<213> ORGANISM: Artificial Sequence
<220> FEATURE:
<223> OTHER INFORMATION: Synthetic primer

<400> SEQUENCE: 960
caagctgaac ggtgtgtcc                                              19

<210> SEQ ID NO 961
<211> LENGTH: 19
<212> TYPE: DNA
<213> ORGANISM: Artificial Sequence
<220> FEATURE:
<223> OTHER INFORMATION: Synthetic primer

<400> SEQUENCE: 961
tgcaagctgt ctttgagcc                                              19

<210> SEQ ID NO 962
<211> LENGTH: 24
<212> TYPE: DNA
<213> ORGANISM: Artificial Sequence
<220> FEATURE:
<223> OTHER INFORMATION: Synthetic probe

<400> SEQUENCE: 962
cagcaccgat ttcttcaggt ccct                                        24

<210> SEQ ID NO 963
<211> LENGTH: 18
<212> TYPE: DNA
<213> ORGANISM: Artificial Sequence
<220> FEATURE:
<223> OTHER INFORMATION: Synthetic primer

<400> SEQUENCE: 963
tacaggatga ggctgggc                                               18

<210> SEQ ID NO 964
<211> LENGTH: 18
```

<212> TYPE: DNA
<213> ORGANISM: Artificial Sequence
<220> FEATURE:
<223> OTHER INFORMATION: Synthetic primer

<400> SEQUENCE: 964
gttgttaggg caagggggc                                          18

<210> SEQ ID NO 965
<211> LENGTH: 24
<212> TYPE: DNA
<213> ORGANISM: Artificial Sequence
<220> FEATURE:
<223> OTHER INFORMATION: Synthetic probe

<400> SEQUENCE: 965
cctgggacag cctatgtaag gcca                                    24

<210> SEQ ID NO 966
<211> LENGTH: 20
<212> TYPE: DNA
<213> ORGANISM: Artificial Sequence
<220> FEATURE:
<223> OTHER INFORMATION: Synthetic primer

<400> SEQUENCE: 966
aatgcctgca cccataattt                                         20

<210> SEQ ID NO 967
<211> LENGTH: 23
<212> TYPE: DNA
<213> ORGANISM: Artificial Sequence
<220> FEATURE:
<223> OTHER INFORMATION: Synthetic primer

<400> SEQUENCE: 967
tgagaactac aggcaaggat agg                                     23

<210> SEQ ID NO 968
<211> LENGTH: 28
<212> TYPE: DNA
<213> ORGANISM: Artificial Sequence
<220> FEATURE:
<223> OTHER INFORMATION: Synthetic probe

<400> SEQUENCE: 968
gccacgacca atttattaac agtcaggg                                28

<210> SEQ ID NO 969
<211> LENGTH: 20
<212> TYPE: DNA
<213> ORGANISM: Artificial Sequence
<220> FEATURE:
<223> OTHER INFORMATION: Synthetic primer

<400> SEQUENCE: 969
aacggactcc ctcaatttgt                                         20

<210> SEQ ID NO 970
<211> LENGTH: 20
<212> TYPE: DNA
<213> ORGANISM: Artificial Sequence
<220> FEATURE:
<223> OTHER INFORMATION: Synthetic primer

<400> SEQUENCE: 970
gaaattgcag ggtccaagat                                          20

<210> SEQ ID NO 971
<211> LENGTH: 24
<212> TYPE: DNA
<213> ORGANISM: Artificial Sequence
<220> FEATURE:
<223> OTHER INFORMATION: Synthetic probe

<400> SEQUENCE: 971
tgtccatggt catgcaaatc ttgc                                     24

<210> SEQ ID NO 972
<211> LENGTH: 20
<212> TYPE: DNA
<213> ORGANISM: Artificial Sequence
<220> FEATURE:
<223> OTHER INFORMATION: Synthetic primer

<400> SEQUENCE: 972
agctggggtg tctgtttcat                                          20

<210> SEQ ID NO 973
<211> LENGTH: 20
<212> TYPE: DNA
<213> ORGANISM: Artificial Sequence
<220> FEATURE:
<223> OTHER INFORMATION: Synthetic primer

<400> SEQUENCE: 973
acagcaaggc gagcataaat                                          20

<210> SEQ ID NO 974
<211> LENGTH: 23
<212> TYPE: DNA
<213> ORGANISM: Artificial Sequence
<220> FEATURE:
<223> OTHER INFORMATION: Synthetic probe

<400> SEQUENCE: 974
cctgacttca ggtcaaggga tgg                                      23

<210> SEQ ID NO 975
<211> LENGTH: 23
<212> TYPE: DNA
<213> ORGANISM: Artificial Sequence
<220> FEATURE:
<223> OTHER INFORMATION: Synthetic primer

<400> SEQUENCE: 975
agttgcagaa tctaagcctg gaa                                      23

<210> SEQ ID NO 976
<211> LENGTH: 25
<212> TYPE: DNA
<213> ORGANISM: Artificial Sequence
<220> FEATURE:
<223> OTHER INFORMATION: Synthetic primer

<400> SEQUENCE: 976
tgagtttttt gcgagagtat tgaca                                    25

<210> SEQ ID NO 977
<211> LENGTH: 20
<212> TYPE: DNA
<213> ORGANISM: Artificial Sequence

```
<220> FEATURE:
<223> OTHER INFORMATION: Synthetic probe

<400> SEQUENCE: 977
cctgcggctt tcggatccca                                              20

<210> SEQ ID NO 978
<211> LENGTH: 20
<212> TYPE: DNA
<213> ORGANISM: Artificial Sequence
<220> FEATURE:
<223> OTHER INFORMATION: Synthetic primer

<400> SEQUENCE: 978
tcctgctgca actggtattc                                              20

<210> SEQ ID NO 979
<211> LENGTH: 20
<212> TYPE: DNA
<213> ORGANISM: Artificial Sequence
<220> FEATURE:
<223> OTHER INFORMATION: Synthetic primer

<400> SEQUENCE: 979
ctttgggtat ggctgactga                                              20

<210> SEQ ID NO 980
<211> LENGTH: 25
<212> TYPE: DNA
<213> ORGANISM: Artificial Sequence
<220> FEATURE:
<223> OTHER INFORMATION: Synthetic probe

<400> SEQUENCE: 980
tcacctgaga tatttgctcc agcca                                        25

<210> SEQ ID NO 981
<211> LENGTH: 20
<212> TYPE: DNA
<213> ORGANISM: Artificial Sequence
<220> FEATURE:
<223> OTHER INFORMATION: Synthetic primer

<400> SEQUENCE: 981
tctgccagtg ctgaattctt                                              20

<210> SEQ ID NO 982
<211> LENGTH: 20
<212> TYPE: DNA
<213> ORGANISM: Artificial Sequence
<220> FEATURE:
<223> OTHER INFORMATION: Synthetic primer

<400> SEQUENCE: 982
ttcgaacctt agcagcttcc                                              20

<210> SEQ ID NO 983
<211> LENGTH: 24
<212> TYPE: DNA
<213> ORGANISM: Artificial Sequence
<220> FEATURE:
<223> OTHER INFORMATION: Synthetic probe

<400> SEQUENCE: 983
tgctgacatt gccctggctc ctat                                         24
```

```
<210> SEQ ID NO 984
<211> LENGTH: 20
<212> TYPE: DNA
<213> ORGANISM: Artificial Sequence
<220> FEATURE:
<223> OTHER INFORMATION: Synthetic primer

<400> SEQUENCE: 984
tcccttggag ctgcatacta                                              20

<210> SEQ ID NO 985
<211> LENGTH: 20
<212> TYPE: DNA
<213> ORGANISM: Artificial Sequence
<220> FEATURE:
<223> OTHER INFORMATION: Synthetic primer

<400> SEQUENCE: 985
tgtgtggatc cctgctgtat                                              20

<210> SEQ ID NO 986
<211> LENGTH: 30
<212> TYPE: DNA
<213> ORGANISM: Artificial Sequence
<220> FEATURE:
<223> OTHER INFORMATION: Synthetic probe

<400> SEQUENCE: 986
aaaaattgaa ttgcactgca gtcaatcact                                   30

<210> SEQ ID NO 987
<211> LENGTH: 18
<212> TYPE: DNA
<213> ORGANISM: Artificial Sequence
<220> FEATURE:
<223> OTHER INFORMATION: Synthetic primer

<400> SEQUENCE: 987
agtcggtcaa ccagggct                                                18

<210> SEQ ID NO 988
<211> LENGTH: 18
<212> TYPE: DNA
<213> ORGANISM: Artificial Sequence
<220> FEATURE:
<223> OTHER INFORMATION: Synthetic primer

<400> SEQUENCE: 988
aagctcatgc ggatggtg                                                18

<210> SEQ ID NO 989
<211> LENGTH: 24
<212> TYPE: DNA
<213> ORGANISM: Artificial Sequence
<220> FEATURE:
<223> OTHER INFORMATION: Synthetic probe

<400> SEQUENCE: 989
tgaggctgtc taccagttga cccg                                         24

<210> SEQ ID NO 990
<211> LENGTH: 19
<212> TYPE: DNA
<213> ORGANISM: Artificial Sequence
<220> FEATURE:
<223> OTHER INFORMATION: Synthetic primer
```

```
<400> SEQUENCE: 990
ggctggccaa acataagca                                                    19

<210> SEQ ID NO 991
<211> LENGTH: 26
<212> TYPE: DNA
<213> ORGANISM: Artificial Sequence
<220> FEATURE:
<223> OTHER INFORMATION: Synthetic primer

<400> SEQUENCE: 991
tccttgtcac agtatttaca gctgaa                                            26

<210> SEQ ID NO 992
<211> LENGTH: 29
<212> TYPE: DNA
<213> ORGANISM: Artificial Sequence
<220> FEATURE:
<223> OTHER INFORMATION: Synthetic probe

<400> SEQUENCE: 992
ctgcactgcg atgcccagtc tagaaaatc                                         29

<210> SEQ ID NO 993
<211> LENGTH: 23
<212> TYPE: DNA
<213> ORGANISM: Artificial Sequence
<220> FEATURE:
<223> OTHER INFORMATION: Synthetic primer

<400> SEQUENCE: 993
tcttccctgt acactggcag ttc                                               23

<210> SEQ ID NO 994
<211> LENGTH: 20
<212> TYPE: DNA
<213> ORGANISM: Artificial Sequence
<220> FEATURE:
<223> OTHER INFORMATION: Synthetic primer

<400> SEQUENCE: 994
agctcggtgt gggagaggta                                                   20

<210> SEQ ID NO 995
<211> LENGTH: 22
<212> TYPE: DNA
<213> ORGANISM: Artificial Sequence
<220> FEATURE:
<223> OTHER INFORMATION: Synthetic probe

<400> SEQUENCE: 995
tggaccagca ccccattgac gg                                                22

<210> SEQ ID NO 996
<211> LENGTH: 20
<212> TYPE: DNA
<213> ORGANISM: Artificial Sequence
<220> FEATURE:
<223> OTHER INFORMATION: Synthetic primer

<400> SEQUENCE: 996
ccatccgcca gtattacaag                                                   20

<210> SEQ ID NO 997
```

```
<211> LENGTH: 19
<212> TYPE: DNA
<213> ORGANISM: Artificial Sequence
<220> FEATURE:
<223> OTHER INFORMATION: Synthetic primer

<400> SEQUENCE: 997
gggtgcacga actggtaga                                                  19

<210> SEQ ID NO 998
<211> LENGTH: 24
<212> TYPE: DNA
<213> ORGANISM: Artificial Sequence
<220> FEATURE:
<223> OTHER INFORMATION: Synthetic probe

<400> SEQUENCE: 998
atcatccgga agccagacat ctcc                                            24

<210> SEQ ID NO 999
<211> LENGTH: 20
<212> TYPE: DNA
<213> ORGANISM: Artificial Sequence
<220> FEATURE:
<223> OTHER INFORMATION: Synthetic primer

<400> SEQUENCE: 999
atttgttccc acaaccaagg                                                 20

<210> SEQ ID NO 1000
<211> LENGTH: 20
<212> TYPE: DNA
<213> ORGANISM: Artificial Sequence
<220> FEATURE:
<223> OTHER INFORMATION: Synthetic primer

<400> SEQUENCE: 1000
cctggctctg gaatctttgt                                                 20

<210> SEQ ID NO 1001
<211> LENGTH: 24
<212> TYPE: DNA
<213> ORGANISM: Artificial Sequence
<220> FEATURE:
<223> OTHER INFORMATION: Synthetic probe

<400> SEQUENCE: 1001
ccatgccact caaaggttcc acaa                                            24

<210> SEQ ID NO 1002
<211> LENGTH: 20
<212> TYPE: DNA
<213> ORGANISM: Artificial Sequence
<220> FEATURE:
<223> OTHER INFORMATION: Synthetic primer

<400> SEQUENCE: 1002
gggctcagct ttcagaagtg                                                 20

<210> SEQ ID NO 1003
<211> LENGTH: 20
<212> TYPE: DNA
<213> ORGANISM: Artificial Sequence
<220> FEATURE:
<223> OTHER INFORMATION: Synthetic primer

<400> SEQUENCE: 1003
```

```
acatgttcag ctggtccaca                                                20

<210> SEQ ID NO 1004
<211> LENGTH: 25
<212> TYPE: DNA
<213> ORGANISM: Artificial Sequence
<220> FEATURE:
<223> OTHER INFORMATION: Synthetic probe

<400> SEQUENCE: 1004
tggcagtttt cttctgtcac caaaa                                          25

<210> SEQ ID NO 1005
<211> LENGTH: 20
<212> TYPE: DNA
<213> ORGANISM: Artificial Sequence
<220> FEATURE:
<223> OTHER INFORMATION: Synthetic primer

<400> SEQUENCE: 1005
ccagtggtgg tgatcgttca                                                20

<210> SEQ ID NO 1006
<211> LENGTH: 21
<212> TYPE: DNA
<213> ORGANISM: Artificial Sequence
<220> FEATURE:
<223> OTHER INFORMATION: Synthetic primer

<400> SEQUENCE: 1006
gcaaaagcat tgtcccagag a                                              21

<210> SEQ ID NO 1007
<211> LENGTH: 23
<212> TYPE: DNA
<213> ORGANISM: Artificial Sequence
<220> FEATURE:
<223> OTHER INFORMATION: Synthetic probe

<400> SEQUENCE: 1007
cagccaggac aacaatgcga cgg                                            23

<210> SEQ ID NO 1008
<211> LENGTH: 19
<212> TYPE: DNA
<213> ORGANISM: Artificial Sequence
<220> FEATURE:
<223> OTHER INFORMATION: Synthetic primer

<400> SEQUENCE: 1008
ctccgaggtg aggaggact                                                 19

<210> SEQ ID NO 1009
<211> LENGTH: 20
<212> TYPE: DNA
<213> ORGANISM: Artificial Sequence
<220> FEATURE:
<223> OTHER INFORMATION: Synthetic primer

<400> SEQUENCE: 1009
acctctccct ggttatgcac                                                20

<210> SEQ ID NO 1010
<211> LENGTH: 24
<212> TYPE: DNA
```

```
<213> ORGANISM: Artificial Sequence
<220> FEATURE:
<223> OTHER INFORMATION: Synthetic probe

<400> SEQUENCE: 1010
cacatcaaac gcacatccca tgag                                               24

<210> SEQ ID NO 1011
<211> LENGTH: 20
<212> TYPE: DNA
<213> ORGANISM: Artificial Sequence
<220> FEATURE:
<223> OTHER INFORMATION: Synthetic primer

<400> SEQUENCE: 1011
catcttccag gaggaccact                                                    20

<210> SEQ ID NO 1012
<211> LENGTH: 20
<212> TYPE: DNA
<213> ORGANISM: Artificial Sequence
<220> FEATURE:
<223> OTHER INFORMATION: Synthetic primer

<400> SEQUENCE: 1012
tccgaccttc aatcatttca                                                    20

<210> SEQ ID NO 1013
<211> LENGTH: 24
<212> TYPE: DNA
<213> ORGANISM: Artificial Sequence
<220> FEATURE:
<223> OTHER INFORMATION: Synthetic probe

<400> SEQUENCE: 1013
ctctgtggca ccctggacta cctg                                               24

<210> SEQ ID NO 1014
<211> LENGTH: 20
<212> TYPE: DNA
<213> ORGANISM: Artificial Sequence
<220> FEATURE:
<223> OTHER INFORMATION: Synthetic primer

<400> SEQUENCE: 1014
gagccatctt cctgcaactt                                                    20

<210> SEQ ID NO 1015
<211> LENGTH: 19
<212> TYPE: DNA
<213> ORGANISM: Artificial Sequence
<220> FEATURE:
<223> OTHER INFORMATION: Synthetic primer

<400> SEQUENCE: 1015
ctgaggtgca acccagtca                                                     19

<210> SEQ ID NO 1016
<211> LENGTH: 24
<212> TYPE: DNA
<213> ORGANISM: Artificial Sequence
<220> FEATURE:
<223> OTHER INFORMATION: Synthetic probe

<400> SEQUENCE: 1016
acctctttcc ctcagatggg gagc                                               24
```

```
<210> SEQ ID NO 1017
<211> LENGTH: 20
<212> TYPE: DNA
<213> ORGANISM: Artificial Sequence
<220> FEATURE:
<223> OTHER INFORMATION: Synthetic primer

<400> SEQUENCE: 1017
cctggaggct gcaacatacc                                                    20

<210> SEQ ID NO 1018
<211> LENGTH: 23
<212> TYPE: DNA
<213> ORGANISM: Artificial Sequence
<220> FEATURE:
<223> OTHER INFORMATION: Synthetic primer

<400> SEQUENCE: 1018
tacaatggct ttggaggata gca                                                23

<210> SEQ ID NO 1019
<211> LENGTH: 25
<212> TYPE: DNA
<213> ORGANISM: Artificial Sequence
<220> FEATURE:
<223> OTHER INFORMATION: Synthetic probe

<400> SEQUENCE: 1019
atcctcctga agccctttc gcagc                                               25

<210> SEQ ID NO 1020
<211> LENGTH: 20
<212> TYPE: DNA
<213> ORGANISM: Artificial Sequence
<220> FEATURE:
<223> OTHER INFORMATION: Synthetic primer

<400> SEQUENCE: 1020
tgttttgatt cccgggctta                                                    20

<210> SEQ ID NO 1021
<211> LENGTH: 24
<212> TYPE: DNA
<213> ORGANISM: Artificial Sequence
<220> FEATURE:
<223> OTHER INFORMATION: Synthetic primer

<400> SEQUENCE: 1021
caaagctgtc agctctagca aaag                                               24

<210> SEQ ID NO 1022
<211> LENGTH: 28
<212> TYPE: DNA
<213> ORGANISM: Artificial Sequence
<220> FEATURE:
<223> OTHER INFORMATION: Synthetic probe

<400> SEQUENCE: 1022
tgccttcttc ctccctcact tctcacct                                           28

<210> SEQ ID NO 1023
<211> LENGTH: 20
<212> TYPE: DNA
<213> ORGANISM: Artificial Sequence
<220> FEATURE:
```

<223> OTHER INFORMATION: Synthetic primer

<400> SEQUENCE: 1023
gatggagcag gtggctcagt                                              20

<210> SEQ ID NO 1024
<211> LENGTH: 25
<212> TYPE: DNA
<213> ORGANISM: Artificial Sequence
<220> FEATURE:
<223> OTHER INFORMATION: Synthetic primer

<400> SEQUENCE: 1024
agtctggaac atgtcagtct tgatg                                        25

<210> SEQ ID NO 1025
<211> LENGTH: 24
<212> TYPE: DNA
<213> ORGANISM: Artificial Sequence
<220> FEATURE:
<223> OTHER INFORMATION: Synthetic probe

<400> SEQUENCE: 1025
cccatagtcc tcagccgcct tcag                                         24

<210> SEQ ID NO 1026
<211> LENGTH: 18
<212> TYPE: DNA
<213> ORGANISM: Artificial Sequence
<220> FEATURE:
<223> OTHER INFORMATION: Synthetic primer

<400> SEQUENCE: 1026
acacggtgcc tctggatg                                                18

<210> SEQ ID NO 1027
<211> LENGTH: 20
<212> TYPE: DNA
<213> ORGANISM: Artificial Sequence
<220> FEATURE:
<223> OTHER INFORMATION: Synthetic primer

<400> SEQUENCE: 1027
caccaatgga gaagtggtca                                              20

<210> SEQ ID NO 1028
<211> LENGTH: 24
<212> TYPE: DNA
<213> ORGANISM: Artificial Sequence
<220> FEATURE:
<223> OTHER INFORMATION: Synthetic probe

<400> SEQUENCE: 1028
atcaggctcc acctcattgc catc                                         24

<210> SEQ ID NO 1029
<211> LENGTH: 22
<212> TYPE: DNA
<213> ORGANISM: Artificial Sequence
<220> FEATURE:
<223> OTHER INFORMATION: Synthetic primer

<400> SEQUENCE: 1029
tcaaggatct gaactgtgga aa                                           22

```
<210> SEQ ID NO 1030
<211> LENGTH: 19
<212> TYPE: DNA
<213> ORGANISM: Artificial Sequence
<220> FEATURE:
<223> OTHER INFORMATION: Synthetic primer

<400> SEQUENCE: 1030
gcctgcccgc tttagtaat                                              19

<210> SEQ ID NO 1031
<211> LENGTH: 24
<212> TYPE: DNA
<213> ORGANISM: Artificial Sequence
<220> FEATURE:
<223> OTHER INFORMATION: Synthetic probe

<400> SEQUENCE: 1031
tcatctcagt cccgatgtca tgga                                        24

<210> SEQ ID NO 1032
<211> LENGTH: 23
<212> TYPE: DNA
<213> ORGANISM: Artificial Sequence
<220> FEATURE:
<223> OTHER INFORMATION: Synthetic primer

<400> SEQUENCE: 1032
gacatggaga acaagctgtt tgc                                         23

<210> SEQ ID NO 1033
<211> LENGTH: 24
<212> TYPE: DNA
<213> ORGANISM: Artificial Sequence
<220> FEATURE:
<223> OTHER INFORMATION: Synthetic primer

<400> SEQUENCE: 1033
gaggtgtcac caacaagaaa tcat                                        24

<210> SEQ ID NO 1034
<211> LENGTH: 21
<212> TYPE: DNA
<213> ORGANISM: Artificial Sequence
<220> FEATURE:
<223> OTHER INFORMATION: Synthetic probe

<400> SEQUENCE: 1034
accaaacgca ggagcagccc g                                           21

<210> SEQ ID NO 1035
<211> LENGTH: 19
<212> TYPE: DNA
<213> ORGANISM: Artificial Sequence
<220> FEATURE:
<223> OTHER INFORMATION: Synthetic primer

<400> SEQUENCE: 1035
ccagcatcag ggaggtttc                                              19

<210> SEQ ID NO 1036
<211> LENGTH: 18
<212> TYPE: DNA
<213> ORGANISM: Artificial Sequence
<220> FEATURE:
<223> OTHER INFORMATION: Synthetic primer
```

```
<400> SEQUENCE: 1036
taagctcagg accgcagg                                                18

<210> SEQ ID NO 1037
<211> LENGTH: 24
<212> TYPE: DNA
<213> ORGANISM: Artificial Sequence
<220> FEATURE:
<223> OTHER INFORMATION: Synthetic probe

<400> SEQUENCE: 1037
ccgtctgaaa ttcaagccat gtcg                                         24

<210> SEQ ID NO 1038
<211> LENGTH: 20
<212> TYPE: DNA
<213> ORGANISM: Artificial Sequence
<220> FEATURE:
<223> OTHER INFORMATION: Synthetic primer

<400> SEQUENCE: 1038
ggtgtgccac agaccttcct                                              20

<210> SEQ ID NO 1039
<211> LENGTH: 24
<212> TYPE: DNA
<213> ORGANISM: Artificial Sequence
<220> FEATURE:
<223> OTHER INFORMATION: Synthetic primer

<400> SEQUENCE: 1039
acggagttct tgacagagtt ttga                                         24

<210> SEQ ID NO 1040
<211> LENGTH: 27
<212> TYPE: DNA
<213> ORGANISM: Artificial Sequence
<220> FEATURE:
<223> OTHER INFORMATION: Synthetic probe

<400> SEQUENCE: 1040
ttggcctgta atcacctgtg cagcctt                                      27

<210> SEQ ID NO 1041
<211> LENGTH: 22
<212> TYPE: DNA
<213> ORGANISM: Artificial Sequence
<220> FEATURE:
<223> OTHER INFORMATION: Synthetic primer

<400> SEQUENCE: 1041
ggatcgagct cttccagatc ct                                           22

<210> SEQ ID NO 1042
<211> LENGTH: 20
<212> TYPE: DNA
<213> ORGANISM: Artificial Sequence
<220> FEATURE:
<223> OTHER INFORMATION: Synthetic primer

<400> SEQUENCE: 1042
gccaccgata tagcgctgtt                                              20

<210> SEQ ID NO 1043
<211> LENGTH: 21
```

```
<212> TYPE: DNA
<213> ORGANISM: Artificial Sequence
<220> FEATURE:
<223> OTHER INFORMATION: Synthetic probe

<400> SEQUENCE: 1043
cggccagatg agcacattgc c                                              21

<210> SEQ ID NO 1044
<211> LENGTH: 19
<212> TYPE: DNA
<213> ORGANISM: Artificial Sequence
<220> FEATURE:
<223> OTHER INFORMATION: Synthetic primer

<400> SEQUENCE: 1044
gctacgagtg ctgtcctgg                                                 19

<210> SEQ ID NO 1045
<211> LENGTH: 19
<212> TYPE: DNA
<213> ORGANISM: Artificial Sequence
<220> FEATURE:
<223> OTHER INFORMATION: Synthetic primer

<400> SEQUENCE: 1045
agtggtaggg ctgctggac                                                 19

<210> SEQ ID NO 1046
<211> LENGTH: 24
<212> TYPE: DNA
<213> ORGANISM: Artificial Sequence
<220> FEATURE:
<223> OTHER INFORMATION: Synthetic probe

<400> SEQUENCE: 1046
ccttctcccc agggaccttt tcat                                           24

<210> SEQ ID NO 1047
<211> LENGTH: 20
<212> TYPE: DNA
<213> ORGANISM: Artificial Sequence
<220> FEATURE:
<223> OTHER INFORMATION: Synthetic primer

<400> SEQUENCE: 1047
aacaccaatg ggttccatct                                                20

<210> SEQ ID NO 1048
<211> LENGTH: 20
<212> TYPE: DNA
<213> ORGANISM: Artificial Sequence
<220> FEATURE:
<223> OTHER INFORMATION: Synthetic primer

<400> SEQUENCE: 1048
cctcttcatc aggccaaact                                                20

<210> SEQ ID NO 1049
<211> LENGTH: 24
<212> TYPE: DNA
<213> ORGANISM: Artificial Sequence
<220> FEATURE:
<223> OTHER INFORMATION: Synthetic probe

<400> SEQUENCE: 1049
```

```
ttctgggctc ctgattgctc aagc                                          24
```

<210> SEQ ID NO 1050
<211> LENGTH: 22
<212> TYPE: DNA
<213> ORGANISM: Artificial Sequence
<220> FEATURE:
<223> OTHER INFORMATION: Synthetic primer

<400> SEQUENCE: 1050

```
catccgcaaa gtgactgaag ag                                            22
```

<210> SEQ ID NO 1051
<211> LENGTH: 27
<212> TYPE: DNA
<213> ORGANISM: Artificial Sequence
<220> FEATURE:
<223> OTHER INFORMATION: Synthetic primer

<400> SEQUENCE: 1051

```
gtactgaact ccgttgtgat agcatag                                       27
```

<210> SEQ ID NO 1052
<211> LENGTH: 22
<212> TYPE: DNA
<213> ORGANISM: Artificial Sequence
<220> FEATURE:
<223> OTHER INFORMATION: Synthetic probe

<400> SEQUENCE: 1052

```
ccaatgagct gaggcggcct cc                                            22
```

<210> SEQ ID NO 1053
<211> LENGTH: 20
<212> TYPE: DNA
<213> ORGANISM: Artificial Sequence
<220> FEATURE:
<223> OTHER INFORMATION: Synthetic primer

<400> SEQUENCE: 1053

```
ggacaagacc ctctcaggct                                               20
```

<210> SEQ ID NO 1054
<211> LENGTH: 18
<212> TYPE: DNA
<213> ORGANISM: Artificial Sequence
<220> FEATURE:
<223> OTHER INFORMATION: Synthetic primer

<400> SEQUENCE: 1054

```
ttggaggctg tgggtcag                                                 18
```

<210> SEQ ID NO 1055
<211> LENGTH: 24
<212> TYPE: DNA
<213> ORGANISM: Artificial Sequence
<220> FEATURE:
<223> OTHER INFORMATION: Synthetic probe

<400> SEQUENCE: 1055

```
caagctccca agagcttcca gagc                                          24
```

<210> SEQ ID NO 1056
<211> LENGTH: 19
<212> TYPE: DNA
<213> ORGANISM: Artificial Sequence

```
<220> FEATURE:
<223> OTHER INFORMATION: Synthetic primer

<400> SEQUENCE: 1056
tccctgcggt cccagatag                                                  19

<210> SEQ ID NO 1057
<211> LENGTH: 20
<212> TYPE: DNA
<213> ORGANISM: Artificial Sequence
<220> FEATURE:
<223> OTHER INFORMATION: Synthetic primer

<400> SEQUENCE: 1057
gtgggaacag ggtggacact                                                 20

<210> SEQ ID NO 1058
<211> LENGTH: 26
<212> TYPE: DNA
<213> ORGANISM: Artificial Sequence
<220> FEATURE:
<223> OTHER INFORMATION: Synthetic probe

<400> SEQUENCE: 1058
atcctgcccg gagtggaagc tgaagc                                          26

<210> SEQ ID NO 1059
<211> LENGTH: 22
<212> TYPE: DNA
<213> ORGANISM: Artificial Sequence
<220> FEATURE:
<223> OTHER INFORMATION: Synthetic primer

<400> SEQUENCE: 1059
tcaccctctg tgacttcatc gt                                              22

<210> SEQ ID NO 1060
<211> LENGTH: 22
<212> TYPE: DNA
<213> ORGANISM: Artificial Sequence
<220> FEATURE:
<223> OTHER INFORMATION: Synthetic primer

<400> SEQUENCE: 1060
tgtggttcag gctcttcttc tg                                              22

<210> SEQ ID NO 1061
<211> LENGTH: 22
<212> TYPE: DNA
<213> ORGANISM: Artificial Sequence
<220> FEATURE:
<223> OTHER INFORMATION: Synthetic probe

<400> SEQUENCE: 1061
ccctgggaca ccctgagcac ca                                              22

<210> SEQ ID NO 1062
<211> LENGTH: 20
<212> TYPE: DNA
<213> ORGANISM: Artificial Sequence
<220> FEATURE:
<223> OTHER INFORMATION: Synthetic primer

<400> SEQUENCE: 1062
ctacctgcct tgctttgtga                                                 20
```

<210> SEQ ID NO 1063
<211> LENGTH: 20
<212> TYPE: DNA
<213> ORGANISM: Artificial Sequence
<220> FEATURE:
<223> OTHER INFORMATION: Synthetic primer

<400> SEQUENCE: 1063
accgaaattg gagagcatgt                                            20

<210> SEQ ID NO 1064
<211> LENGTH: 24
<212> TYPE: DNA
<213> ORGANISM: Artificial Sequence
<220> FEATURE:
<223> OTHER INFORMATION: Synthetic probe

<400> SEQUENCE: 1064
ccaagaacga gtgtctctgg accg                                       24

<210> SEQ ID NO 1065
<211> LENGTH: 20
<212> TYPE: DNA
<213> ORGANISM: Artificial Sequence
<220> FEATURE:
<223> OTHER INFORMATION: Synthetic primer

<400> SEQUENCE: 1065
cggtgctgtt actgcctttc                                            20

<210> SEQ ID NO 1066
<211> LENGTH: 21
<212> TYPE: DNA
<213> ORGANISM: Artificial Sequence
<220> FEATURE:
<223> OTHER INFORMATION: Synthetic primer

<400> SEQUENCE: 1066
aacatggagt agatgcatgg c                                          21

<210> SEQ ID NO 1067
<211> LENGTH: 24
<212> TYPE: DNA
<213> ORGANISM: Artificial Sequence
<220> FEATURE:
<223> OTHER INFORMATION: Synthetic probe

<400> SEQUENCE: 1067
ttgtgtcctg cattaatctg gccg                                       24

<210> SEQ ID NO 1068
<211> LENGTH: 18
<212> TYPE: DNA
<213> ORGANISM: Artificial Sequence
<220> FEATURE:
<223> OTHER INFORMATION: Synthetic primer

<400> SEQUENCE: 1068
cagaaggatg cctgtggc                                              18

<210> SEQ ID NO 1069
<211> LENGTH: 18
<212> TYPE: DNA
<213> ORGANISM: Artificial Sequence
<220> FEATURE:
<223> OTHER INFORMATION: Synthetic primer

```
<400> SEQUENCE: 1069
gtagacctgc ggctctgg                                                 18

<210> SEQ ID NO 1070
<211> LENGTH: 24
<212> TYPE: DNA
<213> ORGANISM: Artificial Sequence
<220> FEATURE:
<223> OTHER INFORMATION: Synthetic probe

<400> SEQUENCE: 1070
attccgttgc ctgacactgt gctc                                          24

<210> SEQ ID NO 1071
<211> LENGTH: 20
<212> TYPE: DNA
<213> ORGANISM: Artificial Sequence
<220> FEATURE:
<223> OTHER INFORMATION: Synthetic primer

<400> SEQUENCE: 1071
ctggctccag aacagaaagg                                               20

<210> SEQ ID NO 1072
<211> LENGTH: 20
<212> TYPE: DNA
<213> ORGANISM: Artificial Sequence
<220> FEATURE:
<223> OTHER INFORMATION: Synthetic primer

<400> SEQUENCE: 1072
gcaaatgctg cagttcctta                                               20

<210> SEQ ID NO 1073
<211> LENGTH: 22
<212> TYPE: DNA
<213> ORGANISM: Artificial Sequence
<220> FEATURE:
<223> OTHER INFORMATION: Synthetic probe

<400> SEQUENCE: 1073
agcctcacgc tggctcacac aa                                            22

<210> SEQ ID NO 1074
<211> LENGTH: 19
<212> TYPE: DNA
<213> ORGANISM: Artificial Sequence
<220> FEATURE:
<223> OTHER INFORMATION: Synthetic primer

<400> SEQUENCE: 1074
gaggtgatgt ggcaaccag                                                19

<210> SEQ ID NO 1075
<211> LENGTH: 20
<212> TYPE: DNA
<213> ORGANISM: Artificial Sequence
<220> FEATURE:
<223> OTHER INFORMATION: Synthetic primer

<400> SEQUENCE: 1075
ttcggacacc atatccttgg                                               20

<210> SEQ ID NO 1076
```

```
<211> LENGTH: 24
<212> TYPE: DNA
<213> ORGANISM: Artificial Sequence
<220> FEATURE:
<223> OTHER INFORMATION: Synthetic probe

<400> SEQUENCE: 1076
tgtaggcctc tcccacgcct aaga                                          24

<210> SEQ ID NO 1077
<211> LENGTH: 20
<212> TYPE: DNA
<213> ORGANISM: Artificial Sequence
<220> FEATURE:
<223> OTHER INFORMATION: Synthetic primer

<400> SEQUENCE: 1077
aatccaaggg ggagagtgat                                               20

<210> SEQ ID NO 1078
<211> LENGTH: 20
<212> TYPE: DNA
<213> ORGANISM: Artificial Sequence
<220> FEATURE:
<223> OTHER INFORMATION: Synthetic primer

<400> SEQUENCE: 1078
gtacagattt tgcccgagga                                               20

<210> SEQ ID NO 1079
<211> LENGTH: 26
<212> TYPE: DNA
<213> ORGANISM: Artificial Sequence
<220> FEATURE:
<223> OTHER INFORMATION: Synthetic probe

<400> SEQUENCE: 1079
catatggact ttgactcagc tgtggc                                        26

<210> SEQ ID NO 1080
<211> LENGTH: 24
<212> TYPE: DNA
<213> ORGANISM: Artificial Sequence
<220> FEATURE:
<223> OTHER INFORMATION: Synthetic primer

<400> SEQUENCE: 1080
ctatatgcag ccagagatgt gaca                                          24

<210> SEQ ID NO 1081
<211> LENGTH: 24
<212> TYPE: DNA
<213> ORGANISM: Artificial Sequence
<220> FEATURE:
<223> OTHER INFORMATION: Synthetic primer

<400> SEQUENCE: 1081
ccacgagttt cttactgaga atgg                                          24

<210> SEQ ID NO 1082
<211> LENGTH: 23
<212> TYPE: DNA
<213> ORGANISM: Artificial Sequence
<220> FEATURE:
<223> OTHER INFORMATION: Synthetic probe

<400> SEQUENCE: 1082
```
acagcctgcc actcatcaca gcc                                              23

<210> SEQ ID NO 1083
<211> LENGTH: 20
<212> TYPE: DNA
<213> ORGANISM: Artificial Sequence
<220> FEATURE:
<223> OTHER INFORMATION: Synthetic primer

<400> SEQUENCE: 1083
tgctgttgct gagtctgttg                                                  20

<210> SEQ ID NO 1084
<211> LENGTH: 20
<212> TYPE: DNA
<213> ORGANISM: Artificial Sequence
<220> FEATURE:
<223> OTHER INFORMATION: Synthetic primer

<400> SEQUENCE: 1084
cttgcctggc ttcacagata                                                  20

<210> SEQ ID NO 1085
<211> LENGTH: 24
<212> TYPE: DNA
<213> ORGANISM: Artificial Sequence
<220> FEATURE:
<223> OTHER INFORMATION: Synthetic probe

<400> SEQUENCE: 1085
ccagtcccca gaagaccatg tctg                                             24

<210> SEQ ID NO 1086
<211> LENGTH: 22
<212> TYPE: DNA
<213> ORGANISM: Artificial Sequence
<220> FEATURE:
<223> OTHER INFORMATION: Synthetic primer

<400> SEQUENCE: 1086
cttcacagtg ctcctgcagt ct                                               22

<210> SEQ ID NO 1087
<211> LENGTH: 21
<212> TYPE: DNA
<213> ORGANISM: Artificial Sequence
<220> FEATURE:
<223> OTHER INFORMATION: Synthetic primer

<400> SEQUENCE: 1087
catctgcttc agctcgttgg t                                                21

<210> SEQ ID NO 1088
<211> LENGTH: 26
<212> TYPE: DNA
<213> ORGANISM: Artificial Sequence
<220> FEATURE:
<223> OTHER INFORMATION: Synthetic probe

<400> SEQUENCE: 1088
aagtacacgt aagttacagc cacaca                                           26

<210> SEQ ID NO 1089
<211> LENGTH: 21
<212> TYPE: DNA

```
<213> ORGANISM: Artificial Sequence
<220> FEATURE:
<223> OTHER INFORMATION: Synthetic primer

<400> SEQUENCE: 1089
tcagcagttc cctctttcag a                                        21

<210> SEQ ID NO 1090
<211> LENGTH: 18
<212> TYPE: DNA
<213> ORGANISM: Artificial Sequence
<220> FEATURE:
<223> OTHER INFORMATION: Synthetic primer

<400> SEQUENCE: 1090
tgaagcactg catggtgg                                            18

<210> SEQ ID NO 1091
<211> LENGTH: 24
<212> TYPE: DNA
<213> ORGANISM: Artificial Sequence
<220> FEATURE:
<223> OTHER INFORMATION: Synthetic probe

<400> SEQUENCE: 1091
ctcactgcca agagccctga acag                                     24

<210> SEQ ID NO 1092
<211> LENGTH: 18
<212> TYPE: DNA
<213> ORGANISM: Artificial Sequence
<220> FEATURE:
<223> OTHER INFORMATION: Synthetic primer

<400> SEQUENCE: 1092
gagtcgaccc tgcacctg                                            18

<210> SEQ ID NO 1093
<211> LENGTH: 18
<212> TYPE: DNA
<213> ORGANISM: Artificial Sequence
<220> FEATURE:
<223> OTHER INFORMATION: Synthetic primer

<400> SEQUENCE: 1093
gcgaatgcca tgactgaa                                            18

<210> SEQ ID NO 1094
<211> LENGTH: 23
<212> TYPE: DNA
<213> ORGANISM: Artificial Sequence
<220> FEATURE:
<223> OTHER INFORMATION: Synthetic probe

<400> SEQUENCE: 1094
aattaacagc caccctcag gcg                                       23

<210> SEQ ID NO 1095
<211> LENGTH: 20
<212> TYPE: DNA
<213> ORGANISM: Artificial Sequence
<220> FEATURE:
<223> OTHER INFORMATION: Synthetic primer

<400> SEQUENCE: 1095
tgtctggcga taaagggatt                                          20
```

<210> SEQ ID NO 1096
<211> LENGTH: 20
<212> TYPE: DNA
<213> ORGANISM: Artificial Sequence
<220> FEATURE:
<223> OTHER INFORMATION: Synthetic primer

<400> SEQUENCE: 1096
atggtcccta cccatttgaa                                              20

<210> SEQ ID NO 1097
<211> LENGTH: 25
<212> TYPE: DNA
<213> ORGANISM: Artificial Sequence
<220> FEATURE:
<223> OTHER INFORMATION: Synthetic probe

<400> SEQUENCE: 1097
tctgccttcc ctgaatcaga caacc                                        25

<210> SEQ ID NO 1098
<211> LENGTH: 20
<212> TYPE: DNA
<213> ORGANISM: Artificial Sequence
<220> FEATURE:
<223> OTHER INFORMATION: Synthetic primer

<400> SEQUENCE: 1098
gtgaagccac cgtcatcatg                                              20

<210> SEQ ID NO 1099
<211> LENGTH: 22
<212> TYPE: DNA
<213> ORGANISM: Artificial Sequence
<220> FEATURE:
<223> OTHER INFORMATION: Synthetic primer

<400> SEQUENCE: 1099
ccttccttct tatcccccaa gt                                           22

<210> SEQ ID NO 1100
<211> LENGTH: 28
<212> TYPE: DNA
<213> ORGANISM: Artificial Sequence
<220> FEATURE:
<223> OTHER INFORMATION: Synthetic probe

<400> SEQUENCE: 1100
ctgaccagga ggcaaaacct tcaactga                                     28

<210> SEQ ID NO 1101
<211> LENGTH: 19
<212> TYPE: DNA
<213> ORGANISM: Artificial Sequence
<220> FEATURE:
<223> OTHER INFORMATION: Synthetic primer

<400> SEQUENCE: 1101
gttctgcaga cacgccttc                                               19

<210> SEQ ID NO 1102
<211> LENGTH: 20
<212> TYPE: DNA
<213> ORGANISM: Artificial Sequence
<220> FEATURE:

<223> OTHER INFORMATION: Synthetic primer

<400> SEQUENCE: 1102
cagctgtgca ctctgcttgt                                               20

<210> SEQ ID NO 1103
<211> LENGTH: 24
<212> TYPE: DNA
<213> ORGANISM: Artificial Sequence
<220> FEATURE:
<223> OTHER INFORMATION: Synthetic probe

<400> SEQUENCE: 1103
ctcagccaca cccaggcact taag                                          24

<210> SEQ ID NO 1104
<211> LENGTH: 19
<212> TYPE: DNA
<213> ORGANISM: Artificial Sequence
<220> FEATURE:
<223> OTHER INFORMATION: Synthetic primer

<400> SEQUENCE: 1104
accatgctcc agaaggagg                                                19

<210> SEQ ID NO 1105
<211> LENGTH: 18
<212> TYPE: DNA
<213> ORGANISM: Artificial Sequence
<220> FEATURE:
<223> OTHER INFORMATION: Synthetic primer

<400> SEQUENCE: 1105
aacccaagcg gagaaagg                                                 18

<210> SEQ ID NO 1106
<211> LENGTH: 24
<212> TYPE: DNA
<213> ORGANISM: Artificial Sequence
<220> FEATURE:
<223> OTHER INFORMATION: Synthetic probe

<400> SEQUENCE: 1106
ccccgagcct tctacaaagg gttc                                          24

<210> SEQ ID NO 1107
<211> LENGTH: 18
<212> TYPE: DNA
<213> ORGANISM: Artificial Sequence
<220> FEATURE:
<223> OTHER INFORMATION: Synthetic primer

<400> SEQUENCE: 1107
tgcggaaatg agctccac                                                 18

<210> SEQ ID NO 1108
<211> LENGTH: 19
<212> TYPE: DNA
<213> ORGANISM: Artificial Sequence
<220> FEATURE:
<223> OTHER INFORMATION: Synthetic primer

<400> SEQUENCE: 1108
cctcagccat tctaaccgc                                                19

```
<210> SEQ ID NO 1109
<211> LENGTH: 24
<212> TYPE: DNA
<213> ORGANISM: Artificial Sequence
<220> FEATURE:
<223> OTHER INFORMATION: Synthetic probe

<400> SEQUENCE: 1109
ccctggccac tggggactac acta                                            24

<210> SEQ ID NO 1110
<211> LENGTH: 19
<212> TYPE: DNA
<213> ORGANISM: Artificial Sequence
<220> FEATURE:
<223> OTHER INFORMATION: Synthetic primer

<400> SEQUENCE: 1110
gtggatgtgc cctgaagga                                                  19

<210> SEQ ID NO 1111
<211> LENGTH: 20
<212> TYPE: DNA
<213> ORGANISM: Artificial Sequence
<220> FEATURE:
<223> OTHER INFORMATION: Synthetic primer

<400> SEQUENCE: 1111
ctgcggatcc agggtaagaa                                                 20

<210> SEQ ID NO 1112
<211> LENGTH: 28
<212> TYPE: DNA
<213> ORGANISM: Artificial Sequence
<220> FEATURE:
<223> OTHER INFORMATION: Synthetic probe

<400> SEQUENCE: 1112
aagccaggcg tctacacgag agtctcac                                        28

<210> SEQ ID NO 1113
<211> LENGTH: 18
<212> TYPE: DNA
<213> ORGANISM: Artificial Sequence
<220> FEATURE:
<223> OTHER INFORMATION: Synthetic primer

<400> SEQUENCE: 1113
ggaacgctgg gaaactcc                                                   18

<210> SEQ ID NO 1114
<211> LENGTH: 18
<212> TYPE: DNA
<213> ORGANISM: Artificial Sequence
<220> FEATURE:
<223> OTHER INFORMATION: Synthetic primer

<400> SEQUENCE: 1114
tgacacacgg tcactgcc                                                   18

<210> SEQ ID NO 1115
<211> LENGTH: 24
<212> TYPE: DNA
<213> ORGANISM: Artificial Sequence
<220> FEATURE:
<223> OTHER INFORMATION: Synthetic probe
```

```
<400> SEQUENCE: 1115
ccgccaccat cttgctttcc ttta                                          24

<210> SEQ ID NO 1116
<211> LENGTH: 19
<212> TYPE: DNA
<213> ORGANISM: Artificial Sequence
<220> FEATURE:
<223> OTHER INFORMATION: Synthetic primer

<400> SEQUENCE: 1116
caggtgtagc ctgccctct                                                19

<210> SEQ ID NO 1117
<211> LENGTH: 20
<212> TYPE: DNA
<213> ORGANISM: Artificial Sequence
<220> FEATURE:
<223> OTHER INFORMATION: Synthetic primer

<400> SEQUENCE: 1117
gggatgtgtc cactgaacct                                               20

<210> SEQ ID NO 1118
<211> LENGTH: 24
<212> TYPE: DNA
<213> ORGANISM: Artificial Sequence
<220> FEATURE:
<223> OTHER INFORMATION: Synthetic probe

<400> SEQUENCE: 1118
atcaatccgt ctgggtgcca gaac                                          24

<210> SEQ ID NO 1119
<211> LENGTH: 21
<212> TYPE: DNA
<213> ORGANISM: Artificial Sequence
<220> FEATURE:
<223> OTHER INFORMATION: Synthetic primer

<400> SEQUENCE: 1119
tggcttcagg agctgaatac c                                             21

<210> SEQ ID NO 1120
<211> LENGTH: 24
<212> TYPE: DNA
<213> ORGANISM: Artificial Sequence
<220> FEATURE:
<223> OTHER INFORMATION: Synthetic primer

<400> SEQUENCE: 1120
tgctgtcgtg atgagaaaat agtg                                          24

<210> SEQ ID NO 1121
<211> LENGTH: 26
<212> TYPE: DNA
<213> ORGANISM: Artificial Sequence
<220> FEATURE:
<223> OTHER INFORMATION: Synthetic probe

<400> SEQUENCE: 1121
caggcacaca caggtgggac acaaat                                        26

<210> SEQ ID NO 1122
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 1122
cctgctacac agccaacaag                                              20

<210> SEQ ID NO 1123
<211> LENGTH: 18
<212> TYPE: DNA
<213> ORGANISM: Artificial Sequence
<220> FEATURE:
<223> OTHER INFORMATION: Synthetic primer

<400> SEQUENCE: 1123
agaaagcgcc tgaggtcc                                                18

<210> SEQ ID NO 1124
<211> LENGTH: 24
<212> TYPE: DNA
<213> ORGANISM: Artificial Sequence
<220> FEATURE:
<223> OTHER INFORMATION: Synthetic probe

<400> SEQUENCE: 1124
cccactgtgg aagacaaaga ggcc                                         24

<210> SEQ ID NO 1125
<211> LENGTH: 18
<212> TYPE: DNA
<213> ORGANISM: Artificial Sequence
<220> FEATURE:
<223> OTHER INFORMATION: Synthetic primer

<400> SEQUENCE: 1125
acccacggac agacttgc                                                18

<210> SEQ ID NO 1126
<211> LENGTH: 18
<212> TYPE: DNA
<213> ORGANISM: Artificial Sequence
<220> FEATURE:
<223> OTHER INFORMATION: Synthetic primer

<400> SEQUENCE: 1126
agctttgcca aggtcagc                                                18

<210> SEQ ID NO 1127
<211> LENGTH: 24
<212> TYPE: DNA
<213> ORGANISM: Artificial Sequence
<220> FEATURE:
<223> OTHER INFORMATION: Synthetic probe

<400> SEQUENCE: 1127
cgcgtccaat gtgtattcct ccat                                         24

<210> SEQ ID NO 1128
<211> LENGTH: 20
<212> TYPE: DNA
<213> ORGANISM: Artificial Sequence
<220> FEATURE:
<223> OTHER INFORMATION: Synthetic primer

<400> SEQUENCE: 1128
```
ctgctgtctt gggtgcattg                                              20

<210> SEQ ID NO 1129
<211> LENGTH: 18
<212> TYPE: DNA
<213> ORGANISM: Artificial Sequence
<220> FEATURE:
<223> OTHER INFORMATION: Synthetic primer

<400> SEQUENCE: 1129
gcagcctggg accacttg                                                18

<210> SEQ ID NO 1130
<211> LENGTH: 25
<212> TYPE: DNA
<213> ORGANISM: Artificial Sequence
<220> FEATURE:
<223> OTHER INFORMATION: Synthetic probe

<400> SEQUENCE: 1130
ttgccttgct gctctacctc cacca                                        25

<210> SEQ ID NO 1131
<211> LENGTH: 23
<212> TYPE: DNA
<213> ORGANISM: Artificial Sequence
<220> FEATURE:
<223> OTHER INFORMATION: Synthetic primer

<400> SEQUENCE: 1131
tgtgaatgca gaccaaagaa aga                                          23

<210> SEQ ID NO 1132
<211> LENGTH: 20
<212> TYPE: DNA
<213> ORGANISM: Artificial Sequence
<220> FEATURE:
<223> OTHER INFORMATION: Synthetic primer

<400> SEQUENCE: 1132
gctttctccg ctctgagcaa                                              20

<210> SEQ ID NO 1133
<211> LENGTH: 28
<212> TYPE: DNA
<213> ORGANISM: Artificial Sequence
<220> FEATURE:
<223> OTHER INFORMATION: Synthetic probe

<400> SEQUENCE: 1133
agagcaagac aagaaaatcc ctgtgggc                                     28

<210> SEQ ID NO 1134
<211> LENGTH: 22
<212> TYPE: DNA
<213> ORGANISM: Artificial Sequence
<220> FEATURE:
<223> OTHER INFORMATION: Synthetic primer

<400> SEQUENCE: 1134
agcttcctac agcacaacaa at                                           22

<210> SEQ ID NO 1135
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 1135
ctcggcttgt cacattttc                                                  20

<210> SEQ ID NO 1136
<211> LENGTH: 29
<212> TYPE: DNA
<213> ORGANISM: Artificial Sequence
<220> FEATURE:
<223> OTHER INFORMATION: Synthetic probe

<400> SEQUENCE: 1136
tgtcttgctc tatctttctt tggtctgca                                       29

<210> SEQ ID NO 1137
<211> LENGTH: 25
<212> TYPE: DNA
<213> ORGANISM: Artificial Sequence
<220> FEATURE:
<223> OTHER INFORMATION: Synthetic primer

<400> SEQUENCE: 1137
cctcagcaag acgttatttg aaatt                                           25

<210> SEQ ID NO 1138
<211> LENGTH: 24
<212> TYPE: DNA
<213> ORGANISM: Artificial Sequence
<220> FEATURE:
<223> OTHER INFORMATION: Synthetic primer

<400> SEQUENCE: 1138
aagtgtgatt ggcaaaactg attg                                            24

<210> SEQ ID NO 1139
<211> LENGTH: 26
<212> TYPE: DNA
<213> ORGANISM: Artificial Sequence
<220> FEATURE:
<223> OTHER INFORMATION: Synthetic probe

<400> SEQUENCE: 1139
cctctctctc aaggccccaa accagt                                          26

<210> SEQ ID NO 1140
<211> LENGTH: 21
<212> TYPE: DNA
<213> ORGANISM: Artificial Sequence
<220> FEATURE:
<223> OTHER INFORMATION: Synthetic primer

<400> SEQUENCE: 1140
tgcccttaaa ggaaccaatg a                                               21

<210> SEQ ID NO 1141
<211> LENGTH: 22
<212> TYPE: DNA
<213> ORGANISM: Artificial Sequence
<220> FEATURE:
<223> OTHER INFORMATION: Synthetic primer

<400> SEQUENCE: 1141
gcttcaacgg caaagttctc tt                                              22
```

-continued

<210> SEQ ID NO 1142
<211> LENGTH: 22
<212> TYPE: DNA
<213> ORGANISM: Artificial Sequence
<220> FEATURE:
<223> OTHER INFORMATION: Synthetic probe

<400> SEQUENCE: 1142
atttcacgca tctggcgttc ca                                              22

<210> SEQ ID NO 1143
<211> LENGTH: 20
<212> TYPE: DNA
<213> ORGANISM: Artificial Sequence
<220> FEATURE:
<223> OTHER INFORMATION: Synthetic primer

<400> SEQUENCE: 1143
gagaactggt ggagcctttc                                                 20

<210> SEQ ID NO 1144
<211> LENGTH: 20
<212> TYPE: DNA
<213> ORGANISM: Artificial Sequence
<220> FEATURE:
<223> OTHER INFORMATION: Synthetic primer

<400> SEQUENCE: 1144
tctggtttgt tttggagctg                                                 20

<210> SEQ ID NO 1145
<211> LENGTH: 29
<212> TYPE: DNA
<213> ORGANISM: Artificial Sequence
<220> FEATURE:
<223> OTHER INFORMATION: Synthetic probe

<400> SEQUENCE: 1145
tcttactccc aggacttcag cacctaaga                                       29

<210> SEQ ID NO 1146
<211> LENGTH: 22
<212> TYPE: DNA
<213> ORGANISM: Artificial Sequence
<220> FEATURE:
<223> OTHER INFORMATION: Synthetic primer

<400> SEQUENCE: 1146
agaggcatcc atgaacttca ca                                              22

<210> SEQ ID NO 1147
<211> LENGTH: 24
<212> TYPE: DNA
<213> ORGANISM: Artificial Sequence
<220> FEATURE:
<223> OTHER INFORMATION: Synthetic primer

<400> SEQUENCE: 1147
caaactccac agtacttggg ttga                                            24

<210> SEQ ID NO 1148
<211> LENGTH: 20
<212> TYPE: DNA
<213> ORGANISM: Artificial Sequence
<220> FEATURE:
<223> OTHER INFORMATION: Synthetic probe

```
<400> SEQUENCE: 1148
cgggctgcat cagcacacgc                                          20

<210> SEQ ID NO 1149
<211> LENGTH: 20
<212> TYPE: DNA
<213> ORGANISM: Artificial Sequence
<220> FEATURE:
<223> OTHER INFORMATION: Synthetic primer

<400> SEQUENCE: 1149
acaaagctac cagggagtcg                                          20

<210> SEQ ID NO 1150
<211> LENGTH: 19
<212> TYPE: DNA
<213> ORGANISM: Artificial Sequence
<220> FEATURE:
<223> OTHER INFORMATION: Synthetic primer

<400> SEQUENCE: 1150
tgagcgtgtc actgcaaag                                           19

<210> SEQ ID NO 1151
<211> LENGTH: 22
<212> TYPE: DNA
<213> ORGANISM: Artificial Sequence
<220> FEATURE:
<223> OTHER INFORMATION: Synthetic probe

<400> SEQUENCE: 1151
tttgtccacg ccattgcctc ag                                       22

<210> SEQ ID NO 1152
<211> LENGTH: 18
<212> TYPE: DNA
<213> ORGANISM: Artificial Sequence
<220> FEATURE:
<223> OTHER INFORMATION: Synthetic primer

<400> SEQUENCE: 1152
cggtggaatc tggctctg                                            18

<210> SEQ ID NO 1153
<211> LENGTH: 20
<212> TYPE: DNA
<213> ORGANISM: Artificial Sequence
<220> FEATURE:
<223> OTHER INFORMATION: Synthetic primer

<400> SEQUENCE: 1153
ccatgaagag ttgacctcgg                                          20

<210> SEQ ID NO 1154
<211> LENGTH: 24
<212> TYPE: DNA
<213> ORGANISM: Artificial Sequence
<220> FEATURE:
<223> OTHER INFORMATION: Synthetic probe

<400> SEQUENCE: 1154
ctccctctgc tcttgacctg gctc                                     24

<210> SEQ ID NO 1155
```

```
<211> LENGTH: 66
<212> TYPE: DNA
<213> ORGANISM: Homo sapiens

<400> SEQUENCE: 1155
atattcctca aggtggccga agagagtggg gtggatgctg agacctcaga tggtaccttg    60
ccagca                                                               66

<210> SEQ ID NO 1156
<211> LENGTH: 83
<212> TYPE: DNA
<213> ORGANISM: Homo sapiens

<400> SEQUENCE: 1156
ctcagaggac attcccaaca cagccacacc tgggaactcc gtgggcttcc tgctccggcc    60
attcaacttc ttcccagagg acc                                            83

<210> SEQ ID NO 1157
<211> LENGTH: 67
<212> TYPE: DNA
<213> ORGANISM: Homo sapiens

<400> SEQUENCE: 1157
tttgccgaga aggagttgtt tcccattgca gcccaggtgg ataaggaaca tctcttccca    60
gcggctc                                                              67

<210> SEQ ID NO 1158
<211> LENGTH: 71
<212> TYPE: DNA
<213> ORGANISM: Homo sapiens

<400> SEQUENCE: 1158
gaagccccca ttcactagaa gcactgagag atgcggcccc ctcgcagggt ctgaatttcc    60
tgctgctgtt c                                                         71

<210> SEQ ID NO 1159
<211> LENGTH: 68
<212> TYPE: DNA
<213> ORGANISM: Homo sapiens

<400> SEQUENCE: 1159
aaggagccac accacctgtg actccagccc tgacttctgc tctggaccag tgtttccata    60
acagggac                                                             68

<210> SEQ ID NO 1160
<211> LENGTH: 73
<212> TYPE: DNA
<213> ORGANISM: Homo sapiens

<400> SEQUENCE: 1160
ggacaggtgc aagctcatct gccaagccaa aggcattggc tacttcttcg ttttgcagcc    60
caaggttgta gat                                                       73

<210> SEQ ID NO 1161
<211> LENGTH: 66
<212> TYPE: DNA
<213> ORGANISM: Homo sapiens

<400> SEQUENCE: 1161
ggagaagggt ggagtgcagc acccagatgg attctgactg tgcggccatc cagagacctg    60
```

```
accctg                                                        66

<210> SEQ ID NO 1162
<211> LENGTH: 80
<212> TYPE: DNA
<213> ORGANISM: Homo sapiens

<400> SEQUENCE: 1162
aggctttcaa cggctacaac cacagcacca accggctcac tctcgccgtg gcatgggtgc   60
ccaagtactc cggcgtgtct                                              80

<210> SEQ ID NO 1163
<211> LENGTH: 78
<212> TYPE: DNA
<213> ORGANISM: Homo sapiens

<400> SEQUENCE: 1163
ttatccggtg gtcctcattc cagctggcgc ccgaagcatc gaaatccagg agctgcaggt   60
ttcctccagt tacctcgc                                                78

<210> SEQ ID NO 1164
<211> LENGTH: 67
<212> TYPE: DNA
<213> ORGANISM: Homo sapiens

<400> SEQUENCE: 1164
caagtggatt gccatggagt ggtctcagtg cacagtgact tgtggccgag ggttacggta   60
ccgggtt                                                            67

<210> SEQ ID NO 1165
<211> LENGTH: 70
<212> TYPE: DNA
<213> ORGANISM: Homo sapiens

<400> SEQUENCE: 1165
agccaacatg tgactaattg gaagaagagc aaagggtggt gacgtgttga tgaggcagat   60
ggagatcaga                                                         70

<210> SEQ ID NO 1166
<211> LENGTH: 69
<212> TYPE: DNA
<213> ORGANISM: Homo sapiens

<400> SEQUENCE: 1166
gcggcataga gaccgactta atacagagtt ggaccgtttg gctagcctgc tgcctttccc   60
acaagatgt                                                          69

<210> SEQ ID NO 1167
<211> LENGTH: 75
<212> TYPE: DNA
<213> ORGANISM: Homo sapiens

<400> SEQUENCE: 1167
tagagagccc ctgacaatcc tgaggcttca tcaggagcta gagccattta acatttcctc   60
tttccaagac caacc                                                   75

<210> SEQ ID NO 1168
<211> LENGTH: 75
<212> TYPE: DNA
```

-continued

<213> ORGANISM: Homo sapiens

<400> SEQUENCE: 1168
ttgtctctgc cttggactat ctacattccg gaaagattgt gtaccgtgat ctcaagttgg    60
agaatctaat gctgg                                                    75

<210> SEQ ID NO 1169
<211> LENGTH: 76
<212> TYPE: DNA
<213> ORGANISM: Homo sapiens

<400> SEQUENCE: 1169
gtgaggcctc tgatgaatga tgaaggcctg aaggtcagat accccccgag cccggccaag    60
atgacccagc actgag                                                   76

<210> SEQ ID NO 1170
<211> LENGTH: 67
<212> TYPE: DNA
<213> ORGANISM: Homo sapiens

<400> SEQUENCE: 1170
ctccaggtgt acctccaacc ctagccttct cccacagctg cctacaacag agtctcccag    60
ccttctc                                                             67

<210> SEQ ID NO 1171
<211> LENGTH: 67
<212> TYPE: DNA
<213> ORGANISM: Homo sapiens

<400> SEQUENCE: 1171
gcccctatcc taccttcaat ccatcctcgg atgtcgctgc cttgcataag gccataatgg    60
ttaaagg                                                             67

<210> SEQ ID NO 1172
<211> LENGTH: 67
<212> TYPE: DNA
<213> ORGANISM: Homo sapiens

<400> SEQUENCE: 1172
tgggagggat gaaggaaatt atctggacga tgctctcgtg agacaggatg cccaggacct    60
gtatgag                                                             67

<210> SEQ ID NO 1173
<211> LENGTH: 81
<212> TYPE: DNA
<213> ORGANISM: Homo sapiens

<400> SEQUENCE: 1173
gactgcaaag atggaaacga ccttctatga cgatgccctc aacgcctcgt tcctcccgtc    60
cgagagcgga ccttatggct a                                             81

<210> SEQ ID NO 1174
<211> LENGTH: 69
<212> TYPE: DNA
<213> ORGANISM: Homo sapiens

<400> SEQUENCE: 1174
ggacagcagg aatgtgtttc tccatacagg tcacggggag ccaatggttc agaaacaaat    60
cgagtgggt                                                           69

```
<210> SEQ ID NO 1175
<211> LENGTH: 83
<212> TYPE: DNA
<213> ORGANISM: Homo sapiens

<400> SEQUENCE: 1175
ccaccttgga ccaaagtaaa gcgtggaatc gttaccgcct ccccaacacg ctgaaacccg    60
attcctaccg ggtgacgctg aga                                           83

<210> SEQ ID NO 1176
<211> LENGTH: 82
<212> TYPE: DNA
<213> ORGANISM: Homo sapiens

<400> SEQUENCE: 1176
tgtgagtgaa atgccttcta gtagtgaacc gtcctcggga gccgactatg actactcaga    60
agagtatgat aacgaaccac aa                                            82

<210> SEQ ID NO 1177
<211> LENGTH: 75
<212> TYPE: DNA
<213> ORGANISM: Homo sapiens

<400> SEQUENCE: 1177
cgcctcatcg agatcaagtc caccacgctg cgagtggacc agtccatcct gacgggtgaa    60
tctgtgtccg tgacc                                                    75

<210> SEQ ID NO 1178
<211> LENGTH: 66
<212> TYPE: DNA
<213> ORGANISM: Homo sapiens

<400> SEQUENCE: 1178
ccgctttcgc tacagcatgg tggcctactg gagacaggct ggactcagct acatccgata    60
ctccca                                                              66

<210> SEQ ID NO 1179
<211> LENGTH: 66
<212> TYPE: DNA
<213> ORGANISM: Homo sapiens

<400> SEQUENCE: 1179
ggctatgtct ttgcaccagc caccagcgcc aacgacagtg agatatccag tgatgcgctg    60
acggat                                                              66

<210> SEQ ID NO 1180
<211> LENGTH: 66
<212> TYPE: DNA
<213> ORGANISM: Homo sapiens

<400> SEQUENCE: 1180
cagcagatgt ggatcagcaa gcaggagtat gacgagtccg gcccctccat cgtccaccgc    60
aaatgc                                                              66

<210> SEQ ID NO 1181
<211> LENGTH: 80
<212> TYPE: DNA
<213> ORGANISM: Homo sapiens
```

```
<400> SEQUENCE: 1181
ggctcttgtg cgtactgtcc ttcgggctgg tgacagggaa gacatcactg agcctgccat    60
ctgtgctctt cgtcatctga                                                80

<210> SEQ ID NO 1182
<211> LENGTH: 70
<212> TYPE: DNA
<213> ORGANISM: Homo sapiens

<400> SEQUENCE: 1182
ccgccgtgga cacagactcc ccccgagagg tcttttccg agtggcagct gacatgtttt     60
ctgacggcaa                                                           70

<210> SEQ ID NO 1183
<211> LENGTH: 73
<212> TYPE: DNA
<213> ORGANISM: Homo sapiens

<400> SEQUENCE: 1183
ccccgagaca acggagataa gtgctgttgc ggatgccaac ggaaagaatc ttgggaaaga    60
ggccaaaccc gag                                                       73

<210> SEQ ID NO 1184
<211> LENGTH: 73
<212> TYPE: DNA
<213> ORGANISM: Homo sapiens

<400> SEQUENCE: 1184
cagatggacc tagtacccac tgagatttcc acgccgaagg acagcgatgg gaaaaatgcc    60
cttaaatcat agg                                                       73

<210> SEQ ID NO 1185
<211> LENGTH: 74
<212> TYPE: DNA
<213> ORGANISM: Homo sapiens

<400> SEQUENCE: 1185
tgtactggcg aagaatattt ggtaaagcag ggcatcgatc tctcaccctg gggcttgtgg    60
aagaatcacg tggc                                                      74

<210> SEQ ID NO 1186
<211> LENGTH: 71
<212> TYPE: DNA
<213> ORGANISM: Homo sapiens

<400> SEQUENCE: 1186
gcctgcagtc ccatgatcac catcctccca gggcaaactc aaggaccaaa ctactgtggc    60
ccaagaggga a                                                         71

<210> SEQ ID NO 1187
<211> LENGTH: 66
<212> TYPE: DNA
<213> ORGANISM: Homo sapiens

<400> SEQUENCE: 1187
gagctccgca aggatgactt caagggtctc cagcacctct acgccctcgt cctggtgaac    60
aacaag                                                               66
```

```
<210> SEQ ID NO 1188
<211> LENGTH: 70
<212> TYPE: DNA
<213> ORGANISM: Homo sapiens

<400> SEQUENCE: 1188
attcctatgg ctctgcaatt gtcaccggtt aactgtggcc tgtgcccagg aagagccatt    60
cactcctgcc                                                          70

<210> SEQ ID NO 1189
<211> LENGTH: 76
<212> TYPE: DNA
<213> ORGANISM: Homo sapiens

<400> SEQUENCE: 1189
cctgcaaaag ggaacaagag cccttcgcct ccagatggct cccctgccgc cacccccgag    60
atcagagtca accacg                                                   76

<210> SEQ ID NO 1190
<211> LENGTH: 67
<212> TYPE: DNA
<213> ORGANISM: Homo sapiens

<400> SEQUENCE: 1190
gaccaagcag gaagctcaga ctggttgagt tcaggtagct gcccctggct ctgaccgaaa    60
cagcgct                                                             67

<210> SEQ ID NO 1191
<211> LENGTH: 68
<212> TYPE: DNA
<213> ORGANISM: Homo sapiens

<400> SEQUENCE: 1191
ctggacggag tagctccaag agctctcact gtgacagccc acctcgctcg cagacaccac    60
aagatacc                                                            68

<210> SEQ ID NO 1192
<211> LENGTH: 75
<212> TYPE: DNA
<213> ORGANISM: Homo sapiens

<400> SEQUENCE: 1192
tatttcttca tgaagacctc acagtaaaaa taggtgattt tggtctagct acagtgaaat    60
ctcgatggag tgggt                                                    75

<210> SEQ ID NO 1193
<211> LENGTH: 76
<212> TYPE: DNA
<213> ORGANISM: Homo sapiens

<400> SEQUENCE: 1193
tatttcttca tgaagacctc acagtaaaaa taggtgattt tggtctagct acagagaaat    60
ctcgatggag tgggtc                                                   76

<210> SEQ ID NO 1194
<211> LENGTH: 65
<212> TYPE: DNA
<213> ORGANISM: Homo sapiens

<400> SEQUENCE: 1194
```

```
tcaggggct agaaatctgt tgctatgggc ccttcaccaa catgcccaca gatcaactgg    60
aatgg                                                              65

<210> SEQ ID NO 1195
<211> LENGTH: 66
<212> TYPE: DNA
<213> ORGANISM: Homo sapiens

<400> SEQUENCE: 1195
gctacgaatg gcacgacctg ctcgagcttg gcagtctcca gttgggctgt gcatggaagc    60
ttggga                                                              66

<210> SEQ ID NO 1196
<211> LENGTH: 68
<212> TYPE: DNA
<213> ORGANISM: Homo sapiens

<400> SEQUENCE: 1196
ccgaggttaa tccagcacgt atggggccaa gtgtaggctc ccagcaggaa ctgagagcgc    60
catgtctt                                                            68

<210> SEQ ID NO 1197
<211> LENGTH: 87
<212> TYPE: DNA
<213> ORGANISM: Homo sapiens

<400> SEQUENCE: 1197
aactcagact tggaaatgcc ttctttaact tccaccccc tcattggtca caaattgact    60
gttacaacac catttcatag agaccag                                       87

<210> SEQ ID NO 1198
<211> LENGTH: 71
<212> TYPE: DNA
<213> ORGANISM: Homo sapiens

<400> SEQUENCE: 1198
tcctcaacag aggtacacat ggtccgccca ggatactctc atcgggtgtc tctgcccaca    60
agccctggga t                                                        71

<210> SEQ ID NO 1199
<211> LENGTH: 65
<212> TYPE: DNA
<213> ORGANISM: Homo sapiens

<400> SEQUENCE: 1199
tcagctgtga gctgcggata ccgcccggca atgggacctg ctcttaacct caaacctagg    60
accgt                                                               65

<210> SEQ ID NO 1200
<211> LENGTH: 67
<212> TYPE: DNA
<213> ORGANISM: Homo sapiens

<400> SEQUENCE: 1200
ccagcactgc tcgttactgt ctgccttcag tggtctgagg tcccagtatg aactgccgtg    60
aagtcaa                                                             67

<210> SEQ ID NO 1201
<211> LENGTH: 81
```

```
<212> TYPE: DNA
<213> ORGANISM: Homo sapiens

<400> SEQUENCE: 1201
aggacaacga taaccgatca gtgctgaaag gtggtccttt ctctgacagc tacaggctct     60
ttcagttcca ttttcactgg g                                               81

<210> SEQ ID NO 1202
<211> LENGTH: 66
<212> TYPE: DNA
<213> ORGANISM: Homo sapiens

<400> SEQUENCE: 1202
ctctctgaag gtgtcctggc cagccctgga gaagcactgg tgtctgcagc acccctcagt     60
tcctgt                                                                66

<210> SEQ ID NO 1203
<211> LENGTH: 69
<212> TYPE: DNA
<213> ORGANISM: Homo sapiens

<400> SEQUENCE: 1203
caacgtggag tttgatgact ctcaggacaa agcagtgctc aagggaggac ccctggatgg     60
cacttacag                                                             69

<210> SEQ ID NO 1204
<211> LENGTH: 72
<212> TYPE: DNA
<213> ORGANISM: Homo sapiens

<400> SEQUENCE: 1204
atcctagccc tggtttttgg cctccttttt gctgtcacca gcgtcgcgtt ccttgtgcag     60
atgagaaggc ag                                                         72

<210> SEQ ID NO 1205
<211> LENGTH: 77
<212> TYPE: DNA
<213> ORGANISM: Homo sapiens

<400> SEQUENCE: 1205
gaaggccaag aaccgagtca aattatattc cagtttaagg ccaatcctcc tgctgtgact     60
tttgaactaa ctgggga                                                    77

<210> SEQ ID NO 1206
<211> LENGTH: 78
<212> TYPE: DNA
<213> ORGANISM: Homo sapiens

<400> SEQUENCE: 1206
cactaaggtt tgagacagtt ccagaaagaa cccaagctca agacgcagga cgagctcagt     60
tgtagagggc taattcgc                                                   78

<210> SEQ ID NO 1207
<211> LENGTH: 70
<212> TYPE: DNA
<213> ORGANISM: Homo sapiens

<400> SEQUENCE: 1207
atgcaaagca ctgtggaaac cttcaacagg gctctgattc tgaaatggat ccttcttgtt     60
```

```
gcagtttgga                                                            70

<210> SEQ ID NO 1208
<211> LENGTH: 69
<212> TYPE: DNA
<213> ORGANISM: Homo sapiens

<400> SEQUENCE: 1208
ccatgtgctg taccaagagt ttgctcctgg ctgctttgat gtcagtgctg ctactccacc    60
tctgcggcg                                                            69

<210> SEQ ID NO 1209
<211> LENGTH: 70
<212> TYPE: DNA
<213> ORGANISM: Homo sapiens

<400> SEQUENCE: 1209
gggtccagga gtacgtgtat gacctggaac tgaactgagc tgctcagaga caggaagtct    60
tcagggaagg                                                           70

<210> SEQ ID NO 1210
<211> LENGTH: 65
<212> TYPE: DNA
<213> ORGANISM: Homo sapiens

<400> SEQUENCE: 1210
aggttctgag ctctggcttt gccttggctt tgccagggct ctgtgaccag gaaggaagtc    60
agcat                                                                65

<210> SEQ ID NO 1211
<211> LENGTH: 79
<212> TYPE: DNA
<213> ORGANISM: Homo sapiens

<400> SEQUENCE: 1211
ccatacctca agtatttgcc atcagttatt gctggagctg cctttcattt agcactctac    60
acagtcacgg gacaaagct                                                 79

<210> SEQ ID NO 1212
<211> LENGTH: 84
<212> TYPE: DNA
<213> ORGANISM: Homo sapiens

<400> SEQUENCE: 1212
ttcaggttgt tgcaggagac catgtacatg actgtctcca ttattgatcg gttcatgcag    60
aataattgtg tgcccaagaa gatg                                           84

<210> SEQ ID NO 1213
<211> LENGTH: 69
<212> TYPE: DNA
<213> ORGANISM: Homo sapiens

<400> SEQUENCE: 1213
gcatgttcgt ggcctctaag atgaaggaga ccatcccccct gacggccgag aagctgtgca   60
tctacaccg                                                            69

<210> SEQ ID NO 1214
<211> LENGTH: 67
<212> TYPE: DNA
<213> ORGANISM: Homo sapiens
```

```
<400> SEQUENCE: 1214
ctcgggaatc ctgaaaaccc tgcttcggtg tcgaaacgag aagaagaggc atagggcagt      60
gagagtc                                                               67

<210> SEQ ID NO 1215
<211> LENGTH: 67
<212> TYPE: DNA
<213> ORGANISM: Homo sapiens

<400> SEQUENCE: 1215
cagactgaat gggggtgggg ggggcgcctt aggtacttat tccagatgcc ttctccagac      60
aaaccag                                                               67

<210> SEQ ID NO 1216
<211> LENGTH: 78
<212> TYPE: DNA
<213> ORGANISM: Homo sapiens

<400> SEQUENCE: 1216
cgatgtctgt gaacccaagt accagactgt ctcggagccc atcaggtgga agctgctgat      60
gttggggctt gagctact                                                   78

<210> SEQ ID NO 1217
<211> LENGTH: 64
<212> TYPE: DNA
<213> ORGANISM: Homo sapiens

<400> SEQUENCE: 1217
ggatgacatg cactcagctc ttggctccac tgggatggga ggagaggaca agggaaatgt      60
cagg                                                                  64

<210> SEQ ID NO 1218
<211> LENGTH: 75
<212> TYPE: DNA
<213> ORGANISM: Homo sapiens

<400> SEQUENCE: 1218
gcaggtgtca gcaagtatga tcagcaatga ggcggtggtc aatatcctgt cgagctcatc      60
accacagcgg aaaaa                                                      75

<210> SEQ ID NO 1219
<211> LENGTH: 81
<212> TYPE: DNA
<213> ORGANISM: Homo sapiens

<400> SEQUENCE: 1219
cgtcaggacc caccatgtct gccccatcac gcggccgaga catggcttgg ccacagctct      60
tgaggatgtc accaattaac c                                               81

<210> SEQ ID NO 1220
<211> LENGTH: 66
<212> TYPE: DNA
<213> ORGANISM: Homo sapiens

<400> SEQUENCE: 1220
ccagctaccc cctcaagccc cagatgccct tgtcctcaga acccaggcca cccagcttcc      60
cattat                                                                66
```

```
<210> SEQ ID NO 1221
<211> LENGTH: 75
<212> TYPE: DNA
<213> ORGANISM: Homo sapiens

<400> SEQUENCE: 1221
tgtatttcaa gacctctgtg cacttattta tgaacctgcc ctgctcccac agaacacagc      60
aattcctcag gctaa                                                      75

<210> SEQ ID NO 1222
<211> LENGTH: 65
<212> TYPE: DNA
<213> ORGANISM: Homo sapiens

<400> SEQUENCE: 1222
agatgaagtg gaaggcgctt ttcaccgcgg ccatcctgca ggcacagttg ccgattacag      60
aggca                                                                 65

<210> SEQ ID NO 1223
<211> LENGTH: 78
<212> TYPE: DNA
<213> ORGANISM: Homo sapiens

<400> SEQUENCE: 1223
ctcataccag ccatccaatg caaggaagga caacaccaag cccagaggac agttcctgga      60
ctgatttctt caacccaa                                                   78

<210> SEQ ID NO 1224
<211> LENGTH: 67
<212> TYPE: DNA
<213> ORGANISM: Homo sapiens

<400> SEQUENCE: 1224
gtcccttagc caagcagttt ctttcaaaga agccagcagg cgaaaagcag ggactgccac      60
tgcattt                                                               67

<210> SEQ ID NO 1225
<211> LENGTH: 74
<212> TYPE: DNA
<213> ORGANISM: Homo sapiens

<400> SEQUENCE: 1225
tggttcccag ccctgtgtcc acctccaagc ccagattcag attcgagtca tgtacacaac      60
ccagggtgga ggag                                                       74

<210> SEQ ID NO 1226
<211> LENGTH: 84
<212> TYPE: DNA
<213> ORGANISM: Homo sapiens

<400> SEQUENCE: 1226
gtgcaggctc aggtgaagtg ctgcggctgg gtcagcttct acaactggac agacaacgct      60
gagctcatga atcgccctga ggtc                                            84

<210> SEQ ID NO 1227
<211> LENGTH: 68
<212> TYPE: DNA
<213> ORGANISM: Homo sapiens

<400> SEQUENCE: 1227
```

```
agggtgaggt gcttgagtct ccaacggcaa gggaacaagt acttcttgat acctgggata    60
ctgtgccc                                                             68

<210> SEQ ID NO 1228
<211> LENGTH: 68
<212> TYPE: DNA
<213> ORGANISM: Homo sapiens

<400> SEQUENCE: 1228
tggattggag ttctgggaat gtactggccg tggcactgga caacagtgtg tacctgtgga    60
gtgcaagc                                                             68

<210> SEQ ID NO 1229
<211> LENGTH: 85
<212> TYPE: DNA
<213> ORGANISM: Homo sapiens

<400> SEQUENCE: 1229
aaacgagcag tttgccatca gacgcttcca gtctatgccg gtgaggctgc tgggccacag    60
ccccgtgctt cggaacatca ccaac                                          85

<210> SEQ ID NO 1230
<211> LENGTH: 67
<212> TYPE: DNA
<213> ORGANISM: Homo sapiens

<400> SEQUENCE: 1230
gagctgaaag acgcacactg tcagaggaaa ctggccatgc aggaattcat ggagatcaat    60
gagcggc                                                              67

<210> SEQ ID NO 1231
<211> LENGTH: 74
<212> TYPE: DNA
<213> ORGANISM: Homo sapiens

<400> SEQUENCE: 1231
gctacctcta ggaagccttc tctgatcctc atccccaagg cctgtgtcgg gatacgtcct    60
actccttccc tttg                                                      74

<210> SEQ ID NO 1232
<211> LENGTH: 81
<212> TYPE: DNA
<213> ORGANISM: Homo sapiens

<400> SEQUENCE: 1232
tgagtgtccc ccggtatctt ccccgccctg ccaatcccga tgaaattgga aattttattg    60
atgaaaatct gaaagcggct g                                              81

<210> SEQ ID NO 1233
<211> LENGTH: 70
<212> TYPE: DNA
<213> ORGANISM: Homo sapiens

<400> SEQUENCE: 1233
gtcggcagaa gcaggacttg taccttctgc ccatagtgat cagcgatggc ggcatcccgc    60
ccatgagtag                                                           70

<210> SEQ ID NO 1234
```

```
<211> LENGTH: 71
<212> TYPE: DNA
<213> ORGANISM: Homo sapiens

<400> SEQUENCE: 1234
acccatgtac cgtcctcggc cagccaaccc agatgaaatc ggcaacttta taattgagaa      60
cctgaaggcg g                                                          71

<210> SEQ ID NO 1235
<211> LENGTH: 76
<212> TYPE: DNA
<213> ORGANISM: Homo sapiens

<400> SEQUENCE: 1235
gagctgaagg aggtggttgt ggggaaccac ctggagagca tcttcctggt gatgggttac      60
tgtgagcagg acctgg                                                     76

<210> SEQ ID NO 1236
<211> LENGTH: 66
<212> TYPE: DNA
<213> ORGANISM: Homo sapiens

<400> SEQUENCE: 1236
agcaacacca gcctcctggc cacctcctct ccaatgcctg tgaaagagga gtttctgcca      60
tagccc                                                                66

<210> SEQ ID NO 1237
<211> LENGTH: 67
<212> TYPE: DNA
<213> ORGANISM: Homo sapiens

<400> SEQUENCE: 1237
gggcaggcaa ggtttacact gcggaagcca aaggcagcta agatagaaag ctggactgac      60
caaagac                                                               67

<210> SEQ ID NO 1238
<211> LENGTH: 71
<212> TYPE: DNA
<213> ORGANISM: Homo sapiens

<400> SEQUENCE: 1238
acttgcctgt tcagagcact cattccttcc cacccccagt cctgtcctat cactctaatt      60
cggatttgcc a                                                          71

<210> SEQ ID NO 1239
<211> LENGTH: 75
<212> TYPE: DNA
<213> ORGANISM: Homo sapiens

<400> SEQUENCE: 1239
ggcctcaata ggaccacagt cacgacgatc acagtctatg cagagccacc caaacccttc      60
atcaccagca acaac                                                      75

<210> SEQ ID NO 1240
<211> LENGTH: 77
<212> TYPE: DNA
<213> ORGANISM: Homo sapiens

<400> SEQUENCE: 1240
actttgcgag aaatgggaac cccaatggcg agggtctgcc acactggccg ctgttcgacc      60
```
aggaggagca atacctg                                              77

<210> SEQ ID NO 1241
<211> LENGTH: 80
<212> TYPE: DNA
<213> ORGANISM: Homo sapiens

<400> SEQUENCE: 1241
ccaccatagg cagaggcagg ccttcctaca ccctactccc tgtgcctcca gcctcgacta    60
gtccctagca ctcgacgact                                              80

<210> SEQ ID NO 1242
<211> LENGTH: 82
<212> TYPE: DNA
<213> ORGANISM: Homo sapiens

<400> SEQUENCE: 1242
gataaattgg tacaagggat cagcttttcc cagcccacat gtcctgatca tatgcttttg    60
aatagtcagt tacttggcac cc                                            82

<210> SEQ ID NO 1243
<211> LENGTH: 67
<212> TYPE: DNA
<213> ORGANISM: Homo sapiens

<400> SEQUENCE: 1243
gtgggagcct ttgaaatcca tggagcagaa tggaccaggc ctagagtaca gagtgacctg    60
gaagcca                                                            67

<210> SEQ ID NO 1244
<211> LENGTH: 71
<212> TYPE: DNA
<213> ORGANISM: Homo sapiens

<400> SEQUENCE: 1244
catgcacccc tgatgttcgc cgtctggcga gcccttagcc ttgctgtaga gacttccgtc    60
acccttggta g                                                       71

<210> SEQ ID NO 1245
<211> LENGTH: 62
<212> TYPE: DNA
<213> ORGANISM: Homo sapiens

<400> SEQUENCE: 1245
ggctggacgt ggttttgtct gctgcgcccg ctcttcgcgc tctcgtttca ttttctgcag    60
cg                                                                 62

<210> SEQ ID NO 1246
<211> LENGTH: 66
<212> TYPE: DNA
<213> ORGANISM: Homo sapiens

<400> SEQUENCE: 1246
acgagtgggg ctggttctga ggacatgggg accacagtca atggagatgt gtttcaggag    60
gccaac                                                             66

<210> SEQ ID NO 1247
<211> LENGTH: 76
<212> TYPE: DNA

<213> ORGANISM: Homo sapiens

<400> SEQUENCE: 1247
ccccaggata cctaccacta cctgcccttc agcctgcccc accggaggcc tcacttcttc    60
tttcccaagt cccgca                                                    76

<210> SEQ ID NO 1248
<211> LENGTH: 86
<212> TYPE: DNA
<213> ORGANISM: Homo sapiens

<400> SEQUENCE: 1248
gacatttcca gtcctgcagt caatgcctct ctgccccacc ctttgttcag tgtggctggt    60
gccacgacaa atgtgtgcga tcggag                                         86

<210> SEQ ID NO 1249
<211> LENGTH: 84
<212> TYPE: DNA
<213> ORGANISM: Homo sapiens

<400> SEQUENCE: 1249
tccctccact cggaaggact atcctgctgc caagagggtc aagttggaca gtgtcagagt    60
cctgagacag atcagcaaca accg                                           84

<210> SEQ ID NO 1250
<211> LENGTH: 66
<212> TYPE: DNA
<213> ORGANISM: Homo sapiens

<400> SEQUENCE: 1250
cgaggctttg gttatgtggt ggccttccgg ccctacggta aaatgatctg gatgctgaca    60
gtgctg                                                               66

<210> SEQ ID NO 1251
<211> LENGTH: 73
<212> TYPE: DNA
<213> ORGANISM: Homo sapiens

<400> SEQUENCE: 1251
tacctctccc tgttgccgcc gcctcagatc tcttcatgcc gctgtaagct cggaggccaa    60
ggatgcggag tag                                                       73

<210> SEQ ID NO 1252
<211> LENGTH: 68
<212> TYPE: DNA
<213> ORGANISM: Homo sapiens

<400> SEQUENCE: 1252
gtggccatcc agctgacctt cctgcgcctg atgtccaccg aggcctccca gaacatcacc    60
taccactg                                                             68

<210> SEQ ID NO 1253
<211> LENGTH: 80
<212> TYPE: DNA
<213> ORGANISM: Homo sapiens

<400> SEQUENCE: 1253
cagccaagaa ctggtatagg agctccaagg acaagaaaca cgtctggcta ggagaaacta    60
tcaatgctgg cagccagttt                                                80

<210> SEQ ID NO 1254
<211> LENGTH: 66
<212> TYPE: DNA
<213> ORGANISM: Homo sapiens

<400> SEQUENCE: 1254
ggaggttctg gacctgctgg tcctcctggt ccccaaggtg tcaaaggtga acgtggcagt    60
cctggt                                                              66

<210> SEQ ID NO 1255
<211> LENGTH: 66
<212> TYPE: DNA
<213> ORGANISM: Homo sapiens

<400> SEQUENCE: 1255
acaaaggcct cccaggattg gatggcatcc ctggtgtcaa aggagaagca ggtcttcctg    60
ggactc                                                              66

<210> SEQ ID NO 1256
<211> LENGTH: 72
<212> TYPE: DNA
<213> ORGANISM: Homo sapiens

<400> SEQUENCE: 1256
ggtcgaggaa cccaaggtcc gcctggtgct acaggatttc ctggttctgc gggcagagtt    60
ggacctccag gc                                                       72

<210> SEQ ID NO 1257
<211> LENGTH: 68
<212> TYPE: DNA
<213> ORGANISM: Homo sapiens

<400> SEQUENCE: 1257
ggagaccctg gtgaagctgg cccgcagggt gatcagggaa gagaaggccc cgttggtgtc    60
cctggaga                                                            68

<210> SEQ ID NO 1258
<211> LENGTH: 66
<212> TYPE: DNA
<213> ORGANISM: Homo sapiens

<400> SEQUENCE: 1258
gagagcaagc gagacattct gttcctcttt gacggctcag ccaatcttgt gggccagttc    60
cctgtt                                                              66

<210> SEQ ID NO 1259
<211> LENGTH: 66
<212> TYPE: DNA
<213> ORGANISM: Homo sapiens

<400> SEQUENCE: 1259
gaatcattca ccaggcaaat tgctggcagg gttgctggtg gtaggaatgt tccacccgca    60
gtacag                                                              66

<210> SEQ ID NO 1260
<211> LENGTH: 66
<212> TYPE: DNA
<213> ORGANISM: Homo sapiens

<400> SEQUENCE: 1260
cttcaaggtt ggggaggagt ttgaggagca gactgtggat gggaggccct gtaagagcct    60
ggtgaa    66

<210> SEQ ID NO 1261
<211> LENGTH: 69
<212> TYPE: DNA
<213> ORGANISM: Homo sapiens

<400> SEQUENCE: 1261
agggtctggt ttgtcgtgag gagctccgcg atgtcctctc aacagagcgc cgtttccgcc    60
aaaggcttt    69

<210> SEQ ID NO 1262
<211> LENGTH: 65
<212> TYPE: DNA
<213> ORGANISM: Homo sapiens

<400> SEQUENCE: 1262
gggtctgtgc cccatgacac ctggctgccc aagaagtgtt ccctgtgtaa atgctggcac    60
ggtca    65

<210> SEQ ID NO 1263
<211> LENGTH: 77
<212> TYPE: DNA
<213> ORGANISM: Homo sapiens

<400> SEQUENCE: 1263
caccagcacc cagacacagg agtccaccaa tggccagaac agagggactg agatccacgg    60
tcaaggcagg agccaga    77

<210> SEQ ID NO 1264
<211> LENGTH: 69
<212> TYPE: DNA
<213> ORGANISM: Homo sapiens

<400> SEQUENCE: 1264
gatgtgattg aggtgcatgg aaaacatgaa gagcgccagg atgaacatgg tttcatctcc    60
agggagttc    69

<210> SEQ ID NO 1265
<211> LENGTH: 72
<212> TYPE: DNA
<213> ORGANISM: Homo sapiens

<400> SEQUENCE: 1265
ttacgcagct catgctcttg aacggctctt tactatgcga gggcctaaca atgccactct    60
ctttacagct gc    72

<210> SEQ ID NO 1266
<211> LENGTH: 74
<212> TYPE: DNA
<213> ORGANISM: Homo sapiens

<400> SEQUENCE: 1266
tgcagcggct gattgacagt cagatggaga cctcgtgcca aattacattt gagtttgtag    60
accaggaaca gttg    74

-continued

```
<210> SEQ ID NO 1267
<211> LENGTH: 76
<212> TYPE: DNA
<213> ORGANISM: Homo sapiens

<400> SEQUENCE: 1267
gagttcaagt gccctgacgg cgaggtcatg aagaagaaca tgatgttcat caagacctgt      60
gcctgccatt acaact                                                      76

<210> SEQ ID NO 1268
<211> LENGTH: 69
<212> TYPE: DNA
<213> ORGANISM: Homo sapiens

<400> SEQUENCE: 1268
tggctcactt cggctaaaat gcagaaatgc atgctgtcag cgttggtatt tcacattcaa      60
tggagctga                                                              69

<210> SEQ ID NO 1269
<211> LENGTH: 62
<212> TYPE: DNA
<213> ORGANISM: Homo sapiens

<400> SEQUENCE: 1269
ggccgagatc tacaaaaacg gccccgtgga gggagctttc tctgtgtatt cggacttcct      60
gc                                                                     62

<210> SEQ ID NO 1270
<211> LENGTH: 78
<212> TYPE: DNA
<213> ORGANISM: Homo sapiens

<400> SEQUENCE: 1270
tgacaacatg atggctcaga acctggtgga cttgccgatg ttttctgtct acatgagcag      60
taacccagaa ggtggtgc                                                    78

<210> SEQ ID NO 1271
<211> LENGTH: 76
<212> TYPE: DNA
<213> ORGANISM: Homo sapiens

<400> SEQUENCE: 1271
tgacaacggc tttccagtac atcattgata caagggcat cgactcagac gcttcctatc       60
cctacaaagc catgga                                                      76

<210> SEQ ID NO 1272
<211> LENGTH: 68
<212> TYPE: DNA
<213> ORGANISM: Homo sapiens

<400> SEQUENCE: 1272
ggagcaaaat cgatgcagtg cttccaagga tggaccacac agaggctgcc tctcccatca      60
cttcccta                                                               68

<210> SEQ ID NO 1273
<211> LENGTH: 84
<212> TYPE: DNA
<213> ORGANISM: Homo sapiens

<400> SEQUENCE: 1273
```

```
cttccccatg ttcaaaagag gacgctgtct ttgcataggc cctggggtaa aagcagtgaa    60
agtggcagat attgagaaag cctc                                          84

<210> SEQ ID NO 1274
<211> LENGTH: 67
<212> TYPE: DNA
<213> ORGANISM: Homo sapiens

<400> SEQUENCE: 1274
gagctacaga tgcccatgcc gattcttcga aagccatgtt gccagagcca acgtcaagca    60
tctcaaa                                                             67

<210> SEQ ID NO 1275
<211> LENGTH: 74
<212> TYPE: DNA
<213> ORGANISM: Homo sapiens

<400> SEQUENCE: 1275
tgcgcccttt cctctgtaca tataccctta agaacgcccc ctccacacac tgcccccag    60 tatatgccgc attg                                                     74

<210> SEQ ID NO 1276
<211> LENGTH: 76
<212> TYPE: DNA
<213> ORGANISM: Homo sapiens

<400> SEQUENCE: 1276
aagaatgggc agaaagcttg tctcaacccc gcatcgccca tggttaagaa aatcatcgaa    60
aagatgctga aaaatg                                                   76

<210> SEQ ID NO 1277
<211> LENGTH: 78
<212> TYPE: DNA
<213> ORGANISM: Homo sapiens

<400> SEQUENCE: 1277
aagaaggcca gcatttatgg tagaatatat aattatatat aaggtggcca cgctggggca    60
agttccctcc ccactcac                                                 78

<210> SEQ ID NO 1278
<211> LENGTH: 70
<212> TYPE: DNA
<213> ORGANISM: Homo sapiens

<400> SEQUENCE: 1278
accagaccat tgtctcagag caggtgctgg ctctttcctg gctactccat gttggctagc    60
ctctggtaac                                                          70

<210> SEQ ID NO 1279
<211> LENGTH: 66
<212> TYPE: DNA
<213> ORGANISM: Homo sapiens

<400> SEQUENCE: 1279
gtctttggct ctggcctctg caaagtggca ggtgccctct tcaacatcaa cttctacgca    60
ggagcc                                                              66

<210> SEQ ID NO 1280
<211> LENGTH: 72
```

```
<212> TYPE: DNA
<213> ORGANISM: Homo sapiens

<400> SEQUENCE: 1280
tgaccgcttc taccccaatg acttgtgggt ggttgtgttc cagtttcagc acatcatggt    60
tggccttatc ct                                                        72

<210> SEQ ID NO 1281
<211> LENGTH: 71
<212> TYPE: DNA
<213> ORGANISM: Homo sapiens

<400> SEQUENCE: 1281
ccagctttgt gcctgtcact attcctcatg ccaccactgc caacacctct gtcttgggct    60
accacattcc c                                                         71

<210> SEQ ID NO 1282
<211> LENGTH: 76
<212> TYPE: DNA
<213> ORGANISM: Homo sapiens

<400> SEQUENCE: 1282
tgctcattct tgaggagcat taaggtattt cgaaactgcc aagggtgctg gtgcggatgg    60
acactaatgc agccac                                                    76

<210> SEQ ID NO 1283
<211> LENGTH: 68
<212> TYPE: DNA
<213> ORGANISM: Homo sapiens

<400> SEQUENCE: 1283
tccaattcca gcatcactgt ggagaaaagc tgtttgtctc cccagcatac tttatcgcct    60
tcactgcc                                                             68

<210> SEQ ID NO 1284
<211> LENGTH: 68
<212> TYPE: DNA
<213> ORGANISM: Homo sapiens

<400> SEQUENCE: 1284
gattcagacg aggatgagcc ttgtgccatc agtggcaaat ggactttcca aagggacagc    60
aagaggtg                                                             68

<210> SEQ ID NO 1285
<211> LENGTH: 76
<212> TYPE: DNA
<213> ORGANISM: Homo sapiens

<400> SEQUENCE: 1285
agacatcagc tcctggttca acgaggccat tgacttcata gactccatca agaatgctgg    60
aggaagggtg tttgtc                                                    76

<210> SEQ ID NO 1286
<211> LENGTH: 76
<212> TYPE: DNA
<213> ORGANISM: Homo sapiens

<400> SEQUENCE: 1286
tatccctgtg gaggacaacc agatggtgga gatcagtgcc tggttccagg aggccatagg    60
```

```
cttcattgac tgggtg                                                    76

<210> SEQ ID NO 1287
<211> LENGTH: 68
<212> TYPE: DNA
<213> ORGANISM: Homo sapiens

<400> SEQUENCE: 1287
tggtgacgat ggaggagctg cgggagatgg actgcagtgt gctcaaaagg ctgatgaacc   60
gggacgag                                                             68

<210> SEQ ID NO 1288
<211> LENGTH: 67
<212> TYPE: DNA
<213> ORGANISM: Homo sapiens

<400> SEQUENCE: 1288
catgcaggga ctgggattcg aggacttcca ggcgcatagg gtagaaccaa atgatagggt   60
aggagca                                                              67

<210> SEQ ID NO 1289
<211> LENGTH: 75
<212> TYPE: DNA
<213> ORGANISM: Homo sapiens

<400> SEQUENCE: 1289
actccctcta cccttgagca agggcagggg tccctgagct gttcttctgc cccatactga   60
aggaactgag gcctg                                                     75

<210> SEQ ID NO 1290
<211> LENGTH: 73
<212> TYPE: DNA
<213> ORGANISM: Homo sapiens

<400> SEQUENCE: 1290
accacctcct ttccagacgg gagcctatac cgcacatgca gcaaccagtc catccacagg   60
cagctcccaa cct                                                       73

<210> SEQ ID NO 1291
<211> LENGTH: 73
<212> TYPE: DNA
<213> ORGANISM: Homo sapiens

<400> SEQUENCE: 1291
tgacattatc atcccgctaa ggactgcgga cagcgtcttc tgccctcact acgagaaggt   60
cagcggggac tac                                                       73

<210> SEQ ID NO 1292
<211> LENGTH: 62
<212> TYPE: DNA
<213> ORGANISM: Homo sapiens

<400> SEQUENCE: 1292
tgtcgatgga cttccagaac cacctgggca gctgccaaaa gtgtgatcca agctgtccca   60
at                                                                   62

<210> SEQ ID NO 1293
<211> LENGTH: 76
<212> TYPE: DNA
<213> ORGANISM: Homo sapiens
```

```
<400> SEQUENCE: 1293
gtccccgctg cagatctctg acccgttcgg atcctttcct cactcgccca ccatggacaa    60
ctaccctaag ctggag                                                    76

<210> SEQ ID NO 1294
<211> LENGTH: 78
<212> TYPE: DNA
<213> ORGANISM: Homo sapiens

<400> SEQUENCE: 1294
ccatgtggat gaatgaggtg tctcctttcc atacccagtc tcaccttctc cccaccctac    60
ctcacctctt ctcaggca                                                  78

<210> SEQ ID NO 1295
<211> LENGTH: 71
<212> TYPE: DNA
<213> ORGANISM: Homo sapiens

<400> SEQUENCE: 1295
gcactgtggg cagatgaaga ggaagtaccg tgtctgcaat gtgacccggc ggcccgccag    60
tcaccaaaca t                                                         71

<210> SEQ ID NO 1296
<211> LENGTH: 75
<212> TYPE: DNA
<213> ORGANISM: Homo sapiens

<400> SEQUENCE: 1296
gctagtactt tgatgctccc ttgatggggt ccagagagcc tccctgcagc caccagactt    60
ggcctccagc tgttc                                                     75

<210> SEQ ID NO 1297
<211> LENGTH: 68
<212> TYPE: DNA
<213> ORGANISM: Homo sapiens

<400> SEQUENCE: 1297
caaggccgtg aacgagaagt cctgcaactg cctcctgctc aaagtcaacc agattggctc    60
cgtgaccg                                                             68

<210> SEQ ID NO 1298
<211> LENGTH: 72
<212> TYPE: DNA
<213> ORGANISM: Homo sapiens

<400> SEQUENCE: 1298
aagccttgga gggtttcatt gccgtggtga cccaagatgg cgacatgatc tttctgtcag    60
aaaacatcag ca                                                        72

<210> SEQ ID NO 1299
<211> LENGTH: 75
<212> TYPE: DNA
<213> ORGANISM: Homo sapiens

<400> SEQUENCE: 1299
gggccctcca gaacaatgat gggctttatg atcctgactg cgatgagagc gggctcttta    60
aggccaagca gtgca                                                     75
```

```
<210> SEQ ID NO 1300
<211> LENGTH: 72
<212> TYPE: DNA
<213> ORGANISM: Homo sapiens

<400> SEQUENCE: 1300
gcggtcagca tcacaactaa tcaggctgct ccatcacctg tcctgacgat taagaaagat    60
cggacctcca ga                                                       72

<210> SEQ ID NO 1301
<211> LENGTH: 66
<212> TYPE: DNA
<213> ORGANISM: Homo sapiens

<400> SEQUENCE: 1301
caaccaggca gctccatcgg cagtgtccat catgcatcag gtgagccgca ccgtggacag    60
cattac                                                              66

<210> SEQ ID NO 1302
<211> LENGTH: 77
<212> TYPE: DNA
<213> ORGANISM: Homo sapiens

<400> SEQUENCE: 1302
tgaacggggt atcctcctta gccacggggc ccgtcccatt tgagcctgtc aatgtcacca    60
ctgaccgaga ggtacct                                                  77

<210> SEQ ID NO 1303
<211> LENGTH: 69
<212> TYPE: DNA
<213> ORGANISM: Homo sapiens

<400> SEQUENCE: 1303
actggtcctc catcggctcc ccaggagctt tggtttgagg tgcaaggctc agcactcatg    60
ctacactgg                                                           69

<210> SEQ ID NO 1304
<211> LENGTH: 66
<212> TYPE: DNA
<213> ORGANISM: Homo sapiens

<400> SEQUENCE: 1304
gccaaaggca aggagacctt gggagtcaga catgaggcca gaggcagagg gagactctga    60
gggtga                                                              66

<210> SEQ ID NO 1305
<211> LENGTH: 91
<212> TYPE: DNA
<213> ORGANISM: Homo sapiens

<400> SEQUENCE: 1305
ataacaaagt gtagctctga catgaatggc tattgtttgc atggacagtg catctatctg    60
gtggacatga gtcaaaacta ctgcaggtgt g                                  91

<210> SEQ ID NO 1306
<211> LENGTH: 70
<212> TYPE: DNA
<213> ORGANISM: Homo sapiens

<400> SEQUENCE: 1306
```

```
acccccagac cggatcaggc aagctggccc tcatgtcccc ttcacggtgt tgaggaagt    60 ctgccctaca                                                         70

<210> SEQ ID NO 1307
<211> LENGTH: 66
<212> TYPE: DNA
<213> ORGANISM: Homo sapiens

<400> SEQUENCE: 1307
cagcagcgtc aggaatctct agaaagaaga acctcggcca cagggcccat cctcccacca   60
ggacat                                                             66

<210> SEQ ID NO 1308
<211> LENGTH: 75
<212> TYPE: DNA
<213> ORGANISM: Homo sapiens

<400> SEQUENCE: 1308
tgcaggccag actcagtatt cggggatgca gcagccagcc gtctacacag cctactcaca   60
gacaggacag cccta                                                   75

<210> SEQ ID NO 1309
<211> LENGTH: 73
<212> TYPE: DNA
<213> ORGANISM: Homo sapiens

<400> SEQUENCE: 1309
gtgaaggatg tgaagcagac gtacttggca cgggtcttct cctacccggc agggaatgtg   60
gagagcaccg gtt                                                     73

<210> SEQ ID NO 1310
<211> LENGTH: 66
<212> TYPE: DNA
<213> ORGANISM: Homo sapiens

<400> SEQUENCE: 1310
gggtccaaag tgatccaaaa cgaattcacg gtggggagg aatgtgagct ggagacaatg    60
acaggg                                                             66

<210> SEQ ID NO 1311
<211> LENGTH: 66
<212> TYPE: DNA
<213> ORGANISM: Homo sapiens

<400> SEQUENCE: 1311
gctttgccac caggaaagtg gctggcatgg ccaaacctaa catgatcatc agtgtgaatg   60
gggatg                                                             66

<210> SEQ ID NO 1312
<211> LENGTH: 66
<212> TYPE: DNA
<213> ORGANISM: Homo sapiens

<400> SEQUENCE: 1312
gccccaggtc tcctgacatt gtgttccagg ctgcgggcta agccagacag tgtttgcctc   60
cggttc                                                             66

<210> SEQ ID NO 1313
```

```
<211> LENGTH: 66
<212> TYPE: DNA
<213> ORGANISM: Homo sapiens

<400> SEQUENCE: 1313
ctgaccagaa ccacggctta tccggcctgt ccacgaacca cttatacacc cacatgaccc    60
acttcc                                                                66

<210> SEQ ID NO 1314
<211> LENGTH: 91
<212> TYPE: DNA
<213> ORGANISM: Homo sapiens

<400> SEQUENCE: 1314
ggattgctca acaaccatgc tgggcatctg gaccctccta cctctggttc ttacgtctgt    60
tgctagatta tcgtccaaaa gtgttaatgc c                                   91

<210> SEQ ID NO 1315
<211> LENGTH: 80
<212> TYPE: DNA
<213> ORGANISM: Homo sapiens

<400> SEQUENCE: 1315
gcactttggg attctttcca ttatgattct ttgttacagg caccgagaat gttgtattca    60
gtgagggtct tcttacatgc                                                80

<210> SEQ ID NO 1316
<211> LENGTH: 66
<212> TYPE: DNA
<213> ORGANISM: Homo sapiens

<400> SEQUENCE: 1316
gcctcttcct gttcgacggc tcgcccacct acgtactggc ctacacccag agctaccggg    60
caaagc                                                                66

<210> SEQ ID NO 1317
<211> LENGTH: 70
<212> TYPE: DNA
<213> ORGANISM: Homo sapiens

<400> SEQUENCE: 1317
caacctcacc acctttgatg gggcccgtgg tgccaccacc tctcctggtg tctatgagct    60
ctcttcccgc                                                            70

<210> SEQ ID NO 1318
<211> LENGTH: 67
<212> TYPE: DNA
<213> ORGANISM: Homo sapiens

<400> SEQUENCE: 1318
cgagcccttt gatgacttcc tgttcccagc atcatccagg cccagtggct ctgagacagc    60
ccgctcc                                                               67

<210> SEQ ID NO 1319
<211> LENGTH: 66
<212> TYPE: DNA
<213> ORGANISM: Homo sapiens

<400> SEQUENCE: 1319
gaagaggaga agcgaagggt gcgccgggaa cgaaataaac tagcagcagc taaatgcagg    60
``` aaccgg 66

<210> SEQ ID NO 1320
<211> LENGTH: 71
<212> TYPE: DNA
<213> ORGANISM: Homo sapiens

<400> SEQUENCE: 1320
catccaagtg gagggaaact ttaaaacaaa acacccagt actgtggctc aggatatgat 60
gcgtgaggag a 71

<210> SEQ ID NO 1321
<211> LENGTH: 83
<212> TYPE: DNA
<213> ORGANISM: Homo sapiens

<400> SEQUENCE: 1321
tgaagtccag gacgatgatg cgcctctctc gcccatgctc tacagcagct cagccagcct 60
gtcaccttca gtaagcaagc cgt 83

<210> SEQ ID NO 1322
<211> LENGTH: 70
<212> TYPE: DNA
<213> ORGANISM: Homo sapiens

<400> SEQUENCE: 1322
cgacagagct tgtgcaccta agctgcagac caagcctttg cccagaattt aaggattcca 60
atggacgacc 70

<210> SEQ ID NO 1323
<211> LENGTH: 66
<212> TYPE: DNA
<213> ORGANISM: Homo sapiens

<400> SEQUENCE: 1323
cagccctgcc agtttgacta tgccgtcttc tgccctaacc tgacagaggt gtcatccaca 60
ggcaac 66

<210> SEQ ID NO 1324
<211> LENGTH: 72
<212> TYPE: DNA
<213> ORGANISM: Homo sapiens

<400> SEQUENCE: 1324
gtaagtcgga tgagcctgtc tgtgccagtg acaatgccac ttatgccagc gagtgtgcca 60
tgaaggaagc tg 72

<210> SEQ ID NO 1325
<211> LENGTH: 70
<212> TYPE: DNA
<213> ORGANISM: Homo sapiens

<400> SEQUENCE: 1325
accctcgaca agaccacact ttgggacttg ggagctgggg ctgaagttgc tctgtaccca 60
tgaactccca 70

<210> SEQ ID NO 1326
<211> LENGTH: 66
<212> TYPE: DNA

<213> ORGANISM: Homo sapiens

<400> SEQUENCE: 1326
gctcacagga cggctaccca tccgcaatgg cttctacacc accaacgccc atgccagaaa    60
cgccta    66

<210> SEQ ID NO 1327
<211> LENGTH: 71
<212> TYPE: DNA
<213> ORGANISM: Homo sapiens

<400> SEQUENCE: 1327
agcaccaatc ccgagaacag cgagctcaag tattcgggtc aagatgggct ctacataggc    60
gtcagtctcg c    71

<210> SEQ ID NO 1328
<211> LENGTH: 83
<212> TYPE: DNA
<213> ORGANISM: Homo sapiens

<400> SEQUENCE: 1328
gcatgggaac catcaaccag caggccatgg accaacttca ctatgtgaca gagctgacag    60
atcgaatcaa ggcaaactcc tca    83

<210> SEQ ID NO 1329
<211> LENGTH: 72
<212> TYPE: DNA
<213> ORGANISM: Homo sapiens

<400> SEQUENCE: 1329
cgctccagac ctatgatgac ttgttagcca aagactgcca ctgcatatga gcagtcctgg    60
tccttccact gt    72

<210> SEQ ID NO 1330
<211> LENGTH: 79
<212> TYPE: DNA
<213> ORGANISM: Homo sapiens

<400> SEQUENCE: 1330
ctgggcctgc tactctgcgg ggcggcgagc ctcgagctgt ctagacccca cggcgacacc    60
gccaagaagc ccatcatcg    79

<210> SEQ ID NO 1331
<211> LENGTH: 68
<212> TYPE: DNA
<213> ORGANISM: Homo sapiens

<400> SEQUENCE: 1331
gttcactggg ggtgtatggg gtagatgggt ggagagggag gggataagag aggtgcatgt    60
tggtattt    68

<210> SEQ ID NO 1332
<211> LENGTH: 74
<212> TYPE: DNA
<213> ORGANISM: Homo sapiens

<400> SEQUENCE: 1332
tgtcatgtac gacggcttct ccatgcagcg gctggtgaag tgcaacgcct ggccttgtcc    60
caacactgtg gact    74

```
<210> SEQ ID NO 1333
<211> LENGTH: 72
<212> TYPE: DNA
<213> ORGANISM: Homo sapiens

<400> SEQUENCE: 1333
gaacgtgcct gactttgact tccctcccga attctatgag catgccaagg ctctgtggga    60
ggatgaagga gt                                                        72

<210> SEQ ID NO 1334
<211> LENGTH: 68
<212> TYPE: DNA
<213> ORGANISM: Homo sapiens

<400> SEQUENCE: 1334
accactagca tctcccaagc caggaaagct gtggagcagc taaagatgga agcctgtatg    60
gacagggt                                                             68

<210> SEQ ID NO 1335
<211> LENGTH: 74
<212> TYPE: DNA
<213> ORGANISM: Homo sapiens

<400> SEQUENCE: 1335
ccacagacac atcgggttac tacatctgta cctccagcaa tgaggagggg acgcagttct    60
gcaacatcac ggtg                                                      74

<210> SEQ ID NO 1336
<211> LENGTH: 67
<212> TYPE: DNA
<213> ORGANISM: Homo sapiens

<400> SEQUENCE: 1336
gcttatgacc gaccccaagc tcatcacctg gtctccggtg tgtcgcaacg atgttgcctg    60
gaacttt                                                              67

<210> SEQ ID NO 1337
<211> LENGTH: 75
<212> TYPE: DNA
<213> ORGANISM: Homo sapiens

<400> SEQUENCE: 1337
cacacagatc tcctactcca tccagtcctg aggagcctta ggatgcagca tgccttcagg    60
agacactgct ggacc                                                     75

<210> SEQ ID NO 1338
<211> LENGTH: 69
<212> TYPE: DNA
<213> ORGANISM: Homo sapiens

<400> SEQUENCE: 1338
gctctaggtc caattgttct gctctaactg atacctcaac cttggggcca gcatctccca    60
ctgcctcca                                                            69

<210> SEQ ID NO 1339
<211> LENGTH: 69
<212> TYPE: DNA
<213> ORGANISM: Homo sapiens
```

```
<400> SEQUENCE: 1339
atctctgcgc ctttctgggg gcgggcaagc tggcggtaga tttgtgatgt cacagtgcaa    60
actgcagtg                                                            69

<210> SEQ ID NO 1340
<211> LENGTH: 73
<212> TYPE: DNA
<213> ORGANISM: Homo sapiens

<400> SEQUENCE: 1340
cgaaaagatg ctgaacagtg acaaatccaa ctgaccagaa gggaggagga agctcactgg    60
tggctgttcc tga                                                       73

<210> SEQ ID NO 1341
<211> LENGTH: 77
<212> TYPE: DNA
<213> ORGANISM: Homo sapiens

<400> SEQUENCE: 1341
gctggaactc cgcgttcacc cgcaaagacg agatcatcac cagcctcgtg tctgccttag    60
actccatgtg ctcagcg                                                   77

<210> SEQ ID NO 1342
<211> LENGTH: 67
<212> TYPE: DNA
<213> ORGANISM: Homo sapiens

<400> SEQUENCE: 1342
tggaagaccg attcagatga ggataggaat tcactcaggc tccgtgctgg ctggagttgt    60
tggggtg                                                              67

<210> SEQ ID NO 1343
<211> LENGTH: 67
<212> TYPE: DNA
<213> ORGANISM: Homo sapiens

<400> SEQUENCE: 1343
cttctcccat gttgccattt ttgaggtgta caaaggtcag gccgtacaca cctctgttag    60
gaggcaa                                                              67

<210> SEQ ID NO 1344
<211> LENGTH: 66
<212> TYPE: DNA
<213> ORGANISM: Homo sapiens

<400> SEQUENCE: 1344
aacagttgcc tggggtagct ctacacaact ctgtccagcc cacagcaatg attccagagg    60
ccatgg                                                               66

<210> SEQ ID NO 1345
<211> LENGTH: 67
<212> TYPE: DNA
<213> ORGANISM: Homo sapiens

<400> SEQUENCE: 1345
gacgatttgc cagctttgag gctcaaggtg cattggccaa catagctgtg gacaaagcca    60
acctgga                                                              67
```

```
<210> SEQ ID NO 1346
<211> LENGTH: 66
<212> TYPE: DNA
<213> ORGANISM: Homo sapiens

<400> SEQUENCE: 1346
aagaggggcc gcagtattgg gagtggacca cagggtacgc caaggccaac gcacagactg      60
accgag                                                                66

<210> SEQ ID NO 1347
<211> LENGTH: 70
<212> TYPE: DNA
<213> ORGANISM: Homo sapiens

<400> SEQUENCE: 1347
cctgcgcggc tactacaacc agagcgaggc cagttctcac accctccagt ggatgattgg      60
ctgcgacctg                                                            70

<210> SEQ ID NO 1348
<211> LENGTH: 71
<212> TYPE: DNA
<213> ORGANISM: Homo sapiens

<400> SEQUENCE: 1348
tggcctgtcc attggtgatg ttgcgaagaa actgggagag atgtggaata acactgctgc      60
agatgacaag c                                                          71

<210> SEQ ID NO 1349
<211> LENGTH: 75
<212> TYPE: DNA
<213> ORGANISM: Homo sapiens

<400> SEQUENCE: 1349
aatggccaca actgtgaagt tagaaaagcc ctgtcaaagc aagagatggc tagtgcttca      60
tccagccaaa gaggt                                                      75

<210> SEQ ID NO 1350
<211> LENGTH: 66
<212> TYPE: DNA
<213> ORGANISM: Homo sapiens

<400> SEQUENCE: 1350
gccagtaaga acgaggagga tgaaggccat tcaaactcct ccccacgaca ctctgaagca      60
gcgacg                                                                66

<210> SEQ ID NO 1351
<211> LENGTH: 68
<212> TYPE: DNA
<213> ORGANISM: Homo sapiens

<400> SEQUENCE: 1351
cagcctcaag ttcggttttc gctaccggag ccttcccaga acaaacttct tgtgcgtttg      60
cttccaac                                                              68

<210> SEQ ID NO 1352
<211> LENGTH: 69
<212> TYPE: DNA
<213> ORGANISM: Homo sapiens

<400> SEQUENCE: 1352
```

```
ccaacctgcc tcaagagctg ctgcaggcct acggcaagga ctacatcgag cacttgcatg    60
ggcagttcc                                                            69
```

<210> SEQ ID NO 1353
<211> LENGTH: 70
<212> TYPE: DNA
<213> ORGANISM: Homo sapiens

<400> SEQUENCE: 1353

```
ctgctgcgac agtccactac cttttcgag agtgactccc gttgtcccaa ggcttcccag     60
agcgaacctg                                                           70
```

<210> SEQ ID NO 1354
<211> LENGTH: 73
<212> TYPE: DNA
<213> ORGANISM: Homo sapiens

<400> SEQUENCE: 1354

```
cctccctctg gtggtgcttc ctcagggccc accattgaag aggttgatta agccaaccaa    60
gtgtagatgt agc                                                       73
```

<210> SEQ ID NO 1355
<211> LENGTH: 78
<212> TYPE: DNA
<213> ORGANISM: Homo sapiens

<400> SEQUENCE: 1355

```
gcaagcaaca gtagtcgctg ttggatcggg ttctaaagga aagggtggag agattcaacc    60
agttagcgtg aaagttgg                                                  78
```

<210> SEQ ID NO 1356
<211> LENGTH: 68
<212> TYPE: DNA
<213> ORGANISM: Homo sapiens

<400> SEQUENCE: 1356

```
gcagacagtg accatctaca gctttccggc gcccaacgtg attctgacga agccagaggt    60
ctcagaag                                                             68
```

<210> SEQ ID NO 1357
<211> LENGTH: 69
<212> TYPE: DNA
<213> ORGANISM: Homo sapiens

<400> SEQUENCE: 1357

```
atcccatgaa gcccagatac acaaaattcc accccatgat caagaatcct gctccactaa    60
gaatggtgc                                                            69
```

<210> SEQ ID NO 1358
<211> LENGTH: 79
<212> TYPE: DNA
<213> ORGANISM: Homo sapiens

<400> SEQUENCE: 1358

```
cacgcagaaa accacacttc tcaaaccttc actcaacact tccttcccca aagccagaag    60
atgcacaagg aggaacatg                                                 79
```

<210> SEQ ID NO 1359
<211> LENGTH: 76

<212> TYPE: DNA
<213> ORGANISM: Homo sapiens

<400> SEQUENCE: 1359

```
ctgagaacca tcccggtaac ccgatcaccg ctggtcacca tgaaccacat tgtgcaaacc    60
ttctctcctg tcaaca                                                    76
```

<210> SEQ ID NO 1360
<211> LENGTH: 72
<212> TYPE: DNA
<213> ORGANISM: Homo sapiens

<400> SEQUENCE: 1360

```
ccgtgcttcc ggacaacttc cccagatacc ccgtgggcaa gttcttccaa tatgcacct     60
ggaagcagtc ca                                                        72
```

<210> SEQ ID NO 1361
<211> LENGTH: 66
<212> TYPE: DNA
<213> ORGANISM: Homo sapiens

<400> SEQUENCE: 1361

```
acatcccaac gcatgctcct ggagctcaca gccttctgtg gtgtcatttc tgaaacaagg    60
gcgtgg                                                               66
```

<210> SEQ ID NO 1362
<211> LENGTH: 69
<212> TYPE: DNA
<213> ORGANISM: Homo sapiens

<400> SEQUENCE: 1362

```
tggacaagta cgggatgaag ctgccaggca tggagtacgt tgacggggac tttcagtgcc    60
acaccttcg                                                            69
```

<210> SEQ ID NO 1363
<211> LENGTH: 68
<212> TYPE: DNA
<213> ORGANISM: Homo sapiens

<400> SEQUENCE: 1363

```
gggtcactat ggagttcaaa ggacagaact cctgcctggt gaccgggaca acctggccat    60
tcagaccc                                                             68
```

<210> SEQ ID NO 1364
<211> LENGTH: 64
<212> TYPE: DNA
<213> ORGANISM: Homo sapiens

<400> SEQUENCE: 1364

```
aaacatgctg gcagttattg atgagctgat gcaggccctg aatttcaaca gtgagactgt    60
gcca                                                                 64
```

<210> SEQ ID NO 1365
<211> LENGTH: 70
<212> TYPE: DNA
<213> ORGANISM: Homo sapiens

<400> SEQUENCE: 1365

```
aaggaaccat ctcactgtgt gtaaacatga cttccaagct ggccgtggct ctcttggcag    60
```
ccttcctgat                                                              70

<210> SEQ ID NO 1366
<211> LENGTH: 79
<212> TYPE: DNA
<213> ORGANISM: Homo sapiens

<400> SEQUENCE: 1366
ggcgctgtca tcgatttctt ccctgtgaaa acaagagcaa ggccgtggag caggtgaaga      60
atgcctttaa taagctcca                                                    79

<210> SEQ ID NO 1367
<211> LENGTH: 67
<212> TYPE: DNA
<213> ORGANISM: Homo sapiens

<400> SEQUENCE: 1367
agctgaggaa gatgctggtt ccctgcccac agaccttcca ggagaatgac ctgagcacct      60
tctttcc                                                                 67

<210> SEQ ID NO 1368
<211> LENGTH: 72
<212> TYPE: DNA
<213> ORGANISM: Homo sapiens

<400> SEQUENCE: 1368
cctgaacctt ccaaagatgg ctgaaaaaga tggatgcttc caatctggat tcaatgagga      60
gacttgcctg gt                                                           72

<210> SEQ ID NO 1369
<211> LENGTH: 68
<212> TYPE: DNA
<213> ORGANISM: Homo sapiens

<400> SEQUENCE: 1369
ccgctccgtc actgatgtct acctgctgaa cctagccttg gccgacctac tctttgccct      60
gaccttgc                                                                68

<210> SEQ ID NO 1370
<211> LENGTH: 63
<212> TYPE: DNA
<213> ORGANISM: Homo sapiens

<400> SEQUENCE: 1370
agccatcact ctcagtgcag ccaggtccta tcgtggcccc tgaggagacc ctgactctgc      60
agt                                                                     63

<210> SEQ ID NO 1371
<211> LENGTH: 67
<212> TYPE: DNA
<213> ORGANISM: Homo sapiens

<400> SEQUENCE: 1371
gaaagtgttt gcggagcaca agatctccta cagcggccag ttcttggtca atccggcta      60 cgccttc                                                                 67

<210> SEQ ID NO 1372
<211> LENGTH: 72
<212> TYPE: DNA
<213> ORGANISM: Homo sapiens

<400> SEQUENCE: 1372
gtgcccgagc catatagcag gcacgtccgg gtcctcactg tccttccact caacagtcat    60
caaccactac cg    72

<210> SEQ ID NO 1373
<211> LENGTH: 77
<212> TYPE: DNA
<213> ORGANISM: Homo sapiens

<400> SEQUENCE: 1373
ccatgatcct cactctgctg gtggactata cactccagac ctcgcttagc atggtaaatc    60
accggctaca aagcttc    77

<210> SEQ ID NO 1374
<211> LENGTH: 66
<212> TYPE: DNA
<213> ORGANISM: Homo sapiens

<400> SEQUENCE: 1374
caacgcttca gtgatcaatc ccggggcgat ttacagatgc aggatcggaa agaatcccgg    60
ccagac    66

<210> SEQ ID NO 1375
<211> LENGTH: 75
<212> TYPE: DNA
<213> ORGANISM: Homo sapiens

<400> SEQUENCE: 1375
aggccagccc tacattatca gagcaagagc cggatagagg acaaggctca gatcttgctg    60
gactgtggag aagac    75

<210> SEQ ID NO 1376
<211> LENGTH: 69
<212> TYPE: DNA
<213> ORGANISM: Homo sapiens

<400> SEQUENCE: 1376
cagtgacaaa cagcccttcc aacccaagga atcccacaaa agatggcgat gacgcccatg    60
aggctaaac    69

<210> SEQ ID NO 1377
<211> LENGTH: 79
<212> TYPE: DNA
<213> ORGANISM: Homo sapiens

<400> SEQUENCE: 1377
gatatgattg gtcgctgctt tgtgctcagc caggacctgg ccatccggga tgagttggat    60
ggtggggaat ggaagttct    79

<210> SEQ ID NO 1378
<211> LENGTH: 79
<212> TYPE: DNA
<213> ORGANISM: Homo sapiens

<400> SEQUENCE: 1378
actcggactg cacaagctat ttttgatgac agctatttgg gttattctgt ggctgtcgga    60
gatttcaatg gtgatggca    79

<210> SEQ ID NO 1379
<211> LENGTH: 74
<212> TYPE: DNA
<213> ORGANISM: Homo sapiens

<400> SEQUENCE: 1379
tcagaattgg atttggctca tttgtggaaa agactgtgat gccttacatt agcacaacac    60
cagctaagct cagg                                                      74

<210> SEQ ID NO 1380
<211> LENGTH: 78
<212> TYPE: DNA
<213> ORGANISM: Homo sapiens

<400> SEQUENCE: 1380
accggggagc cctacatgac gaaaatacct gcaaccgtta ctgccgtgac gagattgagt    60
cagtgaaaga gcttaagg                                                  78

<210> SEQ ID NO 1381
<211> LENGTH: 66
<212> TYPE: DNA
<213> ORGANISM: Homo sapiens

<400> SEQUENCE: 1381
caaggtgccc tcagtggagc tcaccaacct gtacccgtat tgcgactatg agatgaaggt    60
gtgcgc                                                               66

<210> SEQ ID NO 1382
<211> LENGTH: 71
<212> TYPE: DNA
<213> ORGANISM: Homo sapiens

<400> SEQUENCE: 1382
tcgtgaaaga tgaccaggag gctgtgctat gtttctacaa aaccgccaag gactgcgtca    60
tgatgttcac c                                                         71

<210> SEQ ID NO 1383
<211> LENGTH: 68
<212> TYPE: DNA
<213> ORGANISM: Homo sapiens

<400> SEQUENCE: 1383
gcaagaggaa aagcacatga ctgctgtaaa gggactgcct gagcaagaat gtgagcaaca    60
gcagaagg                                                             68

<210> SEQ ID NO 1384
<211> LENGTH: 72
<212> TYPE: DNA
<213> ORGANISM: Homo sapiens

<400> SEQUENCE: 1384
acaacgtctt gggaagatcc ttaagttgaa cagaaatggc catgcacgtt tctttgtgtg    60
acagagctgc tg                                                        72

<210> SEQ ID NO 1385
<211> LENGTH: 71
<212> TYPE: DNA
<213> ORGANISM: Homo sapiens

<400> SEQUENCE: 1385

```
gtcaaaatgg ggagggacta gggcagtttg gatagctcaa caagatacaa tctcactctg    60
tggtggtcct g                                                         71

<210> SEQ ID NO 1386
<211> LENGTH: 66
<212> TYPE: DNA
<213> ORGANISM: Homo sapiens

<400> SEQUENCE: 1386
acgcgcttag ccctactatg cacagtcaag caacacaggt gccaattagt caaagcgatg    60
gctcag                                                               66

<210> SEQ ID NO 1387
<211> LENGTH: 68
<212> TYPE: DNA
<213> ORGANISM: Homo sapiens

<400> SEQUENCE: 1387
gaggacgaag gcctctacac ctgccaggca tgcagtgttc ttggctgtgc aaaagtggag    60
gcattttt                                                             68

<210> SEQ ID NO 1388
<211> LENGTH: 80
<212> TYPE: DNA
<213> ORGANISM: Homo sapiens

<400> SEQUENCE: 1388
cggactttgg gtgcgacttg acgagcggtg gttcgacaag tggccttgcg ggccggatcg    60
tcccagtgga agagttgtaa                                                80

<210> SEQ ID NO 1389
<211> LENGTH: 76
<212> TYPE: DNA
<213> ORGANISM: Homo sapiens

<400> SEQUENCE: 1389
tgcaaaggta aaagtgatgg ttgactcagg agaccggaag cgagccatca gttctgtgtg    60
cacctacatt gtttat                                                    76

<210> SEQ ID NO 1390
<211> LENGTH: 71
<212> TYPE: DNA
<213> ORGANISM: Homo sapiens

<400> SEQUENCE: 1390
atgtgccagt gagcttgagt ccttggagaa acacaagcac ctgctagaaa gtactgttaa    60 ccagggctc a                                                          71

<210> SEQ ID NO 1391
<211> LENGTH: 83
<212> TYPE: DNA
<213> ORGANISM: Homo sapiens

<400> SEQUENCE: 1391
ggcctgctga gatcaaagac tacagtccct acttcaagac cattgaggac ctgaggaaca    60
agattctcac agccacagtg gac                                            83

<210> SEQ ID NO 1392
```

```
<211> LENGTH: 68
<212> TYPE: DNA
<213> ORGANISM: Homo sapiens

<400> SEQUENCE: 1392
agagatcgag gctctcaagg aggagctgct cttcatgaag aagaaccacg aagaggaagt    60
aaaaggcc                                                            68

<210> SEQ ID NO 1393
<211> LENGTH: 68
<212> TYPE: DNA
<213> ORGANISM: Homo sapiens

<400> SEQUENCE: 1393
aggttcaact aacggagctg agacgcacct cccagagcct tgagatagaa ctccagtccc    60
atctcagc                                                            68

<210> SEQ ID NO 1394
<211> LENGTH: 67
<212> TYPE: DNA
<213> ORGANISM: Homo sapiens

<400> SEQUENCE: 1394
agaacgagct gtgtctccgg cagagcgtgg aggctgacat caatggcctg cggaaagtcc    60
tggatga                                                             67

<210> SEQ ID NO 1395
<211> LENGTH: 76
<212> TYPE: DNA
<213> ORGANISM: Homo sapiens

<400> SEQUENCE: 1395
ctctgcctct tggagtttgg tagctacttc ttgatttggg cctggtgacc cacctggaat    60
gggaaggatg tcagct                                                   76

<210> SEQ ID NO 1396
<211> LENGTH: 69
<212> TYPE: DNA
<213> ORGANISM: Homo sapiens

<400> SEQUENCE: 1396
tcagtggaga aggagttgga ccagtcaaca tctctgttgt cacaagcagt gtttcctctg    60
gatatggca                                                           69

<210> SEQ ID NO 1397
<211> LENGTH: 76
<212> TYPE: DNA
<213> ORGANISM: Homo sapiens

<400> SEQUENCE: 1397
tcaaagtcag gtacgaagat gaaattaaca agcgcacagc tgctgagaat gaatttgtag    60
ccctgaaaaa ggacgt                                                   76

<210> SEQ ID NO 1398
<211> LENGTH: 86
<212> TYPE: DNA
<213> ORGANISM: Homo sapiens

<400> SEQUENCE: 1398
ggatgaagct tacatgaaca aggtagagct ggagtctcgc ctggaagggc tgaccgacga    60
```

```
gatcaacttc ctcaggcagc tatatg                                    86

<210> SEQ ID NO 1399
<211> LENGTH: 73
<212> TYPE: DNA
<213> ORGANISM: Homo sapiens

<400> SEQUENCE: 1399
cagatgaggc acatggagac ccaggccaag gacctgagga atcagttgct caactaccgt    60
tctgccattt caa                                                       73

<210> SEQ ID NO 1400
<211> LENGTH: 67
<212> TYPE: DNA
<213> ORGANISM: Homo sapiens

<400> SEQUENCE: 1400
gatgcactgc ggttagcagc gctctccatc gaggaaggca atccggggt gctgagcgta     60 tcctctg                                                              67

<210> SEQ ID NO 1401
<211> LENGTH: 67
<212> TYPE: DNA
<213> ORGANISM: Homo sapiens

<400> SEQUENCE: 1401
ctcctggcca acagcactgc actagaagag gccatgctcc aggaacagca gaggctgggc    60
cttgtgt                                                              67

<210> SEQ ID NO 1402
<211> LENGTH: 80
<212> TYPE: DNA
<213> ORGANISM: Homo sapiens

<400> SEQUENCE: 1402
actcaagcgg aaattgaagc agataggtct tatcagcaca gtctccgcct cctggattca    60
gtgtctcggc ttcagggagt                                                80

<210> SEQ ID NO 1403
<211> LENGTH: 72
<212> TYPE: DNA
<213> ORGANISM: Homo sapiens

<400> SEQUENCE: 1403
atttggtccc ggacagttct ttgatctgtc cattcgctgt ggcttggatc gcttcaaggt    60
ttacgccaat gg                                                        72

<210> SEQ ID NO 1404
<211> LENGTH: 67
<212> TYPE: DNA
<213> ORGANISM: Homo sapiens

<400> SEQUENCE: 1404
cacctggtct gggaagatac ctggaggttt tgattggggt ctcggtggcc ttcgtcctgc    60
tgctctt                                                              67

<210> SEQ ID NO 1405
<211> LENGTH: 66
<212> TYPE: DNA
```

<213> ORGANISM: Homo sapiens

<400> SEQUENCE: 1405
tgcaaacgct ggtgtcacag ccagcccccc aactgacctc atctggaaga accagaactc      60
gtgggg                                                                 66

<210> SEQ ID NO 1406
<211> LENGTH: 66
<212> TYPE: DNA
<213> ORGANISM: Homo sapiens

<400> SEQUENCE: 1406
ccaatgggag aacaacgggc aggtgttcag cttgctgagc ctgggctcac agtaccagcc      60
tcagcg                                                                 66

<210> SEQ ID NO 1407
<211> LENGTH: 66
<212> TYPE: DNA
<213> ORGANISM: Homo sapiens

<400> SEQUENCE: 1407
tcagcgggct cttaaacaac cagctgtccc cgcagtaaag aagcctgcgt ggtcaactcc      60
tgtctt                                                                 66

<210> SEQ ID NO 1408
<211> LENGTH: 75
<212> TYPE: DNA
<213> ORGANISM: Homo sapiens

<400> SEQUENCE: 1408
ccgggagcag ggaatcaccc tgcgcgggag cgccgaaatc gtggccgagt tcttctcatt      60
cggcatcaac agcat                                                       75

<210> SEQ ID NO 1409
<211> LENGTH: 70
<212> TYPE: DNA
<213> ORGANISM: Homo sapiens

<400> SEQUENCE: 1409
gctgcctttg gtaagaacat gtcgtccatc ttgccattca cgccgccagt tgtgaagaga      60
ctgctgggat                                                             70

<210> SEQ ID NO 1410
<211> LENGTH: 76
<212> TYPE: DNA
<213> ORGANISM: Homo sapiens

<400> SEQUENCE: 1410
ggacattact ggcctgttca caatgagctt gcattccagc ctcccatttc caatcatcct      60
gctcctgagt attggt                                                      76

<210> SEQ ID NO 1411
<211> LENGTH: 72
<212> TYPE: DNA
<213> ORGANISM: Homo sapiens

<400> SEQUENCE: 1411
tccatcaagg ctttcgacta cgagaaggcg tacagcctgc agcggcccaa tgaccacgag      60
tttatgcagc ag                                                          72

<210> SEQ ID NO 1412
<211> LENGTH: 66
<212> TYPE: DNA
<213> ORGANISM: Homo sapiens

<400> SEQUENCE: 1412
gttgggagct tgctgtgtct aacctccaac tgctgtgctg tctgctaggg tcacctcctg    60
tttgtg                                                              66

<210> SEQ ID NO 1413
<211> LENGTH: 66
<212> TYPE: DNA
<213> ORGANISM: Homo sapiens

<400> SEQUENCE: 1413
attcggcagc ctcgttcttc gccttcatcg ccacgctgct ctacattctc catgccttca    60
gcatct                                                              66

<210> SEQ ID NO 1414
<211> LENGTH: 67
<212> TYPE: DNA
<213> ORGANISM: Homo sapiens

<400> SEQUENCE: 1414
cggaccacca ggtcagagcc aattcgcaga gcagggaaga gtggtacctc aacacccact    60
acccctg                                                             67

<210> SEQ ID NO 1415
<211> LENGTH: 75
<212> TYPE: DNA
<213> ORGANISM: Homo sapiens

<400> SEQUENCE: 1415
gacttttgcc cgctaccttt cattccggcg tgacaacaat gagctgttgc tcttcatact    60
gaagcagtta gtggc                                                    75

<210> SEQ ID NO 1416
<211> LENGTH: 71
<212> TYPE: DNA
<213> ORGANISM: Homo sapiens

<400> SEQUENCE: 1416
cgctcagcca gatgcaatca atgccccagt cacctgctgt tataacttca ccaataggaa    60
gatctcagtg c                                                        71

<210> SEQ ID NO 1417
<211> LENGTH: 68
<212> TYPE: DNA
<213> ORGANISM: Homo sapiens

<400> SEQUENCE: 1417
ctacagggac gccatcgaat ccggatcttg atgctggtgt aagtgaacat tcaggtgatt    60
ggttggat                                                            68

<210> SEQ ID NO 1418
<211> LENGTH: 86
<212> TYPE: DNA
<213> ORGANISM: Homo sapiens -continued

<400> SEQUENCE: 1418
ccatgatgga gaggcagaca tcatgatcaa ctttggccgc tgggagcatg gcgatggata        60
cccctttgac ggtaaggacg gactcc                                            86

<210> SEQ ID NO 1419
<211> LENGTH: 91
<212> TYPE: DNA
<213> ORGANISM: Homo sapiens

<400> SEQUENCE: 1419
tcatcctggc gatctacttc ctctggcaga acctaggtcc ctctgtcctg gctggagtcg        60
ctttcatggt cttgctgatt ccactcaacg g                                      91

<210> SEQ ID NO 1420
<211> LENGTH: 73
<212> TYPE: DNA
<213> ORGANISM: Homo sapiens

<400> SEQUENCE: 1420
gatgcagaat tgaggcagac tttacaagaa gatttacttc gtcgattccc agatcttaac        60
cgacttgcca aga                                                          73

<210> SEQ ID NO 1421
<211> LENGTH: 70
<212> TYPE: DNA
<213> ORGANISM: Homo sapiens

<400> SEQUENCE: 1421
cccgctccca gatgtaaaga acgcgacttc cacaaacctg gattttttat gtacaaccct        60
gaccgtgacc                                                              70

<210> SEQ ID NO 1422
<211> LENGTH: 66
<212> TYPE: DNA
<213> ORGANISM: Homo sapiens

<400> SEQUENCE: 1422
ctatgagcca tgtgggaacc ggagcttcga gacctgcagg accatcaacg gcatccactc        60
caacat                                                                  66

<210> SEQ ID NO 1423
<211> LENGTH: 69
<212> TYPE: DNA
<213> ORGANISM: Homo sapiens

<400> SEQUENCE: 1423
agtgtgcctg cgtctacaac ggggctgcct atgccccagg ggccacctac tccacagact        60
gcaccaact                                                               69

<210> SEQ ID NO 1424
<211> LENGTH: 67
<212> TYPE: DNA
<213> ORGANISM: Homo sapiens

<400> SEQUENCE: 1424
tgcccttgca ctgtcctaac ggctcagcca tcctgcacac ctacacccac gtggatgagt        60
gtggctg                                                                 67

```
<210> SEQ ID NO 1425
<211> LENGTH: 66
<212> TYPE: DNA
<213> ORGANISM: Homo sapiens

<400> SEQUENCE: 1425
caccttcggg tgcttctgcc cggaaggtac ggtcctgaat gacctctcca ataaccacac    60
ctgcgt                                                               66

<210> SEQ ID NO 1426
<211> LENGTH: 74
<212> TYPE: DNA
<213> ORGANISM: Homo sapiens

<400> SEQUENCE: 1426
gccgagatcg ccaagatgtt gccagggagg acagacaatg ctgtgaagaa tcactggaac    60
tctaccatca aaag                                                      74

<210> SEQ ID NO 1427
<211> LENGTH: 66
<212> TYPE: DNA
<213> ORGANISM: Homo sapiens

<400> SEQUENCE: 1427
atgaaagtgc gcaaacaggt ggcaggaaac gtggcatgtc tcggaggctg gcatcactga    60
ggcact                                                               66

<210> SEQ ID NO 1428
<211> LENGTH: 68
<212> TYPE: DNA
<213> ORGANISM: Homo sapiens

<400> SEQUENCE: 1428
ctgccgggat ggcttctatg aggctgagct ctgcccggac cgctgcatcc acagtttcca    60
gaacctgg                                                             68

<210> SEQ ID NO 1429
<211> LENGTH: 67
<212> TYPE: DNA
<213> ORGANISM: Homo sapiens

<400> SEQUENCE: 1429
gagagagtga gcgaaccctg cccaggctcc aagaagcagc tgaagtttga agagctccag    60
tgcgacg                                                              67

<210> SEQ ID NO 1430
<211> LENGTH: 74
<212> TYPE: DNA
<213> ORGANISM: Homo sapiens

<400> SEQUENCE: 1430
ccaaccctgc agactccaag cctgggacca tccgtggaga cttctgcata caagttggca    60
ggaacattat acat                                                      74

<210> SEQ ID NO 1431
<211> LENGTH: 69
<212> TYPE: DNA
<213> ORGANISM: Homo sapiens

<400> SEQUENCE: 1431
```

```
cacagcttgc ttgtcgatgt ccctgccttc gcctgcctct ctgcccttgt cctcatcacc      60
gaccggcat                                                              69

<210> SEQ ID NO 1432
<211> LENGTH: 76
<212> TYPE: DNA
<213> ORGANISM: Homo sapiens

<400> SEQUENCE: 1432
ctacagccta aacggcaagg actgggaata cattcaggac cccaggaccc agcagccaaa      60
gctgttcgaa gggaac                                                      76

<210> SEQ ID NO 1433
<211> LENGTH: 80
<212> TYPE: DNA
<213> ORGANISM: Homo sapiens

<400> SEQUENCE: 1433
caaccgaagt tttcactcca gttgtcccca cagtagacac atatgatggc cgaggtgata      60
gtgtggttta tggactgagg                                                  80

<210> SEQ ID NO 1434
<211> LENGTH: 72
<212> TYPE: DNA
<213> ORGANISM: Homo sapiens

<400> SEQUENCE: 1434
ccctcgtgct gatgctactg aggagccagc gtctagggca gcagccgctt cctagaagac      60
caggtcatga tg                                                          72

<210> SEQ ID NO 1435
<211> LENGTH: 78
<212> TYPE: DNA
<213> ORGANISM: Homo sapiens

<400> SEQUENCE: 1435
ggtccctcca gaggatttga gggacagggt cggaggggc tcttccgcca gcaccggagg       60
aagaaagagg aggggctg                                                    78

<210> SEQ ID NO 1436
<211> LENGTH: 65
<212> TYPE: DNA
<213> ORGANISM: Homo sapiens

<400> SEQUENCE: 1436
tggagactct cagggtcgaa aacggcggca gaccagcatg acagatttct accactccaa      60
acgcc                                                                  65

<210> SEQ ID NO 1437
<211> LENGTH: 68
<212> TYPE: DNA
<213> ORGANISM: Homo sapiens

<400> SEQUENCE: 1437
ctttgaaccc ttgcttgcaa taggtgtgcg tcagaagcac ccaggacttc catttgcttt      60
gtcccggg                                                               68

<210> SEQ ID NO 1438
<211> LENGTH: 81
```

<212> TYPE: DNA
<213> ORGANISM: Homo sapiens

<400> SEQUENCE: 1438
ccgcaacgtg gttttctcac cctatggggt ggcctcggtg ttggccatgc tccagctgac    60
aacaggagga gaaacccagc a                                              81

<210> SEQ ID NO 1439
<211> LENGTH: 71
<212> TYPE: DNA
<213> ORGANISM: Homo sapiens

<400> SEQUENCE: 1439
gaaggtgttg gaggcactca aggacctcat caacgaggcc tgctgggata ttagctccag    60
cggtgtaaac c                                                         71

<210> SEQ ID NO 1440
<211> LENGTH: 79
<212> TYPE: DNA
<213> ORGANISM: Homo sapiens

<400> SEQUENCE: 1440
agttactaaa aaataccacg aggtccttca gttgagacca agaccggtg tcaggggatt     60 gcacaaatca ctcaccgac                                                 79

<210> SEQ ID NO 1441
<211> LENGTH: 66
<212> TYPE: DNA
<213> ORGANISM: Homo sapiens

<400> SEQUENCE: 1441
ccagctctcc ttccagctac agatcaatgt ccctgtccga gtgctggagc taagtgagag    60
ccaccc                                                               66

<210> SEQ ID NO 1442
<211> LENGTH: 74
<212> TYPE: DNA
<213> ORGANISM: Homo sapiens

<400> SEQUENCE: 1442
agagccagtt gctgtagaac tcaaatctct gctgggcaag gatgttctgt tcttgaagga    60
ctgtgtaggc ccag                                                      74

<210> SEQ ID NO 1443
<211> LENGTH: 67
<212> TYPE: DNA
<213> ORGANISM: Homo sapiens

<400> SEQUENCE: 1443
gtgattgaag agcatgccaa ttggtctgta tcccgagaag caggatttag ctattcccac    60
gcaggac                                                              67

<210> SEQ ID NO 1444
<211> LENGTH: 69
<212> TYPE: DNA
<213> ORGANISM: Homo sapiens

<400> SEQUENCE: 1444
ctccaccaag agcttcacct tcttcaactc catgagcccg ctgtcgtcgc agtccatgtt    60

```
ctcagcacc                                                              69

<210> SEQ ID NO 1445
<211> LENGTH: 66
<212> TYPE: DNA
<213> ORGANISM: Homo sapiens

<400> SEQUENCE: 1445
gatggtccag gactcacagc tggtttcctg aaaggctgcc acaagatggc gacaacgtca      60
cagtgg                                                                 66

<210> SEQ ID NO 1446
<211> LENGTH: 73
<212> TYPE: DNA
<213> ORGANISM: Homo sapiens

<400> SEQUENCE: 1446
gagcgcggtg aagagattgt tttctgaaag ctgcgttgga ggctgtgaca gagctgagag      60
cctgtgtgga gcg                                                         73

<210> SEQ ID NO 1447
<211> LENGTH: 76
<212> TYPE: DNA
<213> ORGANISM: Homo sapiens

<400> SEQUENCE: 1447
cccatggatg ctcctctgaa gagactttcc tcattgactg ccgaggcccc atgaatcaat      60
gtctggtagc caccgg                                                      76

<210> SEQ ID NO 1448
<211> LENGTH: 67
<212> TYPE: DNA
<213> ORGANISM: Homo sapiens

<400> SEQUENCE: 1448
gtggcccaat taggcttggc atctgctctg aggccagatg gagaatacac tttgctggca      60
cctgtga                                                                67

<210> SEQ ID NO 1449
<211> LENGTH: 65
<212> TYPE: DNA
<213> ORGANISM: Homo sapiens

<400> SEQUENCE: 1449
ctcactgagt tcgccaagag catccccagc ttcagcagcc tcttcctcaa cgaccaggtt      60
accct                                                                  65

<210> SEQ ID NO 1450
<211> LENGTH: 72
<212> TYPE: DNA
<213> ORGANISM: Homo sapiens

<400> SEQUENCE: 1450
tgactttatg gagcccaagt ttgagtttgc tgtgaagttc aatgcactgg aattagatga      60
cagcgacttg gc                                                          72

<210> SEQ ID NO 1451
<211> LENGTH: 71
<212> TYPE: DNA
<213> ORGANISM: Homo sapiens
```

```
<400> SEQUENCE: 1451
ccaatacttc catgctgtct tcaagccctg cttcctgcac atctcccagc ccagatgggg    60
agaacccatg t                                                        71

<210> SEQ ID NO 1452
<211> LENGTH: 86
<212> TYPE: DNA
<213> ORGANISM: Homo sapiens

<400> SEQUENCE: 1452
gccctcccag tgtgcaaata agggctgctg tttcgacgac accgttcgtg gggtcccctg    60
gtgcttctat cctaatacca tcgacg                                        86

<210> SEQ ID NO 1453
<211> LENGTH: 81
<212> TYPE: DNA
<213> ORGANISM: Homo sapiens

<400> SEQUENCE: 1453
tggctaagtg aagatgacaa tcatgttgca gcaattcact gtaaagctgg aaagggacga    60
actggtgtaa tgatatgtgc a                                             81

<210> SEQ ID NO 1454
<211> LENGTH: 68
<212> TYPE: DNA
<213> ORGANISM: Homo sapiens

<400> SEQUENCE: 1454
gctcatacga gcaaagggcc cgggccatat agtcccagtg tccagttcag gacactgcct    60
gtggatca                                                            68

<210> SEQ ID NO 1455
<211> LENGTH: 66
<212> TYPE: DNA
<213> ORGANISM: Homo sapiens

<400> SEQUENCE: 1455
tggtctacga ttacgggtgc acctccatcg tcatgctcaa ccagctgaac cagtccaact    60
ccgcct                                                              66

<210> SEQ ID NO 1456
<211> LENGTH: 73
<212> TYPE: DNA
<213> ORGANISM: Homo sapiens

<400> SEQUENCE: 1456
cgtcgtatgc gagagtctgt ttccaggatg cctgttagtt ctcagcacag atattctaca    60
cctcacgcct tca                                                      73

<210> SEQ ID NO 1457
<211> LENGTH: 83
<212> TYPE: DNA
<213> ORGANISM: Homo sapiens

<400> SEQUENCE: 1457
tgctaactcc tgcacagccc cgtcctcttc ctttctgcta gcctggctaa atctgctcat    60
tatttcagag gggaaaccta gca                                           83
```

<210> SEQ ID NO 1458
<211> LENGTH: 71
<212> TYPE: DNA
<213> ORGANISM: Homo sapiens

<400> SEQUENCE: 1458
gcctgtgcag ttcttgtgcc ccaacatcag cgtggcctac aggctcctgg agggtgaggg    60
tctgcccttc c                                                         71

<210> SEQ ID NO 1459
<211> LENGTH: 67
<212> TYPE: DNA
<213> ORGANISM: Homo sapiens

<400> SEQUENCE: 1459
aagcatgaac aggacttgac catctttcca acccctgggg aagacatttg caactgactt    60
ggggagg                                                              67

<210> SEQ ID NO 1460
<211> LENGTH: 81
<212> TYPE: DNA
<213> ORGANISM: Homo sapiens

<400> SEQUENCE: 1460
tcaacatcac agagggagat tcattttccc agtccctggg accctctcga tcttaccaag    60
aaccaggtcg aagactccac c                                              81

<210> SEQ ID NO 1461
<211> LENGTH: 66
<212> TYPE: DNA
<213> ORGANISM: Homo sapiens

<400> SEQUENCE: 1461
gatccgagac cctcgctccc ccatcaacgt ggagagcttg ctggatggct taaattcctt    60
ggtcct                                                               66

<210> SEQ ID NO 1462
<211> LENGTH: 66
<212> TYPE: DNA
<213> ORGANISM: Homo sapiens

<400> SEQUENCE: 1462
gggctactgg cagctacatt gctgggacta atggcaattc caatggcctt gtaccgatgc    60
tgagag                                                               66

<210> SEQ ID NO 1463
<211> LENGTH: 71
<212> TYPE: DNA
<213> ORGANISM: Homo sapiens

<400> SEQUENCE: 1463
cagcgggatt aaacagtcct ttaaccagca cagccagtta aaagatgcag cctcactgct    60
tcaacgcaga t                                                         71

<210> SEQ ID NO 1464
<211> LENGTH: 69
<212> TYPE: DNA
<213> ORGANISM: Homo sapiens

<400> SEQUENCE: 1464

```
aacagagaca ttgccaacca tattggatct gcttgctgtc caaaccagca aacttcctgg    60
gcaaatcac                                                            69

<210> SEQ ID NO 1465
<211> LENGTH: 66
<212> TYPE: DNA
<213> ORGANISM: Homo sapiens

<400> SEQUENCE: 1465
cagcgtgagc tcctccactg cgcaagactg gccaaacaga ccctgccca gtacctcgcc     60 cagcat                                                               66

<210> SEQ ID NO 1466
<211> LENGTH: 83
<212> TYPE: DNA
<213> ORGANISM: Homo sapiens

<400> SEQUENCE: 1466
tgggcgaggg aagagtttca ccctgaccat cactgtgttc accaaccccca cccaagtggc    60 gacctaccac cgagccatca agg                                            83

<210> SEQ ID NO 1467
<211> LENGTH: 73
<212> TYPE: DNA
<213> ORGANISM: Homo sapiens

<400> SEQUENCE: 1467
tggctgtgct ggtcactacc ttccacaagt actcctgcca agagggcgac aagttcaagc    60
tgagtaaggg gga                                                       73

<210> SEQ ID NO 1468
<211> LENGTH: 70
<212> TYPE: DNA
<213> ORGANISM: Homo sapiens

<400> SEQUENCE: 1468
gactgctgtc atggcgtgcc ctctggagaa ggccctggat gtgatggtgt ccaccttcca    60
caagtactcg                                                           70

<210> SEQ ID NO 1469
<211> LENGTH: 75
<212> TYPE: DNA
<213> ORGANISM: Homo sapiens

<400> SEQUENCE: 1469
cctgctgacg atgatgaagg agaacttccc caacttcctt agtgcctgtg acaaaaaggg    60
cacaaattac ctcgc                                                     75

<210> SEQ ID NO 1470
<211> LENGTH: 76
<212> TYPE: DNA
<213> ORGANISM: Homo sapiens

<400> SEQUENCE: 1470
actccctgat aaaggggaat ttccatgccg tctacaggga tgacctgaag aaattgctag    60
agaccgagtg tcctca                                                    76

<210> SEQ ID NO 1471
```

```
<211> LENGTH: 67
<212> TYPE: DNA
<213> ORGANISM: Homo sapiens

<400> SEQUENCE: 1471
caccctgcct ctacccaacc agggccccgg ggcctgttat gtcaaactgt cttggctgtg      60
gggctag                                                                67

<210> SEQ ID NO 1472
<211> LENGTH: 76
<212> TYPE: DNA
<213> ORGANISM: Homo sapiens

<400> SEQUENCE: 1472
gaaattgacg aggggtgtct tgggcagagc tggctctgag cgcctccatc caaggccagg      60
ttctccgtta gctcct                                                      76

<210> SEQ ID NO 1473
<211> LENGTH: 67
<212> TYPE: DNA
<213> ORGANISM: Homo sapiens

<400> SEQUENCE: 1473
ggtaccagcc tcgacacaat gtcatgatca gcactgagtg ggcagctccc aatgtcttac      60
gagatgg                                                                67

<210> SEQ ID NO 1474
<211> LENGTH: 66
<212> TYPE: DNA
<213> ORGANISM: Homo sapiens

<400> SEQUENCE: 1474
caagctgaac ggtgtgtccg aaagggacct gaagaaatcg gtgctgtggc tcaaagacag      60
cttgca                                                                 66

<210> SEQ ID NO 1475
<211> LENGTH: 67
<212> TYPE: DNA
<213> ORGANISM: Homo sapiens

<400> SEQUENCE: 1475
tacaggatga ggctgggcat tgcctgggac agcctatgta aggccatgtg ccccttgccc      60
taacaac                                                                67

<210> SEQ ID NO 1476
<211> LENGTH: 81
<212> TYPE: DNA
<213> ORGANISM: Homo sapiens

<400> SEQUENCE: 1476
aatgcctgca cccataattt tctagtaata gccacgacca atttattaac agtcagggcc      60
tatccttgcc tgtagttctc a                                                81

<210> SEQ ID NO 1477
<211> LENGTH: 77
<212> TYPE: DNA
<213> ORGANISM: Homo sapiens

<400> SEQUENCE: 1477
aacggactcc ctcaatttgt gcaagatttg catgaccatg gacagaaata tgtcatcatc      60
```

```
ttggaccctg caatttc                                              77

<210> SEQ ID NO 1478
<211> LENGTH: 72
<212> TYPE: DNA
<213> ORGANISM: Homo sapiens

<400> SEQUENCE: 1478
agctggggtg tctgtttcat gtggaatacc tgacttcagg tcaagggatg gtatttatgc    60
tcgccttgct gt                                                       72

<210> SEQ ID NO 1479
<211> LENGTH: 71
<212> TYPE: DNA
<213> ORGANISM: Homo sapiens

<400> SEQUENCE: 1479
agttgcagaa tctaagcctg gaaggcctgc ggctttcgga tcccattgtc aatactctcg    60
caaaaaactc a                                                        71

<210> SEQ ID NO 1480
<211> LENGTH: 77
<212> TYPE: DNA
<213> ORGANISM: Homo sapiens

<400> SEQUENCE: 1480
tcctgctgca actggtattc tggctggagc aaatatctca ggtgatcttg cagatcctca    60
gtcagccata cccaaag                                                  77

<210> SEQ ID NO 1481
<211> LENGTH: 64
<212> TYPE: DNA
<213> ORGANISM: Homo sapiens

<400> SEQUENCE: 1481
tctgccagtg ctgaattctt tgctgacatt gccctggctc ctatggaagc tgctaaggtt    60
cgaa                                                                64

<210> SEQ ID NO 1482
<211> LENGTH: 73
<212> TYPE: DNA
<213> ORGANISM: Homo sapiens

<400> SEQUENCE: 1482
tcccttggag ctgcatacta tagtgattga ctgcagtgca attcaatttt tagatacagc    60
agggatccac aca                                                      73

<210> SEQ ID NO 1483
<211> LENGTH: 67
<212> TYPE: DNA
<213> ORGANISM: Homo sapiens

<400> SEQUENCE: 1483
agtcggtcaa ccagggcttt gaggctgtct accagttgac ccgaatgtgc accatccgca    60
tgagctt                                                             67

<210> SEQ ID NO 1484
<211> LENGTH: 76
<212> TYPE: DNA
```

<213> ORGANISM: Homo sapiens

<400> SEQUENCE: 1484
ggctggccaa acataagcag ctgcactgcg atgcccagtc tagaaaatct ttcagctgta    60
aatactgtga caagga    76

<210> SEQ ID NO 1485
<211> LENGTH: 73
<212> TYPE: DNA
<213> ORGANISM: Homo sapiens

<400> SEQUENCE: 1485
tcttccctgt acactggcag ttcggccagc tggaccagca ccccattgac gggtacctct    60
cccacaccga gct    73

<210> SEQ ID NO 1486
<211> LENGTH: 79
<212> TYPE: DNA
<213> ORGANISM: Homo sapiens

<400> SEQUENCE: 1486
ccatccgcca gtattacaag aagggcatca tccggaagcc agacatctcc cagcgcctcg    60
tctaccagtt cgtgcaccc    79

<210> SEQ ID NO 1487
<211> LENGTH: 75
<212> TYPE: DNA
<213> ORGANISM: Homo sapiens

<400> SEQUENCE: 1487
atttgttccc acaaccaagg agccatgcca ctcaaaggtt ccacaacctg gaaacacaaa    60
gattccagag ccagg    75

<210> SEQ ID NO 1488
<211> LENGTH: 81
<212> TYPE: DNA
<213> ORGANISM: Homo sapiens

<400> SEQUENCE: 1488
gggctcagct ttcagaagtg ctgagttggc agttttcttc tgtcaccaaa agaggtctca    60
atgtggacca gctgaacatg t    81

<210> SEQ ID NO 1489
<211> LENGTH: 74
<212> TYPE: DNA
<213> ORGANISM: Homo sapiens

<400> SEQUENCE: 1489
ccagtggtgg tgatcgttca tggcagccag gacaacaatg cgacggccac tgttctctgg    60
gacaatgctt ttgc    74

<210> SEQ ID NO 1490
<211> LENGTH: 72
<212> TYPE: DNA
<213> ORGANISM: Homo sapiens

<400> SEQUENCE: 1490
ctccgaggtg aggaggactc tccctcccac atcaaacgca catcccatga gagtgcataa    60
ccagggagag gt    72

<210> SEQ ID NO 1491
<211> LENGTH: 69
<212> TYPE: DNA
<213> ORGANISM: Homo sapiens

<400> SEQUENCE: 1491
catcttccag gaggaccact ctctgtggca ccctggacta cctgcccct gaaatgattg    60 aaggtcgga                                                          69

<210> SEQ ID NO 1492
<211> LENGTH: 66
<212> TYPE: DNA
<213> ORGANISM: Homo sapiens

<400> SEQUENCE: 1492
gagccatctt cctgcaactt tacctctttc cctcagatgg ggagccatga ctgggttgca    60
cctcag                                                             66

<210> SEQ ID NO 1493
<211> LENGTH: 90
<212> TYPE: DNA
<213> ORGANISM: Homo sapiens

<400> SEQUENCE: 1493
cctggaggct gcaacatacc tcaatcctgt cccaggccgg atcctcctga agcccttttc    60
gcagcactgc tatcctccaa agccattgta                                   90

<210> SEQ ID NO 1494
<211> LENGTH: 80
<212> TYPE: DNA
<213> ORGANISM: Homo sapiens

<400> SEQUENCE: 1494
tgttttgatt cccgggctta ccaggtgaga agtgagggag gaagaaggca gtgtcccttt    60
tgctagagct gacagctttg                                              80

<210> SEQ ID NO 1495
<211> LENGTH: 73
<212> TYPE: DNA
<213> ORGANISM: Homo sapiens

<400> SEQUENCE: 1495
gatggagcag gtggctcagt tcctgaaggc ggctgaggac tatggggtca tcaagactga    60
catgttccag act                                                     73

<210> SEQ ID NO 1496
<211> LENGTH: 69
<212> TYPE: DNA
<213> ORGANISM: Homo sapiens

<400> SEQUENCE: 1496
acacggtgcc tctggatgcc cgggatggca atgaggtgga gcctgatgat gaccacttct    60
ccattggtg                                                          69

<210> SEQ ID NO 1497
<211> LENGTH: 71
<212> TYPE: DNA
<213> ORGANISM: Homo sapiens

<400> SEQUENCE: 1497
tcaaggatct gaactgtgga aaagattcca tgacatcggg actgagatga tcattactaa    60
agcgggcagg c                                                         71

<210> SEQ ID NO 1498
<211> LENGTH: 85
<212> TYPE: DNA
<213> ORGANISM: Homo sapiens

<400> SEQUENCE: 1498
gacatggaga acaagctgtt tgcggggatt cggcgggacg ggctgctcct gcgtttggtg    60
gatgatttct tgttggtgac acctc                                          85

<210> SEQ ID NO 1499
<211> LENGTH: 67
<212> TYPE: DNA
<213> ORGANISM: Homo sapiens

<400> SEQUENCE: 1499
ccagcatcag ggaggtttct gatccgtctg aaattcaagc catgtcgaac ctgcggtcct    60
gagctta                                                              67

<210> SEQ ID NO 1500
<211> LENGTH: 83
<212> TYPE: DNA
<213> ORGANISM: Homo sapiens

<400> SEQUENCE: 1500
ggtgtgccac agaccttcct acttggcctg taatcacctg tgcagccttt tgtgggcctt    60
caaaactctg tcaagaactc cgt                                            83

<210> SEQ ID NO 1501
<211> LENGTH: 65
<212> TYPE: DNA
<213> ORGANISM: Homo sapiens

<400> SEQUENCE: 1501
ggatcgagct cttccagatc cttcggccag atgagcacat tgccaaacag cgctatatcg    60
gtggc                                                                65

<210> SEQ ID NO 1502
<211> LENGTH: 67
<212> TYPE: DNA
<213> ORGANISM: Homo sapiens

<400> SEQUENCE: 1502
gctacgagtg ctgtcctgga tatgaaaagg tccctgggga aagggctgt ccagcagccc     60 taccact                                                              67

<210> SEQ ID NO 1503
<211> LENGTH: 66
<212> TYPE: DNA
<213> ORGANISM: Homo sapiens

<400> SEQUENCE: 1503
aacaccaatg ggttccatct ttctgggctc ctgattgctc aagcacagtt tggcctgatg    60
aagagg                                                               66

```
<210> SEQ ID NO 1504
<211> LENGTH: 85
<212> TYPE: DNA
<213> ORGANISM: Homo sapiens

<400> SEQUENCE: 1504
catccgcaaa gtgactgaag agaacaaaga gttggccaat gagctgaggc ggcctcccct      60
atgctatcac aacggagttc agtac                                           85

<210> SEQ ID NO 1505
<211> LENGTH: 67
<212> TYPE: DNA
<213> ORGANISM: Homo sapiens

<400> SEQUENCE: 1505
ggacaagacc ctctcaggct gtcccaagct cccaagagct tccagagctc tgacccacag      60
cctccaa                                                               67

<210> SEQ ID NO 1506
<211> LENGTH: 76
<212> TYPE: DNA
<213> ORGANISM: Homo sapiens

<400> SEQUENCE: 1506
tccctgcggt cccagatagc ctgaatcctg cccggagtgg aagctgaagc ctgcacagtg      60
tccaccctgt tcccac                                                     76

<210> SEQ ID NO 1507
<211> LENGTH: 69
<212> TYPE: DNA
<213> ORGANISM: Homo sapiens

<400> SEQUENCE: 1507
tcaccctctg tgacttcatc gtgccctggg acaccctgag caccacccag aagaagagcc      60
tgaaccaca                                                             69

<210> SEQ ID NO 1508
<211> LENGTH: 67
<212> TYPE: DNA
<213> ORGANISM: Homo sapiens

<400> SEQUENCE: 1508
ctacctgcct tgctttgtga cttccaagaa cgagtgtctc tggaccgaca tgctctccaa      60
tttcggt                                                               67

<210> SEQ ID NO 1509
<211> LENGTH: 67
<212> TYPE: DNA
<213> ORGANISM: Homo sapiens

<400> SEQUENCE: 1509
cggtgctgtt actgcctttc gttgtgtcct gcattaatct ggccgtgcca tgcatctact      60
ccatgtt                                                               67

<210> SEQ ID NO 1510
<211> LENGTH: 68
<212> TYPE: DNA
<213> ORGANISM: Homo sapiens

<400> SEQUENCE: 1510
```

```
cagaaggatg cctgtggccc tcggagagca cagtgtcagg caacggaatc ccagagccgc    60
aggtctac                                                             68

<210> SEQ ID NO 1511
<211> LENGTH: 79
<212> TYPE: DNA
<213> ORGANISM: Homo sapiens

<400> SEQUENCE: 1511
ctggctccag aacagaaagg gagcctcacg ctggctcaca caaaacagct gacactgact    60
aaggaactgc agcatttgc                                                 79

<210> SEQ ID NO 1512
<211> LENGTH: 67
<212> TYPE: DNA
<213> ORGANISM: Homo sapiens

<400> SEQUENCE: 1512
gaggtgatgt ggcaaccagc tcttaggcgt gggagaggcc tacaggccca aggatatggt    60
gtccgaa                                                              67

<210> SEQ ID NO 1513
<211> LENGTH: 72
<212> TYPE: DNA
<213> ORGANISM: Homo sapiens

<400> SEQUENCE: 1513
aatccaaggg ggagagtgat gacttccata tggactttga ctcagctgtg gctcctcggg    60
caaaatctgt ac                                                        72

<210> SEQ ID NO 1514
<211> LENGTH: 82
<212> TYPE: DNA
<213> ORGANISM: Homo sapiens

<400> SEQUENCE: 1514
ctatatgcag ccagagatgt gacagccacc gtggacagcc tgccactcat cacagcctcc    60
attctcagta agaaactcgt gg                                             82

<210> SEQ ID NO 1515
<211> LENGTH: 74
<212> TYPE: DNA
<213> ORGANISM: Homo sapiens

<400> SEQUENCE: 1515
tgctgttgct gagtctgttg ccagtcccca gaagaccatg tctgtgttga gctgtatctg    60
tgaagccagg caag                                                      74

<210> SEQ ID NO 1516
<211> LENGTH: 73
<212> TYPE: DNA
<213> ORGANISM: Homo sapiens

<400> SEQUENCE: 1516
cttcacagtg ctcctgcagt ctctctgtgt ggctgtaact tacgtgtact ttaccaacga    60
gctgaagcag atg                                                       73

<210> SEQ ID NO 1517
<211> LENGTH: 67
```

```
<212> TYPE: DNA
<213> ORGANISM: Homo sapiens

<400> SEQUENCE: 1517
tcagcagttc cctctttcag aactcactgc caagagccct gaacaggagc caccatgcag    60
tgcttca                                                              67

<210> SEQ ID NO 1518
<211> LENGTH: 522
<212> TYPE: DNA
<213> ORGANISM: Homo sapiens

<400> SEQUENCE: 1518
gagtcgaccc tgcacctggt cctgcgtctg agaggtggta tgcagatctt cgtgaagacc    60
ctgaccggca agaccatcac cctggaagtg gagcccagtg acaccatcga aaatgtgaag   120
gccaagatcc aggataaaga aggcatccct cccgaccagc agaggctcat ctttgcaggc   180
aagcagctgg aagatggccg cactctttct gactacaaca tccagaagga gtcgaccctg   240
cacctggtcc tgcgtctgag aggtggtatg cagatcttcg tgaagaccct gaccggcaag   300
accatcactc tggaagtgga gcccagtgac accatcgaaa atgtgaaggc caagatccaa   360
gataaagaag gcatccctcc cgaccagcag aggctcatct ttgcaggcaa gcagctggaa   420
gatggccgca ctctttctga ctacaacatc cagaaggagt cgaccctgca cctggtcctg   480
cgcctgaggg gtggctgtta attcttcagt catggcattc gc                      522

<210> SEQ ID NO 1519
<211> LENGTH: 67
<212> TYPE: DNA
<213> ORGANISM: Homo sapiens

<400> SEQUENCE: 1519
tgtctggcga taagggatt tctgccttcc ctgaatcaga caaccttttc aaatgggtag     60
ggaccat                                                              67

<210> SEQ ID NO 1520
<211> LENGTH: 73
<212> TYPE: DNA
<213> ORGANISM: Homo sapiens

<400> SEQUENCE: 1520
gtgaagccac cgtcatcatg tctgaccagg aggcaaaacc ttcaactgag gacttggggg    60
ataagaagga agg                                                       73

<210> SEQ ID NO 1521
<211> LENGTH: 66
<212> TYPE: DNA
<213> ORGANISM: Homo sapiens

<400> SEQUENCE: 1521
gttctgcaga cacgccttcc cctcagccac acccaggcac ttaagcacaa gcagagtgca    60
cagctg                                                               66

<210> SEQ ID NO 1522
<211> LENGTH: 70
<212> TYPE: DNA
<213> ORGANISM: Homo sapiens

<400> SEQUENCE: 1522
```

```
accatgctcc agaaggaggg gccccgagcc ttctacaaag ggttcatgcc ctcctttctc    60
cgcttgggtt                                                           70

<210> SEQ ID NO 1523
<211> LENGTH: 71
<212> TYPE: DNA
<213> ORGANISM: Homo sapiens

<400> SEQUENCE: 1523
tgcggaaatg agctccaccg gctccctggc cactggggac tacactagag cagcggttag    60
aatggctgag g                                                         71

<210> SEQ ID NO 1524
<211> LENGTH: 70
<212> TYPE: DNA
<213> ORGANISM: Homo sapiens

<400> SEQUENCE: 1524
gtggatgtgc cctgaaggac aagccaggcg tctacacgag agtctcacac ttcttaccct    60
ggatccgcag                                                           70

<210> SEQ ID NO 1525
<211> LENGTH: 70
<212> TYPE: DNA
<213> ORGANISM: Homo sapiens

<400> SEQUENCE: 1525
ggaacgctgg gaaactcccg gcctccgcca ccatcttgct ttcctttaat ccggcagtga    60
ccgtgtgtca                                                           70

<210> SEQ ID NO 1526
<211> LENGTH: 67
<212> TYPE: DNA
<213> ORGANISM: Homo sapiens

<400> SEQUENCE: 1526
caggtgtagc ctgccctctc atcaatccgt ctgggtgcca gaactcaagg ttcagtggac    60
acatccc                                                              67

<210> SEQ ID NO 1527
<211> LENGTH: 89
<212> TYPE: DNA
<213> ORGANISM: Homo sapiens

<400> SEQUENCE: 1527
tggcttcagg agctgaatac cctcccaggc acacacaggt gggacacaaa taagggtttt    60
ggaaccacta ttttctcatc acgacagca                                      89

<210> SEQ ID NO 1528
<211> LENGTH: 69
<212> TYPE: DNA
<213> ORGANISM: Homo sapiens

<400> SEQUENCE: 1528
cctgctacac agccaacaag accacccact gtggaagaca aagaggcctt tggacctcag    60
gcgctttct                                                            69

<210> SEQ ID NO 1529
<211> LENGTH: 66
```

<212> TYPE: DNA
<213> ORGANISM: Homo sapiens

<400> SEQUENCE: 1529
acccacggac agacttgcgc gcgtccaatg tgtattcctc catcatatgc tgaccttggc    60
aaagct    66

<210> SEQ ID NO 1530
<211> LENGTH: 71
<212> TYPE: DNA
<213> ORGANISM: Homo sapiens

<400> SEQUENCE: 1530
ctgctgtctt gggtgcattg gagccttgcc ttgctgctct acctccacca tgccaagtgg    60
tcccaggctg c    71

<210> SEQ ID NO 1531
<211> LENGTH: 73
<212> TYPE: DNA
<213> ORGANISM: Homo sapiens

<400> SEQUENCE: 1531
tgtgaatgca gaccaaagaa agatagagca agacaagaaa atccctgtgg gccttgctca    60
gagcggagaa agc    73

<210> SEQ ID NO 1532
<211> LENGTH: 77
<212> TYPE: DNA
<213> ORGANISM: Homo sapiens

<400> SEQUENCE: 1532
agcttcctac agcacaacaa atgtgaatgc agaccaaaga agatagagc aagacaagaa    60 aaatgtgaca agccgag    77

<210> SEQ ID NO 1533
<211> LENGTH: 83
<212> TYPE: DNA
<213> ORGANISM: Homo sapiens

<400> SEQUENCE: 1533
cctcagcaag acgttatttg aaattacagt gcctctctct caaggcccca aaccagtaac    60
aatcagtttt gccaatcaca ctt    83

<210> SEQ ID NO 1534
<211> LENGTH: 72
<212> TYPE: DNA
<213> ORGANISM: Homo sapiens

<400> SEQUENCE: 1534
tgcccttaaa ggaaccaatg agtccctgga acgccagatg cgtgaaatgg aagagaactt    60
tgccgttgaa gc    72

<210> SEQ ID NO 1535
<211> LENGTH: 69
<212> TYPE: DNA
<213> ORGANISM: Homo sapiens

<400> SEQUENCE: 1535
gagaactggt ggagcctttc tcttactccc aggacttcag cacctaagac agctccaaaa    60

```
caaaccaga                                                              69

<210> SEQ ID NO 1536
<211> LENGTH: 75
<212> TYPE: DNA
<213> ORGANISM: Homo sapiens

<400> SEQUENCE: 1536
agaggcatcc atgaacttca cacttgcggg ctgcatcagc acacgctcct atcaacccaa      60
gtactgtgga gtttg                                                      75

<210> SEQ ID NO 1537
<211> LENGTH: 74
<212> TYPE: DNA
<213> ORGANISM: Homo sapiens

<400> SEQUENCE: 1537
acaaagctac cagggagtcg gcctttgtcc acgccattgc ctcagccggt gtggcctttg      60
cagtgacacg ctca                                                       74

<210> SEQ ID NO 1538
<211> LENGTH: 67
<212> TYPE: DNA
<213> ORGANISM: Homo sapiens

<400> SEQUENCE: 1538
cggtggaatc tggctctggc tccctctgct cttgacctgg ctcaccccccg aggtcaactc     60 ttcatgg                                                               67
```